US009803218B2

(12) United States Patent
Chatterjee et al.

(10) Patent No.: US 9,803,218 B2
(45) **Date of Patent: *Oct. 31, 2017**

(54) RECOMBINANT ADENO-ASSOCIATED VECTORS FOR TARGETED TREATMENT

(71) Applicant: CITY OF HOPE, Duarte, CA (US)

(72) Inventors: Saswati Chatterjee, Altadena, CA (US); Laura Jane Smith, Westford, MA (US); Kamehameha K. Wong, Jr., Altadena, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/337,499

(22) Filed: Oct. 28, 2016

(65) Prior Publication Data

US 2017/0073703 A1 Mar. 16, 2017

Related U.S. Application Data

(63) Continuation of application No. 14/582,070, filed on Dec. 23, 2014, now Pat. No. 9,623,120, which is a continuation of application No. 13/668,120, filed on Nov. 2, 2012, now Pat. No. 8,927,514, which is a continuation-in-part of application No. 13/097,046, filed on Apr. 28, 2011, now Pat. No. 8,628,966.

(60) Provisional application No. 61/330,272, filed on Apr. 30, 2010.

(51) Int. Cl.

| | |
|---|---|
| ***A61K 48/00*** | (2006.01) |
| ***C12N 15/86*** | (2006.01) |
| ***C07K 14/00*** | (2006.01) |
| ***C12N 7/00*** | (2006.01) |
| ***C07K 14/005*** | (2006.01) |

(52) U.S. Cl.

CPC ............ *C12N 15/86* (2013.01); *A61K 48/005* (2013.01); *A61K 48/0075* (2013.01); *C07K 14/00* (2013.01); *C07K 14/005* (2013.01); *C12N 7/00* (2013.01); *A61K 48/00* (2013.01); *C12N 2750/14122* (2013.01); *C12N 2750/14132* (2013.01); *C12N 2750/14143* (2013.01); *C12N 2810/6027* (2013.01)

(58) Field of Classification Search

CPC .............................. C12N 15/86; A61K 48/005

See application file for complete search history.

(56) References Cited

U.S. PATENT DOCUMENTS

| | | | |
|---|---|---|---|
| 4,866,042 | A | 9/1989 | Neuwelt |
| 8,628,966 | B2 | 1/2014 | Chatterjee et al. |
| 8,927,514 | B2 | 1/2015 | Chatterjee et al. |
| 9,623,120 | B2 | 4/2017 | Chatterjee et al. |
| 2010/0310583 | A1 | 12/2010 | Lieberman et al. |
| 2017/0073703 | A1 | 3/2017 | Chatterjee et al. |

OTHER PUBLICATIONS

Aalbers et al. (2011) "Advancements in adeno-associated viral gene therapy approaches: exploring a new horizon," F1000 Medicine Reports. 3:17. pp. 1-8.

Bainbridge et al. (2008) "Effect of Gene Therapy on Visual Function in Leber's Congenital Amaurosis," N. Eng. J. Med. 358(21):2231-2239.

Batchu et al. (2002) "Adeno-Associated Virus Protects the Retinoblastoma Family of Proteins from Adenoviral-Induced Functional Inactivation," Cancer Res. 62:2982-2985.

Bell et al. (2005) "No Evidence for Tumorigenesis of AAV Vectors in a Large-Scale Study in Mice," Mol. Ther. 12(2):299-306.

Berns et al. (1996) "Biology of Adeno-Associated Virus," Curr. Top. Microbiol. Immunol. 218:1-23.

Biffi et al. (2008) "Human Hematopoietic Stem Cells in Gene Therapy: Pre-Clinical and Clinical Issues," Current Gene Ther. 8:135-146.

Brantly et al. (2009) "Sustained Transgene Expression Despite T Lymphocyte Responses in a Clinical Trial of rAAV1-AAT Gene Therapy," Proc. Natl. Acad. Sci. USA. 106(38):16363-16368.

Chatterjee et al. (1993) "Adeno-Associated Viral Vectors for the Delivery of Antisense RNA," Methods: A Companion to Methods in Enzymology 5:51-59.

Chatterjee et al. (1992) "Dual-Target Inhibition of HIV-1 in Vitro by Means of an Adeno-Associated Virus Antisense Vector," Science 258:1485-1488.

Chatterjee et al. (1999) "Transduction of Primitive Human Marrow and Cord Blood-Derived Hematopoietic Progenitor Cells with Adeno-Associated Virus Vectors," 93:1882-1894.

Cideciyan et al. (2009) "Human RPE65 Gene Therapy for Leber Congenital Amaurosis: Persistence of Early Visual Improvements and Safety at 1 Year," Hum. Gene Ther. 20:999-1004.

Einerhand et al. (1995) "Regulated High-Level Human beta-Globin Gene Expression in Erythroid Cells Following Recombinant Adeno-Associated Virus-Mediated Gene Transfer," Gene Therapy 2: 336-343.

Fisher-Adams et al. (1996) "Integration of Adeno-Associated Virus Vectors in CD34+ Human Hematopoietic Progenitor Cells After Transduction," Blood 88:492-504.

Flotte et al. (2004) "Phase I Trial of Intramuscular Injection of a Recombinant Adeno-Associated Virus Alpha 1-Antitrypsin (rAAV2-CB-hAAT) Gene Vector to AAT-Deficient Adults," Human Gene Therapy 14:93-128.

Fu et al. (Mar. 29, 2013) "A Novel Peptide Delivers Plasminds Across Blood-Brain Barrier into Neuronal Cells as a Single-Component Transfer Vector," PLOS One 8(3):e59642. pp. 1-9.

(Continued)

*Primary Examiner* — Marcia S Noble

(74) *Attorney, Agent, or Firm* — Lathrop Gage LLP; Andrew T. Wilkins; Lily W. Xu

(57) ABSTRACT

Novel adeno-associated virus (AAV) vectors in nucleotide and amino acid forms and uses thereof are provided. The isolates show specific tropism for certain target tissues, such as blood stem cells, liver, heart and joint tissue, and may be used to transduce stem cells for introduction of genes of interest into the target tissues. Certain of the vectors are able to cross tightly controlled biological junctions, such as the blood-brain barrier, which open up additional novel uses and target organs for the vectors, providing for additional methods of gene therapy and drug delivery.

46 Claims, 133 Drawing Sheets

(56) References Cited

OTHER PUBLICATIONS

Gao et al. (2004) "Glades of Adeno-Associated Viruses Are Widely Disseminated in Human Tissues," J. Virol. 78(12):6381-6388.
Hacein-Bey-Abina et al. (2003) "A Serious Adverse Event After Successful Gene Therapy for X-Linked Severe combined Immunodeficiency," N. Eng. J. Med. 348(3):255-266.
Hackel et al. (Jun. 6, 2012) "Modulation of Tight Junction Proteins in the Perineurium for Regional Pain Control," Ann. N. Y. Acad. Sci. 1257:199-206.
Han et al. (2008) "Stable Integration of Recombinant Adeno-Associated Virus Vector Genomes After Transduction of Murine Hematopoietic Stem Cells," Human Gene Therapy 19:267-278.
Jayandharan et al. (2008) "Strategies for Improving the Transduction Efficiency of Single-Stranded Adeno-Associated Virus Vectors In Vitro and In Vivo," Gene Therapy 15:1287-1293.
Jordan et al. (May 7, 2013) "Advanced in the Understanding of Retinal Drug Disposition and the Role of Blood-Ocular Barrier Transporters," Expert Opin. Drug Metab. Toxicol. 9(9):1181-1192.
Kaplitt et al. (2007) "Safety and Tolerability of Gene Therapy with an Adeno-Associated Virus (AAV) Borne GAD Gene for Parkinson's Disease: An Open Label, Phase I Trial," Lancet 369:2097-2105.
Kells et al. (2009) "Efficient Gene Therapy-Based Method for the Delivery of Therapeutics to Primate Cortex," Proc. Natl. Acad. Sci. USA 106(7):2407-2411.
Kessler et al. (1996) "Gene Delivery to Skeletal Muscle Results in Sustained Expression and Systemic Delivery of a Therapeutic Protein," Proc. Natl. Acad. Sci. USA. 93:14082-14087.
Manno et al. (2003) "AAV-Mediated Factor IX Gene Transfer to Skeletal Muscle in Patients with Severe Hemophilia B," Blood 101:2963-2972.
McCormack et al. (2004) "Activation of the T-Cell Oncogenen LMO2 After Gene Therapy for X-Linked Severe Combined Immunodeficiency," N. Eng. J. Med. 350(9):913-922.
Miller et al. (1990) "Gene Transfer by Retrovirus Vectors Occurs Only in Cells that are Actively Replicating at the Time of Infection," Mol. Cell. Biol. 10(8):4239-4242.
Paz et al. (2007) "Quiescent Subpopulations of Human CD34-Positive Hematopoietic Stem Cells are Preferred Targets for Stable Recombinant Adeno-Associated Virus Type 2 Transduction," Human Gene Therapy 18:614-626.
Petrs-Silva et al. (2009) "High-Efficiency Transduction of the Mouse Retina by Tyrosine-Mutant AAV Serotype Vectors," Mol. Ther. 17(3):463-471.
Podsakoff et al. (1994) "Efficient Gene Transfer into Nondividing Cells by Adeno-Associated Virus-based Vectors," J. Virol. 68(9):5656-5666.
Ponnazhagan et al. (1997) "Adeno-Associated Virus Type 2-Mediated Transduction of Murine Hematopoietic Cells with Long-Term Repopulating Ability and Sustained Expression of a Human Globin Gene In Vivo," J. Virol. 71(4):3098-3104.
Raj et al. (2001) "Virus-Mediated Killing of Cells that Lack p53 Activity," Nature 412:914-917.
Santat et al. (2005) "Recombinant AAV2 Transduction of Primitive Human Hematopoietic Stem Cells Capable of Serial Engraftment in Immune-Deficient Mice," Proc. Natl. Acad. Sci. USA. 102(31):11053-11058.
Srivastava (2004) "Hematopoietic Stem and Progenitor Cells by AAV2 Vectors," Methods in Mol Biol 246:245-254.
Towne et al. (2010) "Efficient Transduction of Non-Human Primate Motor Neurons After Intramuscular Delivery of Recombinant AAV Serotype 6," Gene Ther. 17:141-146.
Zhong et al. (2007) "A Dual Role of EGFR Protein Tyrosine Kinase Signaling in Ubiquitination of AAV2 Capsids and Viral Second-Strand DNA Synthesis," Mol. Ther. 15(7):1323-1330.
Zhong et al. (2004) "Impaired Nuclear Transport and Uncoating Limit Recombinant Adeno-Associated Virus 2 Vector-Mediated Transduction of Primary Murine Hematopoietic Cells," Human Gene Therapy 15:1207-1218.
Zhong et al. (2008) "Next Generation of Adeno-Associated Virus 2 Vectors: Point Mutations in Tyrosines Lead to - High-Efficiency Transduction at Lower Doses," Proc. Natl. Acad. Sci. USA. 105(22):7827-7832.
Zhong et al. (2004) "Self-Complementary Adeno-Associated Virus 2 (AAV)-T Cell Protein Tyrosine Phosphatase Vectors as Helper Viruses to Improve Transduction Efficiency of Conventional Single-Stranded AAV Vectors In Vitro and In Vivo," Mol. Ther. 10(5):950-957.
Zhong et al. (2008) "Tyrosine Phosphorylation of AAV2 Vectors and Its Consequences on Viral Intracellular Trafficking and Transgene Expression," Virology 381(2):194-202.
Zhou et al. (1993) "Adeno-Associated Virus 2-Mediated Gene Transfer in Murine Hematopoietic Progenitor Cells," Experimental Hematology 21:928-933.

Figure 1

```
                                      1                                                                         75
SEQ ID NO: 20 HSC1 Rep Cap Seq    (1) ---------------------------------------------------------------------------
SEQ ID NO: 21 HSC2 Rep Cap Seq    (1) ---------------------------------------------------------------------------
SEQ ID NO: 22 HSC3 Rep Cap Seq    (1) ---------------------------------------------------------------------------
SEQ ID NO: 23 HSC4 Rep Cap Seq    (1) ---------------------------------------------------------------------------
SEQ ID NO: 24 HSC6 Rep Cap Seq    (1) ---------------------------------------------------------------------------
SEQ ID NO: 25 HSC5 Rep Cap Seq    (1) ---------------------------------------------------------------------------
SEQ ID NO: 26 HSC11 Rep Cap Seq   (1) ---------------------------------------------------------------------------
SEQ ID NO: 27 HSC7 Rep Cap Seq    (1) ---------------------------------------------------------------------------
SEQ ID NO: 28 HSC8 Rep Cap Seq    (1) ---------------------------------------------------------------------------
SEQ ID NO: 29 HSC9 Rep Cap Seq    (1) ---------------------------------------------------------------------------
SEQ ID NO: 30 HSC12 Rep Cap Seq   (1) ---------------------------------------------------------------------------
SEQ ID NO: 31 HSC13 Rep Cap Seq   (1) ---------------------------------------------------------------------------
SEQ ID NO: 32 HSC14 Rep Cap Seq   (1) ---------------------------------------------------------------------------
SEQ ID NO: 33 HSC15 Rep Cap Seq   (1) ---------------------------------------------------------------------------
SEQ ID NO: 34 HSC16 Rep Cap Seq   (1) ---------------------------------------------------------------------------
SEQ ID NO: 35 HSC17 Rep Cap Seq   (1) ---------------------------------------------------------------------------
SEQ ID NO: 18 AAV9 Capsid         (1) ---------------------------------------------------------------------------
SEQ ID NO: 19 AAV2                (1) TTGGCCACTCCCTCTCTGCGCGCTCGCTCGCTCACTGAGGCCGGGCGACCAAAGGTCGCCCGACGCCCGGGCTTT
```

Figure 1 (cont.)

```
                              76                                                                        150
HSC1 Rep Cap Seq         (1) ---------------------------------------------------------------------------
HSC2 Rep Cap Seq         (1) ---------------------------------------------------------------------------
HSC3 Rep Cap Seq         (1) ---------------------------------------------------------------------------
HSC4 Rep Cap Seq         (1) ---------------------------------------------------------------------------
HSC6 Rep Cap Seq         (1) ---------------------------------------------------------------------------
HSC5 Rep Cap Seq         (1) ---------------------------------------------------------------------------
HSC11 Rep Cap Seq        (1) ---------------------------------------------------------------------------
HSC7 Rep Cap Seq         (1) ---------------------------------------------------------------------------
HSC8 Rep Cap Seq         (1) ---------------------------------------------------------------------------
HSC9 Rep Cap Seq         (1) ---------------------------------------------------------------------------
HSC12 Rep Cap Seq        (1) ---------------------------------------------------------------------------
HSC13 Rep Cap Seq        (1) ---------------------------------------------------------------------------
HSC14 Rep Cap Seq        (1) ---------------------------------------------------------------------------
HSC15 Rep Cap Seq        (1) ---------------------------------------------------------------------------
HSC16 Rep Cap Seq        (1) ---------------------------------------------------------------------------
HSC17 Rep Cap Seq        (1) ---------------------------------------------------------------------------
AAV9 Capsid              (1) ---------------------------------------------------------------------------
AAV2                    (76) GCCCGGGCGGCCTCAGTGAGCGAGCGAGCGCGCAGAGAGGGAGTGGCCAACTCCATCACTAGGGGT--TCCTGGA
```

Figure 1 (cont.)

```
                              151                                                                       225
HSC1 Rep Cap Seq        (1) ---------------------------------------------------------------------------
HSC2 Rep Cap Seq        (1) ---------------------------------------------------------------------------
HSC3 Rep Cap Seq        (1) ---------------------------------------------------------------------------
HSC4 Rep Cap Seq        (1) ---------------------------------------------------------------------------
HSC6 Rep Cap Seq        (1) ---------------------------------------------------------------------------
HSC5 Rep Cap Seq        (1) ---------------------------------------------------------------------------
HSC11 Rep Cap Seq       (1) ---------------------------------------------------------------------------
HSC7 Rep Cap Seq        (1) ---------------------------------------------------------------------------
HSC8 Rep Cap Seq        (1) ---------------------------------------------------------------------------
HSC9 Rep Cap Seq        (1) ---------------------------------------------------------------------------
HSC12 Rep Cap Seq       (1) ---------------------------------------------------------------------------
HSC13 Rep Cap Seq       (1) ---------------------------------------------------------------------------
HSC14 Rep Cap Seq       (1) ---------------------------------------------------------------------------
HSC15 Rep Cap Seq       (1) ---------------------------------------------------------------------------
HSC16 Rep Cap Seq       (1) ---------------------------------------------------------------------------
HSC17 Rep Cap Seq       (1) ---------------------------------------------------------------------------
AAV9 Capsid             (1) ---------------------------------------------------------------------------
AAV2                  (149) GGG-----------GTGGAGTCG----TGACGTGAATTACGTCATAGGGTTAGGGAGGTCCTGTATTAGAGGTCA
```

Figure 1 (cont.)

```
                                226                                                                       300
HSC1 Rep Cap Seq         (1) ---------------------------------------------------------------------------
HSC2 Rep Cap Seq         (1) ---------------------------------------------------------------------------
HSC3 Rep Cap Seq         (1) ---------------------------------------------------------------------------
HSC4 Rep Cap Seq         (1) ---------------------------------------------------------------------------
HSC6 Rep Cap Seq         (1) ---------------------------------------------------------------------------
HSC5 Rep Cap Seq         (1) ---------------------------------------------------------------------------
HSC11 Rep Cap Seq        (1) ---------------------------------------------------------------------------
HSC7 Rep Cap Seq         (1) ---------------------------------------------------------------------------
HSC8 Rep Cap Seq         (1) ---------------------------------------------------------------------------
HSC9 Rep Cap Seq         (1) ---------------------------------------------------------------------------
HSC12 Rep Cap Seq        (1) ---------------------------------------------------------------------------
HSC13 Rep Cap Seq        (1) ---------------------------------------------------------------------------
HSC14 Rep Cap Seq        (1) ---------------------------------------------------------------------------
HSC15 Rep Cap Seq        (1) ---------------------------------------------------------------------------
HSC16 Rep Cap Seq        (1) ---------------------------------------------------------------------------
HSC17 Rep Cap Seq        (1) ---------------------------------------------------------------------------
AAV9 Capsid              (1) ---------------------------------------------------------------------------
AAV2                   (209) CGTGAGTG-TTTTGCGACATTTTGCGACACCATGTGGTCACGCTGGGTATTTAAGCCCGAGTGAGCACGCAGGGT
```

Figure 1 (cont.)

```
                           301                                                                       375
HSC1 Rep Cap Seq     (1)   ---------------------------------------------------------------------------
HSC2 Rep Cap Seq     (1)   ---------------------------------------------------------------------------
HSC3 Rep Cap Seq     (1)   ---------------------------------------------------------------------------
HSC4 Rep Cap Seq     (1)   ---------------------------------------------------------------------------
HSC6 Rep Cap Seq     (1)   ---------------------------------------------------------------------------
HSC5 Rep Cap Seq     (1)   ---------------------------------------------------------------------------
HSC11 Rep Cap Seq    (1)   ---------------------------------------------------------------------------
HSC7 Rep Cap Seq     (1)   ---------------------------------------------------------------------------
HSC8 Rep Cap Seq     (1)   ---------------------------------------------------------------------------
HSC9 Rep Cap Seq     (1)   ---------------------------------------------------------------------------
HSC12 Rep Cap Seq    (1)   ---------------------------------------------------------------------------
HSC13 Rep Cap Seq    (1)   ---------------------------------------------------------------------------
HSC14 Rep Cap Seq    (1)   ---------------------------------------------------------------------------
HSC15 Rep Cap Seq    (1)   ---------------------------------------------------------------------------
HSC16 Rep Cap Seq    (1)   ---------------------------------------------------------------------------
HSC17 Rep Cap Seq    (1)   ---------------------------------------------------------------------------
AAV9 Capsid          (1)   ---------------------------------------------------------------------------
AAV2               (283)   CTCCATTTTGAAGCGGGAGGTTTGAACGCGCAGCCGCCATGCCGGGGTTTTACGAGATTGTGATTAAGGTCCCCA
```

Figure 1 (cont.)

```
                             376                                                                       450
HSC1 Rep Cap Seq      (1)  ---------------------------------------------------------------------------
HSC2 Rep Cap Seq      (1)  ---------------------------------------------------------------------------
HSC3 Rep Cap Seq      (1)  ---------------------------------------------------------------------------
HSC4 Rep Cap Seq      (1)  ---------------------------------------------------------------------------
HSC6 Rep Cap Seq      (1)  ---------------------------------------------------------------------------
HSC5 Rep Cap Seq      (1)  ---------------------------------------------------------------------------
HSC11 Rep Cap Seq     (1)  ---------------------------------------------------------------------------
HSC7 Rep Cap Seq      (1)  ---------------------------------------------------------------------------
HSC8 Rep Cap Seq      (1)  ---------------------------------------------------------------------------
HSC9 Rep Cap Seq      (1)  ---------------------------------------------------------------------------
HSC12 Rep Cap Seq     (1)  ---------------------------------------------------------------------------
HSC13 Rep Cap Seq     (1)  ---------------------------------------------------------------------------
HSC14 Rep Cap Seq     (1)  ---------------------------------------------------------------------------
HSC15 Rep Cap Seq     (1)  ---------------------------------------------------------------------------
HSC16 Rep Cap Seq     (1)  ---------------------------------------------------------------------------
HSC17 Rep Cap Seq     (1)  ---------------------------------------------------------------------------
AAV9 Capsid           (1)  ---------------------------------------------------------------------------
AAV2                (358)  GCGACCTTGACGAGCATCTGCCCGGCATTTCTGACAGCTTTGTGAACTGGGTGGCCGAGAAGGAATGGGAGTTGC
```

Figure 1 (cont.)

```
                               451                                                                       525
HSC1 Rep Cap Seq         (1) ---------------------------------------------------------------------------
HSC2 Rep Cap Seq         (1) ---------------------------------------------------------------------------
HSC3 Rep Cap Seq         (1) ---------------------------------------------------------------------------
HSC4 Rep Cap Seq         (1) ---------------------------------------------------------------------------
HSC6 Rep Cap Seq         (1) ---------------------------------------------------------------------------
HSC5 Rep Cap Seq         (1) ---------------------------------------------------------------------------
HSC11 Rep Cap Seq        (1) ---------------------------------------------------------------------------
HSC7 Rep Cap Seq         (1) ---------------------------------------------------------------------------
HSC8 Rep Cap Seq         (1) ---------------------------------------------------------------------------
HSC9 Rep Cap Seq         (1) ---------------------------------------------------------------------------
HSC12 Rep Cap Seq        (1) ---------------------------------------------------------------------------
HSC13 Rep Cap Seq        (1) ---------------------------------------------------------------------------
HSC14 Rep Cap Seq        (1) ---------------------------------------------------------------------------
HSC15 Rep Cap Seq        (1) ---------------------------------------------------------------------------
HSC16 Rep Cap Seq        (1) ---------------------------------------------------------------------------
HSC17 Rep Cap Seq        (1) ---------------------------------------------------------------------------
AAV9 Capsid              (1) ---------------------------------------------------------------------------
AAV2                   (433) CGCCAGATTCTGACATGGATCTGAATCTGATTGAGCAGGCACCCCTGACCGTGGCCGAGAAGCTGCAGCGCGACT
```

Figure 1 (cont.)

```
                              526                                                                       600
HSC1 Rep Cap Seq       (1)   ---------------------------------------------------------------------------
HSC2 Rep Cap Seq       (1)   ---------------------------------------------------------------------------
HSC3 Rep Cap Seq       (1)   ---------------------------------------------------------------------------
HSC4 Rep Cap Seq       (1)   ---------------------------------------------------------------------------
HSC6 Rep Cap Seq       (1)   ---------------------------------------------------------------------------
HSC5 Rep Cap Seq       (1)   ---------------------------------------------------------------------------
HSC11 Rep Cap Seq      (1)   ---------------------------------------------------------------------------
HSC7 Rep Cap Seq       (1)   ---------------------------------------------------------------------------
HSC8 Rep Cap Seq       (1)   ---------------------------------------------------------------------------
HSC9 Rep Cap Seq       (1)   ---------------------------------------------------------------------------
HSC12 Rep Cap Seq      (1)   ---------------------------------------------------------------------------
HSC13 Rep Cap Seq      (1)   ---------------------------------------------------------------------------
HSC14 Rep Cap Seq      (1)   ---------------------------------------------------------------------------
HSC15 Rep Cap Seq      (1)   ---------------------------------------------------------------------------
HSC16 Rep Cap Seq      (1)   ---------------------------------------------------------------------------
HSC17 Rep Cap Seq      (1)   ---------------------------------------------------------------------------
AAV9 Capsid            (1)   ---------------------------------------------------------------------------
AAV2                 (508)   TTCTGACGGAATGGCGCCGTGTGAGTAAGGCCCCGGAGGCCCTTTTCTTTGTGCAATTTGAGAAGGGAGAGAGCT
```

Figure 1 (cont.)

```
                                601                                                                       675
HSC1 Rep Cap Seq          (1)   ---------------------------------------------------------------------------
HSC2 Rep Cap Seq          (1)   ---------------------------------------------------------------------------
HSC3 Rep Cap Seq          (1)   ---------------------------------------------------------------------------
HSC4 Rep Cap Seq          (1)   ---------------------------------------------------------------------------
HSC6 Rep Cap Seq          (1)   ---------------------------------------------------------------------------
HSC5 Rep Cap Seq          (1)   ---------------------------------------------------------------------------
HSC11 Rep Cap Seq         (1)   ---------------------------------------------------------------------------
HSC7 Rep Cap Seq          (1)   ---------------------------------------------------------------------------
HSC8 Rep Cap Seq          (1)   ---------------------------------------------------------------------------
HSC9 Rep Cap Seq          (1)   ---------------------------------------------------------------------------
HSC12 Rep Cap Seq         (1)   ---------------------------------------------------------------------------
HSC13 Rep Cap Seq         (1)   ---------------------------------------------------------------------------
HSC14 Rep Cap Seq         (1)   ---------------------------------------------------------------------------
HSC15 Rep Cap Seq         (1)   ---------------------------------------------------------------------------
HSC16 Rep Cap Seq         (1)   ---------------------------------------------------------------------------
HSC17 Rep Cap Seq         (1)   ---------------------------------------------------------------------------
AAV9 Capsid               (1)   ---------------------------------------------------------------------------
AAV2                    (583)   ACTTCCACATGCACGTGCTCGTGGAAACCACCGGGGTGAAATCCATGGTTTTGGGACGTTTCCTGAGTCAGATTC
```

Figure 1 (cont.)

```
                          676                                                                       750
HSC1 Rep Cap Seq      (1) ---------------------------------------------------------------------------
HSC2 Rep Cap Seq      (1) ---------------------------------------------------------------------------
HSC3 Rep Cap Seq      (1) ---------------------------------------------------------------------------
HSC4 Rep Cap Seq      (1) ---------------------------------------------------------------------------
HSC6 Rep Cap Seq      (1) ---------------------------------------------------------------------------
HSC5 Rep Cap Seq      (1) ---------------------------------------------------------------------------
HSC11 Rep Cap Seq     (1) ---------------------------------------------------------------------------
HSC7 Rep Cap Seq      (1) ---------------------------------------------------------------------------
HSC8 Rep Cap Seq      (1) ---------------------------------------------------------------------------
HSC9 Rep Cap Seq      (1) ---------------------------------------------------------------------------
HSC12 Rep Cap Seq     (1) ---------------------------------------------------------------------------
HSC13 Rep Cap Seq     (1) ---------------------------------------------------------------------------
HSC14 Rep Cap Seq     (1) ---------------------------------------------------------------------------
HSC15 Rep Cap Seq     (1) ---------------------------------------------------------------------------
HSC16 Rep Cap Seq     (1) ---------------------------------------------------------------------------
HSC17 Rep Cap Seq     (1) ---------------------------------------------------------------------------
AAV9 Capsid           (1) ---------------------------------------------------------------------------
AAV2                (658) GCGAAAAACTGATTCAGAGAATTTACCGCGGGATCGAGCCGACTTTGCCAAACTGGTTCGCGGTCACAAAGACCA
```

Figure 1 (cont.)

```
                                751                                                                     825
HSC1 Rep Cap Seq         (1) ---------------------------------------------------------------------------
HSC2 Rep Cap Seq         (1) ---------------------------------------------------------------------------
HSC3 Rep Cap Seq         (1) ---------------------------------------------------------------------------
HSC4 Rep Cap Seq         (1) ---------------------------------------------------------------------------
HSC6 Rep Cap Seq         (1) ---------------------------------------------------------------------------
HSC5 Rep Cap Seq         (1) ---------------------------------------------------------------------------
HSC11 Rep Cap Seq        (1) ---------------------------------------------------------------------------
HSC7 Rep Cap Seq         (1) ---------------------------------------------------------------------------
HSC8 Rep Cap Seq         (1) ---------------------------------------------------------------------------
HSC9 Rep Cap Seq         (1) ---------------------------------------------------------------------------
HSC12 Rep Cap Seq        (1) ---------------------------------------------------------------------------
HSC13 Rep Cap Seq        (1) ---------------------------------------------------------------------------
HSC14 Rep Cap Seq        (1) ---------------------------------------------------------------------------
HSC15 Rep Cap Seq        (1) ---------------------------------------------------------------------------
HSC16 Rep Cap Seq        (1) ---------------------------------------------------------------------------
HSC17 Rep Cap Seq        (1) ---------------------------------------------------------------------------
AAV9 Capsid              (1) ---------------------------------------------------------------------------
AAV2                   (733) GAAATGGCGCCGGAGGCGGGAACAAGGTGGTGGATGAGTGCTACATCCCCAATTACTTGCTCCCCAAAACCCAGC
```

Figure 1 (cont.)

```
                           826                                                                       900
HSC1 Rep Cap Seq       (1) ---------------------------------------------------------------------------
HSC2 Rep Cap Seq       (1) ---------------------------------------------------------------------------
HSC3 Rep Cap Seq       (1) ---------------------------------------------------------------------------
HSC4 Rep Cap Seq       (1) ---------------------------------------------------------------------------
HSC6 Rep Cap Seq       (1) ---------------------------------------------------------------------------
HSC5 Rep Cap Seq       (1) ---------------------------------------------------------------------------
HSC11 Rep Cap Seq      (1) ---------------------------------------------------------------------------
HSC7 Rep Cap Seq       (1) ---------------------------------------------------------------------------
HSC8 Rep Cap Seq       (1) ---------------------------------------------------------------------------
HSC9 Rep Cap Seq       (1) ---------------------------------------------------------------------------
HSC12 Rep Cap Seq      (1) ---------------------------------------------------------------------------
HSC13 Rep Cap Seq      (1) ---------------------------------------------------------------------------
HSC14 Rep Cap Seq      (1) ---------------------------------------------------------------------------
HSC15 Rep Cap Seq      (1) ---------------------------------------------------------------------------
HSC16 Rep Cap Seq      (1) ---------------------------------------------------------------------------
HSC17 Rep Cap Seq      (1) ---------------------------------------------------------------------------
AAV9 Capsid            (1) ---------------------------------------------------------------------------
AAV2                 (808) CTGAGCTCCAGTGGGCGTGGACTAATATGGAACAGTATTTAAGCGCCTGTTTGAATCTCACGGAGCGTAAACGGT
```

Figure 1 (cont.)

```
                                901                                                                       975
HSC1 Rep Cap Seq        (1)     ---------------------------------------------------------------------------
HSC2 Rep Cap Seq        (1)     ---------------------------------------------------------------------------
HSC3 Rep Cap Seq        (1)     ---------------------------------------------------------------------------
HSC4 Rep Cap Seq        (1)     ---------------------------------------------------------------------------
HSC6 Rep Cap Seq        (1)     ---------------------------------------------------------------------------
HSC5 Rep Cap Seq        (1)     ---------------------------------------------------------------------------
HSC11 Rep Cap Seq       (1)     ---------------------------------------------------------------------------
HSC7 Rep Cap Seq        (1)     ---------------------------------------------------------------------------
HSC8 Rep Cap Seq        (1)     ---------------------------------------------------------------------------
HSC9 Rep Cap Seq        (1)     ---------------------------------------------------------------------------
HSC12 Rep Cap Seq       (1)     ---------------------------------------------------------------------------
HSC13 Rep Cap Seq       (1)     ---------------------------------------------------------------------------
HSC14 Rep Cap Seq       (1)     ---------------------------------------------------------------------------
HSC15 Rep Cap Seq       (1)     ---------------------------------------------------------------------------
HSC16 Rep Cap Seq       (1)     ---------------------------------------------------------------------------
HSC17 Rep Cap Seq       (1)     ---------------------------------------------------------------------------
AAV9 Capsid             (1)     ---------------------------------------------------------------------------
AAV2                  (883)     TGGTGGCGCAGCATCTGACGCACGTGTCGCAGACGCAGGAGCAGAACAAAGAGAATCAGAATCCCAATTCTGATG
```

Figure 1 (cont.)

```
                                 976                                                                    1050
HSC1 Rep Cap Seq          (1) ---------------------------------------------------------------------------
HSC2 Rep Cap Seq          (1) ---------------------------------------------------------------------------
HSC3 Rep Cap Seq          (1) ---------------------------------------------------------------------------
HSC4 Rep Cap Seq          (1) ---------------------------------------------------------------------------
HSC6 Rep Cap Seq          (1) ---------------------------------------------------------------------------
HSC5 Rep Cap Seq          (1) ---------------------------------------------------------------------------
HSC11 Rep Cap Seq         (1) ---------------------------------------------------------------------------
HSC7 Rep Cap Seq          (1) ---------------------------------------------------------------------------
HSC8 Rep Cap Seq          (1) ---------------------------------------------------------------------------
HSC9 Rep Cap Seq          (1) ---------------------------------------------------------------------------
HSC12 Rep Cap Seq         (1) ---------------------------------------------------------------------------
HSC13 Rep Cap Seq         (1) ---------------------------------------------------------------------------
HSC14 Rep Cap Seq         (1) ---------------------------------------------------------------------------
HSC15 Rep Cap Seq         (1) ---------------------------------------------------------------------------
HSC16 Rep Cap Seq         (1) ---------------------------------------------------------------------------
HSC17 Rep Cap Seq         (1) ---------------------------------------------------------------------------
AAV9 Capsid               (1) ---------------------------------------------------------------------------
AAV2                    (958) CGCCGGTGATCAGATCAAAAACTTCAGCCAGGTACATGGAGCTGGTCGGGTGGCTCGTGGACAAGGGGATTACCT
```

Figure 1 (cont.)

```
                                1051                                                                      1125
HSC1 Rep Cap Seq         (1) ---------------------------------------------------------------------------
HSC2 Rep Cap Seq         (1) ---------------------------------------------------------------------------
HSC3 Rep Cap Seq         (1) ---------------------------------------------------------------------------
HSC4 Rep Cap Seq         (1) ---------------------------------------------------------------------------
HSC6 Rep Cap Seq         (1) ---------------------------------------------------------------------------
HSC5 Rep Cap Seq         (1) ---------------------------------------------------------------------------
HSC11 Rep Cap Seq        (1) ---------------------------------------------------------------------------
HSC7 Rep Cap Seq         (1) ---------------------------------------------------------------------------
HSC8 Rep Cap Seq         (1) ---------------------------------------------------------------------------
HSC9 Rep Cap Seq         (1) ---------------------------------------------------------------------------
HSC12 Rep Cap Seq        (1) ---------------------------------------------------------------------------
HSC13 Rep Cap Seq        (1) ---------------------------------------------------------------------------
HSC14 Rep Cap Seq        (1) ---------------------------------------------------------------------------
HSC15 Rep Cap Seq        (1) ---------------------------------------------------------------------------
HSC16 Rep Cap Seq        (1) ---------------------------------------------------------------------------
HSC17 Rep Cap Seq        (1) ---------------------------------------------------------------------------
AAV9 Capsid              (1) ---------------------------------------------------------------------------
AAV2                  (1033) CGGAGAAGCAGTGGATCCAGGAGGACCAGGCCTCATACATCTCCTTCAATGCGGCCTCCAACTCGCGGTCCCAAA
```

Figure 1 (cont.)

```
                             1126                                                                    1200
HSC1 Rep Cap Seq       (1)   ---------------------------------------------------------------------------
HSC2 Rep Cap Seq       (1)   ---------------------------------------------------------------------------
HSC3 Rep Cap Seq       (1)   ---------------------------------------------------------------------------
HSC4 Rep Cap Seq       (1)   ---------------------------------------------------------------------------
HSC6 Rep Cap Seq       (1)   ---------------------------------------------------------------------------
HSC5 Rep Cap Seq       (1)   ---------------------------------------------------------------------------
HSC11 Rep Cap Seq      (1)   ---------------------------------------------------------------------------
HSC7 Rep Cap Seq       (1)   ---------------------------------------------------------------------------
HSC8 Rep Cap Seq       (1)   ---------------------------------------------------------------------------
HSC9 Rep Cap Seq       (1)   ---------------------------------------------------------------------------
HSC12 Rep Cap Seq      (1)   ---------------------------------------------------------------------------
HSC13 Rep Cap Seq      (1)   ---------------------------------------------------------------------------
HSC14 Rep Cap Seq      (1)   ---------------------------------------------------------------------------
HSC15 Rep Cap Seq      (1)   ---------------------------------------------------------------------------
HSC16 Rep Cap Seq      (1)   ---------------------------------------------------------------------------
HSC17 Rep Cap Seq      (1)   ---------------------------------------------------------------------------
AAV9 Capsid            (1)   ---------------------------------------------------------------------------
AAV2                (1108)   TCAAGGCTGCCTTGGACAATGCGGGAAAGATTATGAGCCTGACTAAAACCGCCCCCGACTACCTGGTGGGCCAGC
```

Figure 1 (cont.)

```
                            1201                                                                       1275
HSC1 Rep Cap Seq      (1)   ---------------------------------------------------------------------------
HSC2 Rep Cap Seq      (1)   ---------------------------------------------------------------------------
HSC3 Rep Cap Seq      (1)   ---------------------------------------------------------------------------
HSC4 Rep Cap Seq      (1)   ---------------------------------------------------------------------------
HSC6 Rep Cap Seq      (1)   ---------------------------------------------------------------------------
HSC5 Rep Cap Seq      (1)   ---------------------------------------------------------------------------
HSC11 Rep Cap Seq     (1)   ---------------------------------------------------------------------------
HSC7 Rep Cap Seq      (1)   ---------------------------------------------------------------------------
HSC8 Rep Cap Seq      (1)   ---------------------------------------------------------------------------
HSC9 Rep Cap Seq      (1)   ---------------------------------------------------------------------------
HSC12 Rep Cap Seq     (1)   ---------------------------------------------------------------------------
HSC13 Rep Cap Seq     (1)   ---------------------------------------------------------------------------
HSC14 Rep Cap Seq     (1)   ---------------------------------------------------------------------------
HSC15 Rep Cap Seq     (1)   ---------------------------------------------------------------------------
HSC16 Rep Cap Seq     (1)   ---------------------------------------------------------------------------
HSC17 Rep Cap Seq     (1)   ---------------------------------------------------------------------------
AAV9 Capsid           (1)   ---------------------------------------------------------------------------
AAV2               (1183)   AGCCCGTGGAGGACATTTCCAGCAATCGGATTTATAAAATTTTGGAACTAAACGGGTACGATCCCCAATATGCGG
```

Figure 1 (cont.)

```
                                1276                                                                      1350
HSC1 Rep Cap Seq          (1) ---------------------------------------------------------------------------
HSC2 Rep Cap Seq          (1) ---------------------------------------------------------------------------
HSC3 Rep Cap Seq          (1) ---------------------------------------------------------------------------
HSC4 Rep Cap Seq          (1) ---------------------------------------------------------------------------
HSC6 Rep Cap Seq          (1) ---------------------------------------------------------------------------
HSC5 Rep Cap Seq          (1) ---------------------------------------------------------------------------
HSC11 Rep Cap Seq         (1) ---------------------------------------------------------------------------
HSC7 Rep Cap Seq          (1) ---------------------------------------------------------------------------
HSC8 Rep Cap Seq          (1) ---------------------------------------------------------------------------
HSC9 Rep Cap Seq          (1) ---------------------------------------------------------------------------
HSC12 Rep Cap Seq         (1) ---------------------------------------------------------------------------
HSC13 Rep Cap Seq         (1) ---------------------------------------------------------------------------
HSC14 Rep Cap Seq         (1) ---------------------------------------------------------------------------
HSC15 Rep Cap Seq         (1) ---------------------------------------------------------------------------
HSC16 Rep Cap Seq         (1) ---------------------------------------------------------------------------
HSC17 Rep Cap Seq         (1) ---------------------------------------------------------------------------
AAV9 Capsid               (1) ---------------------------------------------------------------------------
AAV2                   (1258) CTTCCGTCTTTCTGGGATGGGCCACGAAAAAGTTCGGCAAGAGGAACACCATCTGGCTGTTTGGGCCTGCAACTA
```

Figure 1 (cont.)

```
                                1351                                                                   1425
HSC1 Rep Cap Seq          (1) ---------------------------------------------------------------------------
HSC2 Rep Cap Seq          (1) ---------------------------------------------------------------------------
HSC3 Rep Cap Seq          (1) ---------------------------------------------------------------------------
HSC4 Rep Cap Seq          (1) ---------------------------------------------------------------------------
HSC6 Rep Cap Seq          (1) ---------------------------------------------------------------------------
HSC5 Rep Cap Seq          (1) ---------------------------------------------------------------------------
HSC11 Rep Cap Seq         (1) ---------------------------------------------------------------------------
HSC7 Rep Cap Seq          (1) ---------------------------------------------------------------------------
HSC8 Rep Cap Seq          (1) ---------------------------------------------------------------------------
HSC9 Rep Cap Seq          (1) ---------------------------------------------------------------------------
HSC12 Rep Cap Seq         (1) ---------------------------------------------------------------------------
HSC13 Rep Cap Seq         (1) ---------------------------------------------------------------------------
HSC14 Rep Cap Seq         (1) ---------------------------------------------------------------------------
HSC15 Rep Cap Seq         (1) ---------------------------------------------------------------------------
HSC16 Rep Cap Seq         (1) ---------------------------------------------------------------------------
HSC17 Rep Cap Seq         (1) ---------------------------------------------------------------------------
AAV9 Capsid               (1) ---------------------------------------------------------------------------
AAV2                   (1333) CCGGGAAGACCAACATCGCGGAGGCCATAGCCCACACTGTGCCCTTCTACGGGTGCGTAAACTGGACCAATGAGA
```

Figure 1 (cont.)

```
                                1426                                                                    1500
HSC1 Rep Cap Seq         (1)    ---------------------------------------------------------------------------
HSC2 Rep Cap Seq         (1)    ---------------------------------------------------------------------------
HSC3 Rep Cap Seq         (1)    ---------------------------------------------------------------------------
HSC4 Rep Cap Seq         (1)    ---------------------------------------------------------------------------
HSC6 Rep Cap Seq         (1)    ---------------------------------------------------------------------------
HSC5 Rep Cap Seq         (1)    ---------------------------------------------------------------------------
HSC11 Rep Cap Seq        (1)    ---------------------------------------------------------------------------
HSC7 Rep Cap Seq         (1)    ---------------------------------------------------------------------------
HSC8 Rep Cap Seq         (1)    ---------------------------------------------------------------------------
HSC9 Rep Cap Seq         (1)    ---------------------------------------------------------------------------
HSC12 Rep Cap Seq        (1)    ---------------------------------------------------------------------------
HSC13 Rep Cap Seq        (1)    ---------------------------------------------------------------------------
HSC14 Rep Cap Seq        (1)    ---------------------------------------------------------------------------
HSC15 Rep Cap Seq        (1)    ---------------------------------------------------------------------------
HSC16 Rep Cap Seq        (1)    ---------------------------------------------------------------------------
HSC17 Rep Cap Seq        (1)    ---------------------------------------------------------------------------
AAV9 Capsid              (1)    ---------------------------------------------------------------------------
AAV2                  (1408)    ACTTTCCCTTCAACGACTGTGTCGACAAGATGGTGATCTGGTGGGAGGAGGGGAAGATGACCGCCAAGGTCGTGG
```

Figure 1 (cont.)

```
                                1501                                                                       1575
HSC1 Rep Cap Seq           (1) ---------------------------------------------------------------------------
HSC2 Rep Cap Seq           (1) ---------------------------------------------------------------------------
HSC3 Rep Cap Seq           (1) ---------------------------------------------------------------------------
HSC4 Rep Cap Seq           (1) ---------------------------------------------------------------------------
HSC6 Rep Cap Seq           (1) ---------------------------------------------------------------------------
HSC5 Rep Cap Seq           (1) ---------------------------------------------------------------------------
HSC11 Rep Cap Seq          (1) ---------------------------------------------------------------------------
HSC7 Rep Cap Seq           (1) ---------------------------------------------------------------------------
HSC8 Rep Cap Seq           (1) ---------------------------------------------------------------------------
HSC9 Rep Cap Seq           (1) ---------------------------------------------------------------------------
HSC12 Rep Cap Seq          (1) ---------------------------------------------------------------------------
HSC13 Rep Cap Seq          (1) ---------------------------------------------------------------------------
HSC14 Rep Cap Seq          (1) ---------------------------------------------------------------------------
HSC15 Rep Cap Seq          (1) ---------------------------------------------------------------------------
HSC16 Rep Cap Seq          (1) ---------------------------------------------------------------------------
HSC17 Rep Cap Seq          (1) ---------------------------------------------------------------------------
AAV9 Capsid                (1) ---------------------------------------------------------------------------
AAV2                    (1483) AGTCGGCCAAAGCCATTCTCGGAGGAAGCAAGGTGCGCGTGGACCAGAAATGCAAGTCCTCGGCCCAGATAGACC
```

Figure 1 (cont.)

```
                              1576                                                                       1650
HSC1 Rep Cap Seq        (1) ---------------------------------------------------------------------------
HSC2 Rep Cap Seq        (1) ---------------------------------------------------------------------------
HSC3 Rep Cap Seq        (1) ---------------------------------------------------------------------------
HSC4 Rep Cap Seq        (1) ---------------------------------------------------------------------------
HSC6 Rep Cap Seq        (1) ---------------------------------------------------------------------------
HSC5 Rep Cap Seq        (1) ---------------------------------------------------------------------------
HSC11 Rep Cap Seq       (1) ---------------------------------------------------------------------------
HSC7 Rep Cap Seq        (1) ---------------------------------------------------------------------------
HSC8 Rep Cap Seq        (1) ---------------------------------------------------------------------------
HSC9 Rep Cap Seq        (1) ---------------------------------------------------------------------------
HSC12 Rep Cap Seq       (1) ---------------------------------------------------------------------------
HSC13 Rep Cap Seq       (1) ---------------------------------------------------------------------------
HSC14 Rep Cap Seq       (1) ---------------------------------------------------------------------------
HSC15 Rep Cap Seq       (1) ---------------------------------------------------------------------------
HSC16 Rep Cap Seq       (1) ---------------------------------------------------------------------------
HSC17 Rep Cap Seq       (1) ---------------------------------------------------------------------------
AAV9 Capsid             (1) ---------------------------------------------------------------------------
AAV2                 (1558) CGACTCCCGTGATCGTCACCTCCAACACCAACATGTGCGCCGTGATTGACGGGAACTCAACGACCTTCGAACACC
```

Figure 1 (cont.)

```
                              1651                                                                    1725
HSC1 Rep Cap Seq        (1)   ---------------------------------------------------------------------------
HSC2 Rep Cap Seq        (1)   ---------------------------------------------------------------------------
HSC3 Rep Cap Seq        (1)   ---------------------------------------------------------------------------
HSC4 Rep Cap Seq        (1)   ---------------------------------------------------------------------------
HSC6 Rep Cap Seq        (1)   ---------------------------------------------------------------------------
HSC5 Rep Cap Seq        (1)   ---------------------------------------------------------------------------
HSC11 Rep Cap Seq       (1)   ---------------------------------------------------------------------------
HSC7 Rep Cap Seq        (1)   ---------------------------------------------------------------------------
HSC8 Rep Cap Seq        (1)   ---------------------------------------------------------------------------
HSC9 Rep Cap Seq        (1)   ---------------------------------------------------------------------------
HSC12 Rep Cap Seq       (1)   ---------------------------------------------------------------------------
HSC13 Rep Cap Seq       (1)   ---------------------------------------------------------------------------
HSC14 Rep Cap Seq       (1)   ---------------------------------------------------------------------------
HSC15 Rep Cap Seq       (1)   ---------------------------------------------------------------------------
HSC16 Rep Cap Seq       (1)   ---------------------------------------------------------------------------
HSC17 Rep Cap Seq       (1)   ---------------------------------------------------------------------------
AAV9 Capsid             (1)   ---------------------------------------------------------------------------
AAV2                 (1633)   AGCAGCCGTTGCAAGACCGGATGTTCAAATTTGAACTCACCCGCCGTCTGGATCATGACTTTGGGAAGGTCACCA
```

Figure 1 (cont.)

```
                                 1726                                                                     1800
HSC1 Rep Cap Seq          (1)    ---------------------------------------------------------------------------
HSC2 Rep Cap Seq          (1)    ---------------------------------------------------------------------------
HSC3 Rep Cap Seq          (1)    ---------------------------------------------------------------------------
HSC4 Rep Cap Seq          (1)    ---------------------------------------------------------------------------
HSC6 Rep Cap Seq          (1)    ---------------------------------------------------------------------------
HSC5 Rep Cap Seq          (1)    ---------------------------------------------------------------------------
HSC11 Rep Cap Seq         (1)    ---------------------------------------------------------------------------
HSC7 Rep Cap Seq          (1)    ---------------------------------------------------------------------------
HSC8 Rep Cap Seq          (1)    ---------------------------------------------------------------------------
HSC9 Rep Cap Seq          (1)    ---------------------------------------------------------------------------
HSC12 Rep Cap Seq         (1)    ---------------------------------------------------------------------------
HSC13 Rep Cap Seq         (1)    ---------------------------------------------------------------------------
HSC14 Rep Cap Seq         (1)    ---------------------------------------------------------------------------
HSC15 Rep Cap Seq         (1)    ---------------------------------------------------------------------------
HSC16 Rep Cap Seq         (1)    ---------------------------------------------------------------------------
HSC17 Rep Cap Seq         (1)    ---------------------------------------------------------------------------
AAV9 Capsid               (1)    ---------------------------------------------------------------------------
AAV2                   (1708)    AGCAGGAAGTCAAAGACTTTTTCCGGTGGGCAAAGGATCACGTGGTTGAGGTGGAGCATGAATTCTACGTCAAAA
```

Figure 1 (cont.)

```
                             1801                                                                   1875
HSC1 Rep Cap Seq        (1)  ---------------------------------------------------------------------------
HSC2 Rep Cap Seq        (1)  ---------------------------------------------------------------------------
HSC3 Rep Cap Seq        (1)  ---------------------------------------------------------------------------
HSC4 Rep Cap Seq        (1)  ---------------------------------------------------------------------------
HSC6 Rep Cap Seq        (1)  ---------------------------------------------------------------------------
HSC5 Rep Cap Seq        (1)  ---------------------------------------------------------------------------
HSC11 Rep Cap Seq       (1)  ---------------------------------------------------------------------------
HSC7 Rep Cap Seq        (1)  ---------------------------------------------------------------------------
HSC8 Rep Cap Seq        (1)  ---------------------------------------------------------------------------
HSC9 Rep Cap Seq        (1)  ---------------------------------------------------------------------------
HSC12 Rep Cap Seq       (1)  ---------------------------------------------------------------------------
HSC13 Rep Cap Seq       (1)  ---------------------------------------------------------------------------
HSC14 Rep Cap Seq       (1)  ---------------------------------------------------------------------------
HSC15 Rep Cap Seq       (1)  ---------------------------------------------------------------------------
HSC16 Rep Cap Seq       (1)  ---------------------------------------------------------------------------
HSC17 Rep Cap Seq       (1)  ---------------------------------------------------------------------------
AAV9 Capsid             (1)  ---------------------------------------------------------------------------
AAV2                 (1783)  AGGGTGGAGCCAAGAAAAGACCCGCCCCCAGTGACGCAGATATAAGTGAGCCCAAACGGGTGCGCGAGTCAGTTG
```

Figure 1 (cont.)

```
                                  1951                                                                  2025
HSC1 Rep Cap Seq          (68)  ACGTGGGCATGAATCTGATGCTGTTTCCCTGCAGACAATGCGAGAGACTGAATCAGAATTCAAATATCTGCTTCA
HSC2 Rep Cap Seq          (68)  ACGTGGGCATGAATCTGATGCTGTTTCCCTGCAGACAATGCGAGAGACTGAATCAGAATTCAAATATCTGCTTCA
HSC3 Rep Cap Seq          (68)  ACGTGGGCATGAATCTGATGCTGTTTCCCTGCAGACAATGCGAGAGACTGAATCAGAATTCAAATATCTGCTTCA
HSC4 Rep Cap Seq          (68)  ACGTGGGCATGAATCTGATGCTGTTTCCCTGCAGACAATGCGAGAGACTGAATCAGAATTCAAATATCTGCTTCA
HSC6 Rep Cap Seq          (68)  ACGTGGGCATGAATCTGATGCTGTTTCCCTGCAGACAATGCGAGAGACTGAATCAGAATTCAAATATCTGCTTCA
HSC5 Rep Cap Seq          (68)  ACGTGGGCATGAATCTGATGCTGTTTCCCTGCAGACAATGCGAGAGACTGAATCAGAATTCAAATATCTGCTTCA
HSC11 Rep Cap Seq         (68)  ACGTGGGCATGAATCTGATGCTGTTTCCCTGCAGACAATGCGAGAGACTGAATCAGAATTCAAATATCTGCTTCA
HSC7 Rep Cap Seq          (68)  ACGTGGGCATGAATCTGATGCTGTTTCCCTGCAGACAATGCGAGAGACTGAATCAGAATTCAAATATCTGCTTCA
HSC8 Rep Cap Seq          (68)  ACGTGGGCATGAATCTGATGCTGTTTCCCTGCAGACAATGCGAGAGACTGAATCAGAATTCAAATATCTGCTTCA
HSC9 Rep Cap Seq          (68)  ACGTGGGCATGAATCTGATGCTGTTTCCCTGCAGACAATGCGAGAGACTGAATCAGAATTCAAATATCTGCTTCA
HSC12 Rep Cap Seq         (68)  ACGTGGGCATGAATCTGATGCTGTTTCCCTGCAGACAATGCGAGAGACTGAATCAGAATTCAAATATCTGCTTCA
HSC13 Rep Cap Seq         (68)  ACGTGGGCATGAATCTGATGCTGTTTCCCTGCAGACAATGCGAGAGACTGAATCAGAATTCAAATATCTGCTTCA
HSC14 Rep Cap Seq         (68)  ACGTGGGCATGAATCTGATGCTGTTTCCCTGCAGACAATGCGAGAGACTGAATCAGAATTCAAATATCTGCTTCA
HSC15 Rep Cap Seq         (68)  ACGTGGGCATGAATCTGATGCTGTTTCCCTGCAGACAATGCGAGAGACTGAATCAGAATTCAAATATCTGCTTCA
HSC16 Rep Cap Seq         (68)  ACGTGGGCATGAATCTGATGCTGTTTCCCTGCAGACAATGCGAGAGACTGAATCAGAATTCAAATATCTGCTTCA
HSC17 Rep Cap Seq         (68)  ACGTGGGCATGAATCTGATGCTGTTTCCCTGCAGACAATGCGAGAGACTGAATCAGAATTCAAATATCTGCTTCA
AAV9 Capsid                (1)  ---------------------------------------------------------------------------
AAV2                    (1930)  ACGTGGGCATGAATCTGATGCTGTTTCCCTGCAGACAATGCGAGAGAATGAATCAGAATTCAAATATCTGCTTCA
```

Figure 1 (cont.)

```
                                2026                                                                      2100
HSC1 Rep Cap Seq       (143)  CTCACGGTGTCAAAGACTGTTTAGAGTGCTTTCCCG---TGTCAGAATCTCAACCCGTTTCTGTCGTCAAAAAGG
HSC2 Rep Cap Seq       (143)  CTCACGGTGTCAAAGACTGTTTAGAGTGCTTTCCCG---TGTCAGAATCTCAACCCGTTTCTGTCGTCAAAAAGG
HSC3 Rep Cap Seq       (143)  CTCACGGTGTCAAAGACTGTTTAGAGTGCTTTCCCG---TGTCAGAATCTCAACCCGTTTCTGTCGTCAAAAAGG
HSC4 Rep Cap Seq       (143)  CTCACGGTGTCAAAGACTGTTTAGAGTGCTTTCCCG---TGTCAGAATCTCAACCCGTTTCTGTCGTCAAAAAGG
HSC6 Rep Cap Seq       (143)  CTCACGGTGTCAAAGACTGTTTAGAGTGCTTTCCCG---TGTCAGAATCTCAACCCGTTTCTGTCGTCAAAAAGG
HSC5 Rep Cap Seq       (143)  CTCACGGTGTCAAAGACTGTTTAGAGTGCTTTCCCG---TGTCAGAATCTCAACCCGTTTCTGTCGTCAAAAAGG
HSC11 Rep Cap Seq      (143)  CTCACGGTGTCAAAGACTGTTTAGAGTGCTTTCCCG---TGTCAGAATCTCAACCCGTTTCTGTCGTCAAAAAGG
HSC7 Rep Cap Seq       (143)  CTCACGGTGTCAAAGACTGTTTAGAGTGCTTTCCCG---TGTCAGAATCTCAACCCGTTTCTGTCGTCAAAAAGG
HSC8 Rep Cap Seq       (143)  CTCACGGTGTCAAAGACTGTTTAGAGTGCTTTCCCG---TGTCAGAATCTCAACCCGTTTCTGTCGTCAAAAAGG
HSC9 Rep Cap Seq       (143)  CTCACGGTGTCAAAGACTGTTTAGAGTGCTTTCCCG---TGTCAGAATCTCAACCCGTTTCTGTCGTCAAAAAGG
HSC12 Rep Cap Seq      (143)  CTCACGGTGTCAAAGACTGTTTAGAGTGCTTTCCCG---TGTCAGAATCTCAACCCGTTTCTGTCGTCAAAAAGG
HSC13 Rep Cap Seq      (143)  CTCACGGTGTCAAAGACTGTTTAGAGTGCTTTCCCG---TGTCAGAATCTCAACCCGTTTCTGTCGTCAAAAAGG
HSC14 Rep Cap Seq      (143)  CTCACGGTGTCAAAGACTGTTTAGAGTGCTTTCCCG---TGTCAGAATCTCAACCCGTTTCTGTCGTCAAAAAGG
HSC15 Rep Cap Seq      (143)  CTCACGGTGTCAAAGACTGTTTAGAGTGCTTTCCCG---TGTCAGAATCTCAACCCGTTTCTGTCGTCAAAAAGG
HSC16 Rep Cap Seq      (143)  CTCACGGTGTCAAAGACTGTTTAGAGTGCTTTCCCG---TGTCAGAATCTCAACCCGTTTCTGTCGTCAAAAAGG
HSC17 Rep Cap Seq      (143)  CTCACGGTGTCAAAGACTGTTTAGAGTGCTTTCCCG---TGTCAGAATCTCAACCCGTTTCTGTCGTCAAAAAGG
AAV9 Capsid              (1)  ---------------------------------------------------------------------------
AAV2                  (2005)  CTCACGGACAGAAAGACTGTTTAGAGTGCTTTCCCG---TGTCAGAATCTCAACCCGTTTCTGTCGTCAAAAAGG
```

Figure 1 (cont.)

```
                             2101                                                                     2175
HSC1 Rep Cap Seq      (215)  CGTATCAGAAACTGTCCTACATTCATCACATCATGGCAAAGGTGCCACAC---GCTTGCACTGCTTGCGACCTGG
HSC2 Rep Cap Seq      (215)  CGTATCAGAAACTGTCCTACATTCATCACATCATGGCAAAGGTGCCACAC---GCTTGCACTGCTTGCGACCTGG
HSC3 Rep Cap Seq      (215)  CGTATCAGAAACTGTCCTACATTCATCACATCATGGCAAAGGTGCCACAC---GCTTGCACTGCTTGCGACCTGG
HSC4 Rep Cap Seq      (215)  CGTATCAGAAACTGTCCTACATTCATCACATCATGGCAAAGGTGCCACAC---GCTTGCACTGCTTGCGACCTGG
HSC6 Rep Cap Seq      (215)  CGTATCAGAAACTGTCCTACATTCATCACATCATGGCAAAGGTGCCACAC---GCTTGCACTGCTTGCGACCTGG
HSC5 Rep Cap Seq      (215)  CGTATCAGAAACTGTCCTACATTCATCACATCATGGCAAAGGTGCCACAC---GCTTGCACTGCTTGCGACCTGG
HSC11 Rep Cap Seq     (215)  CGTATCAGAAACTGTCCTACATTCATCACATCATGGCAAAGGTGCCACAC---GCTTGCACTGCTTGCGACCTGG
HSC7 Rep Cap Seq      (215)  CGTATCAGAAACTGTCCTACATTCATCACATCATGGCAAAGGTGCCACAC---GCTTGCACTGCTTGCGACCTGG
HSC8 Rep Cap Seq      (215)  CGTATCAGAAACTGTCCTACATTCATCACATCATGGCAAAGGTGCCACAC---GCTTGCACTGCTTGCGACCTGG
HSC9 Rep Cap Seq      (215)  CGTATCAGAAACTGTCCTACATTCATCACATCATGGCAAAGGTGCCACAC---GCTTGCACTGCTTGCGACCTGG
HSC12 Rep Cap Seq     (215)  CGTATCAGAAACTGTCCTACATTCATCACATCATGGCAAAGGTGCCACAC---GCTTGCACTGCTTGCGACCTGG
HSC13 Rep Cap Seq     (215)  CGTATCAGAAACTGTCCTACATTCATCACATCATGGCAAAGGTGCCACAC---GCTTGCACTGCTTGCGACCTGG
HSC14 Rep Cap Seq     (215)  CGTATCAGAAACTGTCCTACATTCATCACATCATGGCAAAGGTGCCACAC---GCTTGCACTGCTTGCGACCTGG
HSC15 Rep Cap Seq     (215)  CGTATCAGAAACTGTCCTACATTCATCACATCATGGCAAAGGTGCCACAC---GCTTGCACTGCTTGCGACCTGG
HSC16 Rep Cap Seq     (215)  CGTATCAGAAACTGTCCTACATTCATCACATCATGGCAAAGGTGCCACAC---GCTTGCACTGCTTGCGACCTGG
HSC17 Rep Cap Seq     (215)  CGTATCAGAAACTGTCCTACATTCATCACATCATGGCAAAGGTGCCACAC---GCTTGCACTGCTTGCGACCTGG
AAV9 Capsid             (1)  ---------------------------------------------------------------------------
AAV2                 (2077)  CGTATCAGAAACTGTCCTACATTCATCATATCATGGCAAAGGTGCCACAC---GCTTGCACTGCCTGCGATCTGG
```

Figure 1 (cont.)

```
                            2176                                                                      2250
HSC1 Rep Cap Seq      (287) TCAATGTGGACTTGCATGACTGTGTTTCTGAACAATAAATGACTTAAACCAGGTATGACTGCCGATGGTTATCTT
HSC2 Rep Cap Seq      (287) TCAATGTGGACTTGCATGACTGTGTTTCTGAACAATAAATGACTTAAACCAGGTATGGCTGCCGATGGTTATCTT
HSC3 Rep Cap Seq      (287) TCAATGTGGACTCGCATGACTGTGTTTCTGAACAATAAATGACTTAAACCAGGTATGGCTGCCGATGGTTATCTT
HSC4 Rep Cap Seq      (287) TCAATGTGGACTTGCATGACTGTGTTTCTGAACAATAAATGACTTAAACCAGGTATGGCTGCCGATGGTTATCTT
HSC6 Rep Cap Seq      (287) TCAATGTGGACTTGCATGACTGTGTTTCTGAACAATAAATGACTTAAACCAGGTATGGCTGCCGATGGTTATCTT
HSC5 Rep Cap Seq      (287) TCAATGTGGACTTGCATGACTGTGTTTCTGAACAATAAATGACTTAAACCAGGTATGGCTGCCGATGGTTATCTT
HSC11 Rep Cap Seq     (287) TCAATGTGGACTTGCATGACTGTGTTTCTGAACAATAAATGACTTAAACCAGGTATGGCTGCCGATGGTTATCTT
HSC7 Rep Cap Seq      (287) TCAATGTGGACTTGCATGACTGTGTTTCTGAACAATAAATGACTTAAACCAGGTATGGCTGCCGATGGTTATCTT
HSC8 Rep Cap Seq      (287) TCAATGTGGACTTGCATGACTGTGTTTCTGAACAATAAATGACTTAAACCAGGTATGGCTGCCGATGGTTATCTT
HSC9 Rep Cap Seq      (287) TCAATGTGGACTTGCATGACTGTGTTTCTGAACAATAAATGACTTAAACCAGGTATGGCTGCCGATGGTTATCTT
HSC12 Rep Cap Seq     (287) TCAATGTGGACTTGCATGACTGTGTTTCTGAACAATAAATGACTTAAACCAGGTATGGCTGCCGATGGTTATCTT
HSC13 Rep Cap Seq     (287) TCAATGTGGACTTGCATGACTGTGTTTCTGAACAATAAATGACTTAAACCAGGTATGGCTGCCGATGGTTATCTT
HSC14 Rep Cap Seq     (287) TCAATGTGGACTTGCATGACTGTGTTTCTGAACAATAAATGACTTAAACCAGGTATGGCTGCCGATGGTTATCTT
HSC15 Rep Cap Seq     (287) TCAATGTGGACTTGCATGACTGTGTTTCTGAACAATAAATGACTTAAACCAGGTATGGCTGCCGATGGTTATCTT
HSC16 Rep Cap Seq     (287) TCAATGTGGACTTGCATGACTGTGTTTCTGAACAATAAATGACTTAAACCAGGTATGGCTGCCGATGGTTATCTT
HSC17 Rep Cap Seq     (287) TCAATGTGGACTTGCATGTCTGTGTTTCTGAACAATAAATGACTTAAACCAGGTATGGCTGCCGATGGTTATCTT
AAV9 Capsid             (1) ------------------------------------------------------ATGGCTGCCGATGGTTATCTT
AAV2                 (2149) TCAATGTGGATTTGCATGACTGCATCTTTGAACAATAAATGATTTAAATCAGGTATGGCTGCCGATGGTTATCTT
```

Figure 1 (cont.)

| | | 2251 … 2325 |
|---|---|---|
| HSC1 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC2 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC3 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC4 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC6 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC5 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC11 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC7 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC8 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC9 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC12 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC13 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC14 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC15 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC16 Rep Cap Seq | (362) | CCAGATTGGCTCGAGGACAACCTTAGTGAAGGAATTCGCGAGTGGTGGGCTTTGAAACCTGCAGCGCCTCAAGCC |
| HSC17 Rep Cap Seq | (362) | CCAGATTGGCTCGAGGACAACCTTAGTGAAGGAATTCGCGAGTGGTGGGCTTTGAAACCTGCAGCGCCTCAAGCC |
| AAV9 Capsid | (22) | CCAGATTGGCTCGAGGACAACCTTAGTGAAGGAATTCGCGAGTGGTGGGCTTTGAAACCTGCAGCGCCTCAAGCC |
| AAV2 | (2224) | CCAGATTGGCTCGAGGACACTCTCTCTGAAGGAATAAGACAGTGGTGGAAGCTCAAACCTGGCCCACC-ACCACC |

Figure 1 (cont.)

```
                            2326                                                                      2400
HSC1 Rep Cap Seq     (437)  AAGGCAAATC-AACAACATCAAGACAACGCTCGAGGTCTTGTGCTTCCGGGTTACAAATACCTTGGACCCGGCAA
HSC2 Rep Cap Seq     (437)  AAGGCAAATC-AACAACATCAAGACAACGCTCGAGGTCTTGTGCTTCCGGGTTACAAATACCTTGGACCCGGCAA
HSC3 Rep Cap Seq     (437)  AAGGCAAATC-AACAACATCAAGACAACGCTCGAGGTCTTGTGCTTCCGGGTTACAAATACCTTGGACCCGGCAA
HSC4 Rep Cap Seq     (437)  AAGGCAAATC-AACAACATCAAGACAACGCTCGAGGTCTTGTGCTTCCGGGTTACAAATACCTTGGACCCGGCAA
HSC6 Rep Cap Seq     (437)  AAGGCAAATC-AACAACATCAAGACAACGCTCGAGGTCTTGTGCTTCCGGGTTACAAATACCTTGGACCCGGCAA
HSC5 Rep Cap Seq     (437)  AAGGCAAATC-AACAACATCAAGACAACGCTCGAGGTCTTGTGCTTCCGGGTTACAAATACCTTGGACCCGGCAA
HSC11 Rep Cap Seq    (437)  AAGGCAAATC-AACAACATCAAGACAACGCTCGAGGTCTTGTGCTTCCGGGTTACAAATACCTTGGACCCGGCAA
HSC7 Rep Cap Seq     (437)  AAGGCAAATC-AACAACATCAAGACAACGCTCGAGGTCTTGTGCTTCCGGGTTACAAATACCTTGGACCCGGCAA
HSC8 Rep Cap Seq     (437)  AAGGCAAATC-AACAACATCAAGACAACGCTCGAGGTCTTGTGCTTCCGGGTTACAAATACCTTGGACCCGGCAA
HSC9 Rep Cap Seq     (437)  AAGGCAAATC-AACAACATCAAGACAACGCTCGAGGTCTTGTGCTTCCGGGTTACAAATACCTTGGACCCGGCAA
HSC12 Rep Cap Seq    (437)  AAGGCAAATC-AACAACATCAAGACAACGCTCGAGGTCTTGTGCTTCCGGGTTACAAATACCTTGGACCCGGCAA
HSC13 Rep Cap Seq    (437)  AAGGCAAATC-AACAACATCAAGACAACGCTCGAGGTCTTGTGCTTCCGGGTTACAAATACCTTGGACCCGGCAA
HSC14 Rep Cap Seq    (437)  AAGGCAAATC-AACAACATCAAGACAACGCTCGAGGTCTTGTGCTTCCGGGTTACAAATACCTTGGACCCGGCAA
HSC15 Rep Cap Seq    (437)  AAGGCAAATC-AACAACATCAAGACAACGCTCGAGGTCTTGTGCTTCCGGGTTACAAATACCTTGGACCCGGCAA
HSC16 Rep Cap Seq    (437)  AAGGCAAATC-AACAACATCAAGACAACGCTCGAGGTCTTGTGCTTCCGGGTTACAAATACCTTGGACCCGGCAA
HSC17 Rep Cap Seq    (437)  AAGGCAAATC-AACAACATCAAGACAACGCTCGAGGTCTTGTGCTTCCGGGTTACAAATACCTTGGACCCGGCAA
AAV9 Capsid           (97)  AAGGCAAATC-AACAACATCAAGACAACGCTCGAGGTCTTGTGCTTCCGGGTTACAAATACCTTGGACCCGGCAA
AAV2                (2298)  AAAGCCCGCAGAGCGGCATAAGGACGACAGCAGGGGTCTTGTGCTTCCTGGGTACAAGTACCTCGGACCCTTCAA
```

Figure 1 (cont.)

| | | 2476 2550 |
|---|---|---|
| HSC1 Rep Cap Seq | (586) | GCTCAAGGCCGGAGACAACCCGTACCTCAAGTACAACCACGCCGACGCCGAGTTCCAGGAGCGGCTCAAAGAAGA |
| HSC2 Rep Cap Seq | (586) | GCTCAAGGCCGGAGACAACCCGTACCTCAAGTACAACCACGCCGACGCCGAGTTCCAGGAGCGGCTCAAAGAAGA |
| HSC3 Rep Cap Seq | (586) | GCTCAAGGCCGGAGACAACCCGTACCTCAAGTACAACCACGCCGACGCCGAGTTCCAGGAGCGGCTCAAAGAAGA |
| HSC4 Rep Cap Seq | (586) | GCTCAAGGCCGGAGACAACCCGTACCTCAAGTACAACCACGCCGACGCCGAGTTCCAGGAGCGGCTCAAAGAAGA |
| HSC6 Rep Cap Seq | (586) | GCTCAAGGCCGGAGACAACCCGTACCTCAAGTACAACCACGCCGACGCCGAGTTCCAGGAGCGGCTCAAAGAAGA |
| HSC5 Rep Cap Seq | (586) | GCTCAAGGCCGGAGACAACCCGTACCTCAAGTACAACCACGCCGACGCCGAGTTCCAGGAGCGGCTCAAAGAAGA |
| HSC11 Rep Cap Seq | (586) | GCTCAAGGCCGGAGACAACCCGTACCTCAAGTACAACCACGCCGACGCCGAGTTCCAGGAGCGGCTCAAAGAAGA |
| HSC7 Rep Cap Seq | (586) | GCTCAAGGCCGGAGACAACCCGTACCTCAAGTACAACCACGCCGACGCCGAGTTCCAGGAGCGGCTCAAAGAAGA |
| HSC8 Rep Cap Seq | (586) | GCTCAAGGCCGGAGACAACCCGTACCTCAAGTACAACCACGCCGACGCCGAGTTCCAGGAGCGGCTCAAAGAAGA |
| HSC9 Rep Cap Seq | (586) | GCTCAAGGCCGGAGACAACCCGTACCTCAAGTACAACCACGCCGACGCCGAGTTCCAGGAGCGGCTCAAAGAAGA |
| HSC12 Rep Cap Seq | (586) | GCTCAAGGCCGGAGACAACCCGTACCTCAAGTACAACCACGCCGACGCCGAGTTCCAGGAGCGGCTCAAAGAAGA |
| HSC13 Rep Cap Seq | (586) | GCTCAAGGCCGGAGACAACCCGTACCTCAAGTACAACCACGCCGACGCCGAGTTCCAGGAGCGGCTCAAAGAAGA |
| HSC14 Rep Cap Seq | (586) | GCTCAAGGCCGGAGACAACCCGTACCTCAAGTACAACCACGCCGACGCCGAGTTCCAGGAGCGGCTCAAAGAAGA |
| HSC15 Rep Cap Seq | (586) | GCTCAAGGCCGGAGACAACCCGTACCTCAAGTACAACCACGCCGACGCCGAGTTCCAGGAGCGGCTCAAAGAAGA |
| HSC16 Rep Cap Seq | (586) | GCTCAAGGCCGGAGACAACCCGTACCTCAAGTACAACCACGCCGACGCCGAGTTCCAGGAGCGGCTCAAAGAAGA |
| HSC17 Rep Cap Seq | (586) | GCTCAAGGCCGGAGACAACCCGTACCTCAAGTACAACCACGCCGACGCCGAGTTCCAGGAGCGGCTCAAAGAAGA |
| AAV9 Capsid | (246) | GCTCAAGGCCGGAGACAACCCGTACCTCAAGTACAACCACGCCGACGCCGAGTTCCAGGAGCGGCTCAAAGAAGA |
| AAV2 | (2448) | GCTCGACAGCGGAGACAACCCGTACCTCAAGTACAACCACGCCGACGCGGAGTTTCAGGAGCGCCTTAAAGAAGA |

Figure 1 (cont.)

| | | 2551 2625 |
|---|---|---|
| HSC1 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC2 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC3 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC4 Rep Cap Seq | (661) | TACGTCTTTTGGGGGCAACCTCGGGCGAGCAGTCCTCCAGGCCAAAAAGAGGCTTCTTGAACCTCTTGGTCTGGT |
| HSC6 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC5 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC11 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC7 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC8 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC9 Rep Cap Seq | (661) | TACGTCTTTTGGGGGCAACCTCGGGCGAGCAGTCTTTCAGGCCAAAAAGAGGCTTCTTGAACCTCTTGGTCTGGT |
| HSC12 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC13 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC14 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC15 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC16 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| HSC17 Rep Cap Seq | (661) | TACGTCTTTTGGGGGCAACCTCGGGCGAGCAGTCTTCCAGGCCAAAAAGAGGCTTCTTGAACCTCTTGGTCTGGT |
| AAV9 Capsid | (321) | TACGTCTTTTGGGGGCAACCTCGGGCGAGCAGTCTTCCAGGCCAAAAAGAGGCTTCTTGAACCTCTTGGTCTGGT |
| AAV2 | (2523) | TACGTCTTTTGGGGGCAACCTCGGACGAGCAGTCTTCCAGGCGAAAAAGAGGGTTCTTGAACCTCTGGGCCTGGT |

Figure 1 (cont.)

```
                            2626                                                                       2700
HSC1 Rep Cap Seq     (736)  TGAGGAAGCGGCTAAGACGGCTCCTGGAAAGAAGAGGCCTGTAGAGCAGTCTCCTCAGGAA---CCGGACTCCTC
HSC2 Rep Cap Seq     (736)  TGAGGAAGCGGCTAAGACGGCTCCTGGAAAGAAGAGGCCTGTAGAGCAGTCTCCTCAGGAA---CCGGACTCCTC
HSC3 Rep Cap Seq     (736)  TGAGGAAGCGGCTAAGACGGCTCCTGGAAAGAAGAGGCCTGTAGAGCAGTCTCCTCAGGAA---CCGGACTCCTC
HSC4 Rep Cap Seq     (736)  TGAGGAAGCGGCTAAGACGGCTCCTGGAAAGAAGAGGCCTGTAGAGCAGTCTCCTCAGGAA---CCGGACTCCTC
HSC6 Rep Cap Seq     (736)  TGAGGAAGCGGCTAAGACGGCTCCTGGAAAGAAGAGGCCTGTAGAGCAGTCTCCTCAGGAA---CCGGACTCCTC
HSC5 Rep Cap Seq     (736)  TGAGGAAGCGGCTAAGACGGCTCCTGGAAAGAAGAGGCCTGTAGAGCAGTCTCCTCAGGAA---CCGGACTCCTC
HSC11 Rep Cap Seq    (736)  TGAGGAAGCGGCTAAGACGGCTCCTGGAAAGAAGAGGCCTGTAGAGCAGTCTCCTCAGGAA---CCGGACTCCTC
HSC7 Rep Cap Seq     (736)  TGAGGAAGCGGCTAAGACGGCTCCTGGAAAGAAGAGGCCTGTAGAGCAGTCTCCTCAGGAA---CCGGACTCCTC
HSC8 Rep Cap Seq     (736)  TGAGGAAGCGGCTAAGACGGCTCCTGGAAAGAAGAGGCCTGTAGAGCAGTCTCCTGAGGAA---CCGGACTCCTC
HSC9 Rep Cap Seq     (736)  TGAGGAAGCGGCTAAGACGGCTCCTGGAAAGAAGAGGCCTGTAGAGCAGTCTCCTCAGGAA---CCGGACTCCTC
HSC12 Rep Cap Seq    (736)  TGAGGAAGCGGCTAAGACGGCTCCTGGAAAGAAGAGGCCTGTAGAGCAGTCTCCTCAGGAA---CCGGACTCCTC
HSC13 Rep Cap Seq    (736)  TGAGGAAGCGGCTAAGACGGCTCCTGGAAAGAAGAGGCCTGTAGAGCAGTCTCCTCAGGAA---CCGGACTCCTC
HSC14 Rep Cap Seq    (736)  TGAGGAAGCGGCTAAGACGGCTCCTGGAAAGAAGAGGCCTGTAGAGCAGTCTCCTCAGGAA---CCGGACTCCTC
HSC15 Rep Cap Seq    (736)  TGAGGAAGCGGCTAAGACGGCTCCTGGAAAGAAGAGGCCTGTAGAGCAGTCTCCTCAGGAA---CCGGACTCCTC
HSC16 Rep Cap Seq    (736)  TGAGGAAGCGGCTAAGACGGCTCCTGGAAAGAAGAGGCCTGTAGAGCAGTCTCCTCAGGAA---CCGGACTCCTC
HSC17 Rep Cap Seq    (736)  TGAGGAAGCGGCTAAGACGGCTCCTGGAAAGAAGAGGCCTGTAGAGCAGTCTCCTCAGGAA---CCGGACTCCTC
AAV9 Capsid          (396)  TGAGGAAGCGGCTAAGACGGCTCCTGGAAAGAAGAGGCCTGTAGAGCAGTCTCCTCAGGAA---CCGGACTCCTC
AAV2                (2598)  TGAGGAACCTGTTAAGACGGCTCCGGGAAAAAAGAGGCCGGTAGAGCACTCTCCTGTGGAG---CCAGACTCCTC
```

Figure 1 (cont.)

| | | 2701 ... 2775 |
|---|---|---|
| HSC1 Rep Cap Seq | (808) | CGCGGGTATTCGCAAATCGGCTGCACAGCCCGCTAAAAAGAGACTCAATTTCGGTCAGACTGGCGACACAGAGTC |
| HSC2 Rep Cap Seq | (808) | CGCGGGTATTCGCAAATCGGCTGCACAGCCCGCTAAAAAGAGACTCAATTTCGGTCAGACTGGCGACACAGAGTC |
| HSC3 Rep Cap Seq | (808) | CGCGGGTATTCACAAATCGGCTGCACAGCCCGCTAAAAAGAGACTCAATTTCGGTCAGACTGGCGACACAGAGTC |
| HSC4 Rep Cap Seq | (808) | CGCGGGTATTCGCAAATCGGCTGCACAGCCCGCTAAAAAGAGACTCAATTTCGGTCAGACTGGCGACACAGAGTC |
| HSC6 Rep Cap Seq | (808) | CGCGGGTATTCGCAAATCGGCTGCACAGCCCGCTAAAAAGAGACTCAATTTCGGTCAGACTGGCGACACAGAGTC |
| HSC5 Rep Cap Seq | (808) | CGCGGGTATTCGCAAATCGGCTGCACAGCCCGCTAAAAAGAGACTCAATTTCGGTCAGACTGGCGACACAGAGTC |
| HSC11 Rep Cap Seq | (808) | CGCGGGTATTCGCAAATCGGCTGCACAGCCCGCTAAAAAGAGACTCAATTTCGGTCAGACTGGCGACACAGAGTC |
| HSC19 Rep Cap Seq | (808) | CGCGGGTATTCGCAAATCGGCTGCACAGCCCGCTAAAAAGAGACTCAATTTCGGTCAGACTGGCGACACAGAGTC |
| HSC8 Rep Cap Seq | (808) | CGCGGGTATTCGCAAATCGGCTGCACAGCCCGCTAAAAAGAGACTCAATTTCGGTCAGACTGGCGACACAGAGTC |
| HSC9 Rep Cap Seq | (808) | CGCGGGTATTCGCAAATCGGCTGCACAGCCCGCTAAAAAGAGACTCAATTTCGGTCAGACTGGCGACACAGAGTC |
| HSC12 Rep Cap Seq | (808) | CGCGGGTATTCGCAAATCGGCTGCACAGCCCGCTAAAAAGAGACTCAATTTCGGTCAGACTGGCGACACAGAGTC |
| HSC13 Rep Cap Seq | (808) | CGCGGGTATTCGCAAATCGGCTGCACAGCCCGCTAAAAAGAGACTCAATTTCGGTCAGACTGGCGACACAGAGTC |
| HSC14 Rep Cap Seq | (808) | CGCGGGTATTCGCAAATCGGCTGCACAGCCCGCTAAAAAGAGACTCAATTTCGGTCAGACTGGCGACACAGAGTC |
| HSC15 Rep Cap Seq | (808) | CGCGGGTATTCGCAAATCGGCTGCACAGCCCGCTAAAAAGAGACTCAATTTCGGTCAGACTGGCGACACAGAGTC |
| HSC16 Rep Cap Seq | (808) | CGCGGGTATTCGCAAATCGGCTGCACAGCCCGCTAAAAAGAGACTCAATTTCGGTCAGACTGGCGACACAGAGTC |
| HSC17 Rep Cap Seq | (808) | CGCGGGTATTCGCAAATCGGCTGCACAGCCCGCTAAAAAGAGACTCAATTTCGGTCAGACTGGCGACACAGAGTC |
| AAV9 Capsid | (468) | CGCGGGTATTCGCAAATCGGCTGCACAGCCCGCTAAAAAGAGACTCAATTTCGGTCAGACTGGCGACACAGAGTC |
| AAV2 | (2670) | CTCGGGAACCGGAAAGGCGGGCCAGCAGCCTGCAAGAAAAAGATTGAATTTTGGTCAGACTGGAGACGCAGACTC |

Figure 1 (cont.)

| | | 2776 … 2850 |
|---|---|---|
| HSC1 Rep Cap Seq | (883) | AGTGCCAGACCCTCAACCAATCGGAGAACCTCCGGCAGCCCCCTCAGGTGTGGGATCTCTTACAATGGCTTCAGG |
| HSC2 Rep Cap Seq | (883) | AGTGCCAGACCCTCAACCAATCGGAGAACCTCCGGCAGCCCCCTCAGGTGTGGGATCTCTTACAATGGCTTCAGG |
| HSC3 Rep Cap Seq | (883) | AGTGCCAGACCCTCAACCAATCGGAGAACCTCCGGCAGCCCCCTCAGGTGTGGGATCTCTTACAATGGCTTCAGG |
| HSC4 Rep Cap Seq | (883) | AGTGCCAGACCCTCAACCAATCGGAGAACCTCCGGCAGCCCCCTCAGGTGTGGGATCTCTTACAATGGCTTCAGG |
| HSC6 Rep Cap Seq | (883) | AGTGCCAGACCCTCAACCAATCGGAGAACCTCCGGCAGCCCCCTCAGGTGTGGGATCTCTTACAATGGCTTCAGG |
| HSC5 Rep Cap Seq | (883) | AGTGCCAGACCCTCAACCAATCGGAGAACCTCCGGCAGCCCCCTCAGGTGTGGGATCTCTTACAATGGCTTCAGG |
| HSC11 Rep Cap Seq | (883) | AGTGCCAGACCCTCAACCAATCGGAGAACCTCCGGCAGCCCCCTCAGGTGTGGGATCTCTTACAATGGCTTCAGG |
| HSC7 Rep Cap Seq | (883) | AGTGCCAGACCCTCAACCAATCGGAGAACCTCCGGCAGCCCCCTCAGGTGTGGGATCTCTTACAATGGCTTCAGG |
| HSC8 Rep Cap Seq | (883) | AGTGCCAGACCCTCAACCAATCGGAGAACCTCCGGCAGCCCCCTCAGGTGTGGGATCTCTTACAATGGCTTCAGG |
| HSC9 Rep Cap Seq | (883) | AGTGCCAGACCCTCAACCAATCGGAGAACCTCCGGCAGCCCCCTCAGGTGTGGGATCTCTTACAATGGCTTCATG |
| HSC12 Rep Cap Seq | (883) | AGTGCCAGACCCTCAACCAATCGGAGAACCTCCGGCTGCCCCCTCAGGTGTGGGATCTCTTACAATGGCTTCAGG |
| HSC13 Rep Cap Seq | (883) | AGTGCCAGACCCTCAACCAATCGGAGAACCTCCGGCAGCCCCCTCAGGTGTGGGATCTCTTACAATGGCTTCAGG |
| HSC14 Rep Cap Seq | (883) | AGTGCCAGACCCTCAACCAATCGGAGAACCTCCGGCAGCCCCCTCAGGTGTGGGATCTCTTACAATGGCTTCAGG |
| HSC15 Rep Cap Seq | (883) | AGTGCCAGACCCTCAACCAATCGGAGAACCTCCGGCAGCCCCCTCAGGTGTGGGATCTCTTACAATGGCTTCAGG |
| HSC16 Rep Cap Seq | (883) | AGTGCCAGACCCTCAACCAATCGGAGAACCTCCGGCAGCCCCCTCAGGTGTGGGATCTCTTACAATGGCTTCAGG |
| HSC17 Rep Cap Seq | (883) | AGTGCCAGACCCTCAACCAATCGGAGAACCTCCGGCAGCCCCCTCAGGTGTGGGATCTCTTACAATGGCTTCAGG |
| AAV9 Capsid | (543) | AGTGCCAGACCCTCAACCAATCGGAGAACCTCCGGCAGCCCCCTCAGGTGTGGGATCTCTTACAATGGCTTCAGG |
| AAV2 | (2745) | AGTACCTGACCCCCAGCCTCTCGGACAGCCACCAGCAGCCCCCTCTGGTCTGGGAACTAATACGATGGCTACAGG |

Figure 1 (cont.)

| | | 2851 2925 |
|---|---|---|
| HSC1 Rep Cap Seq | (958) | TGGTGGCGCACCAGTGGCAGACAATAACGAAGGTGCCGATGGAGTGGGTAGTTCCTCGGAAATTGGCATTGCGA |
| HSC2 Rep Cap Seq | (958) | TGGTGGCGCACCAGTGGCAGACAATAACGAAGGTGCCGATGGAGTGGGTAGTTCCTCGGAAATTGGCATTGCGA |
| HSC3 Rep Cap Seq | (958) | TGGTGGCGCACCAGTGGCAGACAATAACGAAGGTGCCGATGGAGTGGGTAGTTCCTCGGAAATTGGCATTGCGA |
| HSC4 Rep Cap Seq | (958) | TGGTGGCGCACCAGTGGCAGACAATAACGAAGGTGCCGATGGAGTGGGTAGTTCCTCGGAAATTGGCATTGCGA |
| HSC6 Rep Cap Seq | (958) | TGGTGGCGCACCAGTGGCAGACAATAACGAAGGTGCCGATGGAGTGGGTAGTTCCTCGGAAATTGGCATTGCGA |
| HSC5 Rep Cap Seq | (958) | TGGTGGCGCACCAGTGGCAGACAATAACGAAGGTGCCGATGGAGTGGGTAGTTCCTCGGAAATTGGCATTGCGA |
| HSC11 Rep Cap Seq | (958) | TGGTGGCGCACCAGTGGCAGACAATAACGAAGGTGCCGATGGAGTGGGTAGTTCCTCGGAAATTGGCATTGCGA |
| HSC7 Rep Cap Seq | (958) | TGGTGGCGCACCAGTGGCAGACAATAACGAAGGTGCCGATGGAGTGGGTAGTTCCTCGGAAATTGGCATTGCGA |
| HSC8 Rep Cap Seq | (958) | TGGTGGCGCACCAGTGGCAGACAATAACGAAGGTGCCGATGGAGTGGGTAGTTCCTCGGAAATTGGCATTGCGA |
| HSC9 Rep Cap Seq | (958) | TGGTGGCGCACCAGTGGCAGACAATAACGAAGGTGCCGATGGAGTGGGTAGTTCCTCGGAAATTGGCATTGCGA |
| HSC12 Rep Cap Seq | (958) | TGGTGGCGCACCAGTGGCAGACAATAACGAAGGTGCCGATGGAGTGGGTAGTTCCTCGGAAATTGGCATTGCGA |
| HSC13 Rep Cap Seq | (958) | TGGTGGCGCACCAGTGGCAGACAATAACGAAGGTGCCGATGGAGTGGGTAGTTCCTCGGAAATTGGCATTGCGA |
| HSC14 Rep Cap Seq | (958) | TGGTGGCGCACCAGTGGCAGACAATAACGAAGGTGCCGATGGAGTGGGTAGTTCCTCGGAAATTGGCATTGCGA |
| HSC15 Rep Cap Seq | (958) | TGGTGGCGCACCAGTGGCAGACAATAACGAAGGTGCCGATGGAGTGGGTAGTTCCTCGGAAATTGGCATTGCGA |
| HSC16 Rep Cap Seq | (958) | TGGTGGCGCACCAGTGGCAGACAATAACGAAGGTGCCGATGGAGTGGGTAGTTCCTCGGAAATTGGCATTGCGA |
| HSC17 Rep Cap Seq | (958) | TGGTGGCGCACCAGTGGCAGACAATAACGAAGGTGCCGATGGAGTGGGTAGTTCCTCGGAAATTGGCATTGCGA |
| AAV9 Capsid | (618) | TGGTGGCGCACCAGTGGCAGACAATAACGAAGGTGCCGATGGAGTGGGTAGTTCCTCGGAAATTGGCATTGCGA |
| AAV2 | (2820) | CAGTGGCGCACCAATGGCAGACAATAACGAGGGCGCCGACGGAGTGGGTAATTCCTCGGAAATTGGCATTGCGA |

Figure 1 (cont.)

| | | 2926 3000 |
|---|---|---|
| HSC1 Rep Cap Seq | (1033) | TTCCCAATGGCTGGGGGACAGAGTCATCACCACCAGCACCCGAACCTGGGCCCTGCCCACCTACAACAATCACCT |
| HSC2 Rep Cap Seq | (1033) | TTCCCAATGGCTGGGGGACAGAGTCATCACCACCAGCACCCGAACCTGGGCCCTGCCCACCTACAACAATCACCT |
| HSC3 Rep Cap Seq | (1033) | TTCCCAATGGCTGGGGGACAGAGTCATCACCACCAGCACCCGAACCTGGGCCCTGCCCACCTACAACAATCACCT |
| HSC4 Rep Cap Seq | (1033) | TTCCCAATGGCTGGGGGACAGAGTCATCACCACCAGCACCCGAACCTGGGCCCTGCCCACCTACAACAATCACCT |
| HSC6 Rep Cap Seq | (1033) | TTCCCAATGGCTGGGGGACAGAGTCATCACCACCAGCACCCGAACCTGGGCCCTGCCCACCTACAACAATCACCT |
| HSC5 Rep Cap Seq | (1033) | TTCCCAATGGCTGGGGGACAGAGTCATCACCACCAGCACCCGAACCTGGGCCCTGCCCACCTACAACAATCACCT |
| HSC11 Rep Cap Seq | (1033) | TTCCCAATGGCTGGGGGACAGAGTCATCACCACCAGCACCCGAACCTGGGCCCTGCCCACCTACAACAATCACCT |
| HSC7 Rep Cap Seq | (1033) | TTCCCAATGGCTGGGGGACAGAGTCATCACCACCAGCACCCGAACCTGGGCCCTGCCCACCTACAACAATCACCT |
| HSC8 Rep Cap Seq | (1033) | TTCCCAATGGCTGGGGGACAGAGTCATCACCACCAGCACCCGAACCTGGGCCCTGCCCACCTACAACAATCACCT |
| HSC9 Rep Cap Seq | (1033) | TTCCCAATGGCTGGGGGACAGAGTCATCACCACCAGCACCCGAACCTGGGCCCTGCCCACCTACAACAATCACCT |
| HSC12 Rep Cap Seq | (1033) | TTCCCAATGGCTGGGGGACAGAGTCATCACCACCAGCACCCGAACCTGGGCCCTGCCCACCTACAACAATCACCT |
| HSC13 Rep Cap Seq | (1033) | TTCCCAATGGCTGGGGGACAGAGTCATCACCACCAGCACCCGAACCTGGGCCCTGCCCACCTACAACAATCACCT |
| HSC14 Rep Cap Seq | (1033) | TTCCCAATGGCTGGGGGACAGAGTCATCACCACCAGCACCCGAACCTGGGCCCTGCCCACCTACAACAATCACCT |
| HSC15 Rep Cap Seq | (1033) | TTCCCAATGGCTGGGGGACAGAGTCATCACCACCAGCACCCGAACCTGGGCCCTGCCCACCTACAACAATCACCT |
| HSC16 Rep Cap Seq | (1033) | TTCCCAATGGCTGGGGGACAGAGTCATCACCACCAGCACCCGAACCTGGGCCCTGCCCACCTACAACAATCACCT |
| HSC17 Rep Cap Seq | (1033) | TTCCCAATGGCTGGGGGACAGAGTCATCACCACCAGCACCCGAACCTGGGCCCTGCCCACCTACAACAATCACCT |
| AAV9 Capsid | (693) | TTCCCAATGGCTGGGGGACAGAGTCATCACCACCAGCACCCGAACCTGGGCCCTGCCCACCTACAACAATCACCT |
| AAV2 | (2895) | TTCCACATGGATGGGCGACAGAGTCATCACCACCAGCACCCGAACCTGGGCCCTGCCCACCTACAACAACCACCT |

Figure 1 (cont.)

| | | 3001 … 3075 |
|---|---|---|
| HSC1 Rep Cap Seq | (1108) | CTACAAGCAAATCTCCAACAGCACATCTGGAGGATCTTCAAATGACAACGCCTACTTCGGCTACAGCACCCCCTG |
| HSC2 Rep Cap Seq | (1108) | CTACAAGCAAATCTCCAACAGCACATCTGGAGGATCTTCAAATGACAACGCCTACTTCGGCTACAGCACCCCCTG |
| HSC3 Rep Cap Seq | (1108) | CTACAAGCAAATCTCCAACAGCACATCTGGAGGATCTTCAAATGACAACGCCTACTTCGGCTACAGCACCCCCTG |
| HSC4 Rep Cap Seq | (1108) | CTACAAGCAAATCTCCAACAGCACATCTGGAGGATCTTCAAATGACAACGCCTACTTCGGCTACAGCACCCCCTG |
| HSC6 Rep Cap Seq | (1108) | CTACAAGCAAATCTCCAACAGCACATCTGGAGGATCTTCAAATGACAACGCCTACTTCGGCTACAGCACCCCCTG |
| HSC5 Rep Cap Seq | (1108) | CTACAAGCAAATCTCCAACAGCACATCTGGAGGATCTTCAAATGACAACGCCTACTTCGGCTACAGCACCCCCTG |
| HSC11 Rep Cap Seq | (1108) | CTACAAGCAAATCTCCAACAGCACATCTGGAGGATCTTCAAATGACAACGCCTACTTCGGCTACAGCACCCCCTG |
| HSC7 Rep Cap Seq | (1108) | CTACAAGCAAATCTCCAACAGCACATCTGGAGGATCTTCAAATGACAACGCCTACTTCGGCTACAGCACCCCCTG |
| HSC8 Rep Cap Seq | (1108) | CTACAAGCAAATCTCCAACAGCACATCTGGAGGATCTTCAAATGACAACGCCTACTTCGGCTACAGCACCCCCTG |
| HSC9 Rep Cap Seq | (1108) | CTACAAGCAAATCTCCAACAGCACATCTGGAGGATCTTCAAATGACAACGCCTACTTCGGCTACAGCACCCCCTG |
| HSC12 Rep Cap Seq | (1108) | CTACAAGCAAATCTCCAACAGCACATCTGGAGGATCTTCAAATGACAACGCCTACTTCGGCTACAGCACCCCCTG |
| HSC13 Rep Cap Seq | (1108) | CTACAAGCAAATCTCCAACAGCACATCTGGAGGATCTTCAAATGACAACGCCTACTTCGGCTACAGCACCCCCTG |
| HSC14 Rep Cap Seq | (1108) | CTACAAGCAAATCTCCAACAGCACATCTGGAGGATCTTCAAATGACAACGCCTACTTCGGCTACAGCACCCCCTG |
| HSC15 Rep Cap Seq | (1108) | CTACAAGCAAATCTCCAACAGCACATCTGGAGGATCTTCAAATGACAACGCCTACTTCGGCTACAGCACCCCCTG |
| HSC16 Rep Cap Seq | (1108) | CTACAAGCAAATCTCCAACAGCACATCTGGAGGATCTTCAAATGACAACGCCTACTTCGGCTACAGCACCCCCTG |
| HSC17 Rep Cap Seq | (1108) | CTACAAGCAAATCTCCAACAGCACATCTGGAGGATCTTCAAATGACAACGCCTACTTCGGCTACAGCACCCCCTG |
| AAV9 Capsid | (768) | CTACAAGCAAATCTCCAACAGCACATCTGGAGGATCTTCAAATGACAACGCCTACTTCGGCTACAGCACCCCCTG |
| AAV2 | (2970) | CTACAAACAAATTTCCA---GCCAATCAGGAGC---CTCGAACGACAATCACTACTTTGGCTACAGCACCCCTTG |

Figure 1 (cont.)

| | | 3076 … 3150 |
|---|---|---|
| HSC1 Rep Cap Seq | (1183) | GGGGTATTTTGACTTCAACAGATTCCACTGCCACTTCTCACCACGTGACTGGCAGCGACTCATCAACAACAACTG |
| HSC2 Rep Cap Seq | (1183) | GGGGTATTTTGACTTCAACAGATTCCACTGCCACTTCTCACCACGTGACTGGCAGCGACTCATCAACAACAACTG |
| HSC3 Rep Cap Seq | (1183) | GGGGTATTTTGACTTCAACAGATTCCACTGCCACTTCTCACCACGTGACTGGCAGCGACTCATCAACAACAACTG |
| HSC4 Rep Cap Seq | (1183) | GGGGTATTTTGACTTCAACAGATTCCACTGCCACTTCTCACCACGTGACTGGCAGCGACTCATCAACAACAACTG |
| HSC6 Rep Cap Seq | (1183) | GGGGTATTTTGACTTCAACAGATTCCACTGCCACTTCTCACCACGTGACTGGCAGCGACTCATCAACAACAACTG |
| HSC5 Rep Cap Seq | (1183) | GGGGTATTTTGACTTCAACAGATTCCACTGCCACTTCTCACCACGTGACTGGCAGCGACTCATCAACAACAACTG |
| HSC11 Rep Cap Seq | (1183) | GGGGTATTTTGACTTCAACAGATTCCACTGCCACTTCTCACCACGTGACTGGCAGCGACTCATCAACAACAACTG |
| HSC7 Rep Cap Seq | (1183) | GGGGTATTTTGACTTCAACAGATTCCACTGCCACTTCTCACCACGTGACTGGCAGCGACTCATCAACAACAACTG |
| HSC8 Rep Cap Seq | (1183) | GGGGTATTTTGACTTCAACAGATTCCACTGCCACTTCTCACCACGTGACTGGCAGCGACTCATCAACAACAACTG |
| HSC9 Rep Cap Seq | (1183) | GGGGTATTTTGACTTCAACAGATTCCACTGCCACTTCTCACCACGTGACTGGCAGCGACTCATCAACAACAACTG |
| HSC12 Rep Cap Seq | (1183) | GGGGTATTTTGACTTCAACAGATTCCACTGCCACTTCTCACCACATGACTGGCAGCGACTCATCAACAACAACTG |
| HSC13 Rep Cap Seq | (1183) | GGGGTATTTTGACTTCAACAGATTCCACTGCCACTTCTCACCACGTGACTGGCAGCGACTCATCAACAACAACTG |
| HSC14 Rep Cap Seq | (1183) | GGGGTATTTTGACTTCAACAGATTCCACTGCCACTTCTCACCACGTGACTGGCAGCGACTCATCAACAACAACTG |
| HSC15 Rep Cap Seq | (1183) | GGGGTATTTTGACTTCAACAGATTCCACTGCCACTTCTCACCACGTGACTGGCAGCGACTCATCAACAACAACTG |
| HSC16 Rep Cap Seq | (1183) | GGGGTATTTTGACTTCAACAGATTCCACTGCCACTTCTCACCACGTGACTGGCAGCGACTCATCAACAACAACTG |
| HSC17 Rep Cap Seq | (1183) | GGGGTATTTTGACTTCAACAGATTCCACTGCCACTTCTCACCACGTGACTGGCAGCGACTCATCAACAACAACTG |
| AAV9 Capsid | (843) | GGGGTATTTTGACTTCAACAGATTCCACTGCCACTTCTCACCACGTGACTGGCAGCGACTCATCAACAACAACTG |
| AAV2 | (3039) | GGGGTATTTTGACTTCAACAGATTCCACTGCCACTTTTCACCACGTGACTGGCAAAGACTCATCAACAACAACTG |

Figure 1 (cont.)

| | | 3151 … 3225 |
|---|---|---|
| HSC1 Rep Cap Seq | (1258) | GGGATTCCGGCCTAAGCAACTCAACTTCAAGCTCTTCAACATTCAGGTCAAAGAGGTTACGGACAACAATGGAGT |
| HSC2 Rep Cap Seq | (1258) | GGGATTCCGGCCTAAGCGACTCAACTTCAAGCTCTTCAACATTCAGGTCAAAGAGGTTACGGACAACAATGGAGT |
| HSC3 Rep Cap Seq | (1258) | GGGATTCCGGCCTAAGCGACTCAACTTCAAGCTCTTCAACATTCAGGTCAAAGAGGTTACGGACAACAATGGAGT |
| HSC4 Rep Cap Seq | (1258) | GGGATTCCGGCCTAAGCGACTCAACTTCAAGCTCTTCAACATTCAGGTCAAAGAGGTTACGGACAACAATGGAGT |
| HSC6 Rep Cap Seq | (1258) | GGGATTCCGGCCTAAGCGACTCAACTTCAAGCTCTTCAACATTCAGGTCAAAGAGGTTACGGACAACAATGGAGT |
| HSC5 Rep Cap Seq | (1258) | GGGATTCCGGCCTAAGCGACTCAACTTCAAGCTCTTCAACATTCAGGTCAAAGAGGTTACGGACAACAATGGAGT |
| HSC11 Rep Cap Seq | (1258) | GGGATTCCGGCCTAAGCGACTCAACTTCAAGCTCTTCAACATTCAGGTCAAAGAGGTTACGGACAACAATGGAGT |
| HSC7 Rep Cap Seq | (1258) | GGGATTTCGGCCTAAGCGACTCAACTTCAAGCTCTTCAACATTCAGGTCAAAGAGGTTACGGACAACAATGGAGT |
| HSC8 Rep Cap Seq | (1258) | GGGATTCCGGCCTAAGCGACTCAACTTCAAGCTCTTCAACATTCAGGTCAAAGAGGTTACGGACAACAATGGAGT |
| HSC9 Rep Cap Seq | (1258) | GGGATTCCGGCCTAAGCGACTCAACTTCAAGCTCTTCAACATTCAGGTCAAAGAGGTTACGGACAACAATGGAGT |
| HSC12 Rep Cap Seq | (1258) | GGGATTCCGGCCTAAGCGACTCAACTTCAAGCTCTTCAACATTCAGGTCAAAGAGGTTACGGACAACAATGGAGT |
| HSC13 Rep Cap Seq | (1258) | GGGATTCCGGCCTAAGCGACTCAACTTCAAGCTCTTCAACATTCAGGTCAAAGAGGTTACGGACAACAATGGAGT |
| HSC14 Rep Cap Seq | (1258) | GGGATTCCGGCCTAAGCGACTCAACTTCAAGCTCTTCAACATTCAGGTCAAAGAGGTTACGGACAACAATGGAGT |
| HSC15 Rep Cap Seq | (1258) | GGGATTCCGGCCTAAGCGACTCAACTTCAAGCTCTTCAACATTCAGGTCAAAGAGGTTACGGACAACAATGGAGT |
| HSC16 Rep Cap Seq | (1258) | GGGATTCCGGCCTAAGCGACTCAACTTCAAGCTCTTCAACATTCAGGTCAAAGAGGTTACGGACAACAATGGAGT |
| HSC17 Rep Cap Seq | (1258) | GGGATTCCGGCCTAAGCGACTCAACTTCAAGCTCTTCAACATTCAGGTCAAAGAGGTTACGGACAACAATGGAGT |
| AAV9 Capsid | (918) | GGGATTCCGGCCTAAGCGACTCAACTTCAAGCTCTTCAACATTCAGGTCAAAGAGGTTACGGACAACAATGGAGT |
| AAV2 | (3114) | GGGATTCCGACCCAAGAGACTCAACTTCAAGCTCTTTAACATTCAAGTCAAAGAGGTCACGCAGAATGACGGTAC |

Figure 1 (cont.)

| | | 3226 … 3300 |
|---|---|---|
| HSC1 Rep Cap Seq | (1333) | CAAGACCATGGCCAATAACCTTACCAGCACGGTGCAGGTCTTCACGGACTCAGACTATCAGCTGCCGTACGTGCT |
| HSC2 Rep Cap Seq | (1333) | CAAGACCATGGCCAATAACCTTACCAGCACGGTGCAGGTCTTCACGGACTCAGACTATCAGCTGCCGTACGTGCT |
| HSC3 Rep Cap Seq | (1333) | CAAGACCATGGCCAATAACCTTACCAGCACGGTGCAGGTCTTCACGGACTCGGACTATCAGCTGCCGTACGTGCT |
| HSC4 Rep Cap Seq | (1333) | CAAGACCATGGCCAATAACCTTACCAGCACGGTGCAGGTCTTCACGGACTCAGACTATCAGCTGCCGTACGTGCT |
| HSC6 Rep Cap Seq | (1333) | CAAGACCATGGCCAATAACCTTACCAGCACGGTGCAGGTCTTCACGGACTCAGACTATCAGCTGCCGTACGTGCT |
| HSC5 Rep Cap Seq | (1333) | CAAGACCATGGCCAATAACCTTACCAGCACGGTGCAGGTCTTCACGGACTCAGACTATCAGCTGCCGTACGTGCT |
| HSC11 Rep Cap Seq | (1333) | CAAGACCATGGCCAATAACCTTACCAGCACGGTGCAGGTCTTCACGGACTCAGACTATCAGCTGCCGTACGTGCT |
| HSC7 Rep Cap Seq | (1333) | CAAGACCATGGCCAATAACCTTACCAGCACGGTGCAGGTCTTCACGGACTCAGACTATCAGCTGCCGTACGTGCT |
| HSC8 Rep Cap Seq | (1333) | CAAGACCATGGCCAATAACCTTACCAGCACGGTGCAGGTCTTCACGGACTCAGACTATCAGCTGCCGTACGTGCT |
| HSC9 Rep Cap Seq | (1333) | CAAGACCATGGCCAATAACCTTACCAGCACGGTGCAGGTCTTCACGGACTCAGACTATCAGCTGCCGTACGTGCT |
| HSC12 Rep Cap Seq | (1333) | CAAGACCATGGCCAATAACCTTACCAGCACGGTGCAGGTCTTCACGGACTCAGACTATCAGCTGCCGTACGTGCT |
| HSC13 Rep Cap Seq | (1333) | CAAGACCATGGCCAATAACCTTACCAGCACGGTGCAGGTCTTCACGGACTCAGACTATCAGCTGCCGTACGTGCT |
| HSC14 Rep Cap Seq | (1333) | CAAGACCATGGCCAATAACCTTACCAGCACGGTGCAGGTCTTCACGGACTCAGACTATCAGCTGCCGTACGTGCT |
| HSC15 Rep Cap Seq | (1333) | CAAGACCATGGCCAATAACCTTACCAGCACGGTGCAGGTCTTCGCGGACTCAGACTATCAGCTGCCGTACGTGCT |
| HSC16 Rep Cap Seq | (1333) | CAAGACCATGGCCAATAACCTTACCAGCACGGTGCAGGTCTTCACGGACTCAGACTATCAGCTGCCGTACGTGCT |
| HSC17 Rep Cap Seq | (1333) | CAAGACCATGGCCAATAACCTTACCAGCACGGTGCAGGTCTTCACGGACTCAGACTATCAGCTGCCGTACGTGCT |
| AAV9 Capsid | (993) | CAAGACCATGGCCAATAACCTTACCAGCACGGTGCAGGTCTTCACGGACTCAGACTATCAGCTGCCGTACGTGCT |
| AAV2 | (3189) | GACGACGATTGCCAATAACCTTACCAGCACGGTTCAGGTGTTTACTGACTCGGAGTACCAGCTGCCGTACGTCCT |

Figure 1 (cont.)

| | | 3301 3375 |
|---|---|---|
| HSC1 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC2 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC3 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC4 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC6 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC5 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC11 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC7 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC8 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC9 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC12 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC13 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC14 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC15 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC16 Rep Cap Seq | (1408) | CGGGTCGGCTCACGAGGGCTGCCTCCCGCCGTTCCCAGCGGACGTTTTCATGATTCCTCAGTACGGGTATCTGAC |
| HSC17 Rep Cap Seq | (1408) | CGGGTCGGCTCACGAGGGCTGCCTCCCGCCGTTCCCAGCGGACGTTTTCATGATTCCTCAGTACGGGTATCTGAC |
| AAV9 Capsid | (1068) | CGGGTCGGCTCACGAGGGCTGCCTCCCGCCGTTCCCAGCGGACGTTTTCATGATTCCTCAGTACGGGTATCTGAC |
| AAV2 | (3264) | CGGCTCGGCGCATCAAGGATGCCTCCCGCCGTTCCCAGCAGACGTCTTCATGGTGCCACAGTATGGATACCTCAC |

Figure 1 (cont.)

```
                                3376                                                                     3450
HSC1 Rep Cap Seq        (1483) GCTTAATGATGGAAGCCAGGCCGTGGCTCGTTCGTCCTTTTACTGCCTGGAATATTTCCCGTCGCAAATGCTAAG
HSC2 Rep Cap Seq        (1483) GCTTAATGATGGAAGCCAGGCCGTGGCTCGTTCGTCCTTTTACTGCCTGGAATATTTCCCGTCGCAAATGCTAAG
HSC3 Rep Cap Seq        (1483) GCTTAATGATGGAAGCCAGGCCGTGGCTCGTTCGTCCTTTTACTGCCTGGAATATTTCCCGTCGCAAATGCTAAG
HSC4 Rep Cap Seq        (1483) GCTTAATGATGGAAGCCAGGCCGTGGCTCGTTCGTCCTTTTACTGCCTGGAATATTTCCCGTCGCAAATGCTAAG
HSC6 Rep Cap Seq        (1483) GCTTAATGATGGAAGCCAGGCCGTGGCTCGTTCGTCCTTTTACTGCCTGGAATATTTCCCGTCGCAAATGCTAAG
HSC5 Rep Cap Seq        (1483) GCTTAATGATGGAAGCCAGGCCGTGGCTCGTTCGTCCTTTTACTGCCTGGAATATTTCCCGTCGCAAATGCTAAG
HSC11 Rep Cap Seq       (1483) GCTTAATGATGGAAGCCAGGCCGTGGCTCGTTCGTCCTTTTACTGCCTGGAATATTTCCCGTCGCAAATGCTAAG
HSC7 Rep Cap Seq        (1483) GCTTAATGATGGAAGCCAGGCCGTGGCTCGTTCGTCCTTTTACTGCCTGGAATATTTCCCGTCGCAAATGCTAAG
HSC8 Rep Cap Seq        (1483) GCTTAATGATGGAAGCCAGGCCGTGGCTCGTTCGTCCTTTTACTGCCTGGAATATTTCCCGTCGCAAATGCTAAG
HSC9 Rep Cap Seq        (1483) GCTTAATGATGGAAGCCAGGCCGTGGCTCGTTCGTCCTTTTACTGCCTGGAATATTTCCCGTCGCAAATGCTAAG
HSC12 Rep Cap Seq       (1483) GCTTAATGATGGAAGCCAGGCCGTGGCTCGTTCGTCCTTTTACTGCCTGGAATATTTCCCGTCGCAAATGCTAAG
HSC13 Rep Cap Seq       (1483) GCTTAATGATGGAAGCCAGGCCGTGGCTCGTTCGTCCTTTTACTGCCTGGAATATTTCCCGTCGCAAATGCTAAG
HSC14 Rep Cap Seq       (1483) GCTTAATGATGGAAGCCAGGCCGTGGCTCGTTCGTCCTTTTACTGCCTGGAATATTTCCCGTCGCAAATGCTAAG
HSC15 Rep Cap Seq       (1483) GCTTAATGATGGAAGCCAGGCCGTGGCTCGTTCGTCCTTTTACTGCCTGGAATATTTCCCGTCGCAAATGCTAAG
HSC16 Rep Cap Seq       (1483) GCTTAATGATGGAAGCCAGGCCGTGGCTCGTTCGTCCTTTTACTGCCTGGAATATTTCCCGTCGCAAATGCTAAG
HSC17 Rep Cap Seq       (1483) GCTTAATGATGGAAGCCAGGCCGTGGCTCGTTCGTCCTTTTACTGCCTGGAATATTTCCCGTCGCAAATGCTAAG
AAV9 Capsid             (1143) GCTTAATGATGGAAGCCAGGCCGTGGCTCGTTCGTCCTTTTACTGCCTGGAATATTTCCCGTCGCAAATGCTAAG
AAV2                    (3339) CCTGAACAACGGGAGTCAGGCAGTAGGACGCTCTTCATTTTACTGCCTGGAGTACTTTCCTTCTCAGATGCTGCG
```

Figure 1 (cont.)

| | | 3451 3525 |
|---|---|---|
| HSC1 Rep Cap Seq | (1558) | AACGGGTAACAACTTCCAGTTCAGCTACGAGTTTGAGAACGTACCTTTCCATAGCAGCTACGCTCACAGCCAAAG |
| HSC2 Rep Cap Seq | (1558) | AACGGGTAACAACTTCCAGTTCAGCTACGAGTTTGAGAACGTACCTTTCCATAGCAGCTACGCTCACAGCCAAAG |
| HSC3 Rep Cap Seq | (1558) | AACGGGTAACAACTTCCAGTTCAGCTACGAGTTTGAGAACGTACCTTTCCATAGCAGCTACGCTCACAGCCAAAG |
| HSC4 Rep Cap Seq | (1558) | AACGGGTAACAACTTCCAGTTCAGCTACGAGTTTGAGAACGTACCTTTCCATAGCAGCTACGCTCACAGCCAAAG |
| HSC6 Rep Cap Seq | (1558) | AACGGGTAACAACTTCCAGTTCAGCTACGAGTTTGAGAACGTACCTTTCCATAGCAGCTACGCTCACAGCCAAAG |
| HSC5 Rep Cap Seq | (1558) | AACGGGTAACAACTTCCAGTTCAGCTACGAGTTTGAGAACGTACCTTTCCATAGCAGCTACGCTCACAGCCAAAG |
| HSC11 Rep Cap Seq | (1558) | AACGGGTAACAACTTCCAGTTCAGCTACGAGTTTGAGAACGTACCTTTCCATAGCAGCTACGCTCACAGCCAAAG |
| HSC7 Rep Cap Seq | (1558) | AACGGGTAACAACTTCCAGTTCAGCTACGAGTTTGAGAACGTACCTTTCCATAGCAGCTACGCTCACAGCCAAAG |
| HSC8 Rep Cap Seq | (1558) | AACGGGTAACAACTTCCAGTTCAGCTACGAGTTTGAGAACGTACCTTTCCATAGCAGCTACGCTCACAGCCAAAG |
| HSC9 Rep Cap Seq | (1558) | AACGGGTAACAACTTCCAGTTCAGCTACGAGTTTGAGAACGTACCTTTCCATAGCAGCTACGCTCACAGCCAAAG |
| HSC12 Rep Cap Seq | (1558) | AACGGGTAACAACTTCCAGTTCAGCTACGAGTTTGAGAACGTACCTTTCCATAGCAGCTACGCTCACAGCCAAAG |
| HSC13 Rep Cap Seq | (1558) | AACGGGTAACAACTTCCAGTTCAGCTACGAGTTTGAGAACGTACCTTTCCATAGCAGCTACGCTCACAGCCAAAG |
| HSC14 Rep Cap Seq | (1558) | AACGGGTAACAACTTCCAGTTCAGCTACGAGTTTGAGAACGTACCTTTCCATAGCAGCTACGCTCACAGCCAAAG |
| HSC15 Rep Cap Seq | (1558) | AACGGGTAACAACTTCCAGTTCAGCTACGAGTTTGAGAACGTACCTTTCCATAGCAGCTACGCTCACAGCCAAAG |
| HSC16 Rep Cap Seq | (1558) | AACGGGTAACAACTTCCAGTTCAGCTACGAGTTTGAGAACGTACCTTTCCATAGCAGCTACGCTCACAGCCAAAG |
| HSC17 Rep Cap Seq | (1558) | AACGGGTAACAACTTCCAGTTCAGCTACGAGTTTGAGAACGTACCTTTCCATAGCAGCTACGCTCACAGCCAAAG |
| AAV9 Capsid | (1218) | AACGGGTAACAACTTCCAGTTCAGCTACGAGTTTGAGAACGTACCTTTCCATAGCAGCTACGCTCACAGCCAAAG |
| AAV2 | (3414) | TACCGGAAACAACTTTACCTTCAGCTACACTTTTGAGGACGTTCCTTTCCACAGCAGCTACGCTCACAGCCAGAG |

Figure 1 (cont.)

| | | 3526 … 3600 |
|---|---|---|
| HSC1 Rep Cap Seq | (1633) | GCTGGACCGACTAATGAATCCACTCATCGACCAATACTTGTACTATCTCT------CAAAGACTATTAACGGTTC |
| HSC2 Rep Cap Seq | (1633) | GCTGGACCGACTAATGAATCCACTCATCGACCAATACTTGTACTATCTCT------CAAAGACTATTAACGGTTC |
| HSC3 Rep Cap Seq | (1633) | GCTGGACCGACTAATGAATCCACTCATCGACCAATACTTGTACTATCTCT------CAAAGACTATTAACGGTTC |
| HSC4 Rep Cap Seq | (1633) | GCTGGACCGACTAATGAATCCACTCATCGACCAATACTTGTACTATCTCT------CAAAGACTATTAACGGTTC |
| HSC6 Rep Cap Seq | (1633) | GCTGGACCGACTAATGAATCCACTCATCGACCAATACTTGTACTATCTCT------CAAAGACTATTAACGGTTC |
| HSC5 Rep Cap Seq | (1633) | GCTGGACCGACTAATGAATCCACTCATCGACCAATACTTGTACTATCTCT------CAAAGACTATTAACGGTTC |
| HSC11 Rep Cap Seq | (1633) | GCTGGACCGACTAATGAATCCACTCATCGACCAATACTTGTACTATCTCT------CAAAGACTATTAACGGTTC |
| HSC7 Rep Cap Seq | (1633) | GCTGGACCGACTAATGAATCCACTCATCGACCAATACTTGTACTATCTCT------CAAAGACTATTAACGGTTC |
| HSC8 Rep Cap Seq | (1633) | GCTGGACCGACTAATGAATCCACTCATCGACCAATACTTGTACTATCTCT------CAAAGACTATTAACGGTTC |
| HSC9 Rep Cap Seq | (1633) | GCTGGACCGACTAATGAATCCACTCATCGACCAATACTTGTACTATCTCT------CAAAGACTATTAACGGTTC |
| HSC12 Rep Cap Seq | (1633) | GCTGGACCGACTAATGAATCCACTCATCGACCAATACTTGTACTATCTCT------CAAAGACTATTAACGGTTC |
| HSC13 Rep Cap Seq | (1633) | GCTGGACCGACTAATGAATCCACTCATCGACCAATACTTGTACTATCTCT------CAAAGACTATTAACGGTTC |
| HSC14 Rep Cap Seq | (1633) | GCTGGACCGACTAATGAATCCACTCATCGACCAATACTTGTACTATCTCT------CAAAGACTATTAACGGTTC |
| HSC15 Rep Cap Seq | (1633) | GCTGGACCGACTAATGAATCCACTCATCGACCAATACTTGTACTATCTCT------CAAAGACTATTAACGGTTC |
| HSC16 Rep Cap Seq | (1633) | GCTGGACCGACTAATGAATCCACTCATCGACCAATACTTGTACTATCTCT------CAAAGACTATTAACGGTTC |
| HSC17 Rep Cap Seq | (1633) | GCTGGACCGACTAATGAATCCACTCATCGACCAATACTTGTACTATCTCT------CAAAGACTATTAACGGTTC |
| AAV9 Capsid | (1293) | GCTGGACCGACTAATGAATCCACTCATCGACCAATACTTGTACTATCTCT------CAAAGACTATTAACGGTTC |
| AAV2 | (3489) | TCTGGACCGTCTCATGAATCCTCTCATCGACCAGTACCTGTATTACTTGAGCAGAACAAACACTCCAAGTGGAAC |

Figure 1 (cont.)

```
                              3676                                                                       3750
HSC1 Rep Cap Seq     (1777)   ACCTGGACCCAGCTACCGACAACAACGTGTCTCAACCACTGTGACTCAAAACAACAACAGCGAATTTGCTTGGCC
HSC2 Rep Cap Seq     (1777)   ACCTGGACCCAGCTACCGACAACAACGTGTCTCAACCACTGTGACTCAAAACAACAACAGCGAATTTGCTTGGCC
HSC3 Rep Cap Seq     (1777)   ACCTGGACCCAGCTACCGACAACAACGTGTCTCAACCACTGTGACTCAAAACAACAACAGCGAATTTGCTTGGCC
HSC4 Rep Cap Seq     (1777)   ACCTGGACCCAGCTACCGACAACAACGTGTCTCAACCACTGTGACTCAAAACAACAACAGCGAATTTGCTTGGCC
HSC6 Rep Cap Seq     (1777)   ACCTGGACCCAGCTACCGACAACAACGTGTCTCAACCACTGTGACTCAAAACAACAACAGCGAATTTGCTTGGCC
HSC5 Rep Cap Seq     (1777)   ACCTGGACCCAGCTACCGACAACAACGTGTCTCAACCACTGTGACTCAAAACAACAACAGCGAATTTGCTTGGCC
HSC11 Rep Cap Seq    (1777)   ACCTGGACCCAGCTACCGACAACAACGTGTCTCAACCACTGTGACTCAAAACAACAACAGCGAATTTGCTTGGCC
HSC7 Rep Cap Seq     (1777)   ACCTGGACCCAGCTACCGACAACAACGTGTCTCAACCACTGTGACTCAAAACAACAACAGCGAATTTGCTTGGCC
HSC8 Rep Cap Seq     (1777)   ACCTGGACCCAGCTACCGACAACAACGTGTCTCAACCACTGTGACTCAAAACAACAACAGCGAATTTGCTTGGCC
HSC9 Rep Cap Seq     (1777)   ACCTGGACCCAGCTACCGACAACAACGTGTCTCAACCACTGTGACTCAAAACAACAACAGCGAATTTGCTTGGCC
HSC12 Rep Cap Seq    (1777)   ACCTGGACCCAGCTACCGACAACAACGTGTCTCAACCACTGTGACTCAAAACAACAACAGCGAATTTGCCTGGCC
HSC13 Rep Cap Seq    (1777)   ACCTGGACCCAGCTACCGACAACAACGTGTCTCAACCACTGTGACTCAAAACAACAACAGCGAATTTGCTTGGCC
HSC14 Rep Cap Seq    (1777)   ACCTGGACCCAGCTACCGACAACAACGTGTCTCAACCACTGTGACTCAAAACAACAACAGCGAATTTGCTTGGCC
HSC15 Rep Cap Seq    (1777)   ACCTGGACCCAGCTACCGACAACAACGTGTCTCAACCACTGTGACTCAAAACAACAACAGCGAATTTGCTTGGCC
HSC16 Rep Cap Seq    (1777)   ACCTGGACCCAGCTACCGACAACAACGTGTCTCAACCACTGTGACTCAAAACAACAACAGCGAAATTGCTTGGCC
HSC17 Rep Cap Seq    (1777)   ACCTGGACCCAGCTACCGACAACAACGTGTCTCAACCACTGTGACTCAAAACAACAACAGCGAATTTGCTTGGCC
AAV9 Capsid          (1437)   ACCTGGACCCAGCTACCGACAACAACGTGTCTCAACCACTGTGACTCAAAACAACAACAGCGAATTTGCTTGGCC
AAV2                 (3636)   TCCTGGACCCTGTTACCGCCAGCAGCGAGTATCAAAGACATCTGCGGATAACAACAACAGTGAATACTCGTGGAC
```

Figure 1 (cont.)

| | | 3751 … 3825 |
|---|---|---|
| HSC1 Rep Cap Seq | (1852) | TGGAGCTTCTTCTTGGGCTCTCAATGGACGTAATAGCTTGATGAATCCTGGACCTGCTATGGCCAGCCACAAAGA |
| HSC2 Rep Cap Seq | (1852) | TGGGGCTTCTTCTTGGGCTCTCAATGGACGTAATAGCTTGATGAATCCTGGACCTGCTATGGCCAGCCACAAAGA |
| HSC3 Rep Cap Seq | (1852) | TGGAGCTTCTTCTTGGGCTCTCAATGGACGTAATAGCTTGATGAATCCTGGACCTGCTATGGCCAGCCACAAAGA |
| HSC4 Rep Cap Seq | (1852) | TGGAGCTTCTTCTTGGGCTCTCAATGGACGTAATAGCTTGATGAATCCTGGACCTGCTATGGCCAGCCACAAAGA |
| HSC6 Rep Cap Seq | (1852) | TGGAGCTTCTTCTTGGGCTCTCAATGGACGTAATAGCTTGATGAATCCTGGACCTGCTATGGCCAGCCACAAAGA |
| HSC5 Rep Cap Seq | (1852) | TGGAGCTTCTTCTTGGGCTCTCAATGGACGTAATAGCTTGATGAATCCTGGACCTGCTATGGCCAGCCACAAAGA |
| HSC11 Rep Cap Seq | (1852) | TGGAGCTTCTTCTTGGGCTCTCAATGGACGTAATAGCTTGATGAATCCTGGACCTGCTATGGCCAGCCACAAAGA |
| HSC7 Rep Cap Seq | (1852) | TGGAGCTTCTTCTTGGGCTCTCAATGGACGTAATAGCTTGATGAATCCTGGACCTGCTATGGCCAGCCACAAAGA |
| HSC8 Rep Cap Seq | (1852) | TGGAGCTTCTTCTTGGGCTCTCAATGGACGTAATAGCTTGATGAATCCTGGACCTGCTATGGCCAGCCACAAAGA |
| HSC9 Rep Cap Seq | (1852) | TGGAGCTTCTTCTTGGGCTCTCAATGGACGTAATAGCTTGATGAATCCTGGACCTGCTATGGCCAGCCACAAAGA |
| HSC12 Rep Cap Seq | (1852) | TAGAGCTTCTTCTTGGGCTCTCAATGGACGTAATAGCTTGATGAATCCTGGACCTGCTATGGCCAGCCACAAAGA |
| HSC13 Rep Cap Seq | (1852) | TAGAGCTTCTTCTTGGGCTCTCAATGGACGTAATAGCTTGATGAATCCTGGACCTGCTATGGCCAGCCACAAAGA |
| HSC14 Rep Cap Seq | (1852) | TAGAGCTTCTTCTTGGGCTCTCAATGGACGTAATAGCTTGATGAATCCTGGACCTGCTATGGCCAGCCACAAAGA |
| HSC15 Rep Cap Seq | (1852) | TAGAGCTTCTTCTTGGGCTCTCAATGGACGTAATAGCTTGATGAATCCTGGACCTGCTATGGCCAGCCACAAAGA |
| HSC16 Rep Cap Seq | (1852) | TAGAGCTTCTTCTTGGGCTCTCAATGGACGTAATAGCTTGATGAATCCTGGACCTGCTATGGCCAGCCACAAAGA |
| HSC17 Rep Cap Seq | (1852) | TAGAGCTTCTTCTTGGGCTCTCAATGGACGTAATAGCTTGATGAATCCTGGACCTGCTATGGCCAGCCACAAAGA |
| AAV9 Capsid | (1512) | TGGAGCTTCTTCTTGGGCTCTCAATGGACGTAATAGCTTGATGAATCCTGGACCTGCTATGGCCAGCCACAAAGA |
| AAV2 | (3711) | TGGAGCTACCAAGTACCACCTCAATGGCAGAGACTCTCTGGTGAATCCGGGCCCGGCCATGGCAAGCCACAAGGA |

Figure 1 (cont.)

| | | 3826 … 3900 |
|---|---|---|
| HSC1 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC2 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC3 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC4 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC6 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC5 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC11 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC7 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC8 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC9 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC12 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC13 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC14 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC15 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC16 Rep Cap Seq | (1927) | AGGAGAGGACCGTTTCTTTCCTTTGTCTGGATCTTTAATTTTTGGCAAACAAGGAACTGGAAGAGACAACGTGGA |
| HSC17 Rep Cap Seq | (1927) | AGGAGAGGACCGTTTCTTTCCTTTGTCTGGATCTTTAATTTTTGGCAAACAAGGAACTGGAAGAGACAACGTGGA |
| AAV9 Capsid | (1587) | AGGAGAGGACCGTTTCTTTCCTTTGTCTGGATCTTTAATTTTTGGCAAACAAGGAACTGGAAGAGACAACGTGGA |
| AAV2 | (3786) | CGATGAAGAAAAGTTTTTTCCTCAGAGCGGGTTCTCATCTTTGGGAAGCAAGGCTCAGAGAAAACAAATGTGGA |

Figure 1 (cont.)

| | | 3976 ... 4050 |
|---|---|---|
| HSC1 Rep Cap Seq | (2077) | AGTGGCCACAAACCACCAGAGTGCCCAAGCACAGGCGCAGACCGGCTGGGTTCAAAACCAAGGAATACTTCCGGG |
| HSC2 Rep Cap Seq | (2077) | AGTGGCCACAAACCACCAGAGTGCCCAAGCACAGGCGCAGACCGGCTGGGTTCAAAACCAAGGAATACTTCCGGG |
| HSC3 Rep Cap Seq | (2077) | AGTGGCCACAAACCACCAGAGTGCCCAAGCACAGGCGCAGACCGGCTGGGTTCAAAACCAAGGAATACTTCCGGG |
| HSC4 Rep Cap Seq | (2077) | AGTGGCCACAAACCACCAGAGTGCCCAAGCACAGGCGCAGACCGGCTGGGTTCAAAACCAAGGAATACTTCCAGG |
| HSC6 Rep Cap Seq | (2077) | AGTGGCCACAAACCACCAGAGTGCCCAAGCACGGGCGCAGACCGGCTGGGTTCAAAACCAAGGAATACTTCCGGG |
| HSC5 Rep Cap Seq | (2077) | AGTGGCCACAAACCACCAGAGTGCCCAAGCACAGGCGCAGACCGGCTGGGTTCAAAACCAAGGAATACTTCCGGG |
| HSC11 Rep Cap Seq | (2077) | AGTGGCCACAAACCACCAGAGTGCCCAAGCACAGGCGCAGACCGGCTGGGTTCAAAACCAAGGAATACTTCCGGG |
| HSC7 Rep Cap Seq | (2077) | AGTGGCCACAAACCACCAGAGTGCCCAAGCACAGGCGCAGACCGGCTGGGTTCAAAACCAAGGAATACTTCCGGG |
| HSC8 Rep Cap Seq | (2077) | AGTGGCCACAAACCACCAGAGTGCCCAAGCACAGGCGCAGACCGGCTGGGTTCAAAACCAAGGAATACTTCCGGG |
| HSC9 Rep Cap Seq | (2077) | AGTGGCCACAAACCACCAGAGTGCCCAAGCACAGGCGCAGACCGGCTGGGTTCAAAACCAAGGAATACTTCCGGG |
| HSC12 Rep Cap Seq | (2077) | AGTGGCCACAAACCACCAGAGTGCCCAAGCACAGGCGCAGACCGGCTGGGTTCAAAACCAAGGAATACTTCCGGG |
| HSC13 Rep Cap Seq | (2077) | AGTGGCCACAAACCACCAGAGTGCCCAAGCACAGGCGCAGACCGGCTGGGTTCAAAACCAAGGAATACTTCCGGG |
| HSC14 Rep Cap Seq | (2077) | AGTGGCCACAAACCACCAGAGTGCCCAAGCACAGGCGCAGACCGGCTGGGTTCAAAACCAAGGAATACTTCCGGG |
| HSC15 Rep Cap Seq | (2077) | AGTGGCCACAAACCACCAGAGTGCCCAAGCACAGGCGCAGACCGGCTGGGTTCAAAACCAAGGAATACTTCCGGG |
| HSC16 Rep Cap Seq | (2077) | AGTGGCCACAAACCACCAGAGTGCCCAAGCACAGGCGCAGACCGGCTGGGTTCAAAACCAAGGAATACTTCCGGG |
| HSC17 Rep Cap Seq | (2077) | AGTGGCCACAAACCACCAGAGTGCCCAAGCACAGGCGCAGACCGGCTGGGTTCAAAACCAAGGAATACTTCCGGG |
| AAV9 Capsid | (1737) | AGTGGCCACAAACCACCAGAGTGCCCAAGCACAGGCGCAGACCGGCTGGGTTCAAAACCAAGGAATACTTCCGGG |
| AAV2 | (3936) | TGTATCTACCAACCTCCAGAGAGGCAACAGACAAGCAGCTACCGCAGATGTCAACACACAAGGCGTTCTTCCAGG |

Figure 1 (cont.)

```
                                 4051                                                                      4125
HSC1 Rep Cap Seq        (2152)  TATGGTTTGGCAGGACAGAGATGTGTACCTGCAAGGACCCATTTGGGCCAAAATTCCTCACACGGACGGCAACTT
HSC2 Rep Cap Seq        (2152)  TATGGTTTGGCAGGACAGAGATGTGTACCTGCAAGGACCCATTTGGGCCAAAATTCCTCACACGGGCGGCAACTT
HSC3 Rep Cap Seq        (2152)  TATGGTTTGGCAGGACAGAGATGTGTACCTGCAAGGACCCATTTGGGCCAAAATTCCTCACACGGACGGCAACTT
HSC4 Rep Cap Seq        (2152)  TATGGTTTGGCAGGACAGAGATGTGTACCTGCAAGGACCCATTTGGGCCAAAATTCCTCACACGGACGGCAACTT
HSC6 Rep Cap Seq        (2152)  TATGGTTTGGCAGGACAGAGATGTGTACCTGCAAGGACCCATTTGGGCCAAAATTCCTCACACGGACGGCAACTT
HSC5 Rep Cap Seq        (2152)  TATGGTTTGGCAGGACAGAGATGTGTACCTGCAAGGACCCATTTGGGCCAAAATTCCTCACACGGACGGCAACTT
HSC11 Rep Cap Seq       (2152)  TATGGTTTGGCAGGACAGAGATGTGTACCTGCAAGGACCCATTTGGGCCAAAATTCCTCACACGTACGGCAACTT
HSC7 Rep Cap Seq        (2152)  TATGGTTTGGCAGGACAGAGATGTGTACCTGCAAGGACCCATTTGGGCCAAAATTCCTCACACGGACGGCAACTT
HSC8 Rep Cap Seq        (2152)  TATGGTTTGGCAGGACAGAGATGTGTACCTGCAAGGACCCATTTGGGCCAAAATTCCTCACACGGACGGCAACTT
HSC9 Rep Cap Seq        (2152)  TATGGTTTGGCAGGACAGAGATGTGTACCTGCAAGGACCCATTTGGGCCAAAATTCCTCACACGGACGGCAACTT
HSC12 Rep Cap Seq       (2152)  TATGGTTTGGCAGGACAGAGATGTGTACCTGCAAGGACCCATTTGGGCCAAAATTCCTCACACGGACGGCAACTT
HSC13 Rep Cap Seq       (2152)  TATGGTTTGGCAGGACAGAGATGTGTACCTGCAAGGACCCATTTGGGCCAAAATTCCTCACACGGACGGCAACTT
HSC14 Rep Cap Seq       (2152)  TATGGTTTGGCAGGACAGAGATGTGTACCTGCAAGGACCCATTTGGGCCAAAATTCCTCACACGGACGGCAACTT
HSC15 Rep Cap Seq       (2152)  TATGGTTTGGCAGGACAGAGATGTGTACCTGCAAGGACCCATTTGGGCCAAAATTCCTCACACGGACGGCAACTT
HSC16 Rep Cap Seq       (2152)  TATGGTTTGGCAGGACAGAGATGTGTACCTGCAAGGACCCATTTGGGCCAAAATTCCTCACACGGACGGCAACTT
HSC17 Rep Cap Seq       (2152)  TATGGTTTGGCAGGACAGAGATGTGTACCTGCAAGGACCCATTTGGGCCAAAATTCCTCACACGGACGGCAACTT
AAV9 Capsid             (1812)  TATGGTTTGGCAGGACAGAGATGTGTACCTGCAAGGACCCATTTGGGCCAAAATTCCTCACACGGACGGCAACTT
AAV2                    (4011)  CATGGTCTGGCAGGACAGAGATGTGTACCTTCAGGGGCCCATCTGGGCAAAGATTCCACACACGGACGGACATTT
```

Figure 1 (cont.)

| | | 4126 4200 |
|---|---|---|
| HSC1 Rep Cap Seq | (2227) | TCACCCTTCTCCGCTGATGGGAGGGTTTGGAATGAAGCACCCGCCTCCTCAGATCCTCATCAAAAACACACCTGT |
| HSC2 Rep Cap Seq | (2227) | TCACCCTTCTCCGCTGATGGGAGGGTTTGGAATGAAGCACCCGCCTCCTCAGATCCTCATCAAAAACACACCTGT |
| HSC3 Rep Cap Seq | (2227) | TCACCCTTCTCCGCTGATGGGAGGGTTTGGAATGAAGCACCCGCCTCCTCAGATCCTCATCAAAAACACACCTGT |
| HSC4 Rep Cap Seq | (2227) | TCACCCTTCTCCGCTGATGGGAGGGTTTGGAATGAAGCACCCGCCTCCTCAGATCCTCATCAAAAACACACCTGT |
| HSC6 Rep Cap Seq | (2227) | TCACCCTTCTCCGCTGATGGGAGGGTTTGGAATGAAGCACCCGCCTCCTCAGATCCTCATCAAAAACACACCTGT |
| HSC5 Rep Cap Seq | (2227) | TCACCCTTCTCCGCTGATGGGAGGGTTTGGAATGAAGCACCCGCCTCCTCAGATCCTCATCAAAAACACACCTGT |
| HSC11 Rep Cap Seq | (2227) | TCACCCTTCTCCGCTGATGGGAGGGTTTGGAATGAAGCACCCGCCTCCTCAGATCCTCATCAAAAACACACCTGT |
| HSC7 Rep Cap Seq | (2227) | TCACCCTTCTCCGCTGATGGGAGGGTTTGGAATGAAGCACCCGCCTCCTCAGATCCTCATCAAAAACACACCTGT |
| HSC8 Rep Cap Seq | (2227) | TCACCCTTCTCCGCTGATGGGAGGGTTTGGAATGAAGCACCCGCCTCCTCAGATCCTCATCAAAAACACACCTGT |
| HSC9 Rep Cap Seq | (2227) | TCACCCTTCTCCGCTGATGGGAGGGTTTGGAATGAAGCACCCGCCTCCTCAGATCCTCATCAAAAACACACCTGT |
| HSC12 Rep Cap Seq | (2227) | TCACCCTTCTCCGCTGATGGGAGGGTTTGGAATGAAGCACCCGCCTCCTCAGATCCTCATCAAAAACACACCTGT |
| HSC13 Rep Cap Seq | (2227) | TCACCCTTCTCCGCTGATGGGAGGGTTTGGAATGAAGCACCCGCCTCCTCAGATCCTCATCAAAAACACACCTGT |
| HSC14 Rep Cap Seq | (2227) | TCACCCTTCTCCGCTGATGGGAGGGTTTGGAATGAAGCACCCGCCTCCTCAGATCCTCATCAAAAACACACCTGT |
| HSC15 Rep Cap Seq | (2227) | TCACCCTTCTCCGCTGATGGGAGGGTTTGGAATGAAGCACCCGCCTCCTCAGATCCTCATCAAAAACACACCTGT |
| HSC16 Rep Cap Seq | (2227) | TCACCCTTCTCCGCTGATGGGAGGGTTTGGAATGAAGCACCCGCCTCCTCAGATCCTCATCAAAAACACACCTGT |
| HSC17 Rep Cap Seq | (2227) | TCACCCTTCTCCGCTGATGGGAGGGTTTGGAATGAAGCACCCGCCTCCTCAGATCCTCATCAAAAACACACCTGT |
| AAV9 Capsid | (1887) | TCACCCTTCTCCGCTGATGGGAGGGTTTGGAATGAAGCACCCGCCTCCTCAGATCCTCATCAAAAACACACCTGT |
| AAV2 | (4086) | TCACCCCTCTCCCCTCATGGGTGGATTCGGACTTAAACACCCTCCTCCACAGATTCTCATCAAGAACACCCCGGT |

Figure 1 (cont.)

| | | 4201 4275 |
|---|---|---|
| HSC1 Rep Cap Seq | (2302) | ACCTGCGGATCCTCCAACGGCCTTCAACAAGGACAAGCTGAACTCTTTCATCACCCAGTATTCTACTGGCCAAGT |
| HSC2 Rep Cap Seq | (2302) | ACCTGCGGATCCTCCAACGGCCTTCAACAAGGACAAGCTGAACTCTTTCATCACCCAGTATTCTACTGGCCAAGT |
| HSC3 Rep Cap Seq | (2302) | ACCTGCGGATCCTCCAACGGCCTTCAACAAGGACAAGCTGAACTCTTTCATCACCCAGTATTCTACTGGCCAAGT |
| HSC4 Rep Cap Seq | (2302) | ACCTGCGGATCCTCCAACGGCCTTCAACAAGGACAAGCTGAACTCTTTCATCACCCAGTATTCTACTGGCCAAGT |
| HSC6 Rep Cap Seq | (2302) | ACCTGCGGATCCTCCAACGGCCTTCAACAAGGACAAGCTGAACTCTTTCATCACCCAGTATTCTACTGGCCAAGT |
| HSC5 Rep Cap Seq | (2302) | ACCTGCGGATCCTCCAACGGCCTTCAACAAGGACAAGCTGAACTCTTTCATCACCCAGTATTCTACTGGCCAAGT |
| HSC11 Rep Cap Seq | (2302) | ACCTGCGGATCCTCCAACGGCCTTCAACAAGGACAAGCTGAACTCTTTCATCACCCAGTATTCTACTGGCCAAGT |
| HSC7 Rep Cap Seq | (2302) | ACCTGCGGATCCTCCAACGGCCTTCAACAAGGACAAGCTGAACTCTTTCATCACCCAGTATTCTACTGGCCAAGT |
| HSC8 Rep Cap Seq | (2302) | ACCTGCGGATCCTCCAACGGCCTTCAACAAGGACAAGCTGAACTCTTTCATCACCCAGTATTCTACTGGCCAAGT |
| HSC9 Rep Cap Seq | (2302) | ACCTGCGGATCCTCCAACGGCCTTCAACAAGGACAAGCTGAACTCTTTCATCACCCAGTATTCTACTGGCCAAGT |
| HSC12 Rep Cap Seq | (2302) | ACCTGCGGATCCTCCAACGGCCTTCAACAAGGACAAGCTGAACTCTTTCATCACCCAGTATTCTACTGGCCAAGT |
| HSC13 Rep Cap Seq | (2302) | ACCTGCGGATCCTCCAACGGCCTTCAACAAGGACAAGCTGAACTCTTTCATCACCCAGTATTCTACTGGCCAAGT |
| HSC14 Rep Cap Seq | (2302) | ACCTGCGGATCCTCCAACGGCCTTCAACAAGGACAAGCTGAACTCTTTCATCACCCAGTATTCTACTGGCCAAGT |
| HSC15 Rep Cap Seq | (2302) | ACCTGCGGATCCTCCAACGGCCTTCAACAAGGACAAGCTGAACTCTTTCATCACCCAGTATTCTACTGGCCAAGT |
| HSC16 Rep Cap Seq | (2302) | ACCTGCGGATCCTCCAACGGCCTTCAACAAGGACAAGCTGAACTCTTTCATCACCCAGTATTCTACTGGCCAAGT |
| HSC17 Rep Cap Seq | (2302) | ACCTGCGGATCCTCCAACGGCCTTCAACAAGGACAAGCTGAACTCTTTCATCACCCAGTATTCTACTGGCCAAGT |
| AAV9 Capsid | (1962) | ACCTGCGGATCCTCCAACGGCCTTCAACAAGGACAAGCTGAACTCTTTCATCACCCAGTATTCTACTGGCCAAGT |
| AAV2 | (4161) | ACCTGCGAATCCTTCGACCACCTTCAGTGCGGCAAAGTTTGCTTCCTTCATCACACAGTACTCCACGGGACAGGT |

Figure 1 (cont.)

| | | 4276 4350 |
|---|---|---|
| HSC1 Rep Cap Seq | (2377) | CAGCGTGGAGATCGAGTGGGAGCTGCAGAAGGAAAACAGCAAGCGCTGGAACCCGGAGATCCAGTACACTTCCAA |
| HSC2 Rep Cap Seq | (2377) | CAGCGTGGAGATCGAGTGGGAGCTGCAGAAGGAAAACAGCAAGCGCTGGAACCCGGAGATCCAGTACACTTCCAA |
| HSC3 Rep Cap Seq | (2377) | CAGCGTGGAGATCGAGTGGGAGCTGCAGAAGGAAAACAGCAAGCGCTGGAACCCGGAGATCCAGTACACTTCCAA |
| HSC4 Rep Cap Seq | (2377) | CAGCGTGGAGATCGAGTGGGAGCTGCAGAAGGAAAACAGCAAGCGCTGGAACCCGGAGATCCAGTACACTTCCAA |
| HSC6 Rep Cap Seq | (2377) | CAGCGTGGAGATCGAGTGGGAGCTGCAGAAGGAAAACAGCAAGCGCTGGAACCCGGAGATCCAGTACACTTCCAA |
| HSC5 Rep Cap Seq | (2377) | CAGCGTGGAGATCGAGTGGGAGCTGCAGAAAAAAACAGCAAGCGCTGGAACCCGGAGATCCAGTACACTTCCAA |
| HSC11 Rep Cap Seq | (2377) | CAGCGTGGAGATCGAGTGGGAGCTGCAGAAGGAAAACAGCAAGCGCTGGAACCCGGAGATCCAGTACACTTCCAA |
| HSC7 Rep Cap Seq | (2377) | CAGCGTGGAGATCGAGTGGGAGCTGCAGAAGGAAAACAGCAAGCGCTGGAACCCGGAGATCCAGTACACTTCCAA |
| HSC8 Rep Cap Seq | (2377) | CAGCGTGGAGATCGAGTGGGAACTGCAGAAGGAAAACAGCAAGCGCTGGAACCCGGAGATCCAGTACACTTCCAA |
| HSC9 Rep Cap Seq | (2377) | CAGCGTGGAGATCGAGTGGGAGCTGCAGAAGGAAAACAGCAAGCGCTGGAACCCGGAGATCCAGTACACTTCCAA |
| HSC12 Rep Cap Seq | (2377) | CAGCATGGAGATCGAGTGGGAGCTGCAGAAGGAAAACAGCAAGCGCTGGAACCCGGAGATCCAGTACACTTCCAA |
| HSC13 Rep Cap Seq | (2377) | CAGCGTGGAGATCGAGTGGGAGCTGCAGAAGGAAAACAGCAAGCGCTGGAACCCGGAGATCCAGTACACTTCCAA |
| HSC14 Rep Cap Seq | (2377) | CAGCGTGGAGATCGAGTGGGAGCGGCAGAAGGAAAACAGCAAGCGCTGGAACCCGGAGATCCAGTACACTTCCAA |
| HSC15 Rep Cap Seq | (2377) | CAGCGTGGAGATCGAGTGGGAGCTGCAGAAGGAAAACAGCAAGCGCTGGAACCCGGAGATCCAGTACACTTCCAA |
| HSC16 Rep Cap Seq | (2377) | CAGCGTGGAGATCGAGTGGGAGCTGCAGAAGGAAAACAGCAAGCGCTGGAACCCGGAGATCCAGTACACTTCCAA |
| HSC17 Rep Cap Seq | (2377) | CAGCGTGGAGATCGAGTGGGAGCTGCAGAAGGAAAACAGCAAGCGCTGGAACCCGGAGATCCAGTACACTTCCAA |
| AAV9 Capsid | (2037) | CAGCGTGGAGATCGAGTGGGAGCTGCAGAAGGAAAACAGCAAGCGCTGGAACCCGGAGATCCAGTACACTTCCAA |
| AAV2 | (4236) | CAGCGTGGAGATCGAGTGGGAGCTGCAGAAGGAAAACAGCAAACGCTGGAATCCCGAAATTCAGTACACTTCCAA |

Figure 1 (cont.)

```
                            4426                                                                  4500
HSC1 Rep Cap Seq    (2527) CAGATACCTGACTCGTAATCTGTAATTGCTTGTTAATCAATAAACCGTTTAATTCGTTTCAGTTGAACTGCGGCC
HSC2 Rep Cap Seq    (2527) CAGATACCTGACTCGTAATCTGTAATTGCTTGTTAATCAATAAACCGTTTAATTCGTTTCAGTTGAACTGCGGCC
HSC3 Rep Cap Seq    (2527) CAGATACCTGACTCGTAATCTGTAATTGCTTGTTAATCAATAAACCGTTTAATTCGTTTCAGTTGAACTGCGGCC
HSC4 Rep Cap Seq    (2527) CAGATACCTGACTCGTAATCTGTAATTGCTTGTTAATCAATAAACCGTTTAATTCGTTTCAGTTGAACTGCGGCC
HSC6 Rep Cap Seq    (2527) CAGATACCTGACTCGTAATCTGTAATTGCTTGTTAATCAATAAACCGTTTAATTCGTTTCAGTTGAACTGCGGCC
HSC5 Rep Cap Seq    (2527) CAGATACCTGACTCGTAATCTGTAATTGCTTGTTAATCAATAAACCGTTTAATTCGTTTCAGTTGAACTGCGGCC
HSC11 Rep Cap Seq   (2527) CAGATACCTGACTCGTAATCTGTAATTGCTTGTTAATCAATAAACCGTTTAATTCGTTTCAGTTGAACTGCGGCC
HSC7 Rep Cap Seq    (2527) CAGATACCTGACTCGTAATCTGTAATTGCTTGTTAATCAATAAACCGTTTAATTCGTTTCAGTTGAACTGCGGCC
HSC8 Rep Cap Seq    (2527) CAGATACCTGACTCGTAATCTGTAATTGCTTGTTAATCAATAAACCGTTTAATTCGTTTCAGTTGAACTGCGGCC
HSC9 Rep Cap Seq    (2527) CAGATACCTGACTCGTAATCTGTAATTGCTTGTTAATCAATAAACCGTTTAATTCGTTTCAGTTGAACTGCGGCC
HSC12 Rep Cap Seq   (2527) CAGATACCTGACTCGTAATCTGTAATTGCTTGTTAATCAATAAACCGTTTAATTCGTTTCAGTTGAACTGCGGCC
HSC13 Rep Cap Seq   (2527) CAGATACCTGACTCGTAATCTGTAATTGCTTGTTAATCAATAAACCGTTTAATTCGTTTCAGTTGAACTGCGGCC
HSC14 Rep Cap Seq   (2527) CAGATACCTGACTCGTAATCTGTAATTGCTTGTTAATCAATAAACCGTTTAATTCGTTTCAGTTGAACTGCGGCC
HSC15 Rep Cap Seq   (2527) CAGATACCTGACTCGTAATCTGTAATTGCTTGTTAATCAATAAACCGTTTAATTCGTTTCAGTTGAACTGCGGCC
HSC16 Rep Cap Seq   (2527) CAGATACCTGACTCGTAATCTGTAATTGCTTGTTAATCAATAAACCGTTTAATTCGTTTCAGTTGAACTGCGGCC
HSC17 Rep Cap Seq   (2527) CAGATACCTGACTCGTAATCTGTAATTGCTTGTTAATCAATAAACCGTTTAATTCGTTTCAGTTGAACTGCGGCC
AAV9 Capsid         (2187) CAGATACCTGACTCGTAATCTGTAA--------------------------------------------------
AAV2                (4386) CAGATACCTGACTCGTAATCTGTAATTGCTTGTTAATCAATAAACCGTTTAATTCGTTTCAGTTGAACTTTGGTC
```

Figure 1 (cont.)

```
                              4501                                                                    4575
HSC1 Rep Cap Seq     (2602) GC-------------------------------------------------------------------------
HSC2 Rep Cap Seq     (2602) GC-------------------------------------------------------------------------
HSC3 Rep Cap Seq     (2602) GC-------------------------------------------------------------------------
HSC4 Rep Cap Seq     (2602) GC-------------------------------------------------------------------------
HSC6 Rep Cap Seq     (2602) GC-------------------------------------------------------------------------
HSC5 Rep Cap Seq     (2602) GC-------------------------------------------------------------------------
HSC11 Rep Cap Seq    (2602) GC-------------------------------------------------------------------------
HSC7 Rep Cap Seq     (2602) GC-------------------------------------------------------------------------
HSC8 Rep Cap Seq     (2602) GC-------------------------------------------------------------------------
HSC9 Rep Cap Seq     (2602) GC-------------------------------------------------------------------------
HSC12 Rep Cap Seq    (2602) GC-------------------------------------------------------------------------
HSC13 Rep Cap Seq    (2602) GC-------------------------------------------------------------------------
HSC14 Rep Cap Seq    (2602) GC-------------------------------------------------------------------------
HSC15 Rep Cap Seq    (2602) GC-------------------------------------------------------------------------
HSC16 Rep Cap Seq    (2602) GC-------------------------------------------------------------------------
HSC17 Rep Cap Seq    (2602) GC-------------------------------------------------------------------------
AAV9 Capsid          (2212) ---------------------------------------------------------------------------
AAV2                 (4461) TCTGCGTATTTCTTTCTTATCTAGTTTCCATGGCTACGTAGATAAGTAGCATGGCGGGTTAATCATTAACTACAA
```

Figure 1 (cont.)

```
                                 4576                                                                       4650
HSC1 Rep Cap Seq    (2604) ---------------------------------------------------------------------------
HSC2 Rep Cap Seq    (2604) ---------------------------------------------------------------------------
HSC3 Rep Cap Seq    (2604) ---------------------------------------------------------------------------
HSC4 Rep Cap Seq    (2604) ---------------------------------------------------------------------------
HSC6 Rep Cap Seq    (2604) ---------------------------------------------------------------------------
HSC5 Rep Cap Seq    (2604) ---------------------------------------------------------------------------
HSC11 Rep Cap Seq   (2604) ---------------------------------------------------------------------------
HSC7 Rep Cap Seq    (2604) ---------------------------------------------------------------------------
HSC8 Rep Cap Seq    (2604) ---------------------------------------------------------------------------
HSC9 Rep Cap Seq    (2604) ---------------------------------------------------------------------------
HSC12 Rep Cap Seq   (2604) ---------------------------------------------------------------------------
HSC13 Rep Cap Seq   (2604) ---------------------------------------------------------------------------
HSC14 Rep Cap Seq   (2604) ---------------------------------------------------------------------------
HSC15 Rep Cap Seq   (2604) ---------------------------------------------------------------------------
HSC16 Rep Cap Seq   (2604) ---------------------------------------------------------------------------
HSC17 Rep Cap Seq   (2604) ---------------------------------------------------------------------------
AAV9 Capsid         (2212) ---------------------------------------------------------------------------
AAV2                (4536) GGAACCCCTAGTGATGGAGTTGGCCACTCCCTCTCTGCGCGCTCGCTCGCTCACTGAGGCCGGGCGACCAAAGGT
```

Figure 1 (cont.)

```
                                4651                                                              4719
HSC1 Rep Cap Seq    (2604) ---------------------------------------------------------------------
HSC2 Rep Cap Seq    (2604) ---------------------------------------------------------------------
HSC3 Rep Cap Seq    (2604) ---------------------------------------------------------------------
HSC4 Rep Cap Seq    (2604) ---------------------------------------------------------------------
HSC6 Rep Cap Seq    (2604) ---------------------------------------------------------------------
HSC5 Rep Cap Seq    (2604) ---------------------------------------------------------------------
HSC11 Rep Cap Seq   (2604) ---------------------------------------------------------------------
HSC7 Rep Cap Seq    (2604) ---------------------------------------------------------------------
HSC8 Rep Cap Seq    (2604) ---------------------------------------------------------------------
HSC9 Rep Cap Seq    (2604) ---------------------------------------------------------------------
HSC12 Rep Cap Seq   (2604) ---------------------------------------------------------------------
HSC13 Rep Cap Seq   (2604) ---------------------------------------------------------------------
HSC14 Rep Cap Seq   (2604) ---------------------------------------------------------------------
HSC15 Rep Cap Seq   (2604) ---------------------------------------------------------------------
HSC16 Rep Cap Seq   (2604) ---------------------------------------------------------------------
HSC17 Rep Cap Seq   (2604) ---------------------------------------------------------------------
      AAV9 Capsid   (2212) ---------------------------------------------------------------------
             AAV2   (4611) CGCCCGACGCCCGGGCTTTGCCCGGGCGGCCTCAGTGAGCGAGCGAGCGCGCAGAGAGGGAGTGGCCAA
```

Figure 2

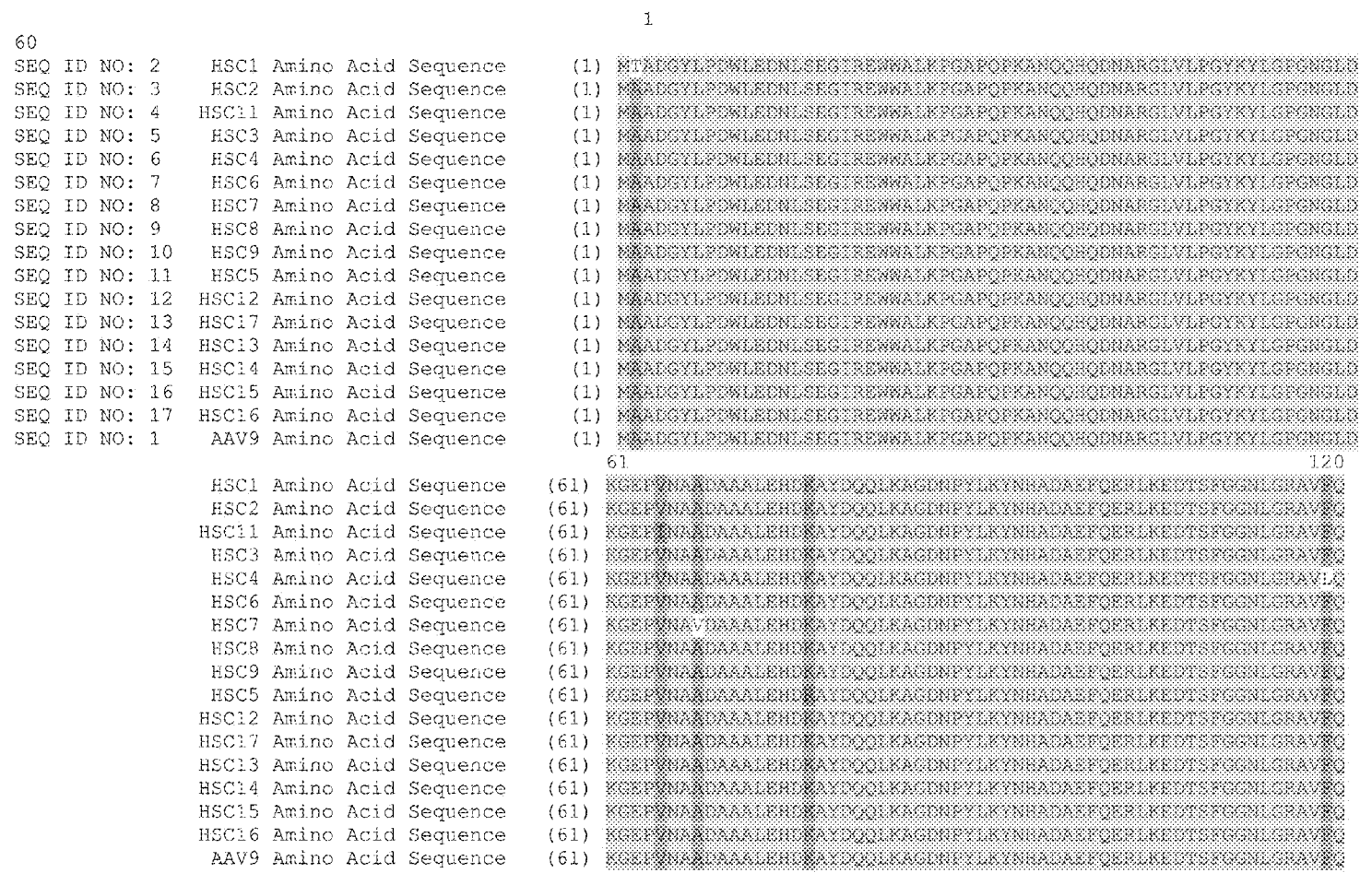

| | | | 1 … 60 |
|---|---|---|---|
| SEQ ID NO: 2 | HSC1 Amino Acid Sequence | (1) | MTADGYLPDWLEDNLSEGIREWWALKPGAPQPKANQQHQDNARGLVLPGYKYLGPGNGLD |
| SEQ ID NO: 3 | HSC2 Amino Acid Sequence | (1) | MAADGYLPDWLEDNLSEGIREWWALKPGAPQPKANQQHQDNARGLVLPGYKYLGPGNGLD |
| SEQ ID NO: 4 | HSC11 Amino Acid Sequence | (1) | MAADGYLPDWLEDNLSEGIREWWALKPGAPQPKANQQHQDNARGLVLPGYKYLGPGNGLD |
| SEQ ID NO: 5 | HSC3 Amino Acid Sequence | (1) | MAADGYLPDWLEDNLSEGIREWWALKPGAPQPKANQQHQDNARGLVLPGYKYLGPGNGLD |
| SEQ ID NO: 6 | HSC4 Amino Acid Sequence | (1) | MAADGYLPDWLEDNLSEGIREWWALKPGAPQPKANQQHQDNARGLVLPGYKYLGPGNGLD |
| SEQ ID NO: 7 | HSC6 Amino Acid Sequence | (1) | MAADGYLPDWLEDNLSEGIREWWALKPGAPQPKANQQHQDNARGLVLPGYKYLGPGNGLD |
| SEQ ID NO: 8 | HSC7 Amino Acid Sequence | (1) | MAADGYLPDWLEDNLSEGIREWWALKPGAPQPKANQQHQDNARGLVLPGYKYLGPGNGLD |
| SEQ ID NO: 9 | HSC8 Amino Acid Sequence | (1) | MAADGYLPDWLEDNLSEGIREWWALKPGAPQPKANQQHQDNARGLVLPGYKYLGPGNGLD |
| SEQ ID NO: 10 | HSC9 Amino Acid Sequence | (1) | MAADGYLPDWLEDNLSEGIREWWALKPGAPQPKANQQHQDNARGLVLPGYKYLGPGNGLD |
| SEQ ID NO: 11 | HSC5 Amino Acid Sequence | (1) | MAADGYLPDWLEDNLSEGIREWWALKPGAPQPKANQQHQDNARGLVLPGYKYLGPGNGLD |
| SEQ ID NO: 12 | HSC12 Amino Acid Sequence | (1) | MAADGYLPDWLEDNLSEGIREWWALKPGAPQPKANQQHQDNARGLVLPGYKYLGPGNGLD |
| SEQ ID NO: 13 | HSC17 Amino Acid Sequence | (1) | MAADGYLPDWLEDNLSEGIREWWALKPGAPQPKANQQHQDNARGLVLPGYKYLGPGNGLD |
| SEQ ID NO: 14 | HSC13 Amino Acid Sequence | (1) | MAADGYLPDWLEDNLSEGIREWWALKPGAPQPKANQQHQDNARGLVLPGYKYLGPGNGLD |
| SEQ ID NO: 15 | HSC14 Amino Acid Sequence | (1) | MAADGYLPDWLEDNLSEGIREWWALKPGAPQPKANQQHQDNARGLVLPGYKYLGPGNGLD |
| SEQ ID NO: 16 | HSC15 Amino Acid Sequence | (1) | MAADGYLPDWLEDNLSEGIREWWALKPGAPQPKANQQHQDNARGLVLPGYKYLGPGNGLD |
| SEQ ID NO: 17 | HSC16 Amino Acid Sequence | (1) | MAADGYLPDWLEDNLSEGIREWWALKPGAPQPKANQQHQDNARGLVLPGYKYLGPGNGLD |
| SEQ ID NO: 1 | AAV9 Amino Acid Sequence | (1) | MAADGYLPDWLEDNLSEGIREWWALKPGAPQPKANQQHQDNARGLVLPGYKYLGPGNGLD |

| | | 61 … 120 |
|---|---|---|
| HSC1 Amino Acid Sequence | (61) | KGEPVNAADAAALEHDKAYDQQLKAGDNPYLKYNHADAEFQERLKEDTSFGGNLGRAVFQ |
| HSC2 Amino Acid Sequence | (61) | KGEPVNAADAAALEHDKAYDQQLKAGDNPYLKYNHADAEFQERLKEDTSFGGNLGRAVFQ |
| HSC11 Amino Acid Sequence | (61) | KGEPVNAADAAALEHDKAYDQQLKAGDNPYLKYNHADAEFQERLKEDTSFGGNLGRAVFQ |
| HSC3 Amino Acid Sequence | (61) | KGEPVNAADAAALEHDKAYDQQLKAGDNPYLKYNHADAEFQERLKEDTSFGGNLGRAVFQ |
| HSC4 Amino Acid Sequence | (61) | KGEPVNAADAAALEHDKAYDQQLKAGDNPYLKYNHADAEFQERLKEDTSFGGNLGRAVLQ |
| HSC6 Amino Acid Sequence | (61) | KGEPVNAADAAALEHDKAYDQQLKAGDNPYLKYNHADAEFQERLKEDTSFGGNLGRAVFQ |
| HSC7 Amino Acid Sequence | (61) | KGEPVNAVDAAALEHDKAYDQQLKAGDNPYLKYNHADAEFQERLKEDTSFGGNLGRAVFQ |
| HSC8 Amino Acid Sequence | (61) | KGEPVNAADAAALEHDKAYDQQLKAGDNPYLKYNHADAEFQERLKEDTSFGGNLGRAVFQ |
| HSC9 Amino Acid Sequence | (61) | KGEPVNAADAAALEHDKAYDQQLKAGDNPYLKYNHADAEFQERLKEDTSFGGNLGRAVFQ |
| HSC5 Amino Acid Sequence | (61) | KGEPVNAADAAALEHDKAYDQQLKAGDNPYLKYNHADAEFQERLKEDTSFGGNLGRAVFQ |
| HSC12 Amino Acid Sequence | (61) | KGEPVNAADAAALEHDKAYDQQLKAGDNPYLKYNHADAEFQERLKEDTSFGGNLGRAVFQ |
| HSC17 Amino Acid Sequence | (61) | KGEPVNAADAAALEHDKAYDQQLKAGDNPYLKYNHADAEFQERLKEDTSFGGNLGRAVFQ |
| HSC13 Amino Acid Sequence | (61) | KGEPVNAADAAALEHDKAYDQQLKAGDNPYLKYNHADAEFQERLKEDTSFGGNLGRAVFQ |
| HSC14 Amino Acid Sequence | (61) | KGEPVNAADAAALEHDKAYDQQLKAGDNPYLKYNHADAEFQERLKEDTSFGGNLGRAVFQ |
| HSC15 Amino Acid Sequence | (61) | KGEPVNAADAAALEHDKAYDQQLKAGDNPYLKYNHADAEFQERLKEDTSFGGNLGRAVFQ |
| HSC16 Amino Acid Sequence | (61) | KGEPVNAADAAALEHDKAYDQQLKAGDNPYLKYNHADAEFQERLKEDTSFGGNLGRAVFQ |
| AAV9 Amino Acid Sequence | (61) | KGEPVNAADAAALEHDKAYDQQLKAGDNPYLKYNHADAEFQERLKEDTSFGGNLGRAVFQ |

Figure 2 (cont.)

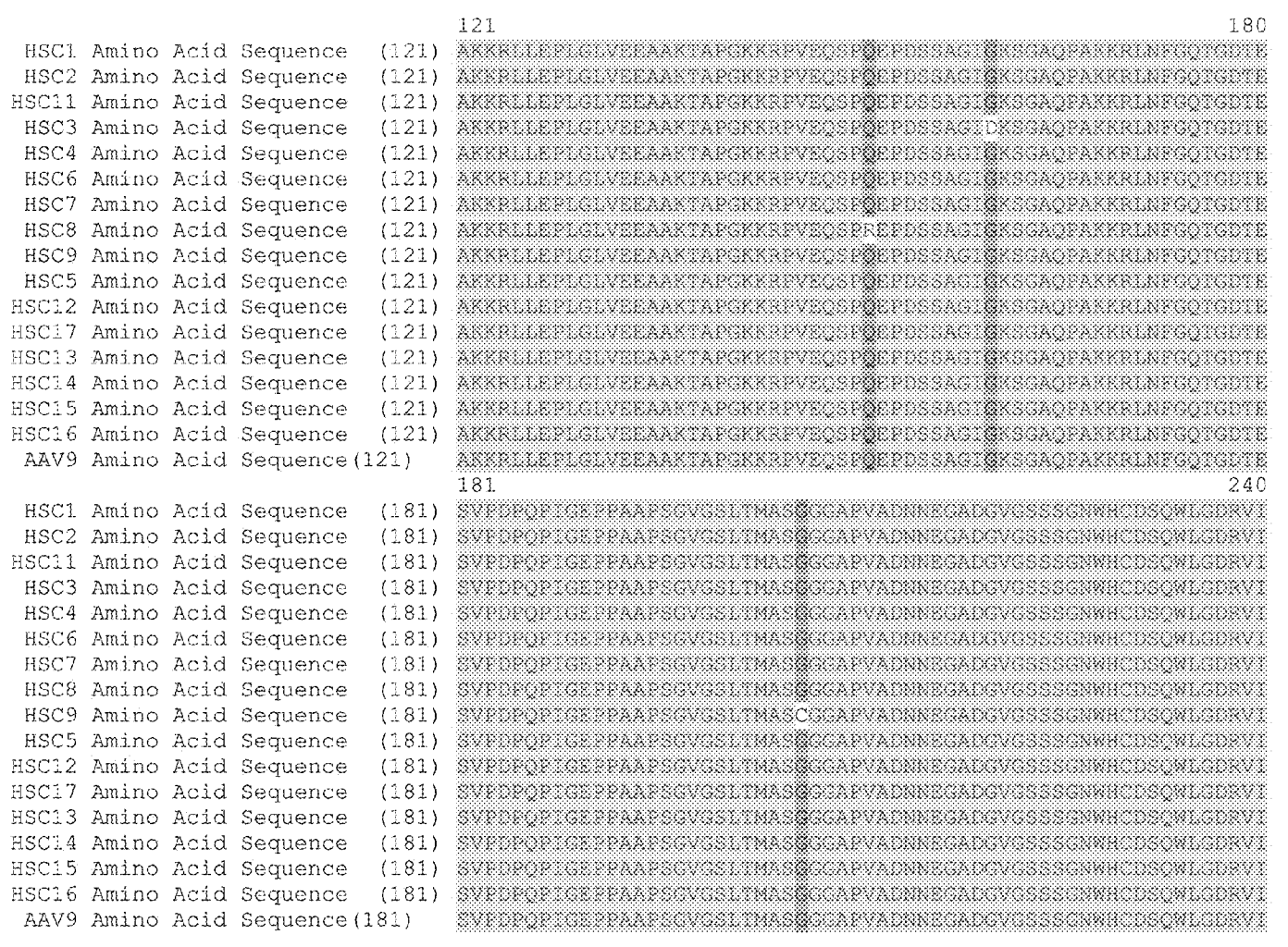

| | | 121 — 180 |
|---|---|---|
| HSC1 Amino Acid Sequence | (121) | AKKRLLEPLGLVEEAAKTAPGKKRPVEQSPQEPDSSAGIGKSGAQPAKKRLNFGQTGDTE |
| HSC2 Amino Acid Sequence | (121) | AKKRLLEPLGLVEEAAKTAPGKKRPVEQSPQEPDSSAGIGKSGAQPAKKRLNFGQTGDTE |
| HSC11 Amino Acid Sequence | (121) | AKKRLLEPLGLVEEAAKTAPGKKRPVEQSPQEPDSSAGIGKSGAQPAKKRLNFGQTGDTE |
| HSC3 Amino Acid Sequence | (121) | AKKRLLEPLGLVEEAAKTAPGKKRPVEQSPQEPDSSAGIDKSGAQPAKKRLNFGQTGDTE |
| HSC4 Amino Acid Sequence | (121) | AKKRLLEPLGLVEEAAKTAPGKKRPVEQSPQEPDSSAGIGKSGAQPAKKRLNFGQTGDTE |
| HSC6 Amino Acid Sequence | (121) | AKKRLLEPLGLVEEAAKTAPGKKRPVEQSPQEPDSSAGIGKSGAQPAKKRLNFGQTGDTE |
| HSC7 Amino Acid Sequence | (121) | AKKRLLEPLGLVEEAAKTAPGKKRPVEQSPQEPDSSAGIGKSGAQPAKKRLNFGQTGDTE |
| HSC8 Amino Acid Sequence | (121) | AKKRLLEPLGLVEEAAKTAPGKKRPVEQSPREPDSSAGIGKSGAQPAKKRLNFGQTGDTE |
| HSC9 Amino Acid Sequence | (121) | AKKRLLEPLGLVEEAAKTAPGKKRPVEQSPQEPDSSAGIGKSGAQPAKKRLNFGQTGDTE |
| HSC5 Amino Acid Sequence | (121) | AKKRLLEPLGLVEEAAKTAPGKKRPVEQSPQEPDSSAGIGKSGAQPAKKRLNFGQTGDTE |
| HSC12 Amino Acid Sequence | (121) | AKKRLLEPLGLVEEAAKTAPGKKRPVEQSPQEPDSSAGIGKSGAQPAKKRLNFGQTGDTE |
| HSC17 Amino Acid Sequence | (121) | AKKRLLEPLGLVEEAAKTAPGKKRPVEQSPQEPDSSAGIGKSGAQPAKKRLNFGQTGDTE |
| HSC13 Amino Acid Sequence | (121) | AKKRLLEPLGLVEEAAKTAPGKKRPVEQSPQEPDSSAGIGKSGAQPAKKRLNFGQTGDTE |
| HSC14 Amino Acid Sequence | (121) | AKKRLLEPLGLVEEAAKTAPGKKRPVEQSPQEPDSSAGIGKSGAQPAKKRLNFGQTGDTE |
| HSC15 Amino Acid Sequence | (121) | AKKRLLEPLGLVEEAAKTAPGKKRPVEQSPQEPDSSAGIGKSGAQPAKKRLNFGQTGDTE |
| HSC16 Amino Acid Sequence | (121) | AKKRLLEPLGLVEEAAKTAPGKKRPVEQSPQEPDSSAGIGKSGAQPAKKRLNFGQTGDTE |
| AAV9 Amino Acid Sequence | (121) | AKKRLLEPLGLVEEAAKTAPGKKRPVEQSPQEPDSSAGIGKSGAQPAKKRLNFGQTGDTE |

| | | 181 — 240 |
|---|---|---|
| HSC1 Amino Acid Sequence | (181) | SVPDPQPIGEPPAAPSGVGSLTMASGGGAPVADNNEGADGVGSSSGNWHCDSQWLGDRVI |
| HSC2 Amino Acid Sequence | (181) | SVPDPQPIGEPPAAPSGVGSLTMASGGGAPVADNNEGADGVGSSSGNWHCDSQWLGDRVI |
| HSC11 Amino Acid Sequence | (181) | SVPDPQPIGEPPAAPSGVGSLTMASGGGAPVADNNEGADGVGSSSGNWHCDSQWLGDRVI |
| HSC3 Amino Acid Sequence | (181) | SVPDPQPIGEPPAAPSGVGSLTMASGGGAPVADNNEGADGVGSSSGNWHCDSQWLGDRVI |
| HSC4 Amino Acid Sequence | (181) | SVPDPQPIGEPPAAPSGVGSLTMASGGGAPVADNNEGADGVGSSSGNWHCDSQWLGDRVI |
| HSC6 Amino Acid Sequence | (181) | SVPDPQPIGEPPAAPSGVGSLTMASGGGAPVADNNEGADGVGSSSGNWHCDSQWLGDRVI |
| HSC7 Amino Acid Sequence | (181) | SVPDPQPIGEPPAAPSGVGSLTMASGGGAPVADNNEGADGVGSSSGNWHCDSQWLGDRVI |
| HSC8 Amino Acid Sequence | (181) | SVPDPQPIGEPPAAPSGVGSLTMASGGGAPVADNNEGADGVGSSSGNWHCDSQWLGDRVI |
| HSC9 Amino Acid Sequence | (181) | SVPDPQPIGEPPAAPSGVGSLTMASCGGAPVADNNEGADGVGSSSGNWHCDSQWLGDRVI |
| HSC5 Amino Acid Sequence | (181) | SVPDPQPIGEPPAAPSGVGSLTMASGGGAPVADNNEGADGVGSSSGNWHCDSQWLGDRVI |
| HSC12 Amino Acid Sequence | (181) | SVPDPQPIGEPPAAPSGVGSLTMASGGGAPVADNNEGADGVGSSSGNWHCDSQWLGDRVI |
| HSC17 Amino Acid Sequence | (181) | SVPDPQPIGEPPAAPSGVGSLTMASGGGAPVADNNEGADGVGSSSGNWHCDSQWLGDRVI |
| HSC13 Amino Acid Sequence | (181) | SVPDPQPIGEPPAAPSGVGSLTMASGGGAPVADNNEGADGVGSSSGNWHCDSQWLGDRVI |
| HSC14 Amino Acid Sequence | (181) | SVPDPQPIGEPPAAPSGVGSLTMASGGGAPVADNNEGADGVGSSSGNWHCDSQWLGDRVI |
| HSC15 Amino Acid Sequence | (181) | SVPDPQPIGEPPAAPSGVGSLTMASGGGAPVADNNEGADGVGSSSGNWHCDSQWLGDRVI |
| HSC16 Amino Acid Sequence | (181) | SVPDPQPIGEPPAAPSGVGSLTMASGGGAPVADNNEGADGVGSSSGNWHCDSQWLGDRVI |
| AAV9 Amino Acid Sequence | (181) | SVPDPQPIGEPPAAPSGVGSLTMASGGGAPVADNNEGADGVGSSSGNWHCDSQWLGDRVI |

Figure 2 (cont.)

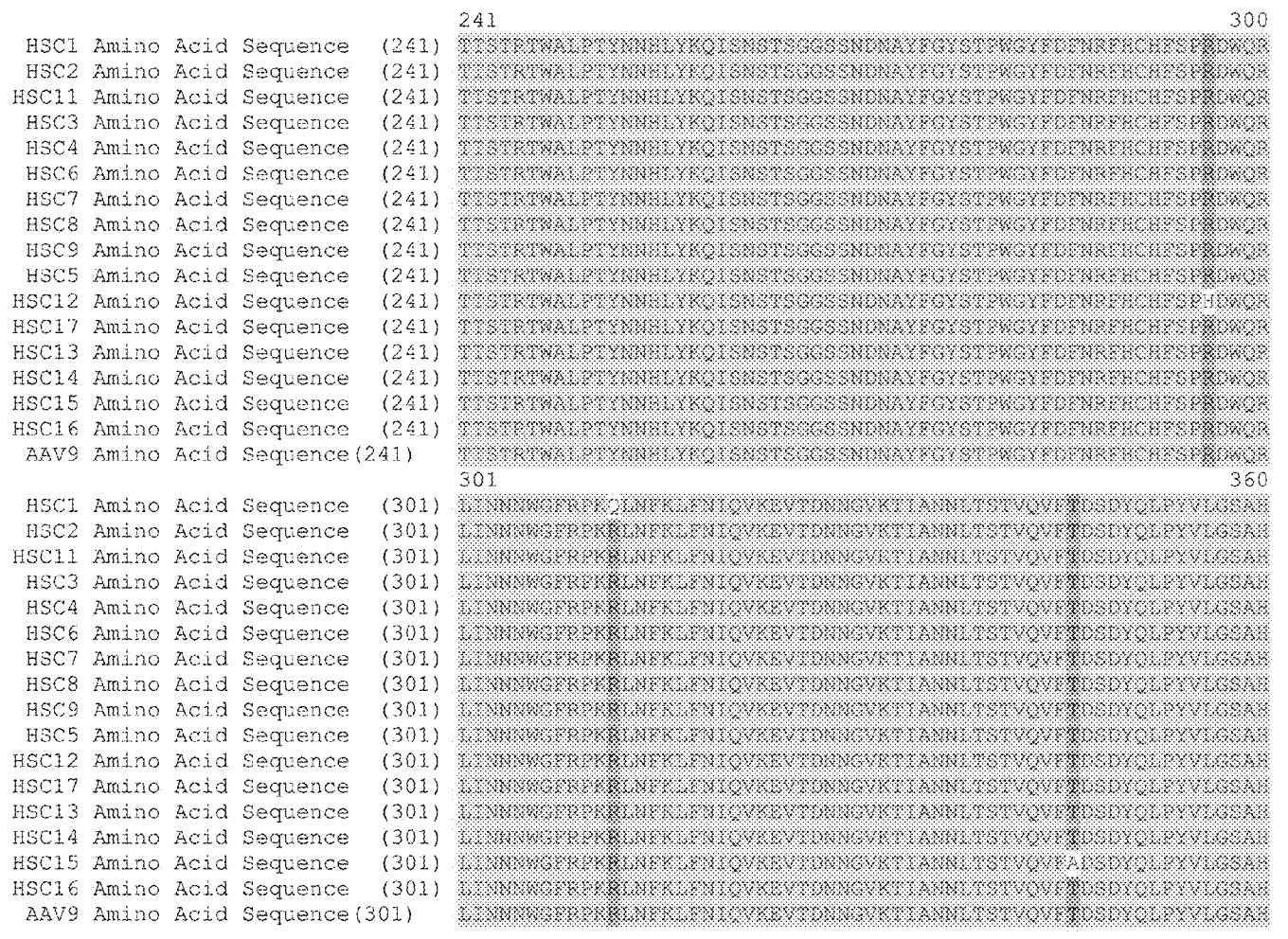

| | | 241 300 |
|---|---|---|
| HSC1 Amino Acid Sequence | (241) | TISTRTWALPTYNNHLYKQISNSTSGGSSNDNAYFGYSTPWGYFDFNRFHCHFSPRDWQR |
| HSC2 Amino Acid Sequence | (241) | TISTRTWALPTYNNHLYKQISNSTSGGSSNDNAYFGYSTPWGYFDFNRFHCHFSPRDWQR |
| HSC11 Amino Acid Sequence | (241) | TISTRTWALPTYNNHLYKQISNSTSGGSSNDNAYFGYSTPWGYFDFNRFHCHFSPRDWQR |
| HSC3 Amino Acid Sequence | (241) | TISTRTWALPTYNNHLYKQISNSTSGGSSNDNAYFGYSTPWGYFDFNRFHCHFSPRDWQR |
| HSC4 Amino Acid Sequence | (241) | TISTRTWALPTYNNHLYKQISNSTSGGSSNDNAYFGYSTPWGYFDFNRFHCHFSPRDWQR |
| HSC6 Amino Acid Sequence | (241) | TISTRTWALPTYNNHLYKQISNSTSGGSSNDNAYFGYSTPWGYFDFNRFHCHFSPRDWQR |
| HSC7 Amino Acid Sequence | (241) | TISTRTWALPTYNNHLYKQISNSTSGGSSNDNAYFGYSTPWGYFDFNRFHCHFSPRDWQR |
| HSC8 Amino Acid Sequence | (241) | TISTRTWALPTYNNHLYKQISNSTSGGSSNDNAYFGYSTPWGYFDFNRFHCHFSPRDWQR |
| HSC9 Amino Acid Sequence | (241) | TISTRTWALPTYNNHLYKQISNSTSGGSSNDNAYFGYSTPWGYFDFNRFHCHFSPRDWQR |
| HSC5 Amino Acid Sequence | (241) | TISTRTWALPTYNNHLYKQISNSTSGGSSNDNAYFGYSTPWGYFDFNRFHCHFSPRDWQR |
| HSC12 Amino Acid Sequence | (241) | TISTRTWALPTYNNHLYKQISNSTSGGSSNDNAYFGYSTPWGYFDFNRFHCHFSPHDWQR |
| HSC17 Amino Acid Sequence | (241) | TISTRTWALPTYNNHLYKQISNSTSGGSSNDNAYFGYSTPWGYFDFNRFHCHFSPRDWQR |
| HSC13 Amino Acid Sequence | (241) | TISTRTWALPTYNNHLYKQISNSTSGGSSNDNAYFGYSTPWGYFDFNRFHCHFSPRDWQR |
| HSC14 Amino Acid Sequence | (241) | TISTRTWALPTYNNHLYKQISNSTSGGSSNDNAYFGYSTPWGYFDFNRFHCHFSPRDWQR |
| HSC15 Amino Acid Sequence | (241) | TISTRTWALPTYNNHLYKQISNSTSGGSSNDNAYFGYSTPWGYFDFNRFHCHFSPRDWQR |
| HSC16 Amino Acid Sequence | (241) | TISTRTWALPTYNNHLYKQISNSTSGGSSNDNAYFGYSTPWGYFDFNRFHCHFSPRDWQR |
| AAV9 Amino Acid Sequence | (241) | TISTRTWALPTYNNHLYKQISNSTSGGSSNDNAYFGYSTPWGYFDFNRFHCHFSPRDWQR |

| | | 301 360 |
|---|---|---|
| HSC1 Amino Acid Sequence | (301) | LINNNWGFRPKQLNFKLFNIQVKEVTDNNGVKTIANNLTSTVQVFTDSDYQLPYVLGSAH |
| HSC2 Amino Acid Sequence | (301) | LINNNWGFRPKRLNFKLFNIQVKEVTDNNGVKTIANNLTSTVQVFTDSDYQLPYVLGSAH |
| HSC11 Amino Acid Sequence | (301) | LINNNWGFRPKRLNFKLFNIQVKEVTDNNGVKTIANNLTSTVQVFTDSDYQLPYVLGSAH |
| HSC3 Amino Acid Sequence | (301) | LINNNWGFRPKRLNFKLFNIQVKEVTDNNGVKTIANNLTSTVQVFTDSDYQLPYVLGSAH |
| HSC4 Amino Acid Sequence | (301) | LINNNWGFRPKRLNFKLFNIQVKEVTDNNGVKTIANNLTSTVQVFTDSDYQLPYVLGSAH |
| HSC6 Amino Acid Sequence | (301) | LINNNWGFRPKRLNFKLFNIQVKEVTDNNGVKTIANNLTSTVQVFTDSDYQLPYVLGSAH |
| HSC7 Amino Acid Sequence | (301) | LINNNWGFRPKRLNFKLFNIQVKEVTDNNGVKTIANNLTSTVQVFTDSDYQLPYVLGSAH |
| HSC8 Amino Acid Sequence | (301) | LINNNWGFRPKRLNFKLFNIQVKEVTDNNGVKTIANNLTSTVQVFTDSDYQLPYVLGSAH |
| HSC9 Amino Acid Sequence | (301) | LINNNWGFRPKRLNFKLFNIQVKEVTDNNGVKTIANNLTSTVQVFTDSDYQLPYVLGSAH |
| HSC5 Amino Acid Sequence | (301) | LINNNWGFRPKRLNFKLFNIQVKEVTDNNGVKTIANNLTSTVQVFTDSDYQLPYVLGSAH |
| HSC12 Amino Acid Sequence | (301) | LINNNWGFRPKRLNFKLFNIQVKEVTDNNGVKTIANNLTSTVQVFTDSDYQLPYVLGSAH |
| HSC17 Amino Acid Sequence | (301) | LINNNWGFRPKRLNFKLFNIQVKEVTDNNGVKTIANNLTSTVQVFTDSDYQLPYVLGSAH |
| HSC13 Amino Acid Sequence | (301) | LINNNWGFRPKRLNFKLFNIQVKEVTDNNGVKTIANNLTSTVQVFTDSDYQLPYVLGSAH |
| HSC14 Amino Acid Sequence | (301) | LINNNWGFRPKRLNFKLFNIQVKEVTDNNGVKTIANNLTSTVQVFTDSDYQLPYVLGSAH |
| HSC15 Amino Acid Sequence | (301) | LINNNWGFRPKRLNFKLFNIQVKEVTDNNGVKTIANNLTSTVQVFADSDYQLPYVLGSAH |
| HSC16 Amino Acid Sequence | (301) | LINNNWGFRPKRLNFKLFNIQVKEVTDNNGVKTIANNLTSTVQVFTDSDYQLPYVLGSAH |
| AAV9 Amino Acid Sequence | (301) | LINNNWGFRPKRLNFKLFNIQVKEVTDNNGVKTIANNLTSTVQVFTDSDYQLPYVLGSAH |

Figure 2 (cont.)

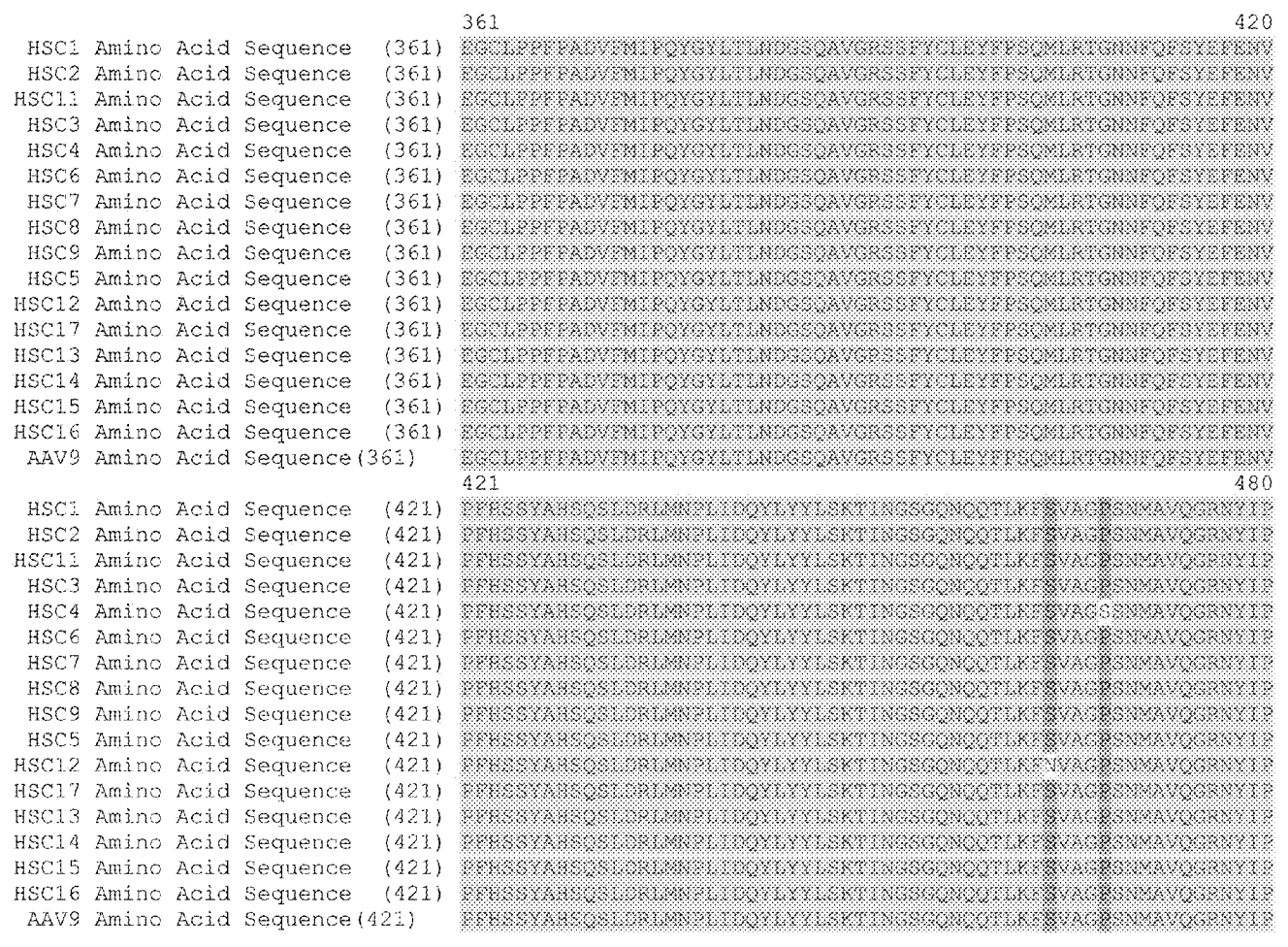

```
                                    361                                                        420
HSC1 Amino Acid Sequence   (361)  EGCLPPFPADVFMIPQYGYLTLNDGSQAVGRSSFYCLEYFPSQMLRTGNNFQFSYEFENV
HSC2 Amino Acid Sequence   (361)  EGCLPPFPADVFMIPQYGYLTLNDGSQAVGRSSFYCLEYFPSQMLRTGNNFQFSYEFENV
HSC11 Amino Acid Sequence  (361)  EGCLPPFPADVFMIPQYGYLTLNDGSQAVGRSSFYCLEYFPSQMLRTGNNFQFSYEFENV
HSC3 Amino Acid Sequence   (361)  EGCLPPFPADVFMIPQYGYLTLNDGSQAVGRSSFYCLEYFPSQMLRTGNNFQFSYEFENV
HSC4 Amino Acid Sequence   (361)  EGCLPPFPADVFMIPQYGYLTLNDGSQAVGRSSFYCLEYFPSQMLRTGNNFQFSYEFENV
HSC6 Amino Acid Sequence   (361)  EGCLPPFPADVFMIPQYGYLTLNDGSQAVGRSSFYCLEYFPSQMLRTGNNFQFSYEFENV
HSC7 Amino Acid Sequence   (361)  EGCLPPFPADVFMIPQYGYLTLNDGSQAVGRSSFYCLEYFPSQMLRTGNNFQFSYEFENV
HSC8 Amino Acid Sequence   (361)  EGCLPPFPADVFMIPQYGYLTLNDGSQAVGRSSFYCLEYFPSQMLRTGNNFQFSYEFENV
HSC9 Amino Acid Sequence   (361)  EGCLPPFPADVFMIPQYGYLTLNDGSQAVGRSSFYCLEYFPSQMLRTGNNFQFSYEFENV
HSC5 Amino Acid Sequence   (361)  EGCLPPFPADVFMIPQYGYLTLNDGSQAVGRSSFYCLEYFPSQMLRTGNNFQFSYEFENV
HSC12 Amino Acid Sequence  (361)  EGCLPPFPADVFMIPQYGYLTLNDGSQAVGRSSFYCLEYFPSQMLRTGNNFQFSYEFENV
HSC17 Amino Acid Sequence  (361)  EGCLPPFPADVFMIPQYGYLTLNDGSQAVGRSSFYCLEYFPSQMLRTGNNFQFSYEFENV
HSC13 Amino Acid Sequence  (361)  EGCLPPFPADVFMIPQYGYLTLNDGSQAVGRSSFYCLEYFPSQMLRTGNNFQFSYEFENV
HSC14 Amino Acid Sequence  (361)  EGCLPPFPADVFMIPQYGYLTLNDGSQAVGRSSFYCLEYFPSQMLRTGNNFQFSYEFENV
HSC15 Amino Acid Sequence  (361)  EGCLPPFPADVFMIPQYGYLTLNDGSQAVGRSSFYCLEYFPSQMLRTGNNFQFSYEFENV
HSC16 Amino Acid Sequence  (361)  EGCLPPFPADVFMIPQYGYLTLNDGSQAVGRSSFYCLEYFPSQMLRTGNNFQFSYEFENV
AAV9 Amino Acid Sequence(361)     EGCLPPFPADVFMIPQYGYLTLNDGSQAVGRSSFYCLEYFPSQMLRTGNNFQFSYEFENV
                                    421                                                        480
HSC1 Amino Acid Sequence   (421)  PFHSSYAHSQSLDRLMNPLIDQYLYYLSKTINGSGQNQQTLKFSVAGPSNMAVQGRNYIP
HSC2 Amino Acid Sequence   (421)  PFHSSYAHSQSLDRLMNPLIDQYLYYLSKTINGSGQNQQTLKFSVAGPSNMAVQGRNYIP
HSC11 Amino Acid Sequence  (421)  PFHSSYAHSQSLDRLMNPLIDQYLYYLSKTINGSGQNQQTLKFSVAGPSNMAVQGRNYIP
HSC3 Amino Acid Sequence   (421)  PFHSSYAHSQSLDRLMNPLIDQYLYYLSKTINGSGQNQQTLKFSVAGPSNMAVQGRNYIP
HSC4 Amino Acid Sequence   (421)  PFHSSYAHSQSLDRLMNPLIDQYLYYLSKTINGSGQNQQTLKFSVAGSSNMAVQGRNYIP
HSC6 Amino Acid Sequence   (421)  PFHSSYAHSQSLDRLMNPLIDQYLYYLSKTINGSGQNQQTLKFSVAGPSNMAVQGRNYIP
HSC7 Amino Acid Sequence   (421)  PFHSSYAHSQSLDRLMNPLIDQYLYYLSKTINGSGQNQQTLKFSVAGPSNMAVQGRNYIP
HSC8 Amino Acid Sequence   (421)  PFHSSYAHSQSLDRLMNPLIDQYLYYLSKTINGSGQNQQTLKFSVAGPSNMAVQGRNYIP
HSC9 Amino Acid Sequence   (421)  PFHSSYAHSQSLDRLMNPLIDQYLYYLSKTINGSGQNQQTLKFSVAGPSNMAVQGRNYIP
HSC5 Amino Acid Sequence   (421)  PFHSSYAHSQSLDRLMNPLIDQYLYYLSKTINGSGQNQQTLKFSVAGPSNMAVQGRNYIP
HSC12 Amino Acid Sequence  (421)  PFHSSYAHSQSLDRLMNPLIDQYLYYLSKTINGSGQNQQTLKFNVAGPSNMAVQGRNYIP
HSC17 Amino Acid Sequence  (421)  PFHSSYAHSQSLDRLMNPLIDQYLYYLSKTINGSGQNQQTLKFSVAGPSNMAVQGRNYIP
HSC13 Amino Acid Sequence  (421)  PFHSSYAHSQSLDRLMNPLIDQYLYYLSKTINGSGQNQQTLKFSVAGPSNMAVQGRNYIP
HSC14 Amino Acid Sequence  (421)  PFHSSYAHSQSLDRLMNPLIDQYLYYLSKTINGSGQNQQTLKFSVAGPSNMAVQGRNYIP
HSC15 Amino Acid Sequence  (421)  PFHSSYAHSQSLDRLMNPLIDQYLYYLSKTINGSGQNQQTLKFSVAGPSNMAVQGRNYIP
HSC16 Amino Acid Sequence  (421)  PFHSSYAHSQSLDRLMNPLIDQYLYYLSKTINGSGQNQQTLKFSVAGPSNMAVQGRNYIP
AAV9 Amino Acid Sequence(421)     PFHSSYAHSQSLDRLMNPLIDQYLYYLSKTINGSGQNQQTLKFSVAGPSNMAVQGRNYIP
```

Figure 2 (cont.)

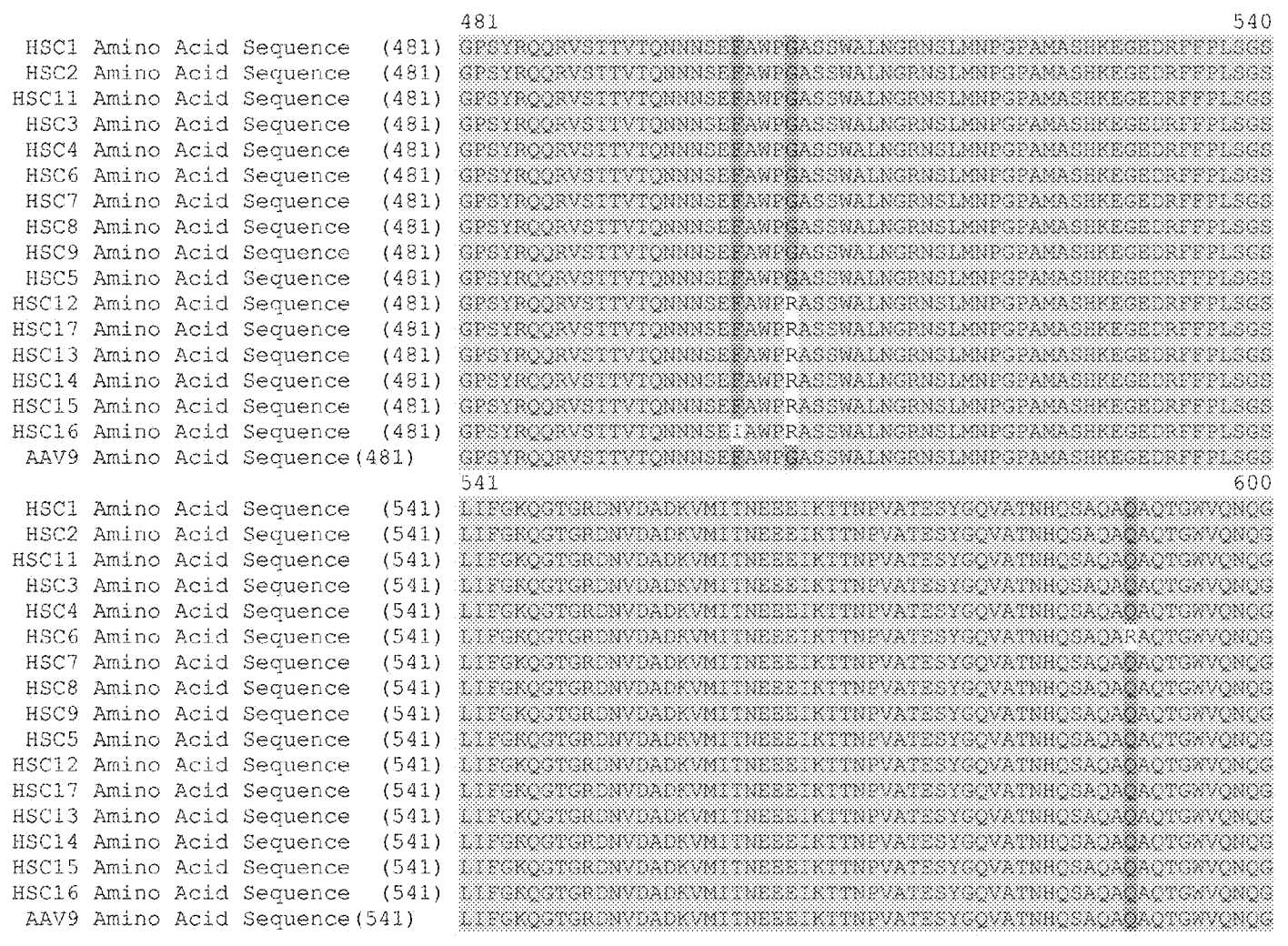

| | | |
|---|---|---|
| | | 481 540 |
| HSC1 Amino Acid Sequence | (481) | GPSYRQQRVSTTVTQNNNSEFAWPGASSWALNGRNSLMNPGPAMASHKEGEDRFFPLSGS |
| HSC2 Amino Acid Sequence | (481) | GPSYRQQRVSTTVTQNNNSEFAWPGASSWALNGRNSLMNPGPAMASHKEGEDRFFPLSGS |
| HSC11 Amino Acid Sequence | (481) | GPSYRQQRVSTTVTQNNNSEFAWPGASSWALNGRNSLMNPGPAMASHKEGEDRFFPLSGS |
| HSC3 Amino Acid Sequence | (481) | GPSYRQQRVSTTVTQNNNSEFAWPGASSWALNGRNSLMNPGPAMASHKEGEDRFFPLSGS |
| HSC4 Amino Acid Sequence | (481) | GPSYRQQRVSTTVTQNNNSEFAWPGASSWALNGRNSLMNPGPAMASHKEGEDRFFPLSGS |
| HSC6 Amino Acid Sequence | (481) | GPSYRQQRVSTTVTQNNNSEFAWPGASSWALNGRNSLMNPGPAMASHKEGEDRFFPLSGS |
| HSC7 Amino Acid Sequence | (481) | GPSYRQQRVSTTVTQNNNSEFAWPGASSWALNGRNSLMNPGPAMASHKEGEDRFFPLSGS |
| HSC8 Amino Acid Sequence | (481) | GPSYRQQRVSTTVTQNNNSEFAWPGASSWALNGRNSLMNPGPAMASHKEGEDRFFPLSGS |
| HSC9 Amino Acid Sequence | (481) | GPSYRQQRVSTTVTQNNNSEFAWPGASSWALNGRNSLMNPGPAMASHKEGEDRFFPLSGS |
| HSC5 Amino Acid Sequence | (481) | GPSYRQQRVSTTVTQNNNSEFAWPGASSWALNGRNSLMNPGPAMASHKEGEDRFFPLSGS |
| HSC12 Amino Acid Sequence | (481) | GPSYRQQRVSTTVTQNNNSEFAWPRASSWALNGRNSLMNPGPAMASHKEGEDRFFPLSGS |
| HSC17 Amino Acid Sequence | (481) | GPSYRQQRVSTTVTQNNNSEFAWPRASSWALNGRNSLMNPGPAMASHKEGEDRFFPLSGS |
| HSC13 Amino Acid Sequence | (481) | GPSYRQQRVSTTVTQNNNSEFAWPRASSWALNGRNSLMNPGPAMASHKEGEDRFFPLSGS |
| HSC14 Amino Acid Sequence | (481) | GPSYRQQRVSTTVTQNNNSEFAWPRASSWALNGRNSLMNPGPAMASHKEGEDRFFPLSGS |
| HSC15 Amino Acid Sequence | (481) | GPSYRQQRVSTTVTQNNNSEFAWPRASSWALNGRNSLMNPGPAMASHKEGEDRFFPLSGS |
| HSC16 Amino Acid Sequence | (481) | GPSYRQQRVSTTVTQNNNSEIAWPRASSWALNGRNSLMNPGPAMASHKEGEDRFFPLSGS |
| AAV9 Amino Acid Sequence | (481) | GPSYRQQRVSTTVTQNNNSEFAWPGASSWALNGRNSLMNPGPAMASHKEGEDRFFPLSGS |
| | | 541 600 |
| HSC1 Amino Acid Sequence | (541) | LIFGKQGTGRDNVDADKVMITNEEEIKTTNPVATESYGQVATNHQSAQAQAQTGWVQNQG |
| HSC2 Amino Acid Sequence | (541) | LIFGKQGTGRDNVDADKVMITNEEEIKTTNPVATESYGQVATNHQSAQAQAQTGWVQNQG |
| HSC11 Amino Acid Sequence | (541) | LIFGKQGTGRDNVDADKVMITNEEEIKTTNPVATESYGQVATNHQSAQAQAQTGWVQNQG |
| HSC3 Amino Acid Sequence | (541) | LIFGKQGTGRDNVDADKVMITNEEEIKTTNPVATESYGQVATNHQSAQAQAQTGWVQNQG |
| HSC4 Amino Acid Sequence | (541) | LIFGKQGTGRDNVDADKVMITNEEEIKTTNPVATESYGQVATNHQSAQAQAQTGWVQNQG |
| HSC6 Amino Acid Sequence | (541) | LIFGKQGTGRDNVDADKVMITNEEEIKTTNPVATESYGQVATNHQSAQARAQTGWVQNQG |
| HSC7 Amino Acid Sequence | (541) | LIFGKQGTGRDNVDADKVMITNEEEIKTTNPVATESYGQVATNHQSAQAQAQTGWVQNQG |
| HSC8 Amino Acid Sequence | (541) | LIFGKQGTGRDNVDADKVMITNEEEIKTTNPVATESYGQVATNHQSAQAQAQTGWVQNQG |
| HSC9 Amino Acid Sequence | (541) | LIFGKQGTGRDNVDADKVMITNEEEIKTTNPVATESYGQVATNHQSAQAQAQTGWVQNQG |
| HSC5 Amino Acid Sequence | (541) | LIFGKQGTGRDNVDADKVMITNEEEIKTTNPVATESYGQVATNHQSAQAQAQTGWVQNQG |
| HSC12 Amino Acid Sequence | (541) | LIFGKQGTGRDNVDADKVMITNEEEIKTTNPVATESYGQVATNHQSAQAQAQTGWVQNQG |
| HSC17 Amino Acid Sequence | (541) | LIFGKQGTGRDNVDADKVMITNEEEIKTTNPVATESYGQVATNHQSAQAQAQTGWVQNQG |
| HSC13 Amino Acid Sequence | (541) | LIFGKQGTGRDNVDADKVMITNEEEIKTTNPVATESYGQVATNHQSAQAQAQTGWVQNQG |
| HSC14 Amino Acid Sequence | (541) | LIFGKQGTGRDNVDADKVMITNEEEIKTTNPVATESYGQVATNHQSAQAQAQTGWVQNQG |
| HSC15 Amino Acid Sequence | (541) | LIFGKQGTGRDNVDADKVMITNEEEIKTTNPVATESYGQVATNHQSAQAQAQTGWVQNQG |
| HSC16 Amino Acid Sequence | (541) | LIFGKQGTGRDNVDADKVMITNEEEIKTTNPVATESYGQVATNHQSAQAQAQTGWVQNQG |
| AAV9 Amino Acid Sequence | (541) | LIFGKQGTGRDNVDADKVMITNEEEIKTTNPVATESYGQVATNHQSAQAQAQTGWVQNQG |

Figure 2 (cont.)

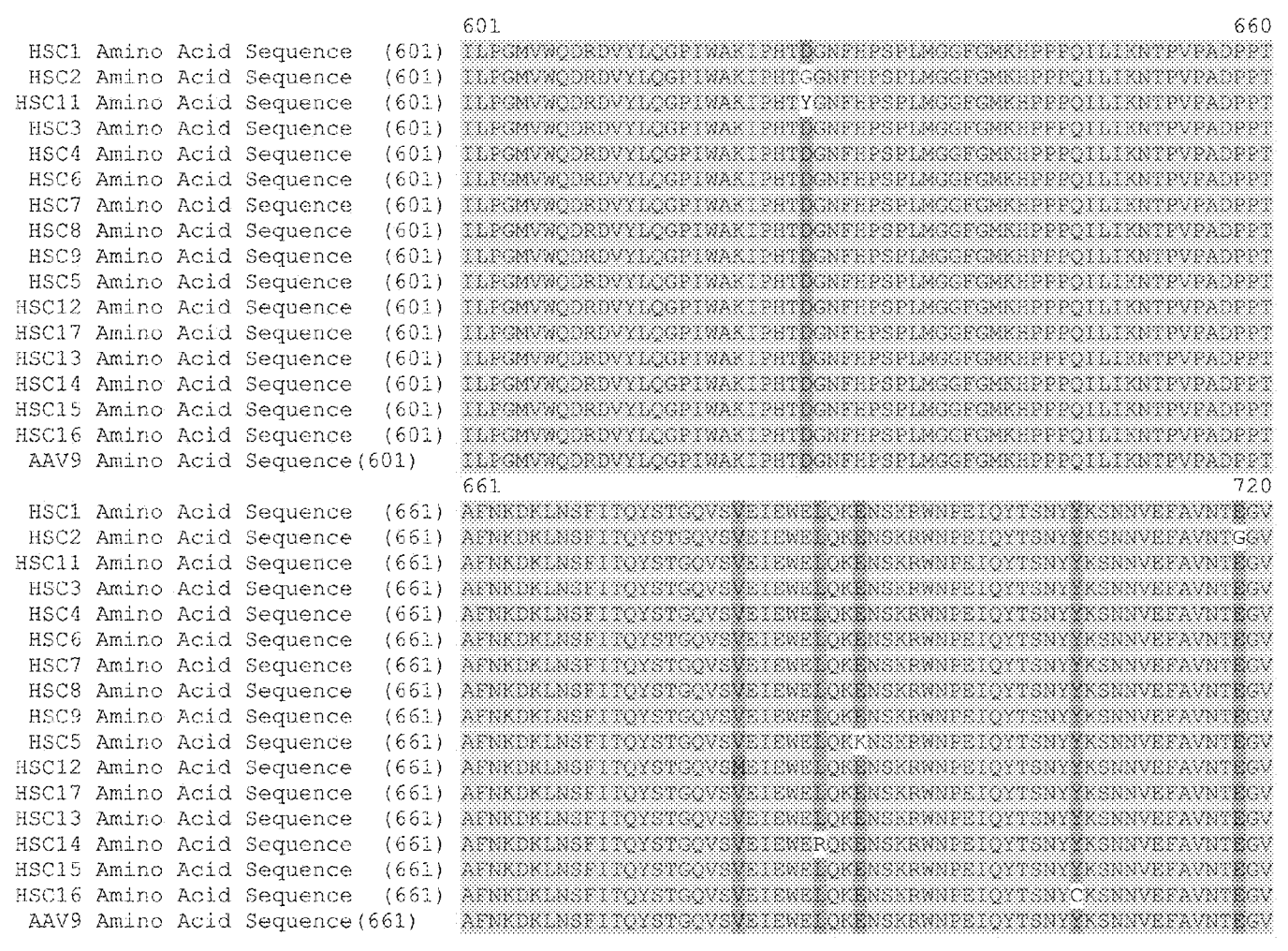

| | 601 | 660 |
|---|---|---|
| HSC1 Amino Acid Sequence (601) | ILPGMVWQDRDVYLQGPIWAKIPHTDGNFHPSPLMGGFGMKHPPPQILIKNTPVPADPPT | |
| HSC2 Amino Acid Sequence (601) | ILPGMVWQDRDVYLQGPIWAKIPHTGGNFHPSPLMGGFGMKHPPPQILIKNTPVPADPPT | |
| HSC11 Amino Acid Sequence (601) | ILPGMVWQDRDVYLQGPIWAKIPHTYGNFHPSPLMGGFGMKHPPPQILIKNTPVPADPPT | |
| HSC3 Amino Acid Sequence (601) | ILPGMVWQDRDVYLQGPIWAKIPHTDGNFHPSPLMGGFGMKHPPPQILIKNTPVPADPPT | |
| HSC4 Amino Acid Sequence (601) | ILPGMVWQDRDVYLQGPIWAKIPHTDGNFHPSPLMGGFGMKHPPPQILIKNTPVPADPPT | |
| HSC6 Amino Acid Sequence (601) | ILPGMVWQDRDVYLQGPIWAKIPHTDGNFHPSPLMGGFGMKHPPPQILIKNTPVPADPPT | |
| HSC7 Amino Acid Sequence (601) | ILPGMVWQDRDVYLQGPIWAKIPHTDGNFHPSPLMGGFGMKHPPPQILIKNTPVPADPPT | |
| HSC8 Amino Acid Sequence (601) | ILPGMVWQDRDVYLQGPIWAKIPHTDGNFHPSPLMGGFGMKHPPPQILIKNTPVPADPPT | |
| HSC9 Amino Acid Sequence (601) | ILPGMVWQDRDVYLQGPIWAKIPHTDGNFHPSPLMGGFGMKHPPPQILIKNTPVPADPPT | |
| HSC5 Amino Acid Sequence (601) | ILPGMVWQDRDVYLQGPIWAKIPHTDGNFHPSPLMGGFGMKHPPPQILIKNTPVPADPPT | |
| HSC12 Amino Acid Sequence (601) | ILPGMVWQDRDVYLQGPIWAKIPHTDGNFHPSPLMGGFGMKHPPPQILIKNTPVPADPPT | |
| HSC17 Amino Acid Sequence (601) | ILPGMVWQDRDVYLQGPIWAKIPHTDGNFHPSPLMGGFGMKHPPPQILIKNTPVPADPPT | |
| HSC13 Amino Acid Sequence (601) | ILPGMVWQDRDVYLQGPIWAKIPHTDGNFHPSPLMGGFGMKHPPPQILIKNTPVPADPPT | |
| HSC14 Amino Acid Sequence (601) | ILPGMVWQDRDVYLQGPIWAKIPHTDGNFHPSPLMGGFGMKHPPPQILIKNTPVPADPPT | |
| HSC15 Amino Acid Sequence (601) | ILPGMVWQDRDVYLQGPIWAKIPHTDGNFHPSPLMGGFGMKHPPPQILIKNTPVPADPPT | |
| HSC16 Amino Acid Sequence (601) | ILPGMVWQDRDVYLQGPIWAKIPHTDGNFHPSPLMGGFGMKHPPPQILIKNTPVPADPPT | |
| AAV9 Amino Acid Sequence (601) | ILPGMVWQDRDVYLQGPIWAKIPHTDGNFHPSPLMGGFGMKHPPPQILIKNTPVPADPPT | |

| | 661 | 720 |
|---|---|---|
| HSC1 Amino Acid Sequence (661) | AFNKDKLNSFITQYSTGQVSVEIEWELQKENSKRWNPEIQYTSNYYKSNNVEFAVNTEGV | |
| HSC2 Amino Acid Sequence (661) | AFNKDKLNSFITQYSTGQVSVEIEWELQKENSKRWNPEIQYTSNYYKSNNVEFAVNTGGV | |
| HSC11 Amino Acid Sequence (661) | AFNKDKLNSFITQYSTGQVSVEIEWELQKENSKRWNPEIQYTSNYYKSNNVEFAVNTEGV | |
| HSC3 Amino Acid Sequence (661) | AFNKDKLNSFITQYSTGQVSVEIEWELQKENSKRWNPEIQYTSNYYKSNNVEFAVNTEGV | |
| HSC4 Amino Acid Sequence (661) | AFNKDKLNSFITQYSTGQVSVEIEWELQKENSKRWNPEIQYTSNYYKSNNVEFAVNTEGV | |
| HSC6 Amino Acid Sequence (661) | AFNKDKLNSFITQYSTGQVSVEIEWELQKENSKRWNPEIQYTSNYYKSNNVEFAVNTEGV | |
| HSC7 Amino Acid Sequence (661) | AFNKDKLNSFITQYSTGQVSVEIEWELQKENSKRWNPEIQYTSNYYKSNNVEFAVNTEGV | |
| HSC8 Amino Acid Sequence (661) | AFNKDKLNSFITQYSTGQVSVEIEWELQKENSKRWNPEIQYTSNYYKSNNVEFAVNTEGV | |
| HSC9 Amino Acid Sequence (661) | AFNKDKLNSFITQYSTGQVSVEIEWELQKENSKRWNPEIQYTSNYYKSNNVEFAVNTEGV | |
| HSC5 Amino Acid Sequence (661) | AFNKDKLNSFITQYSTGQVSVEIEWELQKKNSKRWNPEIQYTSNYYKSNNVEFAVNTEGV | |
| HSC12 Amino Acid Sequence (661) | AFNKDKLNSFITQYSTGQVSVEIEWELQKENSKRWNPEIQYTSNYYKSNNVEFAVNTEGV | |
| HSC17 Amino Acid Sequence (661) | AFNKDKLNSFITQYSTGQVSVEIEWELQKENSKRWNPEIQYTSNYYKSNNVEFAVNTEGV | |
| HSC13 Amino Acid Sequence (661) | AFNKDKLNSFITQYSTGQVSVEIEWELQKENSKRWNPEIQYTSNYYKSNNVEFAVNTEGV | |
| HSC14 Amino Acid Sequence (661) | AFNKDKLNSFITQYSTGQVSVEIEWERQKENSKRWNPEIQYTSNYYKSNNVEFAVNTEGV | |
| HSC15 Amino Acid Sequence (661) | AFNKDKLNSFITQYSTGQVSVEIEWELQKENSKRWNPEIQYTSNYYKSNNVEFAVNTEGV | |
| HSC16 Amino Acid Sequence (661) | AFNKDKLNSFITQYSTGQVSVEIEWELQKENSKRWNPEIQYTSNYCKSNNVEFAVNTEGV | |
| AAV9 Amino Acid Sequence (661) | AFNKDKLNSFITQYSTGQVSVEIEWELQKENSKRWNPEIQYTSNYYKSNNVEFAVNTEGV | |

Figure 2 (cont.)

| | | 721 736 |
|---|---|---|
| HSC1 Amino Acid Sequence | (721) | YSEPRPIGTRYLTRNL |
| HSC2 Amino Acid Sequence | (721) | YSEPRPIGTRYLTRNL |
| HSC11 Amino Acid Sequence | (721) | YSEPRPIGTRYLTRNL |
| HSC3 Amino Acid Sequence | (721) | YSEPRPIGTRYLTRNL |
| HSC4 Amino Acid Sequence | (721) | YSEPRPIGTRYLTRNL |
| HSC6 Amino Acid Sequence | (721) | YSEPRPIGTRYLTRNL |
| HSC7 Amino Acid Sequence | (721) | YSEPRPIGTRYLTRNL |
| HSC8 Amino Acid Sequence | (721) | YSEPRPIGTRYLTRNL |
| HSC9 Amino Acid Sequence | (721) | YSEPRPIGTRYLTRNL |
| HSC5 Amino Acid Sequence | (721) | YSEPRPIGTRYLTRNL |
| HSC12 Amino Acid Sequence | (721) | YSEPRPIGTRYLTRNL |
| HSC17 Amino Acid Sequence | (721) | YSEPRPIGTRYLTRNL |
| HSC13 Amino Acid Sequence | (721) | YSEPRPIGTRYLTRNL |
| HSC14 Amino Acid Sequence | (721) | YSEPRPIGTRYLTRNL |
| HSC15 Amino Acid Sequence | (721) | YSEPRPIGTRYLTRNL |
| HSC16 Amino Acid Sequence | (721) | YSEPRPIGTRYLTRNL |
| AAV9 Amino Acid Sequence | (721) | YSEPRPIGTRYLTRNL |

Figure 3

| Capsid | Base Change | AAV 9 hu. Isolate Amino Acid | Clone New Amino Acid | Difference in Amino Acids | Placement of Amino Acid (HVR = Hypervariable Region) |
|---|---|---|---|---|---|
| HSC1 SEQ ID NO: 2 | G to A | GCT - Alanine | ACT - Threonine | Alanine is nonpolar & neutral; Threonine is polar & neutral | 4 bases into capsid; 2nd amino acid; Not in HVR, VP1 |
| HSC1 SEQ ID NO: 2 | G to A | CGA - Arginine | CAA - Glutamine | Arginine is polar & strongly basic; Glutamine is polar & neutral | 935 bases into the capsid; 312th amino acid; Not in HVR, VP3 |
| HSC2 SEQ ID NO: 3 | A to G | GGA - Glycine | GGG - Glycine | No Amino Acid Difference | 1515 bases into the capsid; 505th amino acid; 1st amino acid after HVR 7, VP3 |
| HSC2 SEQ ID NO: 3 | A to G | GAC- Aspartic Acid | GGC - Glycine | Aspartic Acid is polar & acidic; Glycine is nonpolar & neutral | 1877 bases into the capsid; 626th amino acid; Not in HVR, VP3 |
| HSC2 SEQ ID NO: 3 | A to G | GAA - Glutamic Acid | GGA - Glycine | Glutamic Acid is polar & acidic; Glycine is nonpolar & neutral | 2153 bases into the capsid; 718th amino acid; In HVR 12 last amino acid, VP3 |
| HSC3 SEQ ID NO: 5 | G to A | GGC - Glycine | GAC - Aspartic Acid | Glycine is nonpolar & neutral; Aspartic Acid is polar and acidic | 479 bases into the capsid; 160th amino acid; Not in HVR, VP1 |
| HSC3 SEQ ID NO: 5 | A to G | TCA - Serine | TCG - Serine | No Amino Acid Difference | 1044 bases into the capsid, 348th amino acid; Not in HVR VP3 |
| HSC4 SEQ ID NO: 6 | T to C | TTC - Phenylalanine | CTC - Leucine | Phenylalanine is nonpolar & neutral; Leucine is nonpolar & neutral | 355 bases into the capsid, 119th amino acid; Not in HVR; VP1 |
| HSC4 SEQ ID NO: 6 | C to T | CCC - Proline | TCC - Serine | Proline is nonpolar & neutral; Serine is polar & neutral | 1402 bases into the capsid; 468th amino acid; In HVR 5, VP3 |
| HSC4 SEQ ID NO: 6 | G to A | CCG - Proline | CCA - Proline | No Amino Acid Difference | 1809 bases into the capsid; 603rd amino acid; Not in HVR, VP3 |

Figure 3 (cont.)

| Capsid | Base Change | AAV 9 hu. Isolate Amino Acid | Clone New Amino Acid | Difference in Amino Acids | Placement of Amino Acid (HVR = Hypervariable Region) |
|---|---|---|---|---|---|
| HSC6 SEQ ID NO: 8 | A to G | CAG - Glutamine | CGG - Arginine | Glutamine is polar & neutral; Arginine is polar & strongly basic | 1769 bases into the capsid; 590th amino acid; In HVR 10; VP3 |
| HSC5 SEQ ID NO: 11 | A to G | AAG - Lysine | AGG - Arginine | Lysine is polar & basic; Arginine is polar & strongly basic | 230 bases into the capsid; 77th amino acid; Not in HVR, VP1 |
| HSC5 SEQ ID NO: 11 | C to T | CCC - Proline | CCT - Proline | No Amino Acid Difference | 1404 bases into the capsid; 468th amino acid; In HVR 5, VP3 |
| HSC5 SEQ ID NO: 11 | G to A | GAA - Glutamic Acid | AAA - Lysine | Glutamic Acid is polar & acidic; Lysine is polar & basic | 2068 bases into the capsid; 690th amino acid; Not in HVR, VP3 |
| HSC5 SEQ ID NO: 11 | T to C | AAT - Asparagine | AAC - Asparagine | No Amino Acid Difference | 2148 bases into the capsid; 716th amino acid; In HVR 13, VP3 |
| HSC11 SEQ ID NO: 5 | G to A | GTC - Valine | ATC - Isoleucine | Isoleucine is nonpolar & neutral; valine is nonpolar & neutral | 193 bases into the capsid; 65th amino acid; Not in HVR; VP1 |
| HSC11 SEQ ID NO: 4 | G to T | GAC- Aspartic Acid | TAC - Tyrosine | Aspartic Acid is polar & acidic; Tyrosine is polar & neutral | 1876 bases into the capsid; 626th amino acid; Not in HVR; VP3 |
| HSC7 SEQ ID NO: 8 | C to T | GCA - Alanine | GTA - Valine | Alanine is nonpolar & neutral; Valine is nonpolar & neutral | 203 bases into the capsid; 68th amino acid; Not in HVR; VP1 |
| HSC7 SEQ ID NO: 8 | C to T | TTC - Phenylalanine | TTT - Phenylalanine | No Amino Acid Difference | 924 bases into the capsid; 308th amino acid; Not in HVR; VP3 |
| HSC8 SEQ ID NO: 9 | A to G | CAG - Glutamine | CGG - Arginine | Glutamine is polar & neutral; Arginine is polar & strongly basic | 452 bases into the capsid; 151th amino acid; In HVR 1; VP1 |

Figure 3 (cont.)

| Capsid | Base Change | AAV 9 hu. Isolate Amino Acid | Clone New Amino Acid | Difference in Amino Acids | Placement of Amino Acid (HVR = Hypervariable Region) |
|---|---|---|---|---|---|
| HSC8 SEQ ID NO: 9 | G to A | GAG - Glutamine Acid | GAA - Glutamine Acid | No Amino Acid Difference | 2058 bases into the capsid; 686th amino acid; Not in HVR; VP3 |
| HSC9 SEQ ID NO: 10 | T to C | TTT - Phenylalanine | TTC - Phenylalanine | No Amino Acid Difference | 357 bases into the capsid; 119th amino acid; Not in HVR; VP1 |
| HSC9 SEQ ID NO: 10 | T to G | TGT - Cysteine | GGT - Glycine | Cysteine is polar & neutral; Glycine is nonpolar & neutral | 616 bases into the capsid; 206th amino acid; Not in HVR; Very beginning of VP3 |
| HSC12 SEQ ID NO: 12 | A to T | GCA - Alanine | GCT - Alanine | No Amino Acid Difference | 579 bases into capsid; 193rd amino acid into capsid, in the end of VP2 near HVR 2 |
| HSC12 SEQ ID NO: 12 | G to A | CGT - Arginine | CAT - Histidine | Arginine is polar and strongly basic; Histidine is polar and weakly basic | 887 bases into capsid; 296th amino acid into capsid; in VP3, not in HVR |
| HSC12 SEQ ID NO: 12 | G to A | AGT - Serine | AAT - Asparagine | Serine is polar and neutral; Asparagine is polar and neutral | 1391 bases into capsid; 464th amino acid into capsid; in VP3 in HVR 5 |
| HSC12 SEQ ID NO: 12 | T to C | GCT - Alanine | GCC - Alanine | No Amino Acid Difference | 1506 bases into capsid; 502nd amino acid into capsid; in VP3 in HVR 7 |
| HSC12 SEQ ID NO: 12 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |
| HSC12 SEQ ID NO: 12 | G to A | GTG - Valine | ATG - Methionine | Valine is nonpolar and neutral; Methionine is nonpolar and neutral | 2041 bases into capsid; 681st amino acid into capsid; in VP3; not in HVR |
| HSC13 SEQ ID NO: 14 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |

Figure 3 (cont.)

| Capsid | Base Change | AAV 9 hu. Isolate Amino Acid | Clone New Amino Acid | Difference in Amino Acids | Placement of Amino Acid (HVR = Hypervariable Region) |
|---|---|---|---|---|---|
| HSC14 SEQ ID NO: 15 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |
| HSC14 SEQ ID NO: 15 | T to G | CTG - Leucine | CGG - Arginine | Leucine is nonpolar and neutral; Arginine is polar and strongly basic | 2060 bases into capsid; 687th amino acid into capsid; in VP3; Not in HVR. |
| HSC15 SEQ ID NO: 16 | A to G | ACG - Threonine | GCG - Alanine | Threonine is polar and neutral; Arginine is polar and strongly basic | 1036 bases into capsid; 346th amino acid into the capsid; In VP3; Not in HVR |
| HSC15 SEQ ID NO: 16 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |
| HSC16 SEQ ID NO: 17 | T to A | TTT - Phenylalanine | ATT - Isoleucine | Phenylalanine is nonpolar and neutral; Isoleucine is nonpolar and neutral | 1501 bases into capsid; 501st amino acid into capsid; In VP3, In HVR7 |
| HSC16 SEQ ID NO: 17 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |
| HSC16 SEQ ID NO: 17 | G to A | CCG - Proline | CCA - Proline | No Amino Acid Difference | 1713 bases into capsid; 571st amino acid into capsid; In VP3 Not in HVR |
| HSC16 SEQ ID NO: 17 | A to G | TAC - Tyrosine | TGC - Cysteine | Tyrosine is polar and neutral; Cysteine is polar and neutral | 2117 bases into capsid; 706th amino acid into capsid; In VP3; In HVR 12 and is next to a YF mutation |
| HSC17 SEQ ID NO: 13 | C to T | GAC - Aspartic Acid | GAT - Aspartic Acid | No Amino Acid Difference | 180 bases into the capsid; 60th amino acid into capsid; In VP1; Not in HVR |
| HSC17 SEQ ID NO: 13 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |

Figure 4

Novel Stem Cell AAV Capsids

| Amino Acids Alterations in Stem Cell AAV Capsids Relative to AAV9 | | |
|---|---|---|
| Capsid | Novel Amino Acid | |
| | VP1 | VP3 |
| HSC1 | A2T | R312Q |
| HSC4 | F119L | P468S |
| HSC5 | K77R | E690K |
| HSC7 | A68V | |
| HSC12 | | R296H, S464N, G505R, V681M |
| HSC13 | | G505R |
| HSC15 | | T346R, G505R |
| HSC16 | | F501I, G505R, Y706C |
| HSC17 | | G505R |

NOTE: Chart shows only amino acid alterations in Cap genes

HSC1 HSC4 HSC5 HSC12

HSC13 HSC15 HSC16 HSC17

Figure 14
A
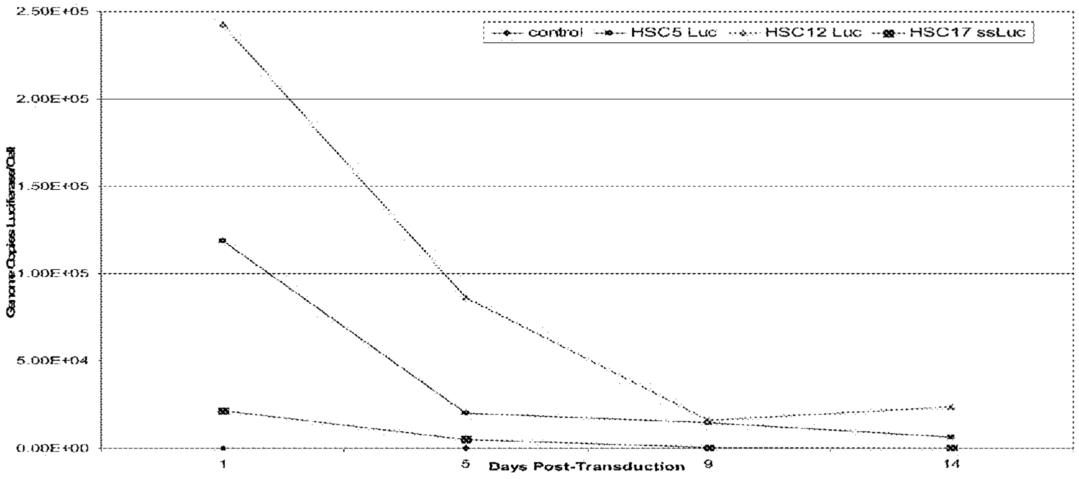
B
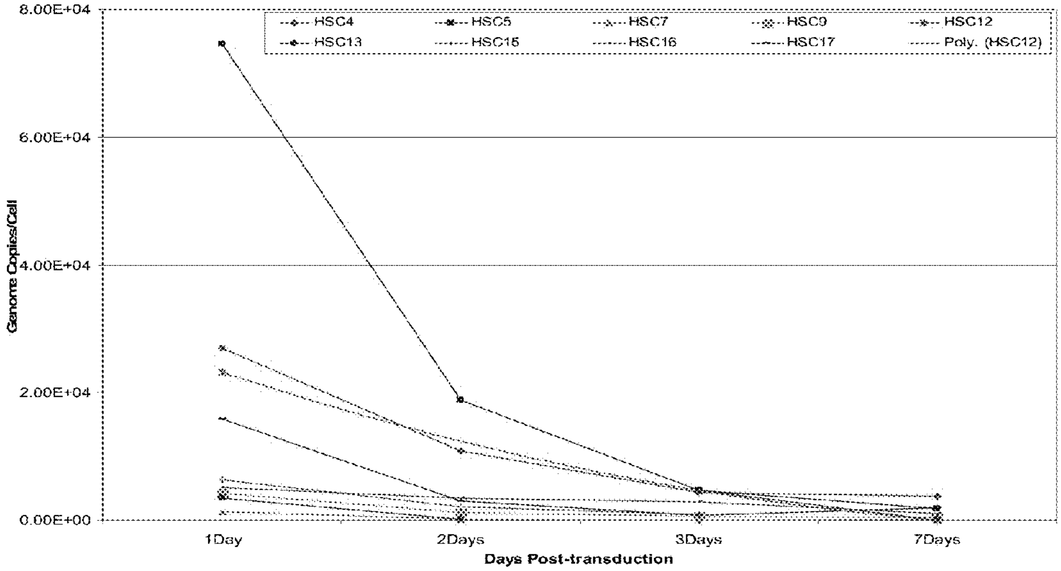

Figure 21

Transduction in Organs Harvested from Mice Injected with $10^{11}$ rAAV-Luc vg

- High Expression:
  - Liver – All isolates, especially HSC15
  - Cartilage/Joints – HSC13, HSC15, HSC17
- Moderate Expression:
  - Heart – HSC13, HSC15, HSC17
  - Lymph Nodes – HSC1, HSC15

Figure 22

Biodistribution of AAV HSCs at 8 Weeks

| | AAV HSC1 | AAV HSC4 | AAV HSC7 | AAV HSC13 | AAV HSC15 | AAV HSC17 | AAV8 | AAV9 |
|---|---|---|---|---|---|---|---|---|
| Heart | ++ | - | - | +++ | ++ | ++ | ++ | + |
| Kidney | ++ | - | - | ++ | ++ | + | + | - |
| Liver | ++ | ++ | ++ | +++ | ++++ | +++ | ++ | + |
| Lung | - | - | - | +++ | + | + | - | - |
| Lymph | + | - | - | + | +++ | + | - | - |
| Muscle | - | + | - | + | + | + | ++ | + |
| Spleen | + | + | - | + | + | + | - | - |
| Testes | - | + | + | + | + | + | - | - |
| Xiphoid | - | + | - | + | ++ | ++ | + | - |

* Based on Taqman Real Time PCR Analysis of Luc and mApoB

Figure 23
A.
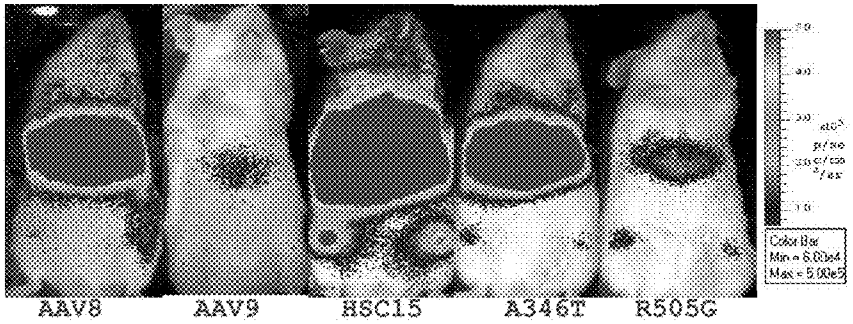
B.
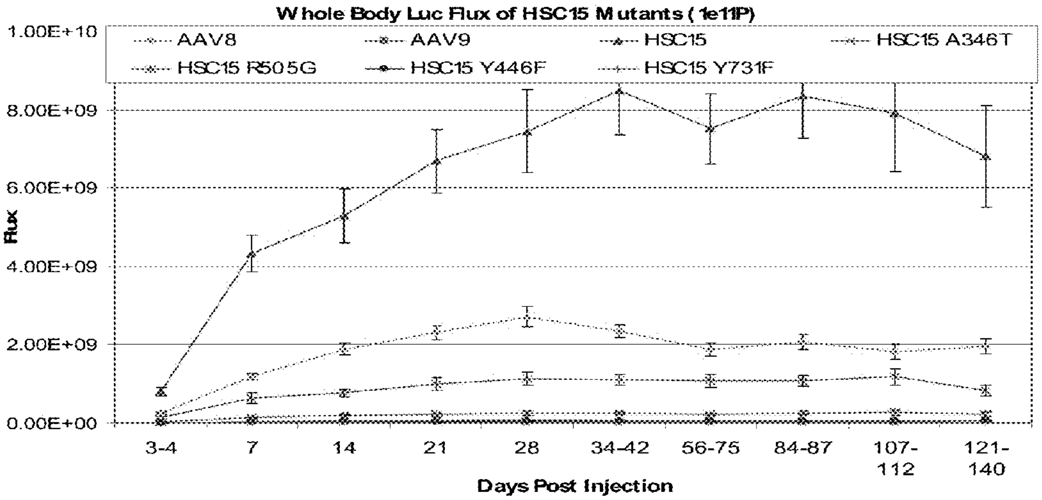

NOD/SCID mice 3-5 days post intravenous injection

Figure 29 rAAV Genome Copies/1000 Cells in the Brain

| Sample | 16 hours | 40 hours | 88 hours | 160 hours |
|---|---|---|---|---|
| AAV9 | 5.06 | 2.12 | 1.37 | 0.23 |
| HSC15 | 83.07 | 11.61 | 6.61 | 10.12 |
| HSC15 A346T | 1.84 | 2.84 | 2.14 | 9.29 |
| HSC15 R505G | 37.72 | 11.43 | 2.78 | 0.31 |

HSC15

Figure 33

Vector Genome Copies in Brains of Mice Injected Systemically with 1E11 Particles of ssrAAV-luc Vector 56 Days Post Injection

| | Vector Copies Per 1E5 Cells |
|---|---|
| AAV8 | 0.08 |
| AAV9 | 0.26 |
| HSC15 | 5.96 |
| HSC15 T346A | 1.37 |
| HSC15 R505G | 1.06 |

Figure 47

Frequency of rAAV Genome Copies in Tissues Harvested from Mice Injected Intra-Muscularly with rAAV

| Sample | Vector Copies Per 1E5 cells |
|---|---|
| HSC15 Liver | 11.63 |
| HSC15 A346T Liver | 3.43 |
| HSC15 R505G Liver | 1.06 |
| AAV9 Liver | 0.74 |
| AAV8 Liver | 0.82 |
| HSC15 Muscle | 8644.44 |
| HSC15 A346T Muscle | 3914.32 |
| HSC15 R505G Muscle | 378.14 |
| AAV9 Muscle | 105.30 |
| AAV8 Muscle | 1.16 |

Figure 52 rAAV Genome Copies in Liver and Muscle of IM Mice with and without IVIG Pretreatment

| Average per 1E5 Cells | Frequency of rAAV Genomes in Liver | Frequency of rAAV Genomes in Muscle |
|---|---|---|
| HSC15 | 11.63 | 864.4 |
| HSC15 + IVIG | 0.01 | 38.2 |
| HSC15 A346T | 3.43 | 391.4 |
| HSC15 A346T + IVIG | 0.00 | 11.2 |
| HSC15 R505G | 1.06 | 37.8 |
| HSC15 R505G + IVIG | 0.03 | 1.4 |
| AAV9 | 0.74 | 10.5 |
| AAV9 + IVIG | 0.25 | 0 |
| AAV8 | 0.82 | 0.1 |
| AAV8 + IVIG | 0.01 | 0 |

Figure 53

Neutralization Titer of AAVHSCs Using Pooled Human IVIG

| Vector | Reciprocal of Nab Titer* |
|---|---|
| HSC1 | 256 |
| HSC4 | 256 |
| HSC7 | 256 |
| HSC9 | 256 |
| HSC13 | 64 |
| HSC15 | 64 |
| HSC16 | 128 |
| HSC17 | 128 |
| AAV8 | 256 |
| AAV9 | 256 |

Figure 54

Frequency of rAAV Genomes per 1000 Cells

| | CD19<br>B Cells | CD33<br>Myeloid cells | CD34<br>Stem/progenitor Cells | GLYCOA<br>Erythroid cells |
|---|---|---|---|---|
| HSC1 | 0.8 | 0 | 0.8 | 4.6 |
| HSC4 | 0.8 | 0.075 | 1.5 | 6.3 |
| HSC5 | 6.7 | 1.4 | 7 | 0 |
| HSC7 | 0.2 | 6 | 0.37 | 10.4 |
| HSC12 | 2.8 | 7.4 | 7.5 | 191.4 |
| HSC13 | 0.2 | 2.2 | 8.7 | 1 |
| HSC15 | 0.2 | 2.8 | 1.1 | 35.9 |
| HSC16 | 0.5 | 0.4 | 0.6 | 7.7 |
| HSC17 | 0.3 | 0.2 | 0.03 | 0.1 |
| AAV9 | 0.8 | 0.2 | 16.3 | 6.1 |

SEQUENCE LISTING

```
<160> NUMBER OF SEQ ID NOS: 67

<210> SEQ ID NO 1
<211> LENGTH: 736
<212> TYPE: PRT
<213> ORGANISM: Artificial Sequence
<220> FEATURE:
<223> OTHER INFORMATION: adeno-associated AAV9

<400> SEQUENCE: 1

Met Ala Ala Asp Gly Tyr Leu Pro Asp Trp Leu Glu Asp Asn Leu Ser
1               5                   10                  15
```

-continued

```
Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430
```

```
Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 2
<211> LENGTH: 736
<212> TYPE: PRT
<213> ORGANISM: Artificial Sequence
<220> FEATURE:
<223> OTHER INFORMATION: novel AAV isolate

<400> SEQUENCE: 2

Met Thr Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60
```

-continued

```
Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Gln Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
```

-continued

```
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

```
<210> SEQ ID NO 3
<211> LENGTH: 736
<212> TYPE: PRT
<213> ORGANISM: Artificial Sequence
<220> FEATURE:
<223> OTHER INFORMATION: novel AAV isolate

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
```

-continued

```
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540
```

Lys Gln Gly Thr Gly Arg Asp Asn Val Asp Ala Asp Lys Val Met Ile
545 550 555 560

Thr Asn Glu Glu Glu Ile Lys Thr Thr Asn Pro Val Ala Thr Glu Ser
565 570 575

Tyr Gly Gln Val Ala Thr Asn His Gln Ser Ala Gln Ala Gln Ala Gln
580 585 590

Thr Gly Trp Val Gln Asn Gln Gly Ile Leu Pro Gly Met Val Trp Gln
595 600 605

Asp Arg Asp Val Tyr Leu Gln Gly Pro Ile Trp Ala Lys Ile Pro His
610 615 620

Thr Gly Gly Asn Phe His Pro Ser Pro Leu Met Gly Gly Phe Gly Met
625 630 635 640

Lys His Pro Pro Pro Gln Ile Leu Ile Lys Asn Thr Pro Val Pro Ala
645 650 655

Asp Pro Pro Thr Ala Phe Asn Lys Asp Lys Leu Asn Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Tyr Lys Ser Asn Asn Val Glu Phe Ala Val Asn Thr Gly Gly Val
705 710 715 720

Tyr Ser Glu Pro Arg Pro Ile Gly Thr Arg Tyr Leu Thr Arg Asn Leu
725 730 735

<210> SEQ ID NO 4
<211> LENGTH: 736
<212> TYPE: PRT
<213> ORGANISM: Artificial Sequence
<220> FEATURE:
<223> OTHER INFORMATION: novel AAV isolate

<400> SEQUENCE: 4

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Ile Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

-continued

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590
```

-continued

```
Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Tyr Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 5
<211> LENGTH: 736
<212> TYPE: PRT
<213> ORGANISM: Artificial Sequence
<220> FEATURE:
<223> OTHER INFORMATION: novel AAV isolate

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Asp
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220
```

-continued

```
Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
```

645 650 655

Asp Pro Pro Thr Ala Phe Asn Lys Asp Lys Leu Asn Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Tyr Lys Ser Asn Asn Val Glu Phe Ala Val Asn Thr Glu Gly Val
705 710 715 720

Tyr Ser Glu Pro Arg Pro Ile Gly Thr Arg Tyr Leu Thr Arg Asn Leu
725 730 735

<210> SEQ ID NO 6
<211> LENGTH: 736
<212> TYPE: PRT
<213> ORGANISM: Artificial Sequence
<220> FEATURE:
<223> OTHER INFORMATION: novel AAV isolate

<400> SEQUENCE: 6

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Leu Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Met Ala Ser Gly Gly Gly
195 200 205

Ala Pro Val Ala Asp Asn Asn Glu Gly Ala Asp Gly Val Gly Ser Ser
210 215 220

Ser Gly Asn Trp His Cys Asp Ser Gln Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Asn Ser Thr Ser Gly Gly Ser Ser Asn Asp Asn
260 265 270

Ala Tyr Phe Gly Tyr Ser Thr Pro Trp Gly Tyr Phe Asp Phe Asn Arg

-continued

```
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Ser Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700
```

```
Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 7
<211> LENGTH: 736
<212> TYPE: PRT
<213> ORGANISM: Artificial Sequence
<220> FEATURE:
<223> OTHER INFORMATION: novel AAV isolate

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335
```

```
Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Arg Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 8
<211> LENGTH: 736

-continued

<212> TYPE: PRT
<213> ORGANISM: Artificial Sequence
<220> FEATURE:
<223> OTHER INFORMATION: novel AAV isolate

<400> SEQUENCE: 8

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Val Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380
```

-continued

Gly Ser Gln Ala Val Gly Arg Ser Ser Phe Tyr Cys Leu Glu Tyr Phe
385 390 395 400

Pro Ser Gln Met Leu Arg Thr Gly Asn Asn Phe Gln Phe Ser Tyr Glu
405 410 415

Phe Glu Asn Val Pro Phe His Ser Ser Tyr Ala His Ser Gln Ser Leu
420 425 430

Asp Arg Leu Met Asn Pro Leu Ile Asp Gln Tyr Leu Tyr Tyr Leu Ser
435 440 445

Lys Thr Ile Asn Gly Ser Gly Gln Asn Gln Gln Thr Leu Lys Phe Ser
450 455 460

Val Ala Gly Pro Ser Asn Met Ala Val Gln Gly Arg Asn Tyr Ile Pro
465 470 475 480

Gly Pro Ser Tyr Arg Gln Gln Arg Val Ser Thr Thr Val Thr Gln Asn
485 490 495

Asn Asn Ser Glu Phe Ala Trp Pro Gly Ala Ser Ser Trp Ala Leu Asn
500 505 510

Gly Arg Asn Ser Leu Met Asn Pro Gly Pro Ala Met Ala Ser His Lys
515 520 525

Glu Gly Glu Asp Arg Phe Phe Pro Leu Ser Gly Ser Leu Ile Phe Gly
530 535 540

Lys Gln Gly Thr Gly Arg Asp Asn Val Asp Ala Asp Lys Val Met Ile
545 550 555 560

Thr Asn Glu Glu Glu Ile Lys Thr Thr Asn Pro Val Ala Thr Glu Ser
565 570 575

Tyr Gly Gln Val Ala Thr Asn His Gln Ser Ala Gln Ala Gln Ala Gln
580 585 590

Thr Gly Trp Val Gln Asn Gln Gly Ile Leu Pro Gly Met Val Trp Gln
595 600 605

Asp Arg Asp Val Tyr Leu Gln Gly Pro Ile Trp Ala Lys Ile Pro His
610 615 620

Thr Asp Gly Asn Phe His Pro Ser Pro Leu Met Gly Gly Phe Gly Met
625 630 635 640

Lys His Pro Pro Pro Gln Ile Leu Ile Lys Asn Thr Pro Val Pro Ala
645 650 655

Asp Pro Pro Thr Ala Phe Asn Lys Asp Lys Leu Asn Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Tyr Lys Ser Asn Asn Val Glu Phe Ala Val Asn Thr Glu Gly Val
705 710 715 720

Tyr Ser Glu Pro Arg Pro Ile Gly Thr Arg Tyr Leu Thr Arg Asn Leu
725 730 735

<210> SEQ ID NO 9
<211> LENGTH: 736
<212> TYPE: PRT
<213> ORGANISM: Artificial Sequence
<220> FEATURE:
<223> OTHER INFORMATION: novel AAV isolate

<400> SEQUENCE: 9

Met Ala Ala Asp Gly Tyr Leu Pro Asp Trp Leu Glu Asp Asn Leu Ser
1 5 10 15

-continued

```
Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Arg Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
```

```
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 10
<211> LENGTH: 736
<212> TYPE: PRT
<213> ORGANISM: Artificial Sequence
<220> FEATURE:
<223> OTHER INFORMATION: novel AAV isolate

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
```

-continued

```
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Cys Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495
```

```
Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 11
<211> LENGTH: 736
<212> TYPE: PRT
<213> ORGANISM: Artificial Sequence
<220> FEATURE:
<223> OTHER INFORMATION: novel AAV isolate

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Arg Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

-continued

```
Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540
```

Lys Gln Gly Thr Gly Arg Asp Asn Val Asp Ala Asp Lys Val Met Ile
545 550 555 560

Thr Asn Glu Glu Glu Ile Lys Thr Thr Asn Pro Val Ala Thr Glu Ser
565 570 575

Tyr Gly Gln Val Ala Thr Asn His Gln Ser Ala Gln Ala Gln Ala Gln
580 585 590

Thr Gly Trp Val Gln Asn Gln Gly Ile Leu Pro Gly Met Val Trp Gln
595 600 605

Asp Arg Asp Val Tyr Leu Gln Gly Pro Ile Trp Ala Lys Ile Pro His
610 615 620

Thr Asp Gly Asn Phe His Pro Ser Pro Leu Met Gly Gly Phe Gly Met
625 630 635 640

Lys His Pro Pro Pro Gln Ile Leu Ile Lys Asn Thr Pro Val Pro Ala
645 650 655

Asp Pro Pro Thr Ala Phe Asn Lys Asp Lys Leu Asn Ser Phe Ile Thr
660 665 670

Gln Tyr Ser Thr Gly Gln Val Ser Val Glu Ile Glu Trp Glu Leu Gln
675 680 685

Lys Lys Asn Ser Lys Arg Trp Asn Pro Glu Ile Gln Tyr Thr Ser Asn
690 695 700

Tyr Tyr Lys Ser Asn Asn Val Glu Phe Ala Val Asn Thr Glu Gly Val
705 710 715 720

Tyr Ser Glu Pro Arg Pro Ile Gly Thr Arg Tyr Leu Thr Arg Asn Leu
725 730 735

<210> SEQ ID NO 12
<211> LENGTH: 736
<212> TYPE: PRT
<213> ORGANISM: Artificial Sequence
<220> FEATURE:
<223> OTHER INFORMATION: novel AAV isolate

<400> SEQUENCE: 12

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

-continued

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro His Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Asn
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
```

595 600 605

Asp Arg Asp Val Tyr Leu Gln Gly Pro Ile Trp Ala Lys Ile Pro His
610 615 620

Thr Asp Gly Asn Phe His Pro Ser Pro Leu Met Gly Gly Phe Gly Met
625 630 635 640

Lys His Pro Pro Pro Gln Ile Leu Ile Lys Asn Thr Pro Val Pro Ala
645 650 655

Asp Pro Pro Thr Ala Phe Asn Lys Asp Lys Leu Asn Ser Phe Ile Thr
660 665 670

Gln Tyr Ser Thr Gly Gln Val Ser Met Glu Ile Glu Trp Glu Leu Gln
675 680 685

Lys Glu Asn Ser Lys Arg Trp Asn Pro Glu Ile Gln Tyr Thr Ser Asn
690 695 700

Tyr Tyr Lys Ser Asn Asn Val Glu Phe Ala Val Asn Thr Glu Gly Val
705 710 715 720

Tyr Ser Glu Pro Arg Pro Ile Gly Thr Arg Tyr Leu Thr Arg Asn Leu
725 730 735

<210> SEQ ID NO 13
<211> LENGTH: 736
<212> TYPE: PRT
<213> ORGANISM: Artificial Sequence
<220> FEATURE:
<223> OTHER INFORMATION: novel AAV isolate

<400> SEQUENCE: 13

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Met Ala Ser Gly Gly Gly
195 200 205

Ala Pro Val Ala Asp Asn Asn Glu Gly Ala Asp Gly Val Gly Ser Ser
210 215 220

Ser Gly Asn Trp His Cys Asp Ser Gln Trp Leu Gly Asp Arg Val Ile

-continued

```
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655
```

```
Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 14
<211> LENGTH: 736
<212> TYPE: PRT
<213> ORGANISM: Artificial Sequence
<220> FEATURE:
<223> OTHER INFORMATION: novel AAV isolate

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700
```

Tyr Tyr Lys Ser Asn Asn Val Glu Phe Ala Val Asn Thr Glu Gly Val
705 710 715 720

Tyr Ser Glu Pro Arg Pro Ile Gly Thr Arg Tyr Leu Thr Arg Asn Leu
725 730 735

<210> SEQ ID NO 15
<211> LENGTH: 736
<212> TYPE: PRT
<213> ORGANISM: Artificial Sequence
<220> FEATURE:
<223> OTHER INFORMATION: novel AAV isolate

<400> SEQUENCE: 15

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Met Ala Ser Gly Gly Gly
195 200 205

Ala Pro Val Ala Asp Asn Asn Glu Gly Ala Asp Gly Val Gly Ser Ser
210 215 220

Ser Gly Asn Trp His Cys Asp Ser Gln Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Asn Ser Thr Ser Gly Gly Ser Ser Asn Asp Asn
260 265 270

Ala Tyr Phe Gly Tyr Ser Thr Pro Trp Gly Tyr Phe Asp Phe Asn Arg
275 280 285

Phe His Cys His Phe Ser Pro Arg Asp Trp Gln Arg Leu Ile Asn Asn
290 295 300

Asn Trp Gly Phe Arg Pro Lys Arg Leu Asn Phe Lys Leu Phe Asn Ile
305 310 315 320

Gln Val Lys Glu Val Thr Asp Asn Asn Gly Val Lys Thr Ile Ala Asn
325 330 335

-continued

```
Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Arg Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 16
<211> LENGTH: 736
<212> TYPE: PRT

<213> ORGANISM: Artificial Sequence
<220> FEATURE:
<223> OTHER INFORMATION: novel AAV isolate

<400> SEQUENCE: 16

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Met Ala Ser Gly Gly Gly
195 200 205

Ala Pro Val Ala Asp Asn Asn Glu Gly Ala Asp Gly Val Gly Ser Ser
210 215 220

Ser Gly Asn Trp His Cys Asp Ser Gln Trp Leu Gly Asp Arg Val Ile
225 230 235 240

Thr Thr Ser Thr Arg Thr Trp Ala Leu Pro Thr Tyr Asn Asn His Leu
245 250 255

Tyr Lys Gln Ile Ser Asn Ser Thr Ser Gly Gly Ser Ser Asn Asp Asn
260 265 270

Ala Tyr Phe Gly Tyr Ser Thr Pro Trp Gly Tyr Phe Asp Phe Asn Arg
275 280 285

Phe His Cys His Phe Ser Pro Arg Asp Trp Gln Arg Leu Ile Asn Asn
290 295 300

Asn Trp Gly Phe Arg Pro Lys Arg Leu Asn Phe Lys Leu Phe Asn Ile
305 310 315 320

Gln Val Lys Glu Val Thr Asp Asn Asn Gly Val Lys Thr Ile Ala Asn
325 330 335

Asn Leu Thr Ser Thr Val Gln Val Phe Ala Asp Ser Asp Tyr Gln Leu
340 345 350

Pro Tyr Val Leu Gly Ser Ala His Glu Gly Cys Leu Pro Pro Phe Pro
355 360 365

Ala Asp Val Phe Met Ile Pro Gln Tyr Gly Tyr Leu Thr Leu Asn Asp
370 375 380

Gly Ser Gln Ala Val Gly Arg Ser Ser Phe Tyr Cys Leu Glu Tyr Phe

```
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 17
<211> LENGTH: 736
<212> TYPE: PRT
<213> ORGANISM: Artificial Sequence
<220> FEATURE:
<223> OTHER INFORMATION: novel AAV isolate

<400> SEQUENCE: 17

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
```

-continued

```
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445
```

-continued

```
Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Ile Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Cys Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 18
<211> LENGTH: 2211
<212> TYPE: DNA
<213> ORGANISM: Artificial Sequence
<220> FEATURE:
<223> OTHER INFORMATION: novel AAV isolate

<400> SEQUENCE: 18

```
atggctgccg atggttatct tccagattgg ctcgaggaca accttagtga aggaattcgc      60

gagtggtggg ctttgaaacc tggagcccct caacccaagg caaatcaaca acatcaagac     120

aacgctcgag gtcttgtgct tccgggttac aaataccttg gacccggcaa cggactcgac     180

aagggggagc cggtcaacgc agcagacgcg gcggccctcg agcacgacaa ggcctacgac     240

cagcagctca aggccggaga caacccgtac ctcaagtaca accacgccga cgccgagttc     300

caggagcggc tcaaagaaga tacgtctttt gggggcaacc tcgggcgagc agtcttccag     360

gccaaaaaga ggcttcttga acctcttggt ctggttgagg aagcggctaa gacggctcct     420
```

```
ggaaagaaga ggcctgtaga gcagtctcct caggaaccgg actcctccgc gggtattggc    480

aaatcgggtg cacagcccgc taaaaagaga ctcaatttcg gtcagactgg cgacacagag    540

tcagtcccag accctcaacc aatcggagaa cctcccgcag ccccctcagg tgtgggatct    600

cttacaatgg cttcaggtgg tggcgcacca gtggcagaca ataacgaagg tgccgatgga    660

gtgggtagtt cctcgggaaa ttggcattgc gattcccaat ggctgggga cagagtcatc    720

accaccagca cccgaacctg ggccctgccc acctacaaca atcacctcta caagcaaatc    780

tccaacagca catctggagg atcttcaaat gacaacgcct acttcggcta cagcaccccc    840

tgggggtatt ttgacttcaa cagattccac tgccacttct caccacgtga ctggcagcga    900

ctcatcaaca acaactgggg attccggcct aagcgactca acttcaagct cttcaacatt    960

caggtcaaag aggttacgga caacaatgga gtcaagacca tcgccaataa ccttaccagc   1020

acggtccagg tcttcacgga ctcagactat cagctcccgt acgtgctcgg gtcggctcac   1080

gagggctgcc tcccgccgtt cccagcggac gttttcatga ttcctcagta cgggtatctg   1140

acgcttaatg atggaagcca ggccgtgggt cgttcgtcct tttactgcct ggaatatttc   1200

ccgtcgcaaa tgctaagaac gggtaacaac ttccagttca gctacgagtt tgagaacgta   1260

cctttccata gcagctacgc tcacagccaa agcctggacc gactaatgaa tccactcatc   1320

gaccaatact tgtactatct ctcaaagact attaacggtt ctggacagaa tcaacaaacg   1380

ctaaaattca gtgtggccgg acccagcaac atggctgtcc agggaagaaa ctacatacct   1440

ggacccagct accgacaaca acgtgtctca accactgtga ctcaaaacaa caacagcgaa   1500

tttgcttggc ctggagcttc ttcttgggct ctcaatggac gtaatagctt gatgaatcct   1560

ggacctgcta tggccagcca caaagaagga gaggaccgtt tctttccttt gtctggatct   1620

ttaatttttg gcaaacaagg aactggaaga gacaacgtgg atgcggacaa agtcatgata   1680

accaacgaag aagaaattaa aactactaac ccggtagcaa cggagtccta tggacaagtg   1740

gccacaaacc accagagtgc ccaagcacag gcgcagaccg gctgggttca aaaccaagga   1800

atacttccgg gtatggtttg gcaggacaga gatgtgtacc tgcaaggacc catttgggcc   1860

aaaattcctc acacggacgg caactttcac ccttctccgc tgatgggagg gtttggaatg   1920

aagcacccgc ctcctcagat cctcatcaaa aacacacctg tacctgcgga tcctccaacg   1980

gccttcaaca aggacaagct gaactctttc atcacccagt attctactgg ccaagtcagc   2040

gtggagatcg agtgggagct gcagaaggaa aacagcaagc gctggaaccc ggagatccag   2100

tacacttcca actattacaa gtctaataat gttgaatttg ctgttaatac tgaaggtgta   2160

tatagtgaac cccgccccat tggcaccaga tacctgactc gtaatctgta a            2211
```

<210> SEQ ID NO 19
<211> LENGTH: 4679
<212> TYPE: DNA
<213> ORGANISM: Artificial Sequence
<220> FEATURE:
<223> OTHER INFORMATION: novel AAV isolate

<400> SEQUENCE: 19

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctggagg ggtggagtcg tgacgtgaat tacgtcatag    180

ggttagggag gtcctgtatt agaggtcacg tgagtgtttt gcgacatttt gcgacaccat    240

gtggtcacgc tgggtattta agcccgagtg agcacgcagg gtctccattt tgaagcggga    300
```

-continued

```
ggtttgaacg cgcagccgcc atgccggggt tttacgagat tgtgattaag gtccccagcg    360
accttgacga gcatctgccc ggcatttctg acagctttgt gaactgggtg gccgagaagg    420
aatgggagtt gccgccagat tctgacatgg atctgaatct gattgagcag gcacccctga    480
ccgtggccga gaagctgcag cgcgactttc tgacggaatg gcgccgtgtg agtaaggccc    540
cggaggccct tttctttgtg caatttgaga agggagagag ctacttccac atgcacgtgc    600
tcgtggaaac caccggggtg aaatccatgg ttttgggacg tttcctgagt cagattcgcg    660
aaaaactgat tcagagaatt taccgcggga tcgagccgac tttgccaaac tggttcgcgg    720
tcacaaagac cagaaatggc gccggaggcg ggaacaaggt ggtggatgag tgctacatcc    780
ccaattactt gctccccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca aagagaatca gaatcccaat tctgatgcgc    960
cggtgatcag atcaaaaact tcagccaggt acatggagct ggtcgggtgg ctcgtggaca   1020
aggggattac ctcggagaag cagtggatcc aggaggacca ggcctcatac atctccttca   1080
atgcggcctc caactcgcgg tcccaaatca aggctgcctt ggacaatgcg ggaaagatta   1140
tgagcctgac taaaaccgcc cccgactacc tggtgggcca gcagcccgtg gaggacattt   1200
ccagcaatcg gatttataaa attttggaac taaacgggta cgatccccaa tatgcggctt   1260
ccgtctttct gggatgggcc acgaaaaagt tcggcaagag gaacaccatc tggctgtttg   1320
ggcctgcaac taccgggaag accaacatcg cggaggccat agcccacact gtgcccttct   1380
acgggtgcgt aaactggacc aatgagaact ttcccttcaa cgactgtgtc gacaagatgg   1440
tgatctggtg ggaggagggg aagatgaccg ccaaggtcgt ggagtcggcc aaagccattc   1500
tcggaggaag caaggtgcgc gtggaccaga aatgcaagtc ctcggcccag atagacccga   1560
ctcccgtgat cgtcacctcc aacaccaaca tgtgcgccgt gattgacggg aactcaacga   1620
ccttcgaaca ccagcagccg ttgcaagacc ggatgttcaa atttgaactc acccgccgtc   1680
tggatcatga ctttgggaag gtcaccaagc aggaagtcaa agactttttc cggtgggcaa   1740
aggatcacgt ggttgaggtg gagcatgaat tctacgtcaa aaagggtgga gccaagaaaa   1800
gacccgcccc cagtgacgca gatataagtg agcccaaacg ggtgcgcgag tcagttgcgc   1860
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag gggtcttgtg   2340
cttcctgggt acaagtacct cggacccttc aacggactcg acaagggaga gccggtcaac   2400
gaggcagacg ccgcggccct cgagcacgac aaagcctacg accggcagct cgacagcgga   2460
gacaacccgt acctcaagta caaccacgcc gacgcggagt ttcaggagcg ccttaaagaa   2520
gatacgtctt ttgggggcaa cctcggacga gcagtcttcc aggcgaaaaa gagggttctt   2580
gaacctctgg gcctggttga ggaacctgtt aagacggctc cgggaaaaaa gaggccggta   2640
```

```
gagcactctc ctgtggagcc agactcctcc tcgggaaccg gaaaggcggg ccagcagcct   2700
gcaagaaaaa gattgaattt tggtcagact ggagacgcag actcagtacc tgacccccag   2760
cctctcggac agccaccagc agccccctct ggtctgggaa ctaatacgat ggctacaggc   2820
agtggcgcac caatggcaga caataacgag ggcgccgacg gagtgggtaa ttcctcggga   2880
aattggcatt gcgattccac atggatgggc gacagagtca tcaccaccag cacccgaacc   2940
tgggccctgc ccacctacaa caaccacctc tacaaacaaa tttccagcca atcaggagcc   3000
tcgaacgaca atcactactt tggctacagc accccttggg ggtattttga cttcaacaga   3060
ttccactgcc acttttcacc acgtgactgg caaagactca tcaacaacaa ctggggattc   3120
cgacccaaga gactcaactt caagctcttt aacattcaag tcaaagaggt cacgcagaat   3180
gacggtacga cgacgattgc caataacctt accagcacgg ttcaggtgtt tactgactcg   3240
gagtaccagc tcccgtacgt cctcggctcg gcgcatcaag gatgcctccc gccgttccca   3300
gcagacgtct tcatggtgcc acagtatgga tacctcaccc tgaacaacgg gagtcaggca   3360
gtaggacgct cttcatttta ctgcctggag tactttcctt ctcagatgct gcgtaccgga   3420
aacaacttta ccttcagcta cacttttgag gacgttcctt tccacagcag ctacgctcac   3480
agccagagtc tggaccgtct catgaatcct ctcatcgacc agtacctgta ttacttgagc   3540
agaacaaaca ctccaagtgg aaccaccacg cagtcaaggc ttcagttttc tcaggccgga   3600
gcgagtgaca ttcgggacca gtctaggaac tggcttcctg gaccctgtta ccgccagcag   3660
cgagtatcaa agacatctgc ggataacaac aacagtgaat actcgtggac tggagctacc   3720
aagtaccacc tcaatggcag agactctctg gtgaatccgg gcccggccat ggcaagccac   3780
aaggacgatg aagaaaagtt ttttcctcag agcggggttc tcatctttgg gaagcaaggc   3840
tcagagaaaa caaatgtgga cattgaaaag gtcatgatta cagacgaaga ggaaatcagg   3900
acaaccaatc ccgtggctac ggagcagtat ggttctgtat ctaccaacct ccagagaggc   3960
aacagacaag cagctaccgc agatgtcaac acacaaggcg ttcttccagg catggtctgg   4020
caggacagag atgtgtacct tcaggggccc atctgggcaa agattccaca cacggacgga   4080
cattttcacc cctctcccct catgggtgga ttcggactta aacaccctcc tccacagatt   4140
ctcatcaaga acaccccggt acctgcgaat ccttcgacca ccttcagtgc ggcaaagttt   4200
gcttccttca tcacacagta ctccacggga caggtcagcg tggagatcga gtgggagctg   4260
cagaaggaaa acagcaaacg ctggaatccc gaaattcagt acacttccaa ctacaacaag   4320
tctgttaatg tggactttac tgtggacact aatggcgtgt attcagagcc tcgccccatt   4380
ggcaccagat acctgactcg taatctgtaa ttgcttgtta atcaataaac cgtttaattc   4440
gtttcagttg aactttggtc tctgcgtatt tctttcttat ctagtttcca tggctacgta   4500
gataagtagc atggcgggtt aatcattaac tacaaggaac ccctagtgat ggagttggcc   4560
actccctctc tgcgcgctcg ctcgctcact gaggccgggc gaccaaaggt cgcccgacgc   4620
ccgggctttg cccgggcggc ctcagtgagc gagcgagcgc gcagagaggg agtggccaa    4679
```

<210> SEQ ID NO 20
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 20

```
ccatcgacgt cagacgcgga agcttcgatc aactacgcgg acaggtacca aaacaaatgt     60
```

```
tctcgtcacg tgggcatgaa tctgatgctg tttccctgca gacaatgcga gagactgaat    120
cagaattcaa atatctgctt cactcacggt gtcaaagact gtttagagtg ctttcccgtg    180
tcagaatctc aacccgtttc tgtcgtcaaa aaggcgtatc agaaactgtg ctacattcat    240
cacatcatgg gaaaggtgcc agacgcttgc actgcttgcg acctggtcaa tgtggacttg    300
gatgactgtg tttctgaaca ataaatgact taaaccaggt atgactgccg atggttatct    360
tccagattgg ctcgaggaca accttagtga aggaattcgc gagtggtggg ctttgaaacc    420
tggagcccct caacccaagg caaatcaaca acatcaagac aacgctcgag gtcttgtgct    480
tccgggttac aaataccttg gacccggcaa cggactcgac aagggggagc cggtcaacgc    540
agcagacgcg gcggccctcg agcacgacaa ggcctacgac cagcagctca aggccggaga    600
caacccgtac ctcaagtaca accacgccga cgccgagttc caggagcggc tcaaagaaga    660
tacgtctttt gggggcaacc tcgggcgagc agtcttccag gccaaaaaga ggcttcttga    720
acctcttggt ctggttgagg aagcggctaa gacggctcct ggaaagaaga ggcctgtaga    780
gcagtctcct caggaaccgg actcctccgc gggtattggc aaatcgggtg cacagcccgc    840
taaaaagaga ctcaatttcg gtcagactgg cgacacagag tcagtcccag accctcaacc    900
aatcggagaa cctcccgcag ccccctcagg tgtgggatct cttacaatgg cttcaggtgg    960
tggcgcacca gtggcagaca ataacgaagg tgccgatgga gtgggtagtt cctcgggaaa   1020
ttggcattgc gattcccaat ggctggggga cagagtcatc accaccagca cccgaacctg   1080
ggccctgccc acctacaaca atcacctcta caagcaaatc tccaacagca catctggagg   1140
atcttcaaat gacaacgcct acttcggcta cagcaccccc tgggggtatt ttgacttcaa   1200
cagattccac tgccacttct caccacgtga ctggcagcga ctcatcaaca acaactgggg   1260
attccggcct aagcaactca acttcaagct cttcaacatt caggtcaaag aggttacgga   1320
caacaatgga gtcaagacca tcgccaataa ccttaccagc acggtccagg tcttcacgga   1380
ctcagactat cagctcccgt acgtgctcgg gtcggctcac gagggctgcc tcccgccgtt   1440
cccagcggac gttttcatga ttcctcagta cgggtatctg acgcttaatg atggaagcca   1500
ggccgtgggt cgttcgtcct tttactgcct ggaatatttc ccgtcgcaaa tgctaagaac   1560
gggtaacaac ttccagttca gctacgagtt tgagaacgta cctttccata gcagctacgc   1620
tcacagccaa agcctggacc gactaatgaa tccactcatc gaccaatact tgtactatct   1680
ctcaaagact attaacggtt ctggacagaa tcaacaaacg ctaaaattca gtgtggccgg   1740
acccagcaac atggctgtcc agggaagaaa ctacatacct ggacccagct accgacaaca   1800
acgtgtctca accactgtga ctcaaaacaa caacagcgaa tttgcttggc ctggagcttc   1860
ttcttgggct ctcaatggac gtaatagctt gatgaatcct ggacctgcta tggccagcca   1920
caaagaagga gaggaccgtt tctttccttt gtctggatct ttaatttttg gcaaacaagg   1980
aactggaaga gacaacgtgg atgcggacaa agtcatgata accaacgaag aagaaattaa   2040
aactactaac ccggtagcaa cggagtccta tggacaagtg gccacaaacc accagagtgc   2100
ccaagcacag gcgcagaccg gctgggttca aaaccaagga atacttccgg gtatggtttg   2160
gcaggacaga gatgtgtacc tgcaaggacc catttgggcc aaaattcctc acacggacgg   2220
caactttcac ccttctccgc tgatgggagg gtttggaatg aagcacccgc ctcctcagat   2280
cctcatcaaa aacacacctg tacctgcgga tcctccaacg gccttcaaca aggacaagct   2340
gaactctttc atcacccagt attctactgg ccaagtcagc gtggagatcg agtgggagct   2400
```

```
gcagaaggaa aacagcaagc gctggaaccc ggagatccag tacacttcca actattacaa   2460

gtctaataat gttgaatttg ctgttaatac tgaaggtgta tatagtgaac cccgccccat   2520

tggcaccaga tacctgactc gtaatctgta attgcttgtt aatcaataaa ccgtttaatt   2580

cgtttcagtt gaactgcggc c                                             2601


<210> SEQ ID NO 21
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 21

ccatcgacgt cagacgcgga agcttcgatc aactacgcgg acaggtacca aaacaaatgt     60

tctcgtcacg tgggcatgaa tctgatgctg tttccctgca gacaatgcga gagactgaat    120

cagaattcaa atatctgctt cactcacggt gtcaaagact gtttagagtg ctttcccgtg    180

tcagaatctc aacccgtttc tgtcgtcaaa aaggcgtatc agaaactgtg ctacattcat    240

cacatcatgg gaaaggtgcc agacgcttgc actgcttgcg acctggtcaa tgtggacttg    300

gatgactgtg tttctgaaca ataaatgact taaaccaggt atggctgccg atggttatct    360

tccagattgg ctcgaggaca accttagtga aggaattcgc gagtggtggg ctttgaaacc    420

tggagcccct caacccaagg caaatcaaca acatcaagac aacgctcgag gtcttgtgct    480

tccgggttac aaataccttg gacccggcaa cggactcgac aagggggagc cggtcaacgc    540

agcagacgcg gcggccctcg agcacgacaa ggcctacgac cagcagctca aggccggaga    600

caacccgtac ctcaagtaca accacgccga cgccgagttc caggagcggc tcaaagaaga    660

tacgtctttt gggggcaacc tcgggcgagc agtcttccag gccaaaaaga ggcttcttga    720

acctcttggt ctggttgagg aagcggctaa gacggctcct ggaaagaaga ggcctgtaga    780

gcagtctcct caggaaccgg actcctccgc gggtattggc aaatcgggtg cacagcccgc    840

taaaaagaga ctcaatttcg gtcagactgg cgacacagag tcagtcccag accctcaacc    900

aatcggagaa cctcccgcag ccccctcagg tgtgggatct cttacaatgg cttcaggtgg    960

tggcgcacca gtggcagaca ataacgaagg tgccgatgga gtgggtagtt cctcgggaaa   1020

ttggcattgc gattcccaat ggctgggga cagagtcatc accaccagca cccgaacctg    1080

ggccctgccc acctacaaca atcacctcta caagcaaatc tccaacagca catctggagg   1140

atcttcaaat gacaacgcct acttcggcta cagcaccccc tgggggtatt ttgacttcaa   1200

cagattccac tgccacttct caccacgtga ctggcagcga ctcatcaaca acaactgggg   1260

attccggcct aagcgactca acttcaagct cttcaacatt caggtcaaag aggttacgga   1320

caacaatgga gtcaagacca tcgccaataa ccttaccagc acggtccagg tcttcacgga   1380

ctcagactat cagctcccgt acgtgctcgg gtcggctcac gagggctgcc tcccgccgtt   1440

cccagcggac gttttcatga ttcctcagta cgggtatctg acgcttaatg atggaagcca   1500

ggccgtgggt cgttcgtcct tttactgcct ggaatatttc ccgtcgcaaa tgctaagaac   1560

gggtaacaac ttccagttca gctacgagtt tgagaacgta cctttccata gcagctacgc   1620

tcacagccaa agcctggacc gactaatgaa tccactcatc gaccaatact tgtactatct   1680

ctcaaagact attaacggtt ctggacagaa tcaacaaacg ctaaaattca gtgtggccgg   1740

acccagcaac atggctgtcc agggaagaaa ctacatacct ggacccagct accgacaaca   1800

acgtgtctca accactgtga ctcaaaacaa caacagcgaa tttgcttggc ctggggcttc   1860
```

```
ttcttgggct ctcaatggac gtaatagctt gatgaatcct ggacctgcta tggccagcca   1920

caaagaagga gaggaccgtt tctttccttt gtctggatct ttaatttttg gcaaacaagg   1980

aactggaaga gacaacgtgg atgcggacaa agtcatgata accaacgaag aagaaattaa   2040

aactactaac ccggtagcaa cggagtccta tggacaagtg gccacaaacc accagagtgc   2100

ccaagcacag gcgcagaccg gctgggttca aaaccaagga atacttccgg gtatggtttg   2160

gcaggacaga gatgtgtacc tgcaaggacc catttgggcc aaaattcctc acacgggcgg   2220

caactttcac ccttctccgc tgatgggagg gtttggaatg aagcacccgc ctcctcagat   2280

cctcatcaaa aacacacctg tacctgcgga tcctccaacg gccttcaaca aggacaagct   2340

gaactctttc atcacccagt attctactgg ccaagtcagc gtggagatcg agtgggagct   2400

gcagaaggaa aacagcaagc gctggaaccc ggagatccag tacacttcca actattacaa   2460

gtctaataat gttgaatttg ctgttaatac tggaggtgta tatagtgaac cccgccccat   2520

tggcaccaga tacctgactc gtaatctgta attgcttgtt aatcaataaa ccgtttaatt   2580

cgtttcagtt gaactgcggc c                                             2601
```

<210> SEQ ID NO 22
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 22

```
ccatcgacgt cagacgcgga agcttcgatc aactacgcgg acaggtacca aaacaaatgt     60

tctcgtcacg tgggcatgaa tctgatgctg tttccctgca gacaatgcga gagactgaat    120

cagaattcaa atatctgctt cactcacggt gtcaaagact gtttagagtg ctttcccgtg    180

tcagaatctc aacccgtttc tgtcgtcaaa aaggcgtatc agaaactgtg ctacattcat    240

cacatcatgg gaaaggtgcc agacgcttgc actgcttgcg acctggtcaa tgtggactcg    300

gatgactgtg tttctgaaca ataaatgact taaaccaggt atggctgccg atggttatct    360

tccagattgg ctcgaggaca accttagtga aggaattcgc gagtggtggg ctttgaaacc    420

tggagcccct caacccaagg caaatcaaca acatcaagac aacgctcgag gtcttgtgct    480

tccgggttac aaataccttg gacccggcaa cggactcgac aagggggagc cggtcaacgc    540

agcagacgcg gcggccctcg agcacgacaa ggcctacgac cagcagctca aggccggaga    600

caacccgtac ctcaagtaca accacgccga cgccgagttc caggagcggc tcaaagaaga    660

tacgtctttt gggggcaacc tcgggcgagc agtcttccag gccaaaaaga ggcttcttga    720

acctcttggt ctggttgagg aagcggctaa gacggctcct ggaaagaaga ggcctgtaga    780

gcagtctcct caggaaccgg actcctccgc gggtattgac aaatcgggtg cacagcccgc    840

taaaaagaga ctcaatttcg gtcagactgg cgacacagag tcagtcccag accctcaacc    900

aatcggagaa cctcccgcag ccccctcagg tgtgggatct cttacaatgg cttcaggtgg    960

tggcgcacca gtggcagaca ataacgaagg tgccgatgga gtgggtagtt cctcgggaaa   1020

ttggcattgc gattcccaat ggctggggga cagagtcatc accaccagca cccgaacctg   1080

ggccctgccc acctacaaca atcacctcta caagcaaatc tccaacagca catctggagg   1140

atcttcaaat gacaacgcct acttcggcta cagcaccccc tgggggtatt ttgacttcaa   1200

cagattccac tgccacttct caccacgtga ctggcagcga ctcatcaaca acaactgggg   1260
```

```
attccggcct aagcgactca acttcaagct cttcaacatt caggtcaaag aggttacgga   1320

caacaatgga gtcaagacca tcgccaataa ccttaccagc acggtccagg tcttcacgga   1380

ctcggactat cagctcccgt acgtgctcgg gtcggctcac gagggctgcc tcccgccgtt   1440

cccagcggac gttttcatga ttcctcagta cgggtatctg acgcttaatg atggaagcca   1500

ggccgtgggt cgttcgtcct tttactgcct ggaatatttc ccgtcgcaaa tgctaagaac   1560

gggtaacaac ttccagttca gctacgagtt tgagaacgta cctttccata gcagctacgc   1620

tcacagccaa agcctggacc gactaatgaa tccactcatc gaccaatact tgtactatct   1680

ctcaaagact attaacggtt ctggacagaa tcaacaaacg ctaaaattca gtgtggccgg   1740

acccagcaac atggctgtcc agggaagaaa ctacatacct ggacccagct accgacaaca   1800

acgtgtctca accactgtga ctcaaaacaa caacagcgaa tttgcttggc ctggagcttc   1860

ttcttgggct ctcaatggac gtaatagctt gatgaatcct ggacctgcta tggccagcca   1920

caaagaagga gaggaccgtt tctttccttt gtctggatct ttaatttttg gcaaacaagg   1980

aactggaaga gacaacgtgg atgcggacaa agtcatgata accaacgaag aagaaattaa   2040

aactactaac ccggtagcaa cggagtccta tggacaagtg gccacaaacc accagagtgc   2100

ccaagcacag gcgcagaccg gctgggttca aaaccaagga atacttccgg gtatggtttg   2160

gcaggacaga gatgtgtacc tgcaaggacc catttgggcc aaaattcctc acacggacgg   2220

caactttcac ccttctccgc tgatgggagg gtttggaatg aagcacccgc ctcctcagat   2280

cctcatcaaa aacacacctg tacctgcgga tcctccaacg gccttcaaca aggacaagct   2340

gaactctttc atcacccagt attctactgg ccaagtcagc gtggagatcg agtgggagct   2400

gcagaaggaa aacagcaagc gctggaaccc ggagatccag tacacttcca actattacaa   2460

gtctaataat gttgaatttg ctgttaatac tgaaggtgta tatagtgaac cccgccccat   2520

tggcaccaga tacctgactc gtaatctgta attgcttgtt aatcaataaa ccgtttaatt   2580

cgtttcagtt gaactgcggc c                                             2601
```

<210> SEQ ID NO 23
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 23

```
ccatcgacgt cagacgcgga agcttcgatc aactacgcgg acaggtacca aaacaaatgt     60

tctcgtcacg tgggcatgaa tctgatgctg tttccctgca gacaatgcga gagactgaat    120

cagaattcaa atatctgctt cactcacggt gtcaaagact gtttagagtg ctttcccgtg    180

tcagaatctc aacccgtttc tgtcgtcaaa aaggcgtatc agaaactgtg ctacattcat    240

cacatcatgg gaaaggtgcc agacgcttgc actgcttgcg acctggtcaa tgtggacttg    300

gatgactgtg tttctgaaca ataaatgact taaaccaggt atggctgccg atggttatct    360

tccagattgg ctcgaggaca accttagtga aggaattcgc gagtggtggg ctttgaaacc    420

tggagcccct caacccaagg caaatcaaca acatcaagac aacgctcgag gtcttgtgct    480

tccgggttac aaataccttg gacccggcaa cggactcgac aagggggagc cggtcaacgc    540

agcagacgcg gcggccctcg agcacgacaa ggcctacgac cagcagctca aggccggaga    600

caacccgtac ctcaagtaca accacgccga cgccgagttc caggagcggc tcaaagaaga    660

tacgtctttt gggggcaacc tcgggcgagc agtcctccag gccaaaaaga ggcttcttga    720
```

```
acctcttggt ctggttgagg aagcggctaa gacggctcct ggaaagaaga ggcctgtaga    780

gcagtctcct caggaaccgg actcctccgc gggtattggc aaatcgggtg cacagcccgc    840

taaaaagaga ctcaatttcg gtcagactgg cgacacagag tcagtcccag accctcaacc    900

aatcggagaa cctcccgcag ccccctcagg tgtgggatct cttacaatgg cttcaggtgg    960

tggcgcacca gtggcagaca ataacgaagg tgccgatgga gtgggtagtt cctcgggaaa   1020

ttggcattgc gattcccaat ggctgggga cagagtcatc accaccagca cccgaacctg   1080

ggccctgccc acctacaaca atcacctcta caagcaaatc tccaacagca catctggagg   1140

atcttcaaat gacaacgcct acttcggcta cagcaccccc tgggggtatt ttgacttcaa   1200

cagattccac tgccacttct caccacgtga ctggcagcga ctcatcaaca acaactgggg   1260

attccggcct aagcgactca acttcaagct cttcaacatt caggtcaaag aggttacgga   1320

caacaatgga gtcaagacca tcgccaataa ccttaccagc acggtccagg tcttcacgga   1380

ctcagactat cagctcccgt acgtgctcgg gtcggctcac gagggctgcc tcccgccgtt   1440

cccagcggac gttttcatga ttcctcagta cgggtatctg acgcttaatg atggaagcca   1500

ggccgtgggt cgttcgtcct tttactgcct ggaatatttc ccgtcgcaaa tgctaagaac   1560

gggtaacaac ttccagttca gctacgagtt tgagaacgta cctttccata gcagctacgc   1620

tcacagccaa agcctggacc gactaatgaa tccactcatc gaccaatact tgtactatct   1680

ctcaaagact attaacggtt ctggacagaa tcaacaaacg ctaaaattca gtgtggccgg   1740

atccagcaac atggctgtcc agggaagaaa ctacatacct ggacccagct accgacaaca   1800

acgtgtctca accactgtga ctcaaaacaa caacagcgaa tttgcttggc ctggagcttc   1860

ttcttgggct ctcaatggac gtaatagctt gatgaatcct ggacctgcta tggccagcca   1920

caaagaagga gaggaccgtt tctttccttt gtctggatct ttaatttttg gcaaacaagg   1980

aactggaaga gacaacgtgg atgcggacaa agtcatgata accaacgaag aagaaattaa   2040

aactactaac ccggtagcaa cggagtccta tggacaagtg gccacaaacc accagagtgc   2100

ccaagcacag gcgcagaccg gctgggttca aaaccaagga atacttccag gtatggtttg   2160

gcaggacaga gatgtgtacc tgcaaggacc catttgggcc aaaattcctc acacggacgg   2220

caactttcac ccttctccgc tgatgggagg gtttggaatg aagcacccgc ctcctcagat   2280

cctcatcaaa aacacacctg tacctgcgga tcctccaacg gccttcaaca aggacaagct   2340

gaactctttc atcacccagt attctactgg ccaagtcagc gtggagatcg agtgggagct   2400

gcagaaggaa aacagcaagc gctggaaccc ggagatccag tacacttcca actattacaa   2460

gtctaataat gttgaatttg ctgttaatac tgaaggtgta tatagtgaac cccgccccat   2520

tggcaccaga tacctgactc gtaatctgta attgcttgtt aatcaataaa ccgtttaatt   2580

cgtttcagtt gaactgcggc c                                             2601
```

<210> SEQ ID NO 24
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 24

```
ccatcgacgt cagacgcgga agcttcgatc aactacgcgg acaggtacca aaacaaatgt     60

tctcgtcacg tgggcatgaa tctgatgctg tttccctgca gacaatgcga gagactgaat    120
```

-continued

```
cagaattcaa atatctgctt cactcacggt gtcaaagact gtttagagtg ctttcccgtg    180

tcagaatctc aacccgtttc tgtcgtcaaa aaggcgtatc agaaactgtg ctacattcat    240

cacatcatgg gaaaggtgcc agacgcttgc actgcttgcg acctggtcaa tgtggacttg    300

gatgactgtg tttctgaaca ataaatgact taaaccaggt atggctgccg atggttatct    360

tccagattgg ctcgaggaca accttagtga aggaattcgc gagtggtggg ctttgaaacc    420

tggagcccct caacccaagg caaatcaaca acatcaagac aacgctcgag gtcttgtgct    480

tccgggttac aaataccttg gacccggcaa cggactcgac aagggggagc cggtcaacgc    540

agcagacgcg gcggccctcg agcacgacaa ggcctacgac cagcagctca aggccggaga    600

caacccgtac ctcaagtaca accacgccga cgccgagttc caggagcggc tcaaagaaga    660

tacgtctttt gggggcaacc tcgggcgagc agtcttccag gccaaaaaga ggcttcttga    720

acctcttggt ctggttgagg aagcggctaa gacggctcct ggaaagaaga ggcctgtaga    780

gcagtctcct caggaaccgg actcctccgc gggtattggc aaatcgggtg cacagcccgc    840

taaaaagaga ctcaatttcg gtcagactgg cgacacagag tcagtcccag accctcaacc    900

aatcggagaa cctcccgcag ccccctcagg tgtgggatct cttacaatgg cttcaggtgg    960

tggcgcacca gtggcagaca ataacgaagg tgccgatgga gtgggtagtt cctcgggaaa   1020

ttggcattgc gattcccaat ggctgggga cagagtcatc accaccagca cccgaacctg   1080

ggccctgccc acctacaaca atcacctcta caagcaaatc tccaacagca catctggagg   1140

atcttcaaat gacaacgcct acttcggcta cagcaccccc tgggggtatt ttgacttcaa   1200

cagattccac tgccacttct caccacgtga ctggcagcga ctcatcaaca acaactgggg   1260

attccggcct aagcgactca acttcaagct cttcaacatt caggtcaaag aggttacgga   1320

caacaatgga gtcaagacca tcgccaataa ccttaccagc acggtccagg tcttcacgga   1380

ctcagactat cagctcccgt acgtgctcgg gtcggctcac gagggctgcc tcccgccgtt   1440

cccagcggac gttttcatga ttcctcagta cgggtatctg acgcttaatg atggaagcca   1500

ggccgtgggt cgttcgtcct tttactgcct ggaatatttc ccgtcgcaaa tgctaagaac   1560

gggtaacaac ttccagttca gctacgagtt tgagaacgta cctttccata gcagctacgc   1620

tcacagccaa agcctggacc gactaatgaa tccactcatc gaccaatact tgtactatct   1680

ctcaaagact attaacggtt ctggacagaa tcaacaaacg ctaaaattca gtgtggccgg   1740

acccagcaac atggctgtcc agggaagaaa ctacatacct ggacccagct accgacaaca   1800

acgtgtctca accactgtga ctcaaaacaa caacagcgaa tttgcttggc ctggagcttc   1860

ttcttgggct ctcaatggac gtaatagctt gatgaatcct ggacctgcta tggccagcca   1920

caaagaagga gaggaccgtt tctttccttt gtctggatct ttaatttttg gcaaacaagg   1980

aactggaaga gacaacgtgg atgcggacaa agtcatgata accaacgaag aagaaattaa   2040

aactactaac ccggtagcaa cggagtccta tggacaagtg gccacaaacc accagagtgc   2100

ccaagcacgg gcgcagaccg gctgggttca aaaccaagga atacttccgg gtatggtttg   2160

gcaggacaga gatgtgtacc tgcaaggacc catttgggcc aaaattcctc acacggacgg   2220

caactttcac ccttctccgc tgatgggagg gtttggaatg aagcacccgc ctcctcagat   2280

cctcatcaaa aacacacctg tacctgcgga tcctccaacg gccttcaaca aggacaagct   2340

gaactctttc atcacccagt attctactgg ccaagtcagc gtggagatcg agtgggagct   2400

gcagaaggaa aacagcaagc gctggaaccc ggagatccag tacacttcca actattacaa   2460

gtctaataat gttgaatttg ctgttaatac tgaaggtgta tatagtgaac cccgccccat   2520
```

tggcaccaga tacctgactc gtaatctgta attgcttgtt aatcaataaa ccgtttaatt 2580
cgtttcagtt gaactgcggc c 2601

<210> SEQ ID NO 25
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 25
ccatcgacgt cagacgcgga agcttcgatc aactacgcgg acaggtacca aaacaaatgt 60
tctcgtcacg tgggcatgaa tctgatgctg tttccctgca gacaatgcga gagactgaat 120
cagaattcaa atatctgctt cactcacggt gtcaaagact gtttagagtg ctttcccgtg 180
tcagaatctc aacccgtttc tgtcgtcaaa aaggcgtatc agaaactgtg ctacattcat 240
cacatcatgg gaaaggtgcc agacgcttgc actgcttgcg acctggtcaa tgtggacttg 300
gatgactgtg tttctgaaca ataaatgact taaaccaggt atggctgccg atggttatct 360
tccagattgg ctcgaggaca accttagtga aggaattcgc gagtggtggg ctttgaaacc 420
tggagcccct caacccaagg caaatcaaca acatcaagac aacgctcgag gtcttgtgct 480
tccgggttac aaataccttg gacccggcaa cggactcgac aagggggagc cggtcaacgc 540
agcagacgcg gcggccctcg agcacgacag ggcctacgac cagcagctca aggccggaga 600
caacccgtac ctcaagtaca accacgccga cgccgagttc caggagcggc tcaaagaaga 660
tacgtctttt gggggcaacc tcgggcgagc agtcttccag gccaaaaaga ggcttcttga 720
acctcttggt ctggttgagg aagcggctaa gacggctcct ggaaagaaga ggcctgtaga 780
gcagtctcct caggaaccgg actcctccgc gggtattggc aaatcgggtg cacagcccgc 840
taaaaagaga ctcaatttcg gtcagactgg cgacacagag tcagtcccag accctcaacc 900
aatcggagaa cctcccgcag ccccctcagg tgtgggatct cttacaatgg cttcaggtgg 960
tggcgcacca gtggcagaca ataacgaagg tgccgatgga gtgggtagtt cctcgggaaa 1020
ttggcattgc gattcccaat ggctgggga cagagtcatc accaccagca cccgaacctg 1080
ggccctgccc acctacaaca atcacctcta caagcaaatc tccaacagca catctggagg 1140
atcttcaaat gacaacgcct acttcggcta cagcaccccc tgggggtatt ttgacttcaa 1200
cagattccac tgccacttct caccacgtga ctggcagcga ctcatcaaca acaactgggg 1260
attccggcct aagcgactca acttcaagct cttcaacatt caggtcaaag aggttacgga 1320
caacaatgga gtcaagacca tcgccaataa ccttaccagc acggtccagg tcttcacgga 1380
ctcagactat cagctcccgt acgtgctcgg gtcggctcac gagggctgcc tcccgccgtt 1440
cccagcggac gttttcatga ttcctcagta cgggtatctg acgcttaatg atggaagcca 1500
ggccgtgggt cgttcgtcct tttactgcct ggaatatttc ccgtcgcaaa tgctaagaac 1560
gggtaacaac ttccagttca gctacgagtt tgagaacgta cctttccata gcagctacgc 1620
tcacagccaa agcctggacc gactaatgaa tccactcatc gaccaatact tgtactatct 1680
ctcaaagact attaacggtt ctggacagaa tcaacaaacg ctaaaattca gtgtggccgg 1740
acctagcaac atggctgtcc agggaagaaa ctacatacct ggacccagct accgacaaca 1800
acgtgtctca accactgtga ctcaaaacaa caacagcgaa tttgcttggc ctggagcttc 1860
ttcttgggct ctcaatggac gtaatagctt gatgaatcct ggacctgcta tggccagcca 1920

```
caaagaagga gaggaccgtt tctttccttt gtctggatct ttaatttttg gcaaacaagg   1980

aactggaaga gacaacgtgg atgcggacaa agtcatgata accaacgaag aagaaattaa   2040

aactactaac ccggtagcaa cggagtccta tggacaagtg gccacaaacc accagagtgc   2100

ccaagcacag gcgcagaccg gctgggttca aaaccaagga atacttccgg gtatggtttg   2160

gcaggacaga gatgtgtacc tgcaaggacc catttgggcc aaaattcctc acacggacgg   2220

caactttcac ccttctccgc tgatgggagg gtttggaatg aagcacccgc ctcctcagat   2280

cctcatcaaa aacacacctg tacctgcgga tcctccaacg gccttcaaca aggacaagct   2340

gaactctttc atcacccagt attctactgg ccaagtcagc gtggagatcg agtgggagct   2400

gcagaagaaa aacagcaagc gctggaaccc ggagatccag tacacttcca actattacaa   2460

gtctaataat gttgaatttg ctgttaacac tgaaggtgta tatagtgaac cccgccccat   2520

tggcaccaga tacctgactc gtaatctgta attgcttgtt aatcaataaa ccgtttaatt   2580

cgtttcagtt gaactgcggc c                                             2601
```

<210> SEQ ID NO 26
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 26

```
ccatcgacgt cagacgcgga agcttcgatc aactacgcgg acaggtacca aaacaaatgt     60

tctcgtcacg tgggcatgaa tctgatgctg tttccctgca gacaatgcga gagactgaat    120

cagaattcaa atatctgctt cactcacggt gtcaaagact gtttagagtg ctttcccgtg    180

tcagaatctc aacccgtttc tgtcgtcaaa aaggcgtatc agaaactgtg ctacattcat    240

cacatcatgg gaaaggtgcc agacgcttgc actgcttgcg acctggtcaa tgtggacttg    300

gatgactgtg tttctgaaca ataaatgact taaaccaggt atggctgccg atggttatct    360

tccagattgg ctcgaggaca accttagtga aggaattcgc gagtggtggg ctttgaaacc    420

tggagcccct caacccaagg caaatcaaca acatcaagac aacgctcgag gtcttgtgct    480

tccgggttac aaataccttg gacccggcaa cggactcgac aagggggagc cgatcaacgc    540

agcagacgcg gcggccctcg agcacgacaa ggcctacgac cagcagctca aggccggaga    600

caacccgtac ctcaagtaca accacgccga cgccgagttc caggagcggc tcaaagaaga    660

tacgtctttt gggggcaacc tcgggcgagc agtcttccag gccaaaaaga ggcttcttga    720

acctcttggt ctggttgagg aagcggctaa gacggctcct ggaaagaaga ggcctgtaga    780

gcagtctcct caggaaccgg actcctccgc gggtattggc aaatcgggtg cacagcccgc    840

taaaaagaga ctcaatttcg gtcagactgg cgacacagag tcagtcccag accctcaacc    900

aatcggagaa cctcccgcag ccccctcagg tgtgggatct cttacaatgg cttcaggtgg    960

tggcgcacca gtggcagaca ataacgaagg tgccgatgga gtgggtagtt cctcgggaaa   1020

ttggcattgc gattcccaat ggctggggga cagagtcatc accaccagca cccgaacctg   1080

ggccctgccc acctacaaca atcacctcta caagcaaatc tccaacagca catctggagg   1140

atcttcaaat gacaacgcct acttcggcta cagcaccccc tgggggtatt ttgacttcaa   1200

cagattccac tgccacttct caccacgtga ctggcagcga ctcatcaaca acaactgggg   1260

attccggcct aagcgactca acttcaagct cttcaacatt caggtcaaag aggttacgga   1320

caacaatgga gtcaagacca tcgccaataa ccttaccagc acggtccagg tcttcacgga   1380
```

-continued

```
ctcagactat cagctcccgt acgtgctcgg gtcggctcac gagggctgcc tcccgccgtt   1440

cccagcggac gttttcatga ttcctcagta cgggtatctg acgcttaatg atggaagcca   1500

ggccgtgggt cgttcgtcct tttactgcct ggaatatttc ccgtcgcaaa tgctaagaac   1560

gggtaacaac ttccagttca gctacgagtt tgagaacgta cctttccata gcagctacgc   1620

tcacagccaa agcctggacc gactaatgaa tccactcatc gaccaatact tgtactatct   1680

ctcaaagact attaacggtt ctggacagaa tcaacaaacg ctaaaattca gtgtggccgg   1740

acccagcaac atggctgtcc agggaagaaa ctacatacct ggacccagct accgacaaca   1800

acgtgtctca accactgtga ctcaaaacaa caacagcgaa tttgcttggc ctggagcttc   1860

ttcttgggct ctcaatggac gtaatagctt gatgaatcct ggacctgcta tggccagcca   1920

caaagaagga gaggaccgtt tctttccttt gtctggatct ttaatttttg gcaaacaagg   1980

aactggaaga gacaacgtgg atgcggacaa agtcatgata accaacgaag aagaaattaa   2040

aactactaac ccggtagcaa cggagtccta tggacaagtg gccacaaacc accagagtgc   2100

ccaagcacag gcgcagaccg gctgggttca aaaccaagga atacttccgg gtatggtttg   2160

gcaggacaga gatgtgtacc tgcaaggacc catttgggcc aaaattcctc acacgtacgg   2220

caactttcac ccttctccgc tgatgggagg gtttggaatg aagcacccgc ctcctcagat   2280

cctcatcaaa aacacacctg tacctgcgga tcctccaacg gccttcaaca aggacaagct   2340

gaactctttc atcacccagt attctactgg ccaagtcagc gtggagatcg agtgggagct   2400

gcagaaggaa aacagcaagc gctggaaccc ggagatccag tacacttcca actattacaa   2460

gtctaataat gttgaatttg ctgttaatac tgaaggtgta tatagtgaac cccgccccat   2520

tggcaccaga tacctgactc gtaatctgta attgcttgtt aatcaataaa ccgtttaatt   2580

cgtttcagtt gaactgcggc c                                             2601
```

<210> SEQ ID NO 27
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 27

```
ccatcgacgt cagacgcgga agcttcgatc aactacgcgg acaggtacca aaacaaatgt     60

tctcgtcacg tgggcatgaa tctgatgctg tttccctgca gacaatgcga gagactgaat    120

cagaattcaa atatctgctt cactcacggt gtcaaagact gtttagagtg ctttcccgtg    180

tcagaatctc aacccgtttc tgtcgtcaaa aaggcgtatc agaaactgtg ctacattcat    240

cacatcatgg gaaaggtgcc agacgcttgc actgcttgcg acctggtcaa tgtggacttg    300

gatgactgtg tttctgaaca ataaatgact taaaccaggt atggctgccg atggttatct    360

tccagattgg ctcgaggaca accttagtga aggaattcgc gagtggtggg ctttgaaacc    420

tggagcccct caacccaagg caaatcaaca acatcaagac aacgctcgag gtcttgtgct    480

tccgggttac aaataccttg gacccggcaa cggactcgac aagggggagc cggtcaacgc    540

agtagacgcg gcggccctcg agcacgacaa ggcctacgac cagcagctca aggccggaga    600

caacccgtac ctcaagtaca accacgccga cgccgagttc caggagcggc tcaaagaaga    660

tacgtctttt gggggcaacc tcgggcgagc agtcttccag gccaaaaaga ggcttcttga    720

acctcttggt ctggttgagg aagcggctaa gacggctcct ggaaagaaga ggcctgtaga    780
```

```
gcagtctcct caggaaccgg actcctccgc gggtattggc aaatcgggtg cacagcccgc    840

taaaaagaga ctcaatttcg gtcagactgg cgacacagag tcagtcccag accctcaacc    900

aatcggagaa cctcccgcag ccccctcagg tgtgggatct cttacaatgg cttcaggtgg    960

tggcgcacca gtggcagaca ataacgaagg tgccgatgga gtgggtagtt cctcgggaaa   1020

ttggcattgc gattcccaat ggctggggga cagagtcatc accaccagca cccgaacctg   1080

ggccctgccc acctacaaca atcacctcta caagcaaatc tccaacagca catctggagg   1140

atcttcaaat gacaacgcct acttcggcta cagcaccccc tgggggtatt ttgacttcaa   1200

cagattccac tgccacttct caccacgtga ctggcagcga ctcatcaaca acaactgggg   1260

atttcggcct aagcgactca acttcaagct cttcaacatt caggtcaaag aggttacgga   1320

caacaatgga gtcaagacca tcgccaataa ccttaccagc acggtccagg tcttcacgga   1380

ctcagactat cagctcccgt acgtgctcgg gtcggctcac gagggctgcc tcccgccgtt   1440

cccagcggac gttttcatga ttcctcagta cgggtatctg acgcttaatg atggaagcca   1500

ggccgtgggt cgttcgtcct ttactgcct ggaatatttc ccgtcgcaaa tgctaagaac    1560

gggtaacaac ttccagttca gctacgagtt tgagaacgta cctttccata gcagctacgc   1620

tcacagccaa agcctggacc gactaatgaa tccactcatc gaccaatact tgtactatct   1680

ctcaaagact attaacggtt ctggacagaa tcaacaaacg ctaaaattca gtgtggccgg   1740

acccagcaac atggctgtcc agggaagaaa ctacatacct ggacccagct accgacaaca   1800

acgtgtctca accactgtga ctcaaaacaa caacagcgaa tttgcttggc ctggagcttc   1860

ttcttgggct ctcaatggac gtaatagctt gatgaatcct ggacctgcta tggccagcca   1920

caaagaagga gaggaccgtt tctttccttt gtctggatct ttaatttttg gcaaacaagg   1980

aactggaaga gacaacgtgg atgcggacaa agtcatgata accaacgaag aagaaattaa   2040

aactactaac ccggtagcaa cggagtccta tggacaagtg gccacaaacc accagagtgc   2100

ccaagcacag gcgcagaccg gctgggttca aaaccaagga atacttccgg gtatggtttg   2160

gcaggacaga gatgtgtacc tgcaaggacc catttgggcc aaaattcctc acacggacgg   2220

caactttcac ccttctccgc tgatgggagg gtttggaatg aagcacccgc ctcctcagat   2280

cctcatcaaa aacacacctg tacctgcgga tcctccaacg gccttcaaca aggacaagct   2340

gaactctttc atcacccagt attctactgg ccaagtcagc gtggagatcg agtgggagct   2400

gcagaaggaa aacagcaagc gctggaaccc ggagatccag tacacttcca actattacaa   2460

gtctaataat gttgaatttg ctgttaatac tgaaggtgta tatagtgaac cccgccccat   2520

tggcaccaga tacctgactc gtaatctgta attgcttgtt aatcaataaa ccgtttaatt   2580

cgtttcagtt gaactgcggc c                                             2601
```

<210> SEQ ID NO 28
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 28

```
ccatcgacgt cagacgcgga agcttcgatc aactacgcgg acaggtacca aaacaaatgt     60

tctcgtcacg tgggcatgaa tctgatgctg tttccctgca gacaatgcga gagactgaat    120

cagaattcaa atatctgctt cactcacggt gtcaaagact gtttagagtg ctttcccgtg    180

tcagaatctc aacccgtttc tgtcgtcaaa aaggcgtatc agaaactgtg ctacattcat    240
```

```
cacatcatgg gaaaggtgcc agacgcttgc actgcttgcg acctggtcaa tgtggacttg    300
gatgactgtg tttctgaaca ataaatgact taaaccaggt atggctgccg atggttatct    360
tccagattgg ctcgaggaca accttagtga aggaattcgc gagtggtggg ctttgaaacc    420
tggagcccct caacccaagg caaatcaaca acatcaagac aacgctcgag gtcttgtgct    480
tccgggttac aaatacc ttg gacccggcaa cggactcgac aagggggagc cggtcaacgc    540
agcagacgcg gcggccctcg agcacgacaa ggcctacgac cagcagctca aggccggaga    600
caacccgtac ctcaagtaca accacgccga cgccgagttc caggagcggc tcaaagaaga    660
tacgtctttt gggggcaacc tcgggcgagc agtcttccag gccaaaaaga ggcttcttga    720
acctcttggt ctggttgagg aagcggctaa gacggctcct ggaaagaaga ggcctgtaga    780
gcagtctcct cgggaaccgg actcctccgc gggtattggc aaatcgggtg cacagcccgc    840
taaaaagaga ctcaatttcg gtcagactgg cgacacagag tcagtcccag accctcaacc    900
aatcggagaa cctcccgcag ccccctcagg tgtgggatct cttacaatgg cttcaggtgg    960
tggcgcacca gtggcagaca ataacgaagg tgccgatgga gtgggtagtt cctcgggaaa   1020
ttggcattgc gattcccaat ggctggggga cagagtcatc accaccagca cccgaacctg   1080
ggccctgccc acctacaaca atcacctcta caagcaaatc tccaacagca catctggagg   1140
atcttcaaat gacaacgcct acttcggcta cagcaccccc tgggggtatt ttgacttcaa   1200
cagattccac tgccacttct caccacgtga ctggcagcga ctcatcaaca acaactgggg   1260
attccggcct aagcgactca acttcaagct cttcaacatt caggtcaaag aggttacgga   1320
caacaatgga gtcaagacca tcgccaataa ccttaccagc acggtccagg tcttcacgga   1380
ctcagactat cagctcccgt acgtgctcgg gtcggctcac gagggctgcc tcccgccgtt   1440
cccagcggac gttttcatga ttcctcagta cgggtatctg acgcttaatg atggaagcca   1500
ggccgtgggt cgttcgtcct tttactgcct ggaatatttc ccgtcgcaaa tgctaagaac   1560
gggtaacaac ttccagttca gctacgagtt tgagaacgta cctttccata gcagctacgc   1620
tcacagccaa agcctggacc gactaatgaa tccactcatc gaccaatact tgtactatct   1680
ctcaaagact attaacggtt ctggacagaa tcaacaaacg ctaaaattca gtgtggccgg   1740
acccagcaac atggctgtcc agggaagaaa ctacatacct ggacccagct accgacaaca   1800
acgtgtctca accactgtga ctcaaaacaa caacagcgaa tttgcttggc ctggagcttc   1860
ttcttgggct ctcaatggac gtaatagctt gatgaatcct ggacctgcta tggccagcca   1920
caaagaagga gaggaccgtt tctttccttt gtctggatct ttaatttttg gcaaacaagg   1980
aactggaaga gacaacgtgg atgcggacaa agtcatgata accaacgaag aagaaattaa   2040
aactactaac ccggtagcaa cggagtccta tggacaagtg gccacaaacc accagagtgc   2100
ccaagcacag gcgcagaccg gctgggttca aaaccaagga atacttccgg gtatggtttg   2160
gcaggacaga gatgtgtacc tgcaaggacc catttgggcc aaaattcctc acacggacgg   2220
caactttcac ccttctccgc tgatgggagg gtttggaatg aagcacccgc ctcctcagat   2280
cctcatcaaa aacacacctg tacctgcgga tcctccaacg gccttcaaca aggacaagct   2340
gaactctttc atcacccagt attctactgg ccaagtcagc gtggagatcg agtgggaact   2400
gcagaaggaa aacagcaagc gctggaaccc ggagatccag tacacttcca actattacaa   2460
gtctaataat gttgaatttg ctgttaatac tgaaggtgta tatagtgaac cccgccccat   2520
tggcaccaga tacctgactc gtaatctgta attgcttgtt aatcaataaa ccgtttaatt   2580
```

cgtttcagtt gaactgcggc c 2601

<210> SEQ ID NO 29
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 29
ccatcgacgt cagacgcgga agcttcgatc aactacgcgg acaggtacca aaacaaatgt 60
tctcgtcacg tgggcatgaa tctgatgctg tttccctgca gacaatgcga gagactgaat 120
cagaattcaa atatctgctt cactcacggt gtcaaagact gtttagagtg ctttcccgtg 180
tcagaatctc aacccgtttc tgtcgtcaaa aaggcgtatc agaaactgtg ctacattcat 240
cacatcatgg gaaaggtgcc agacgcttgc actgcttgcg acctggtcaa tgtggacttg 300
gatgactgtg tttctgaaca ataaatgact taaaccaggt atggctgccg atggttatct 360
tccagattgg ctcgaggaca accttagtga aggaattcgc gagtggtggg ctttgaaacc 420
tggagcccct caacccaagg caaatcaaca acatcaagac aacgctcgag gtcttgtgct 480
tccgggttac aaataccttg gacccggcaa cggactcgac aagggggagc cggtcaacgc 540
agcagacgcg gcggccctcg agcacgacaa ggcctacgac cagcagctca aggccggaga 600
caacccgtac ctcaagtaca accacgccga cgccgagttc caggagcggc tcaaagaaga 660
tacgtctttt gggggcaacc tcgggcgagc agtctttcag gccaaaaaga ggcttcttga 720
acctcttggt ctggttgagg aagcggctaa gacggctcct ggaaagaaga ggcctgtaga 780
gcagtctcct caggaaccgg actcctccgc gggtattggc aaatcgggtg cacagcccgc 840
taaaaagaga ctcaatttcg gtcagactgg cgacacagag tcagtcccag accctcaacc 900
aatcggagaa cctcccgcag ccccctcagg tgtgggatct cttacaatgg cttcatgtgg 960
tggcgcacca gtggcagaca ataacgaagg tgccgatgga gtgggtagtt cctcgggaaa 1020
ttggcattgc gattcccaat ggctggggga cagagtcatc accaccagca cccgaacctg 1080
ggccctgccc acctacaaca atcacctcta caagcaaatc tccaacagca catctggagg 1140
atcttcaaat gacaacgcct acttcggcta cagcaccccc tgggggtatt ttgacttcaa 1200
cagattccac tgccacttct caccacgtga ctggcagcga ctcatcaaca acaactgggg 1260
attccggcct aagcgactca acttcaagct cttcaacatt caggtcaaag aggttacgga 1320
caacaatgga gtcaagacca tcgccaataa ccttaccagc acggtccagg tcttcacgga 1380
ctcagactat cagctcccgt acgtgctcgg gtcggctcac gagggctgcc tcccgccgtt 1440
cccagcggac gttttcatga ttcctcagta cgggtatctg acgcttaatg atggaagcca 1500
ggccgtgggt cgttcgtcct tttactgcct ggaatatttc ccgtcgcaaa tgctaagaac 1560
gggtaacaac ttccagttca gctacgagtt tgagaacgta cctttccata gcagctacgc 1620
tcacagccaa agcctggacc gactaatgaa tccactcatc gaccaatact tgtactatct 1680
ctcaaagact attaacggtt ctggacagaa tcaacaaacg ctaaaattca gtgtggccgg 1740
acccagcaac atggctgtcc agggaagaaa ctacatacct ggacccagct accgacaaca 1800
acgtgtctca accactgtga ctcaaaacaa caacagcgaa tttgcttggc ctggagcttc 1860
ttcttgggct ctcaatggac gtaatagctt gatgaatcct ggacctgcta tggccagcca 1920
caaagaagga gaggaccgtt tctttccttt gtctggatct ttaatttttg gcaaacaagg 1980
aactggaaga gacaacgtgg atgcggacaa agtcatgata accaacgaag aagaaattaa 2040
aactactaac ccggtagcaa cggagtccta tggacaagtg gccacaaacc accagagtgc 2100
ccaagcacag gcgcagaccg gctgggttca aaaccaagga atacttccgg gtatggtttg 2160
gcaggacaga gatgtgtacc tgcaaggacc catttgggcc aaaattcctc acacggacgg 2220
caactttcac ccttctccgc tgatgggagg gtttggaatg aagcacccgc ctcctcagat 2280
cctcatcaaa aacacacctg tacctgcgga tcctccaacg gccttcaaca aggacaagct 2340
gaactctttc atcacccagt attctactgg ccaagtcagc gtggagatcg agtgggagct 2400
gcagaaggaa aacagcaagc gctggaaccc ggagatccag tacacttcca actattacaa 2460
gtctaataat gttgaatttg ctgttaatac tgaaggtgta tatagtgaac cccgccccat 2520
tggcaccaga tacctgactc gtaatctgta attgcttgtt aatcaataaa ccgtttaatt 2580
cgtttcagtt gaactgcggc c 2601

<210> SEQ ID NO 30
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 30
ccatcgacgt cagacgcgga agcttcgatc aactacgcgg acaggtacca aaacaaatgt 60
tctcgccacg tgggcatgaa tctgatgctg tttccctgca gacaatgcga gagactgaat 120
cagaattcaa atatctgctt cactcacggt gtcaaagact gtttagagtg ctttcccgtg 180
tcagaatctc aacccgtttc tgtcgtcaaa aaggcgtatc agaaactgtg ctacattcat 240
cacatcatgg gaaaggtgcc agacgcttgc actgcttgcg acctggtcaa tgtggacttg 300
gatgactgtg tttctgaaca ataaatgact taaaccaggt atggctgccg atggttatct 360
tccagattgg ctcgaggaca accttagtga aggaattcgc gagtggtggg ctttgaaacc 420
tggagcccct caacccaagg caaatcaaca acatcaagac aacgctcgag gtcttgtgct 480
tccgggttac aaataccttg gacccggcaa cggactcgac aagggggagc cggtcaacgc 540
agcagacgcg gcggccctcg agcacgacaa ggcctacgac cagcagctca aggccggaga 600
caacccgtac ctcaagtaca accacgccga cgccgagttc caggagcggc tcaaagaaga 660
tacgtctttt gggggcaacc tcgggcgagc agtcttccag gccaaaaaga ggcttcttga 720
acctcttggt ctggttgagg aagcggctaa gacggctcct ggaaagaaga ggcctgtaga 780
gcagtctcct caggaaccgg actcctccgc gggtattggc aaatcgggtg cacagcccgc 840
taaaaagaga ctcaatttcg gtcagactgg cgacacagag tcagtcccag accctcaacc 900
aatcggagaa cctcccgctg ccccctcagg tgtgggatct cttacaatgg cttcaggtgg 960
tggcgcacca gtggcagaca ataacgaagg tgccgatgga gtgggtagtt cctcgggaaa 1020
ttggcattgc gattcccaat ggctgggga cagagtcatc accaccagca cccgaacctg 1080
ggccctgccc acctacaaca atcacctcta caagcaaatc tccaacagca catctggagg 1140
atcttcaaat gacaacgcct acttcggcta cagcaccccc tgggggtatt ttgacttcaa 1200
cagattccac tgccacttct caccacatga ctggcagcga ctcatcaaca acaactgggg 1260
attccggcct aagcgactca acttcaagct cttcaacatt caggtcaaag aggttacgga 1320
caacaatgga gtcaagacca tcgccaataa ccttaccagc acggtccagg tcttcacgga 1380
ctcagactat cagctcccgt acgtgctcgg gtcggctcac gagggctgcc tcccgccgtt 1440
cccagcggac gttttcatga ttcctcagta cgggtatctg acgcttaatg atggaagcca 1500
ggccgtgggt cgttcgtcct tttactgcct ggaatatttc ccgtcgcaaa tgctaagaac 1560
gggtaacaac ttccagttca gctacgagtt tgagaacgta cctttccata gcagctacgc 1620
tcacagccaa agcctggacc gactaatgaa tccactcatc gaccaatact tgtactatct 1680
ctcaaagact attaacggtt ctggacagaa tcaacaaacg ctaaaattca atgtggccgg 1740
acccagcaac atggctgtcc agggaagaaa ctacatacct ggacccagct accgacaaca 1800
acgtgtctca accactgtga ctcaaaacaa caacagcgaa tttgcctggc ctagagcttc 1860
ttcttgggct ctcaatggac gtaatagctt gatgaatcct ggacctgcta tggccagcca 1920
caaagaagga gaggaccgtt tctttccttt gtctggatct ttaatttttg gcaaacaagg 1980
aactggaaga gacaacgtgg atgcggacaa agtcatgata accaacgaag aagaaattaa 2040
aactactaac ccggtagcaa cggagtccta tggacaagtg gccacaaacc accagagtgc 2100
ccaagcacag gcgcagaccg gctgggttca aaaccaagga atacttccgg gtatggtttg 2160
gcaggacaga gatgtgtacc tgcaaggacc catttgggcc aaaattcctc acacggacgg 2220
caactttcac ccttctccgc tgatgggagg gtttggaatg aagcacccgc ctcctcagat 2280
cctcatcaaa aacacacctg tacctgcgga tcctccaacg gccttcaaca aggacaagct 2340
gaactctttc atcacccagt attctactgg ccaagtcagc atggagatcg agtgggagct 2400
gcagaaggaa aacagcaagc gctggaaccc ggagatccag tacacttcca actattacaa 2460
gtctaataat gttgaatttg ctgttaatac tgaaggtgta tatagtgaac cccgccccat 2520
tggcaccaga tacctgactc gtaatctgta attgcttgtt aatcaataaa ccgtttaatt 2580
cgtttcagtt gaactgcggc c 2601

<210> SEQ ID NO 31
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 31
ccatcgacgt cagacgcgga agcttcgatc aactacgcgg acaggtacca aaacaaatgt 60
tctcgtcacg tgggcatgaa tctgatgctg tttccctgca gacaatgcga gagactgaat 120
cagaattcaa atatctgctt cactcacggt gtcaaagact gtttagagtg ctttcccgtg 180
tcagaatctc aacccgtttc tgtcgtcaaa aaggcgtatc agaaactgtg ctacattcat 240
cacatcatgg gaaaggtgcc agacgcttgc actgcttgcg acctggtcaa tgtggacttg 300
gatgactgtg tttctgaaca ataaatgact taaaccaggt atggctgccg atggttatct 360
tccagattgg ctcgaggaca accttagtga aggaattcgc gagtggtggg ctttgaaacc 420
tggagcccct caacccaagg caaatcaaca acatcaagac aacgctcgag gtcttgtgct 480
tccgggttac aaataccttg gacccggcaa cggactcgac aagggggagc cggtcaacgc 540
agcagacgcg gcggccctcg agcacgacaa ggcctacgac cagcagctca aggccggaga 600
caacccgtac ctcaagtaca accacgccga cgccgagttc caggagcggc tcaaagaaga 660
tacgtctttt gggggcaacc tcgggcgagc agtcttccag gccaaaaaga ggcttcttga 720
acctcttggt ctggttgagg aagcggctaa gacggctcct ggaaagaaga ggcctgtaga 780
gcagtctcct caggaaccgg actcctccgc gggtattggc aaatcgggtg cacagcccgc 840
taaaaagaga ctcaatttcg gtcagactgg cgacacagag tcagtcccag accctcaacc 900

```
aatcggagaa cctcccgcag ccccctcagg tgtgggatct cttacaatgg cttcaggtgg    960

tggcgcacca gtggcagaca ataacgaagg tgccgatgga gtgggtagtt cctcgggaaa   1020

ttggcattgc gattcccaat ggctggggga cagagtcatc accaccagca cccgaacctg   1080

ggccctgccc acctacaaca atcacctcta caagcaaatc tccaacagca catctggagg   1140

atcttcaaat gacaacgcct acttcggcta cagcaccccc tgggggtatt ttgacttcaa   1200

cagattccac tgccacttct caccacgtga ctggcagcga ctcatcaaca acaactgggg   1260

attccggcct aagcgactca acttcaagct cttcaacatt caggtcaaag aggttacgga   1320

caacaatgga gtcaagacca tcgccaataa ccttaccagc acggtccagg tcttcacgga   1380

ctcagactat cagctcccgt acgtgctcgg gtcggctcac gagggctgcc tcccgccgtt   1440

cccagcggac gttttcatga ttcctcagta cgggtatctg acgcttaatg atggaagcca   1500

ggccgtgggt cgttcgtcct tttactgcct ggaatatttc ccgtcgcaaa tgctaagaac   1560

gggtaacaac ttccagttca gctacgagtt tgagaacgta cctttccata gcagctacgc   1620

tcacagccaa agcctggacc gactaatgaa tccactcatc gaccaatact tgtactatct   1680

ctcaaagact attaacggtt ctggacagaa tcaacaaacg ctaaaattca gtgtggccgg   1740

acccagcaac atggctgtcc agggaagaaa ctacatacct ggacccagct accgacaaca   1800

acgtgtctca accactgtga ctcaaaacaa caacagcgaa tttgcttggc ctagagcttc   1860

ttcttgggct ctcaatggac gtaatagctt gatgaatcct ggacctgcta tggccagcca   1920

caaagaagga gaggaccgtt tctttccttt gtctggatct ttaatttttg gcaaacaagg   1980

aactggaaga gacaacgtgg atgcggacaa agtcatgata accaacgaag aagaaattaa   2040

aactactaac ccggtagcaa cggagtccta tggacaagtg gccacaaacc accagagtgc   2100

ccaagcacag gcgcagaccg gctgggttca aaaccaagga atacttccgg gtatggtttg   2160

gcaggacaga gatgtgtacc tgcaaggacc catttgggcc aaaattcctc acacggacgg   2220

caactttcac ccttctccgc tgatgggagg gtttggaatg aagcacccgc ctcctcagat   2280

cctcatcaaa aacacacctg tacctgcgga tcctccaacg gccttcaaca aggacaagct   2340

gaactctttc atcacccagt attctactgg ccaagtcagc gtggagatcg agtgggagct   2400

gcagaaggaa aacagcaagc gctggaaccc ggagatccag tacacttcca actattacaa   2460

gtctaataat gttgaatttg ctgttaatac tgaaggtgta tatagtgaac ccgccccat    2520

tggcaccaga tacctgactc gtaatctgta attgcttgtt aatcaataaa ccgtttaatt   2580

cgtttcagtt gaactgcggc c                                             2601
```

```
<210> SEQ ID NO 32
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 32

ccatcgacgt cagacgcgga agcttcgatc aactacgcgg acaggtacca aaacaaatgt     60

tctcgtcacg tgggcatgaa tctgatgctg tttccctgca gacaatgcga gagactgaat    120

cagaattcaa atatctgctt cactcacggt gtcaaagact gtttagagtg ctttcccgtg    180

tcagaatctc aacccgtttc tgtcgtcaaa aaggcgtatc agaaactgtg ctacattcat    240

cacatcatgg gaaaggtgcc agacgcttgc actgcttgcg acctggtcaa tgtggacttg    300
```

-continued

```
gatgactgtg tttctgaaca ataaatgact taaaccaggt atggctgccg atggttatct    360
tccagattgg ctcgaggaca accttagtga aggaattcgc gagtggtggg ctttgaaacc    420
tggagcccct caacccaagg caaatcaaca acatcaagac aacgctcgag gtcttgtgct    480
tccgggttac aaataccttg gacccggcaa cggactcgac aagggggagc cggtcaacgc    540
agcagacgcg gcggccctcg agcacgacaa ggcctacgac cagcagctca aggccggaga    600
caacccgtac ctcaagtaca accacgccga cgccgagttc caggagcggc tcaaagaaga    660
tacgtctttt gggggcaacc tcgggcgagc agtcttccag gccaaaaaga ggcttcttga    720
acctcttggt ctggttgagg aagcggctaa gacggctcct ggaaagaaga ggcctgtaga    780
gcagtctcct caggaaccgg actcctccgc gggtattggc aaatcgggtg cacagcccgc    840
taaaaagaga ctcaatttcg gtcagactgg cgacacagag tcagtcccag accctcaacc    900
aatcggagaa cctcccgcag ccccctcagg tgtgggatct cttacaatgg cttcaggtgg    960
tggcgcacca gtggcagaca ataacgaagg tgccgatgga gtgggtagtt cctcgggaaa   1020
ttggcattgc gattcccaat ggctgggga cagagtcatc accaccagca cccgaacctg   1080
ggccctgccc acctacaaca atcacctcta caagcaaatc tccaacagca catctggagg   1140
atcttcaaat gacaacgcct acttcggcta cagcaccccc tgggggtatt ttgacttcaa   1200
cagattccac tgccacttct caccacgtga ctggcagcga ctcatcaaca acaactgggg   1260
attccggcct aagcgactca acttcaagct cttcaacatt caggtcaaag aggttacgga   1320
caacaatgga gtcaagacca tcgccaataa ccttaccagc acggtccagg tcttcacgga   1380
ctcagactat cagctcccgt acgtgctcgg gtcggctcac gagggctgcc tcccgccgtt   1440
cccagcggac gttttcatga ttcctcagta cgggtatctg acgcttaatg atggaagcca   1500
ggccgtgggt cgttcgtcct tttactgcct ggaatatttc ccgtcgcaaa tgctaagaac   1560
gggtaacaac ttccagttca gctacgagtt tgagaacgta cctttccata gcagctacgc   1620
tcacagccaa agcctggacc gactaatgaa tccactcatc gaccaatact tgtactatct   1680
ctcaaagact attaacggtt ctggacagaa tcaacaaacg ctaaaattca gtgtggccgg   1740
acccagcaac atggctgtcc agggaagaaa ctacatacct ggacccagct accgacaaca   1800
acgtgtctca accactgtga ctcaaaacaa caacagcgaa tttgcttggc ctagagcttc   1860
ttcttgggct ctcaatggac gtaatagctt gatgaatcct ggacctgcta tggccagcca   1920
caaagaagga gaggaccgtt tctttccttt gtctggatct ttaatttttg gcaaacaagg   1980
aactggaaga gacaacgtgg atgcggacaa agtcatgata accaacgaag aagaaattaa   2040
aactactaac ccggtagcaa cggagtccta tggacaagtg gccacaaacc accagagtgc   2100
ccaagcacag gcgcagaccg gctgggttca aaaccaagga atacttccgg gtatggtttg   2160
gcaggacaga gatgtgtacc tgcaaggacc catttgggcc aaaattcctc acacggacgg   2220
caactttcac ccttctccgc tgatgggagg gtttggaatg aagcacccgc ctcctcagat   2280
cctcatcaaa aacacacctg tacctgcgga tcctccaacg gccttcaaca aggacaagct   2340
gaactctttc atcacccagt attctactgg ccaagtcagc gtggagatcg agtgggagcg   2400
gcagaaggaa aacagcaagc gctggaaccc ggagatccag tacacttcca actattacaa   2460
gtctaataat gttgaatttg ctgttaatac tgaaggtgta tatagtgaac cccgccccat   2520
tggcaccaga tacctgactc gtaatctgta attgcttgtt aatcaataaa ccgtttaatt   2580
cgtttcagtt gaactgcggc c                                             2601
```

<210> SEQ ID NO 33
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 33
ccatcgacgt cagacgcgga agcttcgatc aactacgcgg acaggtacca aaacaaatgt 60
tctcgtcacg tgggcatgaa tctgatgctg tttccctgca gacaatgcga gagactgaat 120
cagaattcaa atatctgctt cactcacggt gtcaaagact gtttagagtg ctttcccgtg 180
tcagaatctc aacccgtttc tgtcgtcaaa aaggcgtatc agaaactgtg ctacattcat 240
cacatcatgg gaaaggtgcc agacgcttgc actgcttgcg acctggtcaa tgtggacttg 300
gatgactgtg tttctgaaca ataaatgact taaaccaggt atggctgccg atggttatct 360
tccagattgg ctcgaggaca accttagtga aggaattcgc gagtggtggg ctttgaaacc 420
tggagcccct caacccaagg caaatcaaca acatcaagac aacgctcgag gtcttgtgct 480
tccgggttac aaataccttg gacccggcaa cggactcgac aagggggagc cggtcaacgc 540
agcagacgcg gcggccctcg agcacgacaa ggcctacgac cagcagctca aggccggaga 600
caacccgtac ctcaagtaca accacgccga cgccgagttc caggagcggc tcaaagaaga 660
tacgtctttt gggggcaacc tcgggcgagc agtcttccag gccaaaaaga ggcttcttga 720
acctcttggt ctggttgagg aagcggctaa gacggctcct ggaaagaaga ggcctgtaga 780
gcagtctcct caggaaccgg actcctccgc gggtattggc aaatcgggtg cacagcccgc 840
taaaaagaga ctcaatttcg gtcagactgg cgacacagag tcagtcccag accctcaacc 900
aatcggagaa cctcccgcag ccccctcagg tgtgggatct cttacaatgg cttcaggtgg 960
tggcgcacca gtggcagaca ataacgaagg tgccgatgga gtgggtagtt cctcgggaaa 1020
ttggcattgc gattcccaat ggctgggga cagagtcatc accaccagca cccgaacctg 1080
ggccctgccc acctacaaca atcacctcta caagcaaatc tccaacagca catctggagg 1140
atcttcaaat gacaacgcct acttcggcta cagcaccccc tgggggtatt ttgacttcaa 1200
cagattccac tgccacttct caccacgtga ctggcagcga ctcatcaaca acaactgggg 1260
attccggcct aagcgactca acttcaagct cttcaacatt caggtcaaag aggttacgga 1320
caacaatgga gtcaagacca tcgccaataa ccttaccagc acggtccagg tcttcgcgga 1380
ctcagactat cagctcccgt acgtgctcgg gtcggctcac gagggctgcc tcccgccgtt 1440
cccagcggac gttttcatga ttcctcagta cgggtatctg acgcttaatg atggaagcca 1500
ggccgtgggt cgttcgtcct tttactgcct ggaatatttc ccgtcgcaaa tgctaagaac 1560
gggtaacaac ttccagttca gctacgagtt tgagaacgta cctttccata gcagctacgc 1620
tcacagccaa agcctggacc gactaatgaa tccactcatc gaccaatact tgtactatct 1680
ctcaaagact attaacggtt ctggacagaa tcaacaaacg ctaaaattca gtgtggccgg 1740
acccagcaac atggctgtcc agggaagaaa ctacatacct ggacccagct accgacaaca 1800
acgtgtctca accactgtga ctcaaaacaa caacagcgaa tttgcttggc ctagagcttc 1860
ttcttgggct ctcaatggac gtaatagctt gatgaatcct ggacctgcta tggccagcca 1920
caaagaagga gaggaccgtt tctttccttt gtctggatct ttaatttttg gcaaacaagg 1980
aactggaaga gacaacgtgg atgcggacaa agtcatgata accaacgaag aagaaattaa 2040
aactactaac ccggtagcaa cggagtccta tggacaagtg gccacaaacc accagagtgc 2100

```
ccaagcacag gcgcagaccg gctgggttca aaaccaagga atacttccgg gtatggtttg   2160

gcaggacaga gatgtgtacc tgcaaggacc catttgggcc aaaattcctc acacggacgg   2220

caactttcac ccttctccgc tgatgggagg gtttggaatg aagcacccgc ctcctcagat   2280

cctcatcaaa aacacacctg tacctgcgga tcctccaacg gccttcaaca aggacaagct   2340

gaactctttc atcacccagt attctactgg ccaagtcagc gtggagatcg agtgggagct   2400

gcagaaggaa aacagcaagc gctggaaccc ggagatccag tacacttcca actattacaa   2460

gtctaataat gttgaatttg ctgttaatac tgaaggtgta tatagtgaac cccgccccat   2520

tggcaccaga tacctgactc gtaatctgta attgcttgtt aatcaataaa ccgtttaatt   2580

cgtttcagtt gaactgcggc c                                             2601


<210> SEQ ID NO 34
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 34

ccatcgacgt cagacgcgga agcttcgatc aactacgcgg acaggtacca aaacaaatgt     60

tctcgtcacg tgggcatgaa tctgatgctg tttccctgca gacaatgcga gagactgaat    120

cagaattcaa atatctgctt cactcacggt gtcaaagact gtttagagtg ctttcccgtg    180

tcagaatctc aacccgtttc tgtcgtcaaa aaggcgtatc agaaactgtg ctacattcat    240

cacatcatgg gaaaggtgcc agacgcttgc actgcttgcg acctggtcaa tgtggacttg    300

gatgactgtg tttctgaaca ataaatgact taaaccaggt atggctgccg atggttatct    360

tccagattgg ctcgaggaca accttagtga aggaattcgc gagtggtggg ctttgaaacc    420

tggagcccct caacccaagg caaatcaaca acatcaagac aacgctcgag gtcttgtgct    480

tccgggttac aaataccttg gacccggcaa cggactcgac aagggggagc cggtcaacgc    540

agcagacgcg gcggccctcg agcacgacaa ggcctacgac cagcagctca aggccggaga    600

caacccgtac ctcaagtaca accacgccga cgccgagttc caggagcggc tcaaagaaga    660

tacgtctttt gggggcaacc tcgggcgagc agtcttccag gccaaaaaga ggcttcttga    720

acctcttggt ctggttgagg aagcggctaa gacggctcct ggaaagaaga ggcctgtaga    780

gcagtctcct caggaaccgg actcctccgc gggtattggc aaatcgggtg cacagcccgc    840

taaaaagaga ctcaatttcg gtcagactgg cgacacagag tcagtcccag accctcaacc    900

aatcggagaa cctcccgcag ccccctcagg tgtgggatct cttacaatgg cttcaggtgg    960

tggcgcacca gtggcagaca ataacgaagg tgccgatgga gtgggtagtt cctcgggaaa   1020

ttggcattgc gattcccaat ggctggggga cagagtcatc accaccagca cccgaacctg   1080

ggccctgccc acctacaaca atcacctcta caagcaaatc tccaacagca catctggagg   1140

atcttcaaat gacaacgcct acttcggcta cagcaccccc tgggggtatt ttgacttcaa   1200

cagattccac tgccacttct caccacgtga ctggcagcga ctcatcaaca acaactgggg   1260

attccggcct aagcgactca acttcaagct cttcaacatt caggtcaaag aggttacgga   1320

caacaatgga gtcaagacca tcgccaataa ccttaccagc acggtccagg tcttcacgga   1380

ctcagactat cagctcccgt acgtgctcgg gtcggctcac gagggctgcc tcccgccgtt   1440

cccagcggac gttttcatga ttcctcagta cgggtatctg acgcttaatg atggaagcca   1500

ggccgtgggt cgttcgtcct tttactgcct ggaatatttc ccgtcgcaaa tgctaagaac   1560
```

gggtaacaac ttccagttca gctacgagtt tgagaacgta cctttccata gcagctacgc 1620
tcacagccaa agcctggacc gactaatgaa tccactcatc gaccaatact tgtactatct 1680
ctcaaagact attaacggtt ctggacagaa tcaacaaacg ctaaaattca gtgtggccgg 1740
acccagcaac atggctgtcc agggaagaaa ctacatacct ggacccagct accgacaaca 1800
acgtgtctca accactgtga ctcaaaacaa caacagcgaa attgcttggc ctagagcttc 1860
ttcttgggct ctcaatggac gtaatagctt gatgaatcct ggacctgcta tggccagcca 1920
caaagaagga gaggaccgtt tctttccttt gtctggatct ttaatttttg gcaaacaagg 1980
aactggaaga gacaacgtgg atgcggacaa agtcatgata accaacgaag aagaaattaa 2040
aactactaac ccagtagcaa cggagtccta tggacaagtg gccacaaacc accagagtgc 2100
ccaagcacag gcgcagaccg gctgggttca aaaccaagga atacttccgg gtatggtttg 2160
gcaggacaga gatgtgtacc tgcaaggacc catttgggcc aaaattcctc acacggacgg 2220
caactttcac ccttctccgc tgatgggagg gtttggaatg aagcacccgc ctcctcagat 2280
cctcatcaaa aacacacctg tacctgcgga tcctccaacg gccttcaaca aggacaagct 2340
gaactctttc atcacccagt attctactgg ccaagtcagc gtggagatcg agtgggagct 2400
gcagaaggaa aacagcaagc gctggaaccc ggagatccag tacacttcca actattgcaa 2460
gtctaataat gttgaatttg ctgttaatac tgaaggtgta tatagtgaac cccgccccat 2520
tggcaccaga tacctgactc gtaatctgta attgcttgtt aatcaataaa ccgtttaatt 2580
cgtttcagtt gaactgcggc c 2601

<210> SEQ ID NO 35
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 35
ccatcgacgt cagacgcgga agcttcgatc aactacgcgg acaggtacca aaacaaatgt 60
tctcgtcacg tgggcatgaa tctgatgctg tttccctgca gacaatgcga gagactgaat 120
cagaattcaa atatctgctt cactcacggt gtcaaagact gtttagagtg ctttcccgtg 180
tcagaatctc aacccgtttc tgtcgtcaaa aaggcgtatc agaaactgtg ctacattcat 240
cacatcatgg gaaaggtgcc agacgcttgc actgcttgcg acctggtcaa tgtggacttg 300
gatgtctgtg tttctgaaca ataaatgact taaaccaggt atggctgccg atggttatct 360
tccagattgg ctcgaggaca accttagtga aggaattcgc gagtggtggg ctttgaaacc 420
tggagcccct caacccaagg caaatcaaca acatcaagac aacgctcgag gtcttgtgct 480
tccgggttac aaataccttg gacccggcaa cggactcgat aagggggagc cggtcaacgc 540
agcagacgcg gcggccctcg agcacgacaa ggcctacgac cagcagctca aggccggaga 600
caacccgtac ctcaagtaca accacgccga cgccgagttc caggagcggc tcaaagaaga 660
tacgtctttt gggggcaacc tcgggcgagc agtcttccag gccaaaaaga ggcttcttga 720
acctcttggt ctggttgagg aagcggctaa gacggctcct ggaaagaaga ggcctgtaga 780
gcagtctcct caggaaccgg actcctccgc gggtattggc aaatcgggtg cacagcccgc 840
taaaaagaga ctcaatttcg gtcagactgg cgacacagag tcagtcccag accctcaacc 900
aatcggagaa cctcccgcag ccccctcagg tgtgggatct cttacaatgg cttcaggtgg 960

-continued

```
tggcgcacca gtggcagaca ataacgaagg tgccgatgga gtgggtagtt cctcgggaaa   1020

ttggcattgc gattcccaat ggctggggga cagagtcatc accaccagca cccgaacctg   1080

ggccctgccc acctacaaca atcacctcta caagcaaatc tccaacagca catctggagg   1140

atcttcaaat gacaacgcct acttcggcta cagcaccccc tgggggtatt ttgacttcaa   1200

cagattccac tgccacttct caccacgtga ctggcagcga ctcatcaaca acaactgggg   1260

attccggcct aagcgactca acttcaagct cttcaacatt caggtcaaag aggttacgga   1320

caacaatgga gtcaagacca tcgccaataa ccttaccagc acggtccagg tcttcacgga   1380

ctcagactat cagctcccgt acgtgctcgg gtcggctcac gagggctgcc tcccgccgtt   1440

cccagcggac gttttcatga ttcctcagta cgggtatctg acgcttaatg atggaagcca   1500

ggccgtgggt cgttcgtcct tttactgcct ggaatatttc ccgtcgcaaa tgctaagaac   1560

gggtaacaac ttccagttca gctacgagtt tgagaacgta cctttccata gcagctacgc   1620

tcacagccaa agcctggacc gactaatgaa tccactcatc gaccaatact tgtactatct   1680

ctcaaagact attaacggtt ctggacagaa tcaacaaacg ctaaaattca gtgtggccgg   1740

acccagcaac atggctgtcc agggaagaaa ctacatacct ggacccagct accgacaaca   1800

acgtgtctca accactgtga ctcaaaacaa caacagcgaa tttgcttggc ctagagcttc   1860

ttcttgggct ctcaatggac gtaatagctt gatgaatcct ggacctgcta tggccagcca   1920

caaagaagga gaggaccgtt tctttccttt gtctggatct ttaatttttg gcaaacaagg   1980

aactggaaga gacaacgtgg atgcggacaa agtcatgata accaacgaag aagaaattaa   2040

aactactaac ccggtagcaa cggagtccta tggacaagtg gccacaaacc accagagtgc   2100

ccaagcacag gcgcagaccg gctgggttca aaaccaagga atacttccgg gtatggtttg   2160

gcaggacaga gatgtgtacc tgcaaggacc catttgggcc aaaattcctc acacggacgg   2220

caactttcac ccttctccgc tgatgggagg gtttggaatg aagcacccgc ctcctcagat   2280

cctcatcaaa aacacacctg tacctgcgga tcctccaacg gccttcaaca aggacaagct   2340

gaactctttc atcacccagt attctactgg ccaagtcagc gtggagatcg agtgggagct   2400

gcagaaggaa aacagcaagc gctggaaccc ggagatccag tacacttcca actattacaa   2460

gtctaataat gttgaatttg ctgttaatac tgaaggtgta tatagtgaac cccgccccat   2520

tggcaccaga tacctgactc gtaatctgta attgcttgtt aatcaataaa ccgtttaatt   2580

cgtttcagtt gaactgcggc c                                               2601
```

<210> SEQ ID NO 36
<211> LENGTH: 23
<212> TYPE: DNA
<213> ORGANISM: Artificial Sequence
<220> FEATURE:
<223> OTHER INFORMATION: forward primer

<400> SEQUENCE: 36

```
ccacctacaa caaccacctc tac                                               23
```

<210> SEQ ID NO 37
<211> LENGTH: 25
<212> TYPE: DNA
<213> ORGANISM: Artificial Sequence
<220> FEATURE:
<223> OTHER INFORMATION: reverse primer

<400> SEQUENCE: 37

```
cgtggcagtg gattctgttg aagtc                                             25
```

<210> SEQ ID NO 38
<211> LENGTH: 26
<212> TYPE: DNA
<213> ORGANISM: Artificial Sequence
<220> FEATURE:
<223> OTHER INFORMATION: forward primer

<400> SEQUENCE: 38
gctgcgtcaa ctggaccaat gagaac 26

<210> SEQ ID NO 39
<211> LENGTH: 28
<212> TYPE: DNA
<213> ORGANISM: Artificial Sequence
<220> FEATURE:
<223> OTHER INFORMATION: reverse primer

<400> SEQUENCE: 39
cgcagagacc aaagttcaac tgaaacga 28

<210> SEQ ID NO 40
<211> LENGTH: 34
<212> TYPE: DNA
<213> ORGANISM: Artificial Sequence
<220> FEATURE:
<223> OTHER INFORMATION: forward primer

<400> SEQUENCE: 40
atcgatacta gtccatcgac gtcagacgcg gaag 34

<210> SEQ ID NO 41
<211> LENGTH: 40
<212> TYPE: DNA
<213> ORGANISM: Artificial Sequence
<220> FEATURE:
<223> OTHER INFORMATION: reverse primer

<400> SEQUENCE: 41
atcgatgcgg ccgcagttca actgaaacga atcaaccggt 40

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42
cgtcttttgg gggcaacctc g 21

<210> SEQ ID NO 43
<211> LENGTH: 28
<212> TYPE: DNA
<213> ORGANISM: Artificial Sequence
<220> FEATURE:
<223> OTHER INFORMATION: primer

<400> SEQUENCE: 43
gactcatcaa caacaactgg ggattccg 28

<210> SEQ ID NO 44
<211> LENGTH: 28
<212> TYPE: DNA
<213> ORGANISM: Artificial Sequence
<220> FEATURE:

<223> OTHER INFORMATION: primer

<400> SEQUENCE: 44
gactcatcaa caacaattgg ggattccg 28

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
ccgtcgcaaa tgctaagaac g 21

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
ccttctcaga tgctgcgtac c 21

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
ccttcgcaga tgctgagaac c 21

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
ccttctcaga tgctgagaac g 21

<210> SEQ ID NO 49
<211> LENGTH: 22
<212> TYPE: DNA
<213> ORGANISM: Artificial Sequence
<220> FEATURE:
<223> OTHER INFORMATION: primer

<400> SEQUENCE: 49
cggtagcaac ggagtcctat gg 22

<210> SEQ ID NO 50
<211> LENGTH: 22
<212> TYPE: DNA
<213> ORGANISM: Artificial Sequence
<220> FEATURE:
<223> OTHER INFORMATION: primer

<400> SEQUENCE: 50
gctgttttcc ttctgcagct cc 22

<210> SEQ ID NO 51
<211> LENGTH: 22
<212> TYPE: DNA
<213> ORGANISM: Artificial Sequence
<220> FEATURE:
<223> OTHER INFORMATION: primer

<400> SEQUENCE: 51
gctgttttct ttctgcagct cc 22

<210> SEQ ID NO 52
<211> LENGTH: 28
<212> TYPE: DNA
<213> ORGANISM: Artificial Sequence
<220> FEATURE:
<223> OTHER INFORMATION: primer

<400> SEQUENCE: 52
cgtactgagg aatcatgaaa acgtccgc 28

<210> SEQ ID NO 53
<211> LENGTH: 24
<212> TYPE: DNA
<213> ORGANISM: Artificial Sequence
<220> FEATURE:
<223> OTHER INFORMATION: primer

<400> SEQUENCE: 53
cgttattgtc tgccattggt gcgc 24

<210> SEQ ID NO 54
<211> LENGTH: 24
<212> TYPE: DNA
<213> ORGANISM: Artificial Sequence
<220> FEATURE:
<223> OTHER INFORMATION: primer

<400> SEQUENCE: 54
cgttattgtc tgccactggt gcgc 24

<210> SEQ ID NO 55
<211> LENGTH: 22
<212> TYPE: DNA
<213> ORGANISM: Artificial Sequence
<220> FEATURE:
<223> OTHER INFORMATION: primer

<400> SEQUENCE: 55
cgagccaatc tggaagataa cc 22

<210> SEQ ID NO 56
<211> LENGTH: 36
<212> TYPE: DNA
<213> ORGANISM: Artificial Sequence
<220> FEATURE:
<223> OTHER INFORMATION: forward primer

<400> SEQUENCE: 56
gatcatatcg atggtggagt cgtgacgtga attacg 36

<210> SEQ ID NO 57
<211> LENGTH: 31
<212> TYPE: DNA

<213> ORGANISM: Artificial Sequence
<220> FEATURE:
<223> OTHER INFORMATION: reverse primer

<400> SEQUENCE: 57
gatcataagc ttccgcgtct gacgtcgatg g 31

<210> SEQ ID NO 58
<211> LENGTH: 22
<212> TYPE: DNA
<213> ORGANISM: Artificial Sequence
<220> FEATURE:
<223> OTHER INFORMATION: primer

<400> SEQUENCE: 58
ggagagagct acttccacat gc 22

<210> SEQ ID NO 59
<211> LENGTH: 23
<212> TYPE: DNA
<213> ORGANISM: Artificial Sequence
<220> FEATURE:
<223> OTHER INFORMATION: primer

<400> SEQUENCE: 59
ccttcaatgc ggcctccaac tcg 23

<210> SEQ ID NO 60
<211> LENGTH: 25
<212> TYPE: DNA
<213> ORGANISM: Artificial Sequence
<220> FEATURE:
<223> OTHER INFORMATION: primer

<400> SEQUENCE: 60
cgtcacctcc aacaccaaca tgtgg 25

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
cgtgtcagaa tctcaacccg 20

<210> SEQ ID NO 62
<211> LENGTH: 25
<212> TYPE: DNA
<213> ORGANISM: Artificial Sequence
<220> FEATURE:
<223> OTHER INFORMATION: primer

<400> SEQUENCE: 62
ccacctcaac cacgtgatcc tttgc 25

<210> SEQ ID NO 63
<211> LENGTH: 24
<212> TYPE: DNA
<213> ORGANISM: Artificial Sequence
<220> FEATURE:
<223> OTHER INFORMATION: primer

<400> SEQUENCE: 63
cgattgctgg aaatgtcctc cacg 24

<210> SEQ ID NO 64
<211> LENGTH: 21
<212> TYPE: DNA
<213> ORGANISM: Artificial Sequence
<220> FEATURE:
<223> OTHER INFORMATION: primer

<400> SEQUENCE: 64
gcacaaagaa aagggcctcc g 21

<210> SEQ ID NO 65
<211> LENGTH: 21
<212> TYPE: DNA
<213> ORGANISM: Artificial Sequence
<220> FEATURE:
<223> OTHER INFORMATION: forward primer

<400> SEQUENCE: 65
aactgcacaa ggccatgaag a 21

<210> SEQ ID NO 66
<211> LENGTH: 27
<212> TYPE: DNA
<213> ORGANISM: Artificial Sequence
<220> FEATURE:
<223> OTHER INFORMATION: reverse primer

<400> SEQUENCE: 66
ctcaaagtat tcagcatagg tgatgtc 27

<210> SEQ ID NO 67
<211> LENGTH: 28
<212> TYPE: DNA
<213> ORGANISM: Artificial Sequence
<220> FEATURE:
<223> OTHER INFORMATION: probe

<400> SEQUENCE: 67
ttgccttcac tgatgctcac attgaggt 28

RECOMBINANT ADENO-ASSOCIATED VECTORS FOR TARGETED TREATMENT

PRIORITY CLAIM

This application is a continuation of U.S. patent application Ser. No. 14/582,070, filed Dec. 23, 2014, which is a continuation of U.S. patent application Ser. No. 13/668,120, filed Nov. 2, 2012, now U.S. Pat. No. 8,927,514, which is a continuation-in-part of U.S. patent application Ser. No. 13/097,046, filed Apr. 28, 2011, now U.S. Pat. No. 8,628,966, which claims priority to U.S. Provisional Patent Application Ser. No. 61/330,272, filed Apr. 30, 2010, each of which is incorporated herein by reference in its entirety.

STATEMENT REGARDING FEDERALLY FUNDED RESEARCH

This invention was made with government support under Grant No. R01 HL087285 awarded by the National Institutes of Health. The government has certain rights in the invention.

BACKGROUND

The adeno-associated virus (AAV) genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. Rep is composed of four overlapping genes encoding rep proteins required for the AAV life cycle, and cap contains overlapping nucleotide sequences of capsid proteins: VP1, VP2 and VP3, which interact together to form a capsid of an icosahedral symmetry.

Recombinant adeno-associated virus (rAAV) vectors derived from the replication defective human parvovirus AAV2 are proving to be safe and effective gene transfer vehicles that have yet to be definitively identified as either pathogenic or oncogenic [3-4, 6, 18-19, 26, 31]. rAAV transduce non-dividing primary cells, are low in immunogenicity, and direct sustained transgene expression in vivo [6, 10, 20]. Infection with wild type AAV is associated with inhibition of oncogenic transformation and AAV inverted terminal repeats may actually confer oncoprotection [2, 28, 52-55]. A recent survey of panels of human tissues found that the marrow and liver were the two most common sites of naturally occurring AAV isolates in humans, suggesting that infection of marrow cells by AAV is not rare.

Use of viral vectors for gene therapy has been long considered. Due to its potential for long-lived correction and the ease of ex vivo manipulation, the hematopoietic system was one of the earliest targets of gene therapy. Despite significant effort, however, actual therapeutic success remains elusive [5]. This is due to the recognized inability of most viral vectors to efficiently transduce quiescent, non-dividing hematopoietic stem cells (HSC) [23] as well as safety concerns arising from insertional oncogenesis [15, 22]. However, stable gene transfer has been successfully demonstrated to both murine and human HSC by rAAV [8, 11-12, 24, 27, 29-30, 37].

It has been additionally difficult to effectively use viral vectors in gene therapy for treating neurological conditions, particularly central nervous system diseases or disorders due to the difficulty of crossing the blood-brain barrier, a cellular and metabolic separation of the circulating blood from the brain extracellular fluid created by tight junctions between endothelial cells that restrict the passage of solutes.

CD34 is cell surface glycoprotein and a cell-cell adhesion factor. CD34 protein is expressed in early hematopoietic and vascular tissue and a cell expressing CD34 is designated $CD34^+$. Chromosomal integration of rAAV in human $CD34^+$ HSC [8, 12, 16, 29] and efficient transduction of primitive, pluripotent, self-renewing human HSC capable of supporting primary and secondary multi-lineage engraftment has been demonstrated in immune-deficient NOD-SCID mice [29]. Transduction of primitive HSC capable of supporting serial engraftment was shown to be attributable to the propensity of rAAV to efficiently transduce primitive, quiescent CD34+CD38− cells residing in GO [24]. Despite several reports of successful rAAV-mediated gene transfer into human HSC in vitro and in murine and non-human primate HSC in vivo, controversy regarding the utility of rAAV for HSC transduction still persists. These discrepancies arose primarily from short-term in vitro studies that assessed transduction by expression profiling and are attributable to the identified restrictions to transgene expression from rAAV2, including viral uncoating [35], intracellular trafficking [33], nuclear transport and second strand synthesis [36].

While AAV2 remains the best-studied prototypic virus for AAV-based vectors [1, 13, 18, 21], the identification of a large number of new AAV serotypes significantly enhances the repertoire of potential gene transfer vectors [14]. AAV1, 3 and 4 were isolated as contaminants of adenovirus stocks, and AAV5 was isolated from a human condylomatous wart. AAV6 arose as a laboratory recombinant between AAV1 and AAV2. Recently, more than 100 novel distinct isolates of naturally occurring AAV in human and non-human primate tissues were identified. This led to the use of capsids derived from some of these isolates for pseudotyping, replacing the envelope proteins of AAV2 with the novel envelopes, whereby rAAV2 genomes are then packaged using AAV2 rep and novel capsid genes. The use of novel capsids, the proteins as part of the viral shell, resulted in the circumvention of many limitations in transgene expression associated with AAV2 [32, 35-36].

In an effort to circumvent these restrictions, recent research has shown that novel capsid sequences result in reduced proteasome-mediated capsid degradation, increased nuclear trafficking and retention. Novel capsids, many of which utilize novel receptors, broadens the tropism of rAAV allowing for efficient transduction of previously refractory tissues and provides a means of circumventing highly prevalent pre-existing serologic immunity to AAV2, which posed major clinical limitations in a recent trial. Notably, some novel capsids appear to alter the intracellular processing of rAAV. For example, uncoating and transgene expression is accelerated in the context of AAV8 as compared to native AAV2 capsids. Recently, transgene expression was shown to be based upon capsid proteins, regardless of the serotype origin of the inverted terminal repeats (ITRs).

Naturally occurring AAV is readily identified in cytokine-primed peripheral blood stem cells. Capsid sequences of these AAV are unique. These capsids are capable of pseudotyping recombinant AAV2 genomes. Any improvement in the area of gene therapy regarding both permanent and reversible gene transfer and expression for therapeutic purposes, particularly if such advances targeted previously unsuccessfully targeted tissues like the central nervous system tissues including the brain, would be a significant improvement in the art. Moreover, safe and efficient gene delivery to stem cells remains a significant challenge in the field despite decades of research. Therefore the ability to genetically modify stem cells safely would represent a significant advance.

SUMMARY

In a first aspect, a set of novel, highly efficient, adeno-associated virus (AAV) isolates from human $CD34^+$ hematopoietic stem cells (HSC) is provided. The novel isolates may be represented and used as either nucleotide sequences, amino acid sequences, or both. The novel isolate sequences or portions thereof may be determined by comparison to an AAV reference sequence, such as AAV9 (including AAV9 hu. 14 sequence of SEQ ID NO: 1), AAV2, another AAV reference sequence or portion thereof, or another relevant sequence or portion thereof. In one embodiment, novel AAV isolate sequences are represented as amino acid sequences in SEQ ID NOS: 2-17 and as nucleotide sequences as SEQ ID NOS: 20-35. The isolates may be used alone or a part of a larger expression cassette. Additionally, the colinear genes comprising the novel capsid genes, VP1, VP2, and VP3, may be recombined from the various novel capsid genes to create additional novel capsid genes. Sequences that are a certain percentage identical to these sequences such as sequences that are about 95%, 96%, 97%, 98%, or 99% identical are also contemplated. Preferably, the sequences may be used in cell transduction. The transduction may be either transient or permanent. In one embodiment, if the transduction is transient, the length of time for which the cell is transduced is programmed into the vector.

In another aspect, the novel AAV capsid isolates or portions thereof, from $CD34^+$ HSC or from another source, may be used for high efficiency transduction of stem cells, including HSC and iPSC, and other cells, such as those of the heart, joint, central nervous system, including the brain, muscle, and liver. If the AAV isolates are used in vitro, they may be used for research and investigation purposes or to prepare cells or tissues that will later be implanted into a subject. Preferably, the subject is a mammal, such as a human, but may be any other animal that has tissues that can be transduced by the present vectors and methods of using those vectors. The present vectors are well suited for both human and veterinary use. The AAV isolates may also be used in vitro for the transient transduction of stem cells, such as HSC. The length of transduction may be controlled by culture conditions. If the AAV isolates are used in vivo, they may be directly administered to the subject receiving the therapy for uptake or use in the target cells, such as liver or cartilage cells. If the AAV isolates are used for transducing cells of the central nervous system, they are preferably able to traverse the blood-brain barrier and maintain their efficacy.

Members of the novel AAV capsid family transduce HSC, e.g. HSC 15 and HSC 17, giving rise to long-term engraftment with sustained gene expression and are thus strong candidates for stem cell gene therapy vectors. AAVHSC17 and 15 (also referred in abbreviated form as "HSC17" and "HSC15") supported the highest levels of long-term in vivo transduction, up to 22 weeks post-transplantation. Serial bioluminescent imaging following intravenous injection of the novel AAVs revealed that HSC15 generally supported the highest levels of long-term transgene expression in vivo. Other novel AAVs including HSC13 and 17 also supported strong in vivo transduction.

HSC15 was found to be highly liver tropic, about 5-10 fold higher than AAV9. HSC13 and HSC15 also transduced the heart and skeletal muscle at least 10-fold better than AAV9. In vitro neutralization titers revealed that the prevalence of antibodies to HSC1-9 in pooled human IVIG were similar to AAV9, while antibodies to HSC13, HSC15, HSC16 and HSC17 were somewhat less prevalent. In vivo neutralization assays confirmed that over 100-fold higher vector genome copies/cell were found in liver and muscle following IVIG administration with HSC15 compared to AAV9, suggesting that pre-existing antibodies did not completely neutralize HSC15. Muscle diseases or disorders may comprise any cell, tissue, organ, or system containing muscle cells which have a disease or disorder, including the heart, such as coronary heart disease or cardiomyopathy.

In addition, site-specific mutagenesis experiments indicate that the R505G mutation in HSC15 is responsible for the enhanced liver tropism. The AAV isolates may be used to treat a whole host of genetic diseases such as hemophilia, atherosclerosis and a variety of inborn errors of metabolism. In one instance, HSC 15 effectively treats hemophilia B. Some members of this family also target the joints after systemic injection, which may be used to treat joint and cartilage diseases such as arthritis. Other members of the family target the heart upon intravenous injection. Yet other members of the family target the brain.

In yet another aspect, the novel AAV isolates may be used in screens, binding assay, or as part of test kits. The novel isolate sequences may be used alone or as part of a replication-competent vector, which may be accompanied by a helper virus. The screens may be used to detect novel AAV isolate binding partners in samples and/or to detect AAV sequences in cells.

The present experiments demonstrate the efficacy of the novel AAV isolates, including the efficacy of individual capsid nucleotides and proteins for use in cell transduction and gene therapy. AAV isolates from donors were analyzed and mapped to the same AAV clade. Gene transfer vectors derived from these isolates are shown to transduce human $CD34^+$ HSC at high efficiency. Thus, $CD34^+$ HSC indicates a CD34 expressing hematopoetic stem cell.

Demonstrating the efficacy of vivo applications, transplantation of transduced cells to immune-deficient mice with the novel isolates resulted in prolonged and sustained transgene expression and may be used for gene therapy. Under different conditions, these vectors may be used to transduce cells transiently, resulting in short term gene expression without genomic integration, a property of enormous importance for the applications such as derivation of induced pluripotent stem cells, expression of zinc finger proteins, or reprogramming genes. In addition, when delivered systemically, these vectors display a tropism for the liver and cartilage, with implications for therapy of inherited, acquired, infectious and oncologic diseases. With respect to the liver transduction, the present AAV isolates have up to approximately 10-fold higher liver transduction levels than the current gold standard for systemic gene delivery to the liver, AAV8. This property can be exploited for gene-based enzyme replacement therapy from the liver for diseases such as hemophilia, enzyme deficiency diseases, and atherosclerosis. The additional tropism of the present AAV isolates for cartilaginous tissue in joints may be exploited for the treatment of bone disorders such as arthritis, osteoporosis or other cartilage/bone based diseases. The novel sequences and methods may accordingly be used for transient transduction where long term integration is not desirable.

When gene therapy is desired, the target protein may be any protein that is therapeutically effective, including therapeutic antibodies. For example, in a subject with brain cancer, a clinician may administer a HSC15 vector comprising an apoptotic antibody specific for proteins expressed only by the brain cancer cells.

In another aspect, nucleic acid comprising the novel AAV capsid isolates may be inserted into the genome of a new virus, where in the addition of the novel genes transmits the same or similar tissue or organ tropisms of the AAV capsid isolates to the new virus. Such gene therapy may be effected using in vivo and ex vivo gene therapy procedures; see, e.g., U.S. Pat. No. 5,474,935; Okada, Gene Ther. 3:957-964, 1996. Gene therapy using the novel AAV capsid gene will typically involve introducing the target gene in vitro into the new virus, either alone or with another gene intended for therapeutic purposes. If the tropic gene is introduced with one or more additional genes, preferably the resulting polypeptides are administered for therapeutic purposes in the tissue for which the AAV isolate has a tropism. The virus may then be administered to patient in need of such therapy or may be administered ex vivo, such as to an organ awaiting transplant. The virus may be a retrovirus, an RNA virus, a DNA virus such as an adenovirus vector, an adeno-associated virus vector, a vaccinia virus vector, a herpes virus vector, and the like. A transfection method using a virus vector that uses a liposome for administration in which the new virus vector is encapsulated is also contemplated.

In another aspect, novel AAV isolate proteins may be used as markers. The proteins are labeled, as with radioactive moieties, such as a radioactive isotope, phosphorescence, or other detectable labels for tagging siRNA, small molecules, antibodies, aptamers, or the like to track the localization of these molecules. This use can assist in developing therapies for targeting the tissues for which the novel isolates show a tropism. For example, the label facilitates viewing the therapeutic molecule reaching the desired location, the in vivo circulation, biological path, half-life, and other elements that are important factors to consider in developing a therapeutic molecule.

One skilled in the art will appreciate these and other aspects of the invention from the disclosure and experiments described herein.

BRIEF DESCRIPTION OF THE DRAWINGS

FIG. 2 shows the alignment of novel capsid amino acid sequences in comparison to AAV9.

FIG. 3 is a chart listing some of the nucleotide mutations in the capsid of each sequence, including the base change, the amino acid change, and whether it is in VP1 or VP3.

FIG. 4 is a table showing amino acid substitutions of the major novel stem cell-derived AAV capsids.

FIG. 13A is a plot of human cell engraftment in NOD/SCID mice as determined by the frequency of $CD45^+$ cells in the marrow. Each point represents an individual xenograft recipient. A total of 40 mice were analyzed. FIG. 13B is a graph showing the frequency of human hematopoietic lineages derived from transplanted $CD45^+$ cells at 12-22 weeks post transplantation. Bars represent standard errors of the mean. Total number of mice (n) analyzed for CD34, CD33, CD19, CD14 and Glycophorin A lineages, were 25, 24, 23, 13 and 18, respectively.

FIG. 14: HSCs transiently transduce human stem cells at high efficiency (particularly HSC 5 and HSC 12) and then decline in genome copy number per cell over time for cells in culture as shown in two experiments (FIGS. 14A and B). These rAAV are ideal for the expression of transgenes such as zinc finger endonucleases and reprogramming genes. In these cases, stable long term expression is undesirable because of potential genotoxicity. This figure shows the decline in genome copies per cell as estimated by real time PCR analysis following transduction of $CD34^+$ cells with the stem cell-derived rAAV. Importantly, the initial level of transduction was noted to be very high.

FIG. 21 indicates the level of transduction in organs harvested from mice injected with $10^{11}$ rAAV-Luc vg. Transgene expression was assessed in individual organs harvested from mice given intra-venous injection of the stem cell-derived rAAV. All isolates transduced the liver however HSC15 was clearly the most efficient. HSC13, HSC15 and HSC17 also transduced the joints/cartilaginous areas strongly. HSC13 was the most efficient at transducing the heart.

FIG. 22 shows the biodistribution of AAV HSCs at 8 weeks in various types of tissue.

FIG. 23 shows mapping of HSC15 capsid determinants of liver tropism. Although HSC15 is greater than 100-fold more efficient than AAV9 at targeting genes to the liver, the capsid only differs by two amino acids, R505G and A346T. The roles of these two amino acid changes were tested by site-directed mutagenesis experiments. Each amino acid was altered one at a time and the resulting capsids were used to generate recombinant AAV vectors encoding luciferase. While the presence of both changes was found to be necessary for optimal liver transduction, the contribution of amino acid 505 was clearly most important for liver tropism. FIG. 23A is an image of luciferase expression in representative mice after systemic administration of rAAV-luciferase packaged in HSC15, mutant capsids and AAV9 and AAV8 controls. FIG. 23B shows serial expression over time.

FIG. 29 shows rAAV genome copies per 1000 cells in the brain. Brains were harvested from mice injected intravenously via tail vein with 1E11P of AAV9, HSC15 or HSC15 mutants at given time points post injection. Genomic DNA was isolated from harvested brain and vector genome copies were assayed through qPCR using primers specific for the transgene and housekeeping gene. HSC15 has over a 40 fold increase in vector genome copies when compared to AAV9 in the brain 160 hours post IV injection of 1E11 particles or rAAV.

FIG. 33 shows vector genome copies in brains of mice injected systemically with 1E11 particles of ssrAAV-luc vector 56 days post injection. Mice were injected with 1E11P of ssluc via tail vein. 56 days post injection, brains were harvested and homogenized. Genomic DNA isolated from brains was analyzed for vector genome copies through qPCR using vector specific and housekeeping gene primers and probes. HSC15 has over 20 fold increase in average vector genome copies compared to AAV9 at 56 days post 1E11P IV injection. N=4 mice.

FIG. 47 shows the frequency of rAAV genome copies in tissues harvested from mice injected intra-muscularly with rAAV. Brain, muscle and liver were harvested from mice injected intramuscularly in the gastronemius with 1E10P of ssluc vector approximately 6 weeks post injection. Organs were homogenized and isolated genomic DNA was assayed for vector genome copies per cell by qPCR using vector and housekeeping specific primers and probes. AAVHSC15 is 80-fold higher than AAV9 in muscle and 15-fold greater than AAV9 in the liver when comparing the frequency of rAAV genome copies in the tissues at 6 weeks post-injection.

Two hours later, mice are injected intramuscularly into the gastronemius with ssluc vector.

Figure 49:
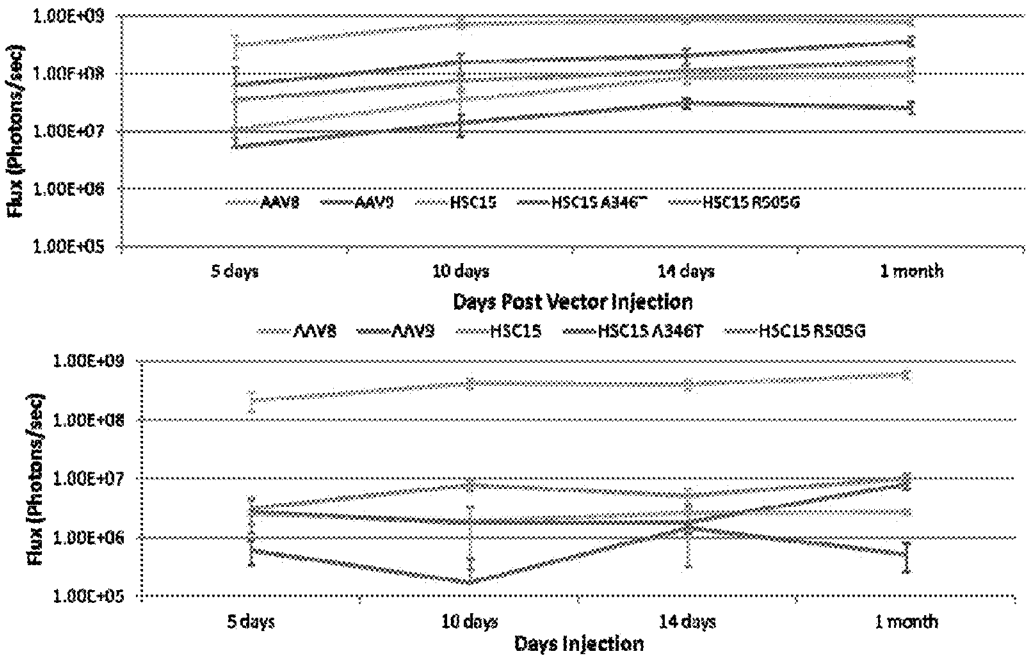

FIG. 49 shows systemic transgene expression in mice injected intra-muscularly with and without human IVIG pre-treatment. Average whole body flux was measured from bioluminescent images taken at given time points post IVIG and vector or vector alone injections. AAVHSC15 has high whole body transgene expression even after pretreatment with 12 mg of pooled human IVIG (high dose) indicating neutralization does not fully eliminate transduction. N=4 mice.

Figure 50:
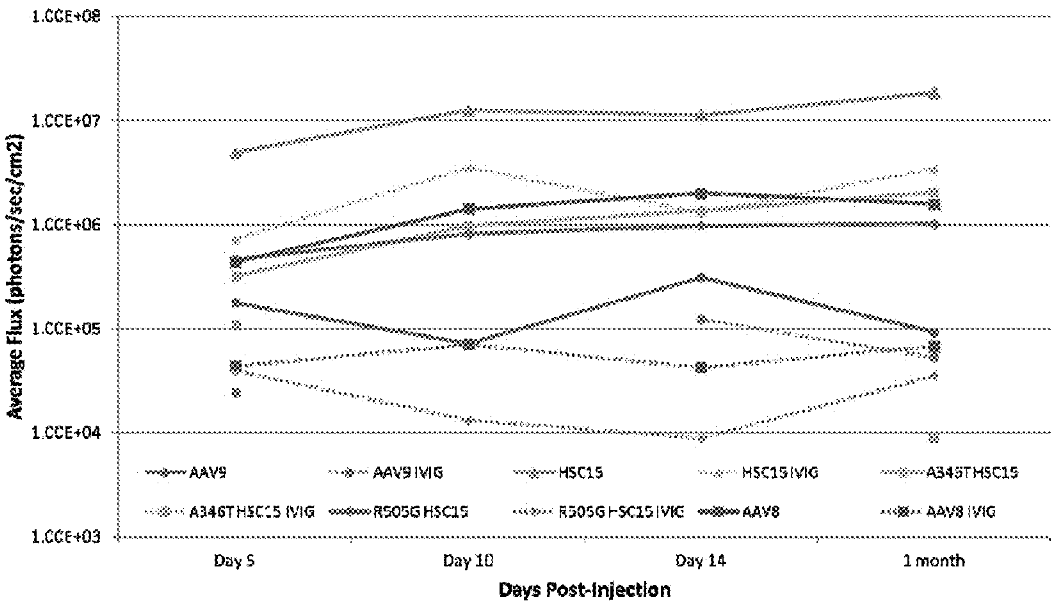

FIG. 50 shows transgene expression in liver in mice injected intra-muscularly with and without human IVIG pretreatment. Consistent regions around the liver were measured for flux from bioluminescent images taken at given time points post IVIG and vector or vector alone injections. Transgene expression in the liver of mice pretreated with pooled human IVIG is comparable between AAVHSC15 and AAV8 and higher than AAV9 in mice not pretreated with IVIG. N=4 mice.

Figure 51:
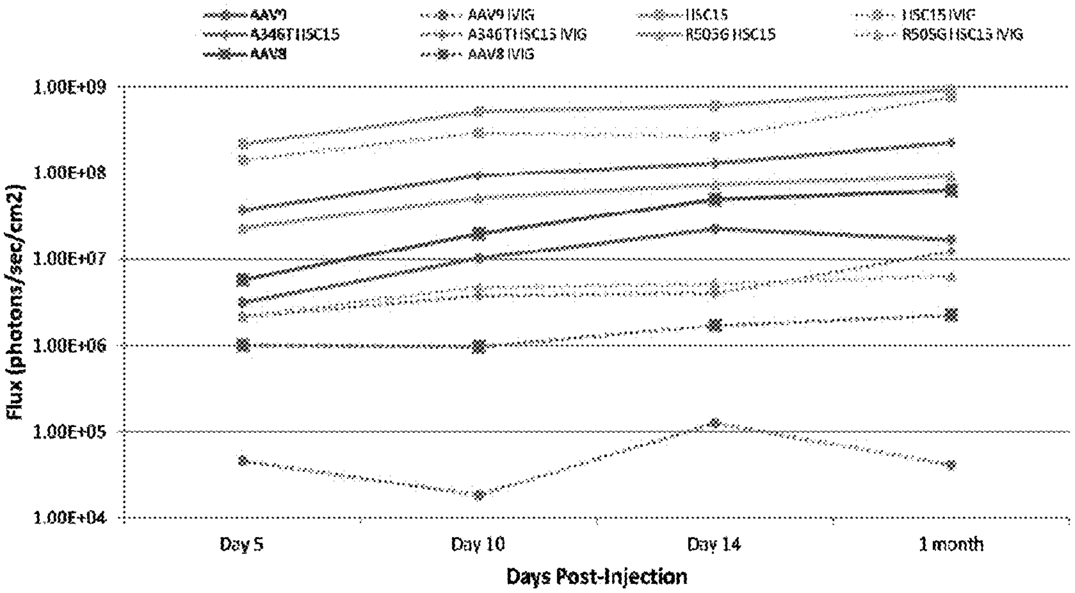

FIG. 51 shows transgene expression in muscle in mice injected intra-muscularly with and without IVIG pretreatment. Consistent regions around intramuscular injection of the gastronemius were measured for flux from bioluminescent images taken at given points post IVIG and vector or vector alone injections. Transgene expression in the muscle of mice pretreated with pooled human IVIG is higher with AAVHSC15 than with AAV8 or AAV9 in mice not pretreated with IVIG. N=4 mice.

FIG. 52 shows rAAV genome copies in the liver and muscle of IM mice with and without IVIG pretreatment. Muscle and liver were harvested from mice injected with either IVIG and ssluc vector or vector alone and at approximately 6 weeks after injection. Organs were homogenized and isolate genomic DNA analyzed for vector genome copies through qPCR using vector and housekeeping gene specific primer and probes. AAVHSC15 vector genome copies in the muscle of mice pretreated with pooled human IVIG is greater than AAV9 vector copies in the muscle of mice not pretreated with IVIG. N=4 mice.

FIG. 53 shows neutralization titer of AAVHSCs using pooled human IVIG. AAVHSC13 and AAVHSC15, followed by AAVHSC16 and AAVHSC17 have the lowest neutralizing antibody titer, indicating that they have the lowest seroprevalence of neutralizing antibodies in pooled human IVIG. Antibody titer was determined as the highest IVIG dilution that inhibited transduction 50%.

FIG. 54 shows the frequency of rAAV genomes per 1000 cells.

DETAILED DESCRIPTION

Certain embodiments of the invention are described in detail, using specific examples, sequences, and drawings. The enumerated embodiments are not intended to limit the invention to those embodiments, as the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. Unless defined otherwise, all technical and scientific terms used herein have the same meaning as commonly understood by one of ordinary skill in the art to which this invention belongs. All publications and/or patents are incorporated by reference as though fully set forth herein.

"AAV" is an adeno-associated virus. The term may be used to refer to the virus or derivatives thereof, virus subtypes, and naturally occurring and recombinant forms, unless otherwise indicated. AAV has over 100 different subtypes, which are referred to as AAV-1, AAV-2, etc., and includes both human and non-human derived AAV. There are about a dozen AAV serotypes. The various subtypes of AAVs can be used as recombinant gene transfer viruses to transduce many different cell types.

"Recombinant," as applied to a polynucleotide means that the polynucleotide is the product of various combinations of cloning, restriction or ligation steps, and other procedures that result in a construct that is distinct from a naturally-occurring polynucleotide. A recombinant virus is a viral particle comprising a recombinant polynucleotide, including replicates of the original polynucleotide construct and progeny of the original virus construct. A "rAAV vector" refers to a recombinant AAV vector comprising a polynucleotide sequence not of AAV origin (i.e., a polynucleotide heterologous to AAV), which is usually a sequence of interest for the genetic transformation of a cell.

A "helper virus" for AAV as used herein is virus that allows AAV to be replicated and packaged by a mammalian cell. Helper viruses for AAV are known in the art, and include, for example, adenoviruses (such as Adenovirus type 5 of subgroup C), herpes viruses (such as herpes simplex viruses, Epstein-Bar viruses, and cytomegaloviruses) and poxviruses.

"Joint tissue" is comprised of a number of tissues including cartilage, synovial fluid, and mature, progenitor and stem cells that give rise to, or are: (i) cartilage producing cells; (ii) Type I synoviocytes; (iii) Type II synoviocytes; (iv) resident or circulating leukocytes; (v) fibroblasts; (vi) vascular endothelial cells; and (vii) pericytes.

A "replication-competent" virus refers to a virus that is infectious and capable of being replicated in an infected cell. In the case of AAV, replication competence generally requires the presence of functional AAV packaging genes, as well as helper virus genes, such as adenovirus and herpes simplex virus. In general, rAAV vectors are replication-incompetent because they lack of one or more AAV packaging genes.

The term "therapeutic" refers to a substance or process that results in the treatment of a disease or disorder. "Therapeutic nucleotide sequence" is a nucleotide sequence that provides a therapeutic effect. "Treatment" of a disease or disorder means improving the condition of the disease or disorder, and may including curing, improving, stalling or stopping the progress of further worsening due to the disease or disorder, or to generally counteract the disease or disorder. The vectors comprising the therapeutic nucleotide sequences are preferably administered in a therapeutically effective amount via an suitable route of administration, such as injection, inhalation, absorption, ingestion or other methods.

In some embodiments, a composition comprising novel AAV isolates is a cell-free composition. The composition is generally free of cellular proteins and/or other contaminants and may comprise additional elements such as a buffer (e.g., a phosphate buffer, a Tris buffer), a salt (e.g., NaCl, MgCl2), ions (e.g., magnesium ions, manganese ions, zinc ions), a preservative, a solubilizing agent, or a detergent, (e.g., a non-ionic detergent; dimethylsulfoxide).

In another embodiment, an expression cassette comprises a polynucleotide sequence encoding a polypeptide comprising one or more of the novel AAV isolates, wherein the polynucleotide sequence encoding the polypeptide comprises a sequence having at least about 95%, 96%, 97%, more preferably about 98%, and most preferably about 99% sequence identity to the sequences taught in the present specification. Percentage identity may be calculated using any of a number of sequence comparison programs or methods such as the Pearson & Lipman, Proc. Natl. Acad. Sci. USA, 85:2444 (1988), and programs implementing comparison algorithms such as GAP, BESTFIT, FASTA, or TFASTA (from the Wisconsin Genetics Software Package, Genetics Computer Group, 575 Science Drive, Madison, Wis.), or BLAST, available through the National Center for Biotechnology Information web site.

In another aspect, an expression cassette comprises a polynucleotide sequence encoding a polypeptide comprising one or more of the novel AAV isolates, wherein the sequence is comprised of portions of the three genes comprising the capsid protein, V1-V3. For example, the cassette may comprise V1 from capsid HSC1, a standard V2 as compared to AAV9 hu.14, and V3 from HSC17. In yet another embodiment, a capsid may comprise more than one of each of the capsid gene components. For example, novel capsids may be selected from any of the V1-V3 for the capsid sequences set forth herein and may be combined in any order and in any combination so long as the desired property of increased transduction is achieved. For example, the capsid sequence could be V1A-V1B-V2-V3, V3-V1-V2, or V1-V2-V3A-V3B.

Another aspect includes cells comprising one or more of the novel expression cassettes where the polynucleotide sequences are operably linked to control elements compatible with expression in the selected cell. The expression cassette preferably comprises a promoter, open reading frame, and 3' untranslated region containing a polyadenylation site, and target polynucleotide sequence.

Another embodiment includes methods of immunization of a subject. Compositions comprising the novel capsids maybe introduced into a subject in a manner that causes an immunological reaction resulting in immunity in the subject. The novel capsids may be in the composition alone or as part of an expression cassette. In one embodiment, the expression cassettes (or polynucleotides) can be introduced using a gene delivery vector. The gene delivery vector can, for example, be a non-viral vector or a viral vector. Exemplary viral vectors include, but are not limited to Sindbis-virus derived vectors, retroviral vectors, and lentiviral vectors. Compositions useful for generating an immunological response can also be delivered using a particulate carrier. Further, such compositions can be coated on, for example, gold or tungsten particles and the coated particles delivered to the subject using, for example, a gene gun. The compositions can also be formulated as liposomes. In one embodiment of this method, the subject is a mammal and can, for example, be a human.

Figure 1:
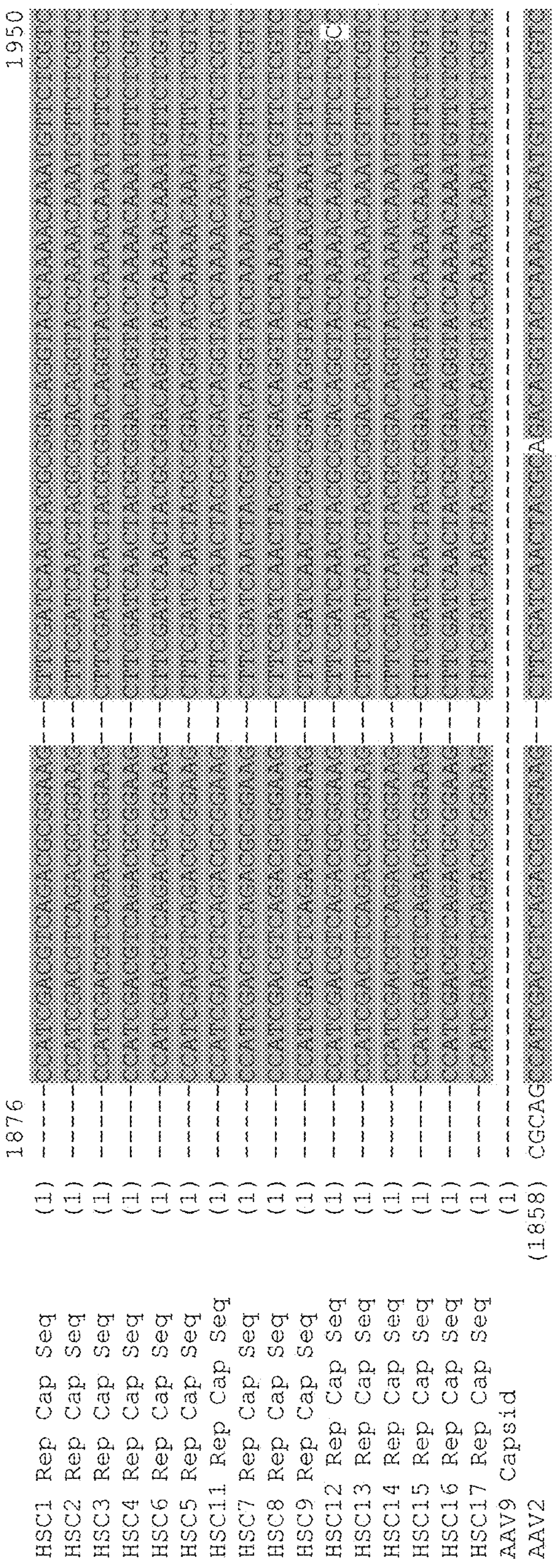
FIG. 1 shows the alignment of novel AAV capsids with AAV2 and AAV9 hu.14.
Figure 1:
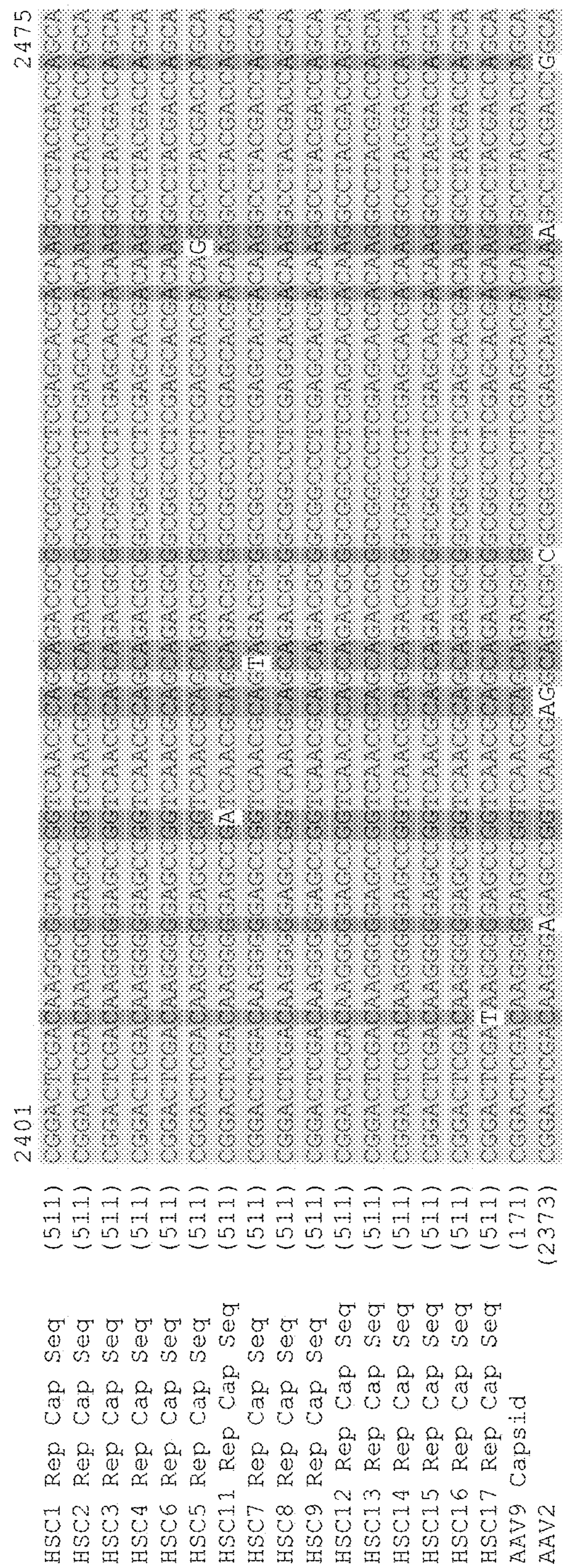
Figure 1:
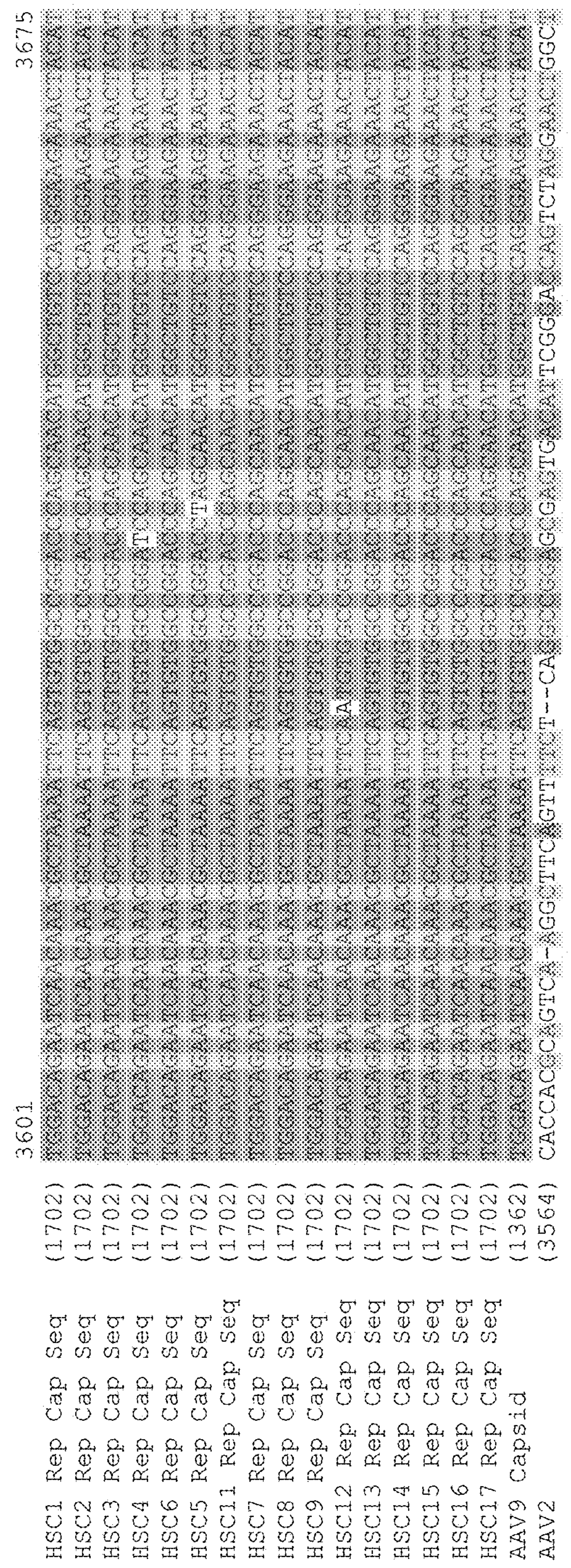
Figure 1:
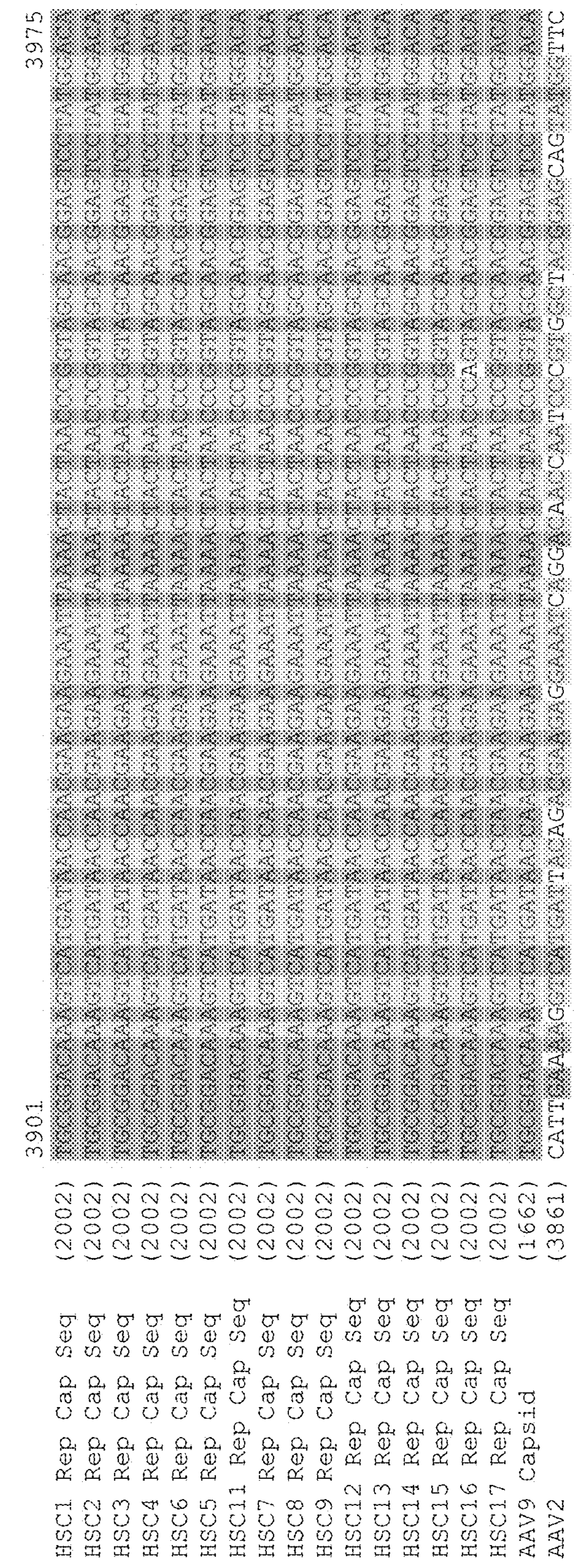
Figure 1:
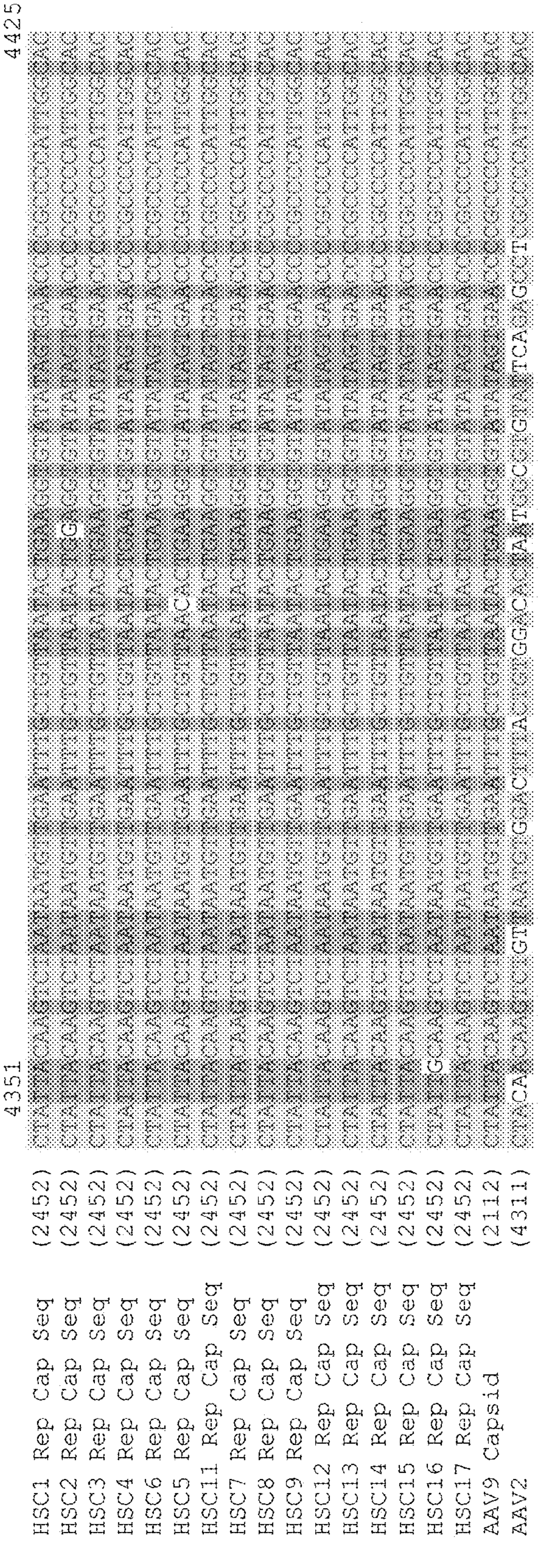

Novel AAV capsids may be represented as nucleotide sequences, such as SEQ ID NOS: 20-35 (FIG. 1) and nucleotide sequence encoding amino acid sequences, such as SEQ ID NOS: 2-17 (FIGS. 2-4). The novel capsid sequences are typically modified at one or more positions in the V1 and/or V3 cap genes, these genes or functional portions of the genes can be used separately or together in any of the methods described herein. Cap genes, V1, V2, and V3, may be substituted out from multiple mutated sequences, and are typically used in a colinear fashion V1-V2-V3. However the sequences may be truncated such as partial V1-V2-V3 or V1-V3 or V1-V1-V2-V3. For example, one sequence could be V1 of (HSC8)-V2 of (HSC4)-V3 of HSC14. Preferably, the novel capsids transduce the target cells on a level at or higher than AAV2.

The novel sequences may be used alone or a part of a vector, which is preferably isolated and purified. The sequences may be used to transduce cells. The cells may be either stem cells, such as HSC, a CD34+ HSC, or induced pluripotent stem cells or other types of cells, or they may be somatic cells, such as liver, cartilage, or bone cells. When the transduced cells are, for example, liver cells, the introduced sequence is directed to treating (improving or curing a disease or disorder or stopping further progression of a disease or disorder) or preventing a condition. When the cell transduced with the novel capsid sequences is a liver cell, the liver conditions treated or prevented comprise hemophilia, enzyme delivery, cirrhosis, cancer, or atherosclerosis, among other liver conditions.

The AAVs described herein may be used for transducing a wide variety of mammalian cells, for example, cells of the liver, lung, cartilage and other connective tissue, eye, central and peripheral nervous system, lymphatic system, bone, muscle, blood, brain, skin, heart, and digestive tract. In addition, AAVs may have a tropism for cells containing various tags, such as a six-His tag or an affinity tag, or for interferon responses, such as naturally occurring antibodies elicited or introduced monoclonal antibodies administered in response to a pathogen or tumor cell.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A (Nilsson et al., EMBO J. 4:1075, 1985; Nilsson et al., Methods Enzymol. 198:3, 1991), glutathione S transferase (Smith and Johnson, Gene 67:31, 1988), Glu-Glu affinity tag (Grussenmeyer et al., Proc. Natl. Acad. Sci. USA 82:7952-4, 1985), substance P, Flag™ peptide (Hopp et al., Biotechnology 6:1204-10, 1988), streptavidin binding peptide, or other antigenic epitope or binding domain. See, in general, Ford et al., Protein Expression and Purification 2: 95-107, 1991, DNAs encoding affinity tags are available from commercial suppliers (e.g., Pharmacia Biotech, Piscataway, N.J.).

Figure 5:
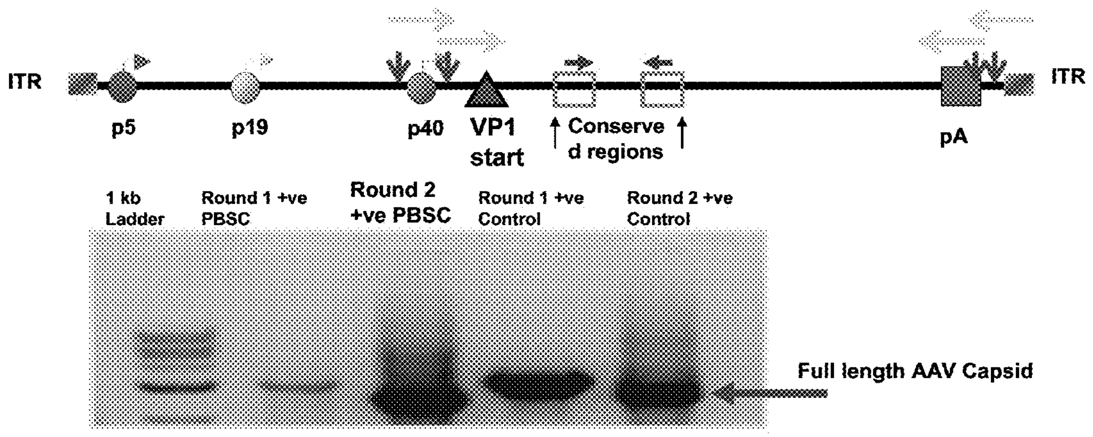
FIG. 5 shows identification and isolation of endogenous AAV in $CD34^+$ cells. The AAV genome is represented in a linear fashion. Primers are used to identify positive cells. Light gray arrows represent primers used to amplify full length AAV capsid genes. Vertical arrows show the exact location of primers on the AAV genome. Also shown are the AAV ITRs, the three AAV promoters, the start of the capsid transcripts and the polyadenylation signal. "PBSC" are the peripheral blood stem cells used in the experiment.

Of the number of affinity tag purification systems available, the most frequently employed utilize polyhistidine (His) or glutathione S-transferase (GST) tags. His binds with good selectivity to matrices incorporating Ni+2 ions, typically immobilized with either iminodiacetic acid or nitrilotriacetic acid chelating groups. The technique is known as immobilized metal affinity chromatography (FIG. 5, gel image). Absorption of the His-tagged protein is performed at neutral to slightly alkaline pH to prevent protonation and loss of binding capacity of the weakly basic histidine imidazole groups. Elution of the bound protein is caused by displacement with imidazole or low pH conditions.

Methods of generating induced pluripotent stem cells from somatic cells without permanent introduction of foreign DNA are also described. The method involved transiently transducing stem cells with vectors comprising a novel capsid nucleotide sequence as described herein encoding an amino acid sequence, or V1 or V3 portion thereof.

Methods of testing for a novel capsid in target tissue comprising are also described herein. The methods comprise isolating nucleic acid from the target tissue, detecting one or more AAV sequences, cloning the AAV sequences, sequencing the AAV sequences, amplifying the capsid gene(s), and comparing the amplified capsid gene to a reference sequence, wherein if the sequence differs as compared to the reference sequence and has at least the same, if not greater tropism for the target tissue, it is a desirable novel capsid for additional in vitro and in vivo testing and use.

For these and other experiments, a person skilled in the art knows how to modify and propagate AAV. For example, AAV-2 can be propagated both as lytic virus and as a provirus. For lytic growth, AAV requires co-infection with a helper virus. Either adenovirus or herpes simplex can supply helper function. When no helper is available, AAV can persist as an integrated provirus, which involves recombination between AAV termini and host sequences and most of the AAV sequences remain intact in the provirus. The ability of AAV to integrate into host DNA allows propagation absent a helper virus. When cells carrying an AAV provirus are subsequently infected with a helper, the integrated AAV genome is rescued and a productive lytic cycle occurs. The construction of rAAV vectors carrying particular modifications and the production of rAAV particles, e.g., with modified capsids, is described, e.g., in Shi et al. (2001), Human Gene Therapy 12:1697-1711; Rabinowitz et al. (1999), Virology 265:274-285; Nicklin et al. (2001), Molecular Therapy 4:174-181; Wu et al. (2000), J. Virology 74:8635-8647; and Grifman et al. (2001), Molecular Therapy 3:964-974.

Yet another aspect relates to a pharmaceutical composition containing a rAAV vector or AAV particle. The pharmaceutical composition containing an AAV vector or particle, preferably, contains a pharmaceutically acceptable excipient, diluent or carrier. A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well known conventional methods such as those set forth in Remington's Pharmaceutical Sciences, current Ed., Mack Publishing Co., Easton Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., 7th ed., Lippincott, Williams, & Wilkins; and Handbook of Pharmaceutical Excipients (2000) A. H. Kibbe et al., 3rd ed. Amer. Pharmaceutical Assoc. Such carriers can be formulated by conventional methods and can be administered to the subject at a suitable dose. Administration of the suitable compositions may be effected by different ways, e.g. by intravenous, intraperitoneal, subcutaneous, intramuscular, topical or intradermal administration. The route of administration, of course, depends, inter alia, on the kind of vector contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind and stage of infection or disease, general health and other drugs being administered concurrently.

Some of the novel capsids are capable of highly efficient transient in vitro transduction and may be useful for transient expression of transgenes such as zinc fingers and reprogramming genes for the induction of induced pluripotent stem cells (iPSC), while others are capable of supporting long-term stable transgene expression in vivo after transplantation of transduced hematopoietic stem cells or after direct systemic delivery of rAAV.

In one embodiment, a method of treating a neurological disease or disorder in a subject comprises administering a vector capable of crossing the blood-brain barrier, blood-ocular barrier, or blood-nerve barrier. Certain of the novel vectors disclosed herein have the unique ability to traverse the biological junctions that were previously unknown to be accessible to any vector for gene therapy or other diagnostic or therapeutic purposes using a modified viral vector. These junctions have common characteristics. The blood-brain barrier is a separation between blood circulating in the body and the brain extracellular fluid in the central nervous system and is created by tight junctions around capillaries. The blood-brain barrier generally allows only the passage of by diffusion of small hydrophobic molecules. The blood-ocular barrier is a separation made by between the local blood vessels and most parts of the eye and is made by endothelium of capillaries of the retina and iris. The blood-nerve barrier is the physiological space within which the axons, Schwann cells, and other associated cells of a peripheral nerve function and is made of endoneurial microvessels within the nerve fascicle and the investing perineurium. As with three of these barriers, there is restricted permeability to protect in the internal environment, here, the nerve, from drastic concentration changes in the vascular and other extracellular spaces. The vector that traverses any of these barriers has a unique ability to deliver one or more therapeutic nucleotide sequences for treating the neurological disease or disorder or to act as a labeled and or diagnostic agent. Certain of the novel vectors that have been experimentally validated as being particularly well suited for crossing these biological barriers include AAVHSC15, AAVHSC15 A346T, and AAVHSC15 R505G.

There are many neurological diseases or disorders that are well known to one of skill in the art, which may be generally classified by cell or organ-type such as a disease or disorder of the brain, spinal cord, ganglia, motor nerve, sensory nerve, autonomic nerve, optic nerve, retinal nerve, and auditory nerve. By way of example, brain diseases or disorders may include cancer or other brain tumor, inflammation, bacterial infections, viral infections, including rabies, amoeba or parasite infections, stroke, paralysis, neurodegenerative disorders such as Alzheimer's Disease, Parkinson's Disease, or other dementia or reduction in cognitive functioning, plaques, encephalopathy, Huntington's Disease, aneurysm, genetic or acquired malformations, acquired brain injury, Tourette Syndrome, narcolepsy, muscular dystrophy, tremors, cerebral palsy, autism, Down Syndrome, attention deficit and attention deficit hyperactivity disorder, chronic inflammation, epilepsy, coma, meningitis, multiple sclerosis, myasthenia gravis, various neuropathies, restless leg syndrome, and Tay-Sachs disease.

Muscle diseases or disorders include, by way of example only, myopathies, chronic fatigue syndrome, fibromyalgia, muscular dystrophy, multiple sclerosis, atrophy, spasms, cramping, rigidity, various inflammations, such as dermatomyositis, rhabdomyolysis, myofacial pain syndrome, swelling, compartment syndrome, eosinophilia-myalgia syndrome, mitochondrial myopathies, myotonic disorder, paralysis, tendinitis, polymyalgia rheumatic, cancer, and tendon disorders such as tendinitis and tenosynovitis.

Heart diseases or disorders include, by way of example only, coronary artery disease, coronary heart disease, congestive heart failure, cardiomyopathy, myocarditis, pericardial disease, congenital heart disease, cancer, endocartditis, and valve disease.

Lung diseases or disorders include, by way of example only, asthma, allergies, chronic obstructive pulmonary disease, bronchitis, emphysema, cystic fibrosis, pneumonia, tuberculosis, pulmonary edema, cancer, acute respiratory distress syndrome, pneumonconiosis, and interstitial lung disease.

Liver diseases or disorders include, by way of example only, cancer, hepatitis A, B, and C, cirrhosis, jaundice, and liver disease. Kidney diseases or disorders include, by way of example only, cancer, diabetes, nephrotic syndrome, kidney stones, acquired kidney disease, congenital disease, polycystic kidney disease, nephritis, primary hyperoxaluria, and cystinuria. Spleen diseases or disorders include, by way of example only, cncer, splenic infarction, sarcoidosis, and Gaucher's disease. Bone diseases or disorders include, by way of example only, ooseoporosis, cancer, low bone density, Paget's disease, and infection.

With any of these diseases or disorders treated using therapeutic nucleotide sequences or even small molecules transported by or with the novel vectors, the therapeutic nucleotide sequence may be, by way of example, a nucleic acid encoding a protein therapeutic, such as for cancer—an apoptotic protein, miRNA, shRNA, sRNA, other RNA-subtypes or a combination thereof. In some embodiments, the vectors are isolated an purified as described herein. Isolation and purification are preferred in vivo administration to increase efficacy and reduce contamination. The vector may permanent or transiently transduce a transgene, which is a gene or other genetic material that has been isolated from one organism and introduced into another. Here, the other organism may be the subject receiving the vector.

The vector may transduce a stem cell either in vitro or in vivo. The stem cell may be any type of stem cell including a hematopoietic stem cell, a pluripotent stem cell, an embryonic stem cell or a mesenchymal stem cell. Transduction of the stem cell may be either transient or permanent (also called persistent). If transient, one embodiment allows for the length of time the therapeutic nucleotide is used or expressed to be controlled either by the vector, by substance attached to the vector, or by external factors or forces.

In another embodiment, the vector is selected based on experimental results of the highest efficacy in the given target cell or tissue for the given disease or disorder. One such method of treating a disease or disorder in a subject comprises administering a vector comprising one or more therapeutic nucleotide sequences selected from the following: a) for muscle disease or disorders and for antibody genes or other vaccine treatments administered to the subject via the muscle, the vector selected from the group of AAVHSC7, AAVHSC13, AAVHSC15, and AAVHSC17; b) for heart and lung disease or disorders, the vector selected from the group of AAVHSC13, AAVHSC15, and AAVHSC17; c) for liver or neurological diseases or disorders, vector AAVHSC15; d) for conditions treated by engrafting stem cells, vector AAVHSC17; e) for conditions treated by transducing B cell progenitors, vector AAVHSC5; f) for conditions treated by transducing myeloid and erythroid progenitors, vector AAVHSC12; and g) for lymph node, kidney, spleen, cartilage and bone, the vector selected from the group of the vector selected from the group of AAVHSC7, AAVHSC13, AAVHSC15, and AAVHSC17; wherein the vector transduces the target cell or tissue and the therapeutic nucleotide sequences treat the disease or disorder. The subject is any animal for which the method works, but is preferably a mammal, which may be a human. If the vector contains an antibody gene or other vaccine treatment it may be administered via injection in the muscle and may provide immunological protection against diseases including from HIV, influenza, malaria, tetanus, measles, mumps, rubella, HPV, pertussis, or any other vaccine. The vector may be packaged, isolated, and purified and may transduce a stem cell of any type with the at least one therapeutic nucleotide sequence. The vector may also transduce a transgene or carry corrective genes endogenous to the subject and/or to the other subjects of the same species.

Various methods of gene therapy or genome editing systems are well known in the art and are cited in the background and detailed description section of this document. Such methods may include a zinc finger-based targeting system, which uses zinc finger nucleases to target genes. Other methods are TALENs technology, which allows precise changes to nucleotide sequences using site directed transcription activator-like effector nucleases (TALEN). TALENs are artificial restriction enzymes generated by fusing a DNA cleavage domain to a TAL effector binding domain. These gene therapy systems may be used in vitro or in vivo. The methods may be used to reprogram genes for inducing pluripotent stem cells from somatic cells.

Materials and Methods

Cell and DNA Isolation

Umbilical cord blood (CB) was collected at Huntington Memorial Hospital or by Stemcyte and cytokine primed peripheral blood samples were obtained from healthy donors by informed consent under IRB approved protocols. $CD34^+$ cells were isolated from mononuclear cells by two successive rounds of immunomagnetic selection using $CD34^+$ isolation kits (Miltenyi Biotech, Auburn, Calif.) to a final purity of 96-98%. Aliquots of $10^6$ cells were frozen at −80 C prior to genomic extraction. Subsequent to RNase treatment, the cells were digested in Proteinase K/SDS overnight, and genomic DNA was extracted using a three-step process of phenol, phenol-chloroform, and chloroform extractions. Genomic DNA was precipitated overnight at −80 C in Ammonium Acetate and Ethanol solution. Salts were cleaned from the genomic DNA using 70% Ethanol solution, and DNA was resuspended in Tris-EDTA.

Detection of AAV in Genomic DNA

Detection of integrated AAV sequences was done using PCR. Primers were designed to hybridize to highly conserved regions which flanked a hypervariable region of the AAV capsid. The sequence of the forward and reverse primers used were 5'-CCACCTACAACAACCACCTC-TAC-3' (SEQ ID NO: 36) and 5'-CGTGGCAGTGGATTCT-GTTGAAGTC-3' (SEQ ID NO: 37) respectively. The PCR reaction was done according to Qiagen HotStar HiFidelity PCR protocol, using Qiagen Hotstar polymerase and Q-Solution to optimize sensitivity of detection and fidelity of product, 200 ng of genomic DNA per 25 ul reaction was used, and each reaction underwent 40 cycles of amplification. 10 ul of PCR reaction was run on a 2.5% gel, post-stained with Biotium GelRed Nucleic Acid Gel Stain, 3×, to determine if sample was positive. Positive bands were excised from gel and purified with Qiagen's QIAquick Gel Extraction Kit.

Cloning and Sequencing of the AAV Signature Regions

Purified PCR products were first cloned into a TOPO vector using Invitrogen TOPO TA Cloning kit. Competent cells were transformed with 2 ul of TOPO cloning reaction and then plated on Luria Agar plates, containing 100 ug/ml ampicillin, with 40 ul of 2% X-gal and 40 uL of 100 um IPTG. Blue colonies are selected and cultured overnight in 5 ml of Terrific Broth with 200 ug/ml of ampicillin. 1 ml of culture is phenol/chloroform miniprepped, washed with 1 ml of 70% ethanol, dried and resuspended into 50 ul ddH20 with 1 ul DNase free RNase. Clones cut with EcoR1 to drop out inserted PCR product were then run on a 2% gel post-stained with Biotium GelRed Nucleic Acid Gel Stain, 3×. Clone DNA was then sequenced with M13F and M13R primers.

Amplification of Full Length AAV Capsid Genes

Full capsids were amplified from signature region positive genomic DNA by PCR using nested primers. The PCR reaction was done according to Qiagen HotStar HiFidelity PCR protocol, using Qiagen Hotstar polymerase and Q-Solution to optimize sensitivity of detection and fidelity of product, 200 ng of genomic DNA per 25 ul reaction was used, and each reaction underwent 40 cycles of amplification. The first round PCR used forward and reverse primers GaoCapF, 5'-GCTGCGTCAACTGGACCAATGAGAAC-3' (SEQ ID NO: 38) and GaoCapR, 5'-CGCAGAGACCAAAGTTCAACTGAAACGA-3' (SEQ ID NO: 39) respectively. The second round PCR, using 1 ul of the first round PCR, used forward and reverse primers McapF3SpeI, 5'-ATCGATACTAGTCCATCGACGTCAGACGCGGAAG-3' (SEQ ID NO: 40) and McapR1NotI, 5'-ATCGATGCGGCCGCAGTTCAACTGAAACGAATCAACCGGT-3' (SEQ ID NO: 41) respectively. 10 ul of each PCR reaction were run on a 1% gel post-stained with Biotium GelRed Nucleic Acid Gel Stain, 3× to screen for correct amplicon size. Appropriately sized capsid genomes were excised and purified using Qiagen QIAquick Gel Extraction Kit.

Cloning and Sequencing of Full Length Novel AAV Capsid Genes 325 ng of the full length capsid PCR product and 125 ng of pBluescript SK+ was cut with restriction enzymes SpeI and NotI and run on a 1% gel post-stained with Biotium GelRed Nucleic Acid Gel Stain, 3×. Appropriately sized bands were excised and gel purified using QIAquick Gel Extraction Kit, and ligated at 16 C with New England Biolabs T4 DNA Ligase and 10× ligation buffer overnight. DH5 Alphas were transformed with ligation reaction and plated on Luria Agar plates containing 100 mg/ml of ampicillin. 1 ml of culture was phenol/chloroform miniprepped, washed with 1 ml of 70% ethanol, dried and resuspended into 50 ul $H_2O$ with 1 ul DNase free RNase. Clones were cut with EcoR1 to linearize plasmid. Cut plasmid clones were run on 1% gel post-stained with Biotium GelRed Nucleic Acid Gel Stain, 3× to determine correct plasmid size.

Correct Sized Plasmid is Sequenced with Degenerative Primers:

| | | |
|---|---|---|
| LCapSeqF1: | CGTCTTTTGGGGGCAACCTCG | (SEQ ID NO: 42) |
| LCapSeqF2C: | GACTCATCAACAACAACTGGGGATTCCG | (SEQ ID NO: 43) |

-continued

| | | |
|---|---|---|
| LCapSeqF2T: | GACTCATCAACAACAATTGGGGATTCCG | (SEQ ID NO: 44) |
| LCapSeqF3A: | CCGTCGCAAATGCTAAGAACG | (SEQ ID NO: 45) |
| LCapSeqF3B: | CCTTCTCAGATGCTGCGTACC | (SEQ ID NO: 46) |
| LCapSeqF3C: | CCTTCGCAGATGCTGAGAACC | (SEQ ID NO: 47) |
| LCapSeqF3D: | CCTTCTCAGATGCTGAGAACG | (SEQ ID NO: 48) |
| LCapSeqF4: | CGGTAGCAACGGAGTCCTATGG | (SEQ ID NO: 49) |
| LCapSeqR1G: | GCTGTTTTCCTTCTGCAGCTCC | (SEQ ID NO: 50) |
| LCapSeqR1A: | GCTGTTTTCTTTCTGCAGCTCC | (SEQ ID NO: 51) |
| LCapSeqR2: | CGTACTGAGGAATCATGAAAACGTCCGC | (SEQ ID NO: 52) |
| LCapSeqR3A: | CGTTATTGTCTGCCATTGGTGCGC | (SEQ ID NO: 53) |
| LCapSeqR3G: | CGTTATTGTCTGCCACTGGTGCGC | (SEQ ID NO: 54) |
| LCapSeqR4: | CGAGCCAATCTGGAAGATAACC | (SEQ ID NO: 55) |

M13F and M13R.

Amplification AAV2 Rep for Creation of the Packaging Plasmids

To create a packaging plasmid first, AAV2 Rep was isolated from a plasmid containing the entire AAV2 genome. The rep genome isolated was after the first ITR but before the p5 promoter until before the p40 promoter. The forward and reverse primers are AAV2RepF, 5'-GATCATATCGATGGTGGAGTCGTGACGTGAATTACG-3' (SEQ ID NO: 56) and AAV2RepR 5'-GATCATAAGCTTCCGCGTCTGACGTCGATGG-3' (SEQ ID NO: 57) respectively. The PCR reaction was done according to Qiagen HotStar HiFidelity PCR protocol, using Qiagen Hotstar polymerase and Q-Solution to optimize sensitivity of detection and fidelity of product, genomic DNA was used, and each 25 ul reaction underwent 40 cycles of amplification. 10 ul of PCR reaction was run on a 1% gel post-stained with Biotium GelRed Nucleic Acid Gel Stain, 3× and appropriate sized PCR product was excised and gel purified by Qiagen QIAquick Gel Extraction Kit [7, 9].

Cloning and Sequencing of Novel Packaging Plasmids

PCR product and plasmid containing full length capsid clone and pBluescript SK+ were then cut with restriction enzymes ClaI and HindIII. Each digest was run on a 1% gel and appropriately sized band were excised and gel purified with QIAquick Gel Extraction Kit. 50 ng of the ClaI and HindIII digested capsid clone and pBluescript SK+ vector and 75 ng of the ClaI and HindIII digest AAV2 Rep were ligated at 16 C using New England Biolabs T4 DNA Ligase and 10× Ligation Buffer overnight. DH5 Alphas were transformed with ligation reaction and plated on Luria Agar plates containing 100 mg/ml of ampicillin. 1 ml of culture is phenol/chloroform miniprepped, washed with 1 ml of 70% ethanol, dried and resuspended into 50 ul ddH20 with 1 ul DNase free RNase. Clones were cut with EcoR1 to linearize plasmid. Ran cut plasmid clones on 1% gel post-stained with Biotium GelRed Nucleic Acid Gel Stain, 3× to determine correct plasmid size. Packaging plasmids were sequenced using primers:

```
                                     (SEQ ID NO: 42)
LCapSeqF1:       CGTCTTTTGGGGGCAACCTCG

                                     (SEQ ID NO: 43)
LCapSeqF2C:      GACTCATCAACAACAACTGGGGATTCCG

                                     (SEQ ID NO: 44)
LCapSeqF2T:      GACTCATCAACAACAATTGGGGATTCCG

                                     (SEQ ID NO: 45)
LCapSeqF3A:      CCGTCGCAAATGCTAAGAACG

                                     (SEQ ID NO: 46)
LCapSeqF3B:      CCTTCTCAGATGCTGCGTACC

                                     (SEQ ID NO: 47)
LCapSeqF3C:      CCTTCGCAGATGCTGAGAACC

                                     (SEQ ID NO: 48)
LCapSeqF3D:      CCTTCTCAGATGCTGAGAACG

                                     (SEQ ID NO: 49)
LCapSeqF4:       CGGTAGCAACGGAGTCCTATGG

                                     (SEQ ID NO: 50)
LCapSeqR1G:      GCTGTTTTCCTTCTGCAGCTCC

                                     (SEQ ID NO: 51)
LCapSeqR1A:      GCTGTTTTCTTTCTGCAGCTCC

                                     (SEQ ID NO: 52)
LCapSeqR2:       CGTACTGAGGAATCATGAAAACGTCCGC

                                     (SEQ ID NO: 53)
LCapSeqR3A:      CGTTATTGTCTGCCATTGGTGCGC

                                     (SEQ ID NO: 54)
LCapSeqR3G:      CGTTATTGTCTGCCACTGGTGCGC

                                     (SEQ ID NO: 55)
LCapSeqR4:       CGAGCCAATCTGGAAGATAACC

                                     (SEQ ID NO: 58)
LRepSeqF1:       GGAGAGAGCTACTTCCACATGC

                                     (SEQ ID NO: 59)
LRepSeqF2:       CCTTCAATGCGGCCTCCAACTCG

                                     (SEQ ID NO: 60)
LRepSeqF3:       CGTCACCTCCAACACCAACATGTGG

                                     (SEQ ID NO: 61)
LRepSeqF4:       CGTGTCAGAATCTCAACCCG

                                     (SEQ ID NO: 62)
LRepSeqR1:       CCACCTCAACCACGTGATCCTTTGC

                                     (SEQ ID NO: 63)
LRepSeqR2:       CGATTGCTGGAAATGTCCTCCACG

                                     (SEQ ID NO: 64)
LRepSeqR3:       GCACAAAGAAAAGGGCCTCCG

M13F and M13R.
```

rAAV Production, Purification and Titration

Self complementary Enhanced Green Fluorescent Protein (scEGFP) or single stranded Firefly Luciferase (ssLuc) was packaged in capsid clones. 20 ng of capsid clone packaging plasmid and 20 ng of vector plasmid containing reporter gene and AAV2 ITRs were transfected into 70% confluent, HSV infected, 293 cells in using OZ Bioscience $CaPO_4$ Transfection Kits. Cells were harvested at appropriate cytopathic effect (CPE) level. Cell lysate was processed and vector was purified using a CsCl2 gradients. Vector was purified from CsCl2 gradient using Millipore Amicon Ultra-4 Centrifugal Filter Units and protocol. Membrane of centrifugal unit was washed and collected twice with 500 ul of PBS. 25 ul of vector was treated with DNase, then SDS and proteinase K overnight. The vector DNA was extracted using phenol and chloroform and DNA was titered using quantitative real time PCR.

In Vitro Transductions

Mononuclear cells were isolated using a Ficoll-paque gradient on human cord blood. Hematopoietic stem cells were double purified from the mononuclear cells by magnetic column, using CD34 as a cell surface marker. Approximately $10^6$ $CD34^+$ cells were plated in media containing human cytokines and antibiotics. Cells were transduced with EGFP $CD34^+$ capsid vector at a multiplicity of infection (MOI) of 20,000. Transduced cells were harvested at approximately 20 to 24 hours, washed in a sodium azide buffer, and percent of EGFP positive cells was determined by flow cytometry.

rAAV Transductions

Purified CB $CD34^+$ cells were transduced at a MOI of 20,000 in Iscove's Modified Dulbecco's Medium (IMDM) containing 20% FCS, 100 ug/mL streptomycin, 100 U/mL penicillin, 2 mmol/L L-glutamine, IL-3 (10 ng/mL; R&D Systems, Minneapolis, Minn.), IL-6 (10 ng/mL; R&D Systems, Minneapolis, Minn.), and SCF (1 ng/mL; R&D Systems, Minneapolis, Minn.). Cells were incubated in humidified CO2 at 37° C. After 24 hours, cells were washed 3 times in Hanks Balanced Salt Solution (HBSS) and resuspended in approximately 150-300 ul of HBSS for transplantation into NOD/SCID mice (8, 12, 29).

HSC Transplantations

NOD/SCID mice (The Jackson Laboratory, Bar Harbor, Me.) were maintained in micro isolators at the Animal Resources Center, City of Hope National Medical Center. All animal care and experiments were performed under protocols approved by the Institutional Animal Care and Use Committee, City of Hope. 6-8 week old male NOD/SCID mice were placed on Sulfatrim antibiotic (10 mL/500 mL $H_2O$) for at least 48 hours before transplant. Mice were irradiated with a sublethal dose of 350cGy from a $^{137}Cs$ source and allowed to recover for a minimum of 4 hours prior to transplantation. For the majority of transplants, $7\times10^5$-$1\times10^6$ transduced $CD34^+$ cells were infused via the tail vein in a total volume of 150-300 ul. Mice were sacrificed at 5-20 weeks post-transplant. Marrow from femurs and tibiae, spleen and thymus were harvested from each mouse. For secondary transplants, total marrow cells were harvested from primary recipients at 5-14 weeks post-transplant and infused into secondary recipients.

Serial Bioluminescent Analysis of Luciferase Expression

Luciferase expression in xenografted mice was monitored by serial biweekly bioluminescent imaging using a Xenogen In Vivo Imaging System (Caliper Life Sciences, Hopkinton, Mass.). Mice were anesthetized with oxygen containing 4% isoflurane (Phoenix Pharmaceuticals, St. Joseph, Mo.) for induction, and 2.5% for maintenance. Luciferin (Caliper Life Sciences, Hopkinton, Mass.) was injected intraperitoneally at a dose of 0.15 mg/gram of mouse weight. Photons were accumulated over a five-minute exposure from the ventral aspect, ten minutes post-injection. Living Image 3.0 software (Caliper Life Sciences, Hopkinton, Mass.) was used to calculate light emission.

Flow Cytometric Analysis

Human engraftment in NOD/SCID mice was determined by flow cytometry following staining of marrow, spleen and thymus cells with human-specific monoclonal antibodies and analysis of 50,000 events. Human-specific engraftment was evaluated following staining with anti-human CD45 antibody (Becton Dickinson, Mountain View, Calif.). Human $CD34^+$, $CD19^+$ and $CD14^+$ or $CD33^+$ cells from primary and secondary recipients were analyzed and flow-sorted following staining with human-specific antibodies.

Cell suspensions were incubated with human-specific monoclonal antibodies for 30-60 minutes at 4° C. as per the manufacturer's protocol. The samples were analyzed on a MoFlo flow cytometer (Cytomation, Fort Collins, Colo.). 50,000 events were acquired using triple laser excitation. Bone marrow, spleen and thymus cells were labeled with anti-human CD45 antibody conjugated with PerCP or FITC (Becton Dickinson, Mountain View, Calif.) to evaluate human-specific engraftment. Lineage distribution was assessed following staining with human specific antibodies: PerCP-anti-CD45, APC-anti-CD34, FITC-anti-CD45, -anti-CD34, -anti-CD19, -anti-CD3, and PE-anti-CD38, -anti-CD14, -anti-CD33 (Becton Dickinson, Mountain View, Calif.). Human $CD34^+$, $CD19^+$ and $CD14^+$ or $CD33^+$ cells from the marrow and human $CD19^+$ cells from the spleen of primary and secondary recipients were flow sorted following staining with APC-anti-CD34, FITC-anti-CD19, and PE-anti-CD33 antibodies for vector genome analysis.

In vitro expression was analyzed 24 hours after rAAV-EGFP transduction on 20,000 cells. Cells were washed in a 5% FCS, 0.1% sodium azide PBS (Mediatech, Manassas, Va.) solution before analysis on a Cyan ADP Flow Cytometer (Dako, Denmark). Specific EGFP was quantified following the subtraction of autofluorescence. In vivo engraftment of human cells in both the bone marrow and spleen of xenografted mice was analyzed as described previously (29). Lineage distribution was assessed in bone marrow and spleen cell suspensions following staining with human specific antibodies: FITC-conjugated anti-CD45, FITC- or APC-conjugated anti-CD34, APC-conjugated anti-CD33 and anti-CD14, anti-Glycophorin A, PE-conjugated anti-CD19, and FITC-, PE- and APC-conjugated IgG controls (Becton Dickinson, Mountain View, Calif.). Bone marrow lineages were sorted by Fluorescence Activated Cell Sorting (FACS) using FITC-CD34, APC-CD33, PE-CD19 and Glycophorin A-APC, as well as the appropriate controls. FITC and PE fluorescence was excited by a 488 nm laser, and APC fluorescence was excited by a 670 nm laser. Flow cytometry data was then analyzed for specific populations with FlowJo software (Treestar, Ashland, Oreg.).

rAAV Frequency Detention rAAV2 frequencies were detected by quantitative real-time PCR with vector-specific primers and probe on a 7900HT Sequence Detection System (Applied Biosystems, Foster City, Calif.). High molecular weight DNA was extracted from human lineages isolated from the murine marrow using standard methods. Vector-specific sequences were amplified by real-time Taqman PCR analysis using the following primers: Luc1: 5'-AACTGCACAAGGCCATGAAGA-3' (SEQ ID NO: 65), Luc2: 5'-CTCAAAGTATTCAGCATAGGTGATGTC-3' (SEQ ID NO: 66), and were detected with the Taqman probe 5'FAM-TTGCCTTCACTGATGCTCACATTGAGGT-TAMRA-3' (SEQ ID NO: 67). Samples were also evaluated for the single-copy human gene ApoB, which served to quantitate human cell equivalents and as a template integrity control (Santat et al., 2005).

Results

Identification of Novel Human Stem Cell-Derived AAV

While evaluating AAV-mediated gene transfer to human hematopoietic stem cells (HSC), it was discovered that 9 out of 26 samples tested, about 35% of cytokine-primed peripheral blood $CD34^+$ stem cells from healthy donors harbored endogenous natural AAV sequences in their genome. The presence of endogenous AAV was detected using primers that hybridized to highly conserved regions and which flanked a hypervariable region of the AAV capsids. Since AAV isolates from $CD34^+$ HSC must have tropism for these cells reasoned that therefore would serve as highly efficient gene delivery vectors for HSC.

Sequence Analysis of Full-Length AAV Capsids.

Full-length natural AAV capsids genes were then amplified and sequenced from the AAV-positive stem cell samples (FIG. 5). 16 full-length AAV capsid clones were amplified from two donors. Sequence analysis of multiple clones of each type in both directions using an overlapping sequence strategy together with homology analysis of the AAV sequences obtained from stem cells revealed that the isolates from both donors mapped to AAV clade F.

Figure 6:
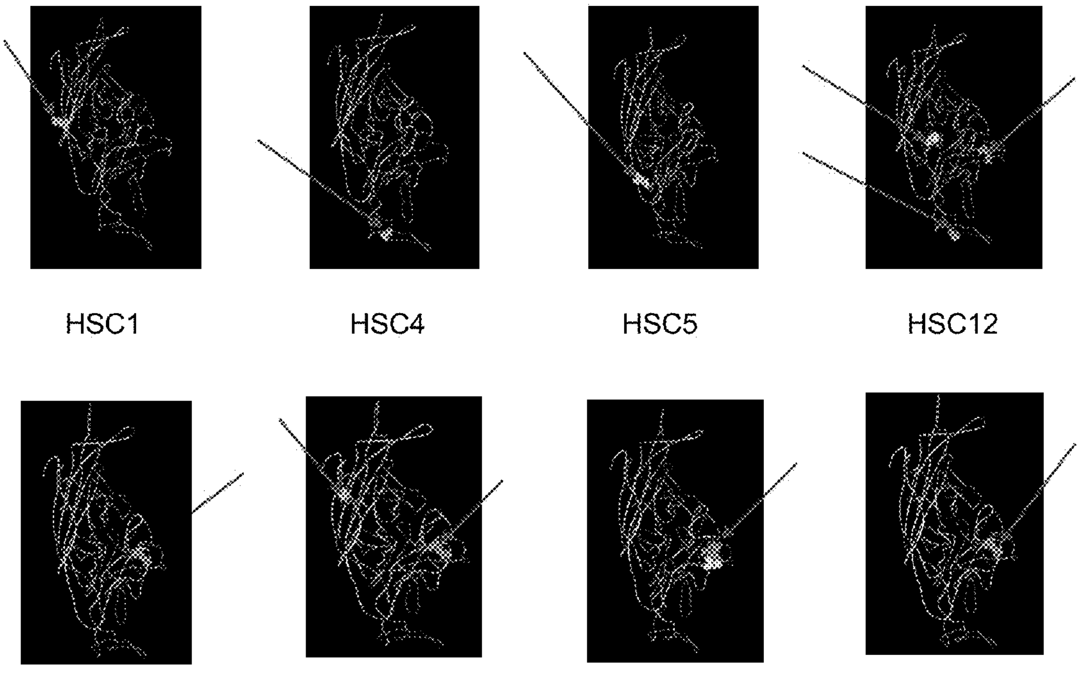
FIG. 6 shows 3D models of VP3 capsid proteins of stem cell AAVs showing novel amino acids. Arrows represent the novel amino acids. Only amino acid changes in VP3 are shown.

Sequence analysis revealed that the novel stem cell isolates of AAV possess unique amino acids in their capsid genes. Table 1 shows the amino acid differences relative to AAV9, a member of the same clade. While the majority of changes mapped to VP3 (FIG. 6), the most predominant protein of the AAV capsids, several isolates had additional novel amino acids in VP1. Some isolates had multiple amino acid differences, for example HSC12, HSC16. Many of the amino acid substitutions in the stem cell derived capsids were found to be located on the outside aspect of the capsid, showing they may be involved in the binding of the AAV virions to their cognate receptor(s) on stem cells. Other amino acids alterations map to the internal aspect of the virion and may play a role in accelerating uncoating after intracellular entry.

TABLE 1

Amino Acids Alterations in Stem Cell AAV Capsids Relative to AAV9

| Capsid | AA Change (Location on Capsid) |
|---|---|
| HSC1 | A2T (VP1), R312Q (VP3) |
| HSC2 | D626G (VP3), E718G (VP3) |
| HSC3 | G160D (VP1) |
| HSC4 | F119L (VP1), P468S (VP3) |
| HSC5 | K77R (VP1), E690K (VP3) |
| HSC6 | Q590R (VP3) |
| HSC7 | A68V (VP1) |
| HSC8 | Q151R (VP1) |
| HSC9 | C206G (VP3) |
| HSC10 | D626G (VP3), E718G (VP3) |
| HSC11 | D626Y (VP3) |
| HSC12 | R296H (VP3), S464N (VP3 HVR 5), G505R (VP3), V681M (VP3) |
| HSC13 | G505R (VP3) |
| HSC14 | G505R (VP3), L687R (VP3) |
| HSC15 | T346R (VP3), G505R (VP3) |
| HSC16 | F501I (VP3 HVR 7), G505R (VP3), Y706C (VP3 HVR12) |
| HSC17 | G505R (VP3) |

Figure 7:
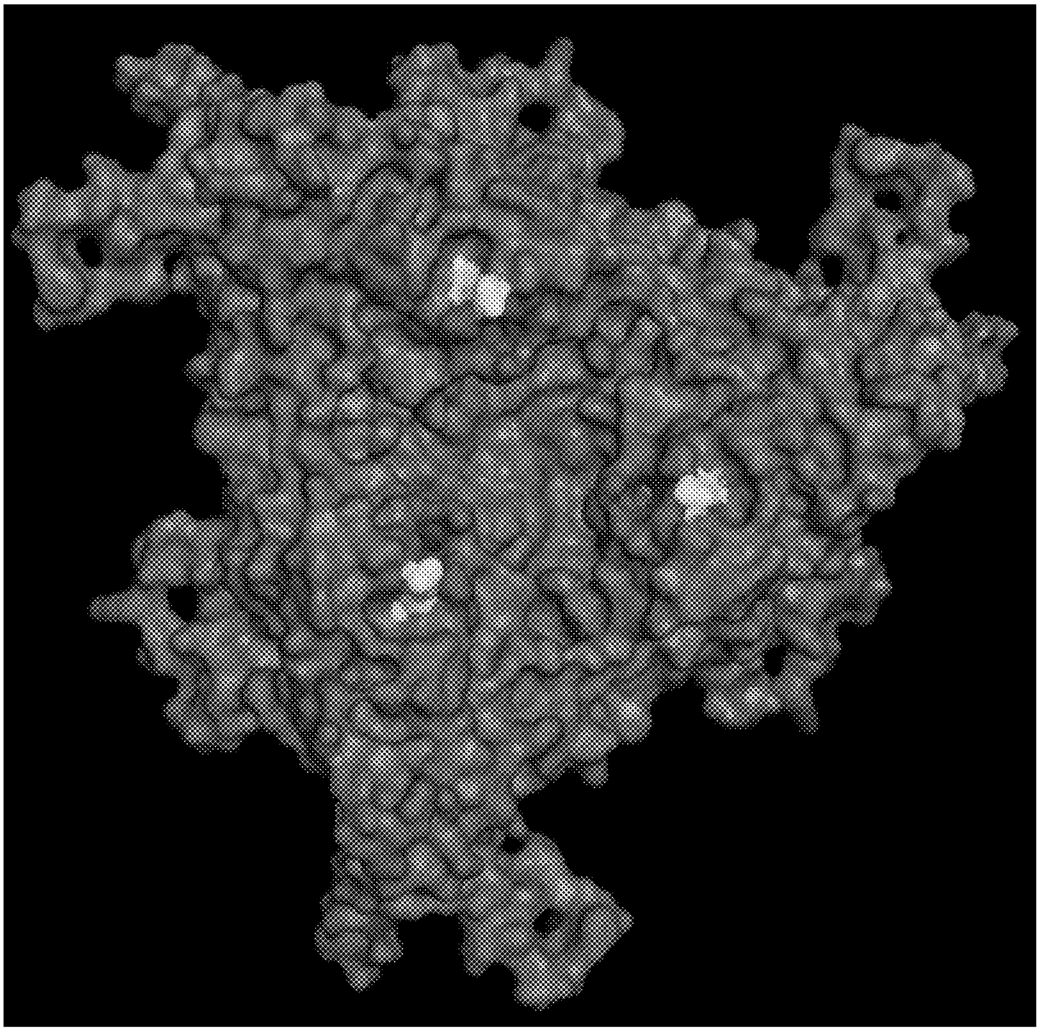
FIG. 7 is a three-dimensional representation of a HSC1 trimer with R312 shown in lighter grey.

These changes were mapped onto the crystal structure of AAV to determine the role possible of these changes. Of the two altered amino acid residues in HSC1, the A2T, in VP1, is not ordered on the crystal structure and R312Q in VP3 is pointing into the capsid on the inside surface (FIG. 7). For HSC4, F119L, in VP1 is not ordered in the crystal structure and P468S in VP3, is located on the wall of the 3-fold mounds towards the 2-fold axes. For HSC5, amino acid K77R, in VP1, is not in the crystal structure and E690K, inVP3, is located at a monomer-monomer interface placed to interact with an arginine residue, 296. For HSC15, amino acid 346 is located on the inside of the capsid and buried while 505 is surface exposed. Both amino acids are located in VP3. Interestingly, a number of other variants display the G505R change, including HSC12, HSC13, HSC16 and HSC17.

Pseudotyping of rAAV Genomes in Stem Cell-Derived AAV Capsids.

Figure 8:
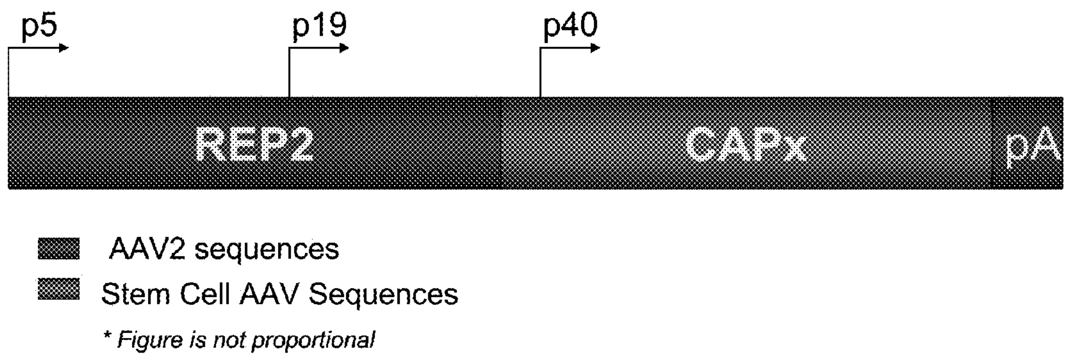
FIG. 8 shows packaging plasmid: Rep2/Capx. Dark gray areas represent AAV2 sequences. Light gray area represents stem cell AAV sequences.

A series of packaging plasmids composed of AAV2 rep genes and the novel stem cell capsid genes were created to package infectious rAAV consisting of the novel capsid shells. These new infectious rAAV were then tested for enhanced tropism for the $CD34^+$ HSC (FIG. 8). The endogenous p40 promoter derived from the novel AAV isolates was used to drive the three colinear capsids genes, VP1, VP2 and VP3. A single stranded rAAV2 genome encoding either the firefly luciferase gene or a self-complementary rAAV encoding the EGFP gene was packaged in the stem cell-derived AAV capsids. The titers of the majority of the purified pseudotyped stem cell rAAV vectors ranged from $10^{10}$-$10^{12}$ vg/ml, comparable to other rAAV vectors routinely packaged in the laboratory, showing that these capsids are capable of packaging AAV genomes and generating infectious particles. Table 2 shows that the stem cell-derived capsids package to titers comparable to that of the standard AAV serotypes.

TABLE 2

Titers of rAAV HSC Vectors

| rAAV Pseudotype | scEGFP | ssLuc |
|---|---|---|
| HSC1 | 3.8E+11 | 4.37E+11 |
| HSC4 | 7.1E+11 | 2.05E+11 |
| HSC5 | 5.45E+10 | 1.31E+12 |
| HSC7 | 8.58E+10 | 4.52E+12 |
| HSC12 | 9.65E+10 | 8.85E+10 |
| HSC13 | 4.01E+10 | 1.09E+12 |
| HSC15 | 6.42E+10 | 9.81E+11 |
| HSC16 | 8.04E+10 | 1.86E+12 |
| HSC17 | 5.93E+11 | 1.95E+12 |
| AAV2 | 3.58E+11 | 1.00E+11 |
| AAV7 | 1.79E+11 | 7.00E+11 |
| AAV8 | 7.13E+11 | 9.20E+12 |
| AAV9 | 3.38E+10 | 7.5E+12 |

Human $CD34^+$ cells harbor novel endogenous AAVs which map to AAV clade F. Many of the novel amino acids in these new AAV isolates are in VP3 and/or in VP1 and located on the outside of the capsids. Novel capsids are capable of generating infectious particles when used to pseudotype AAV genomes.

High Efficiency Transduction of Human $CD34^+$ HSC In Vivo and In Vitro

Figure 9A:
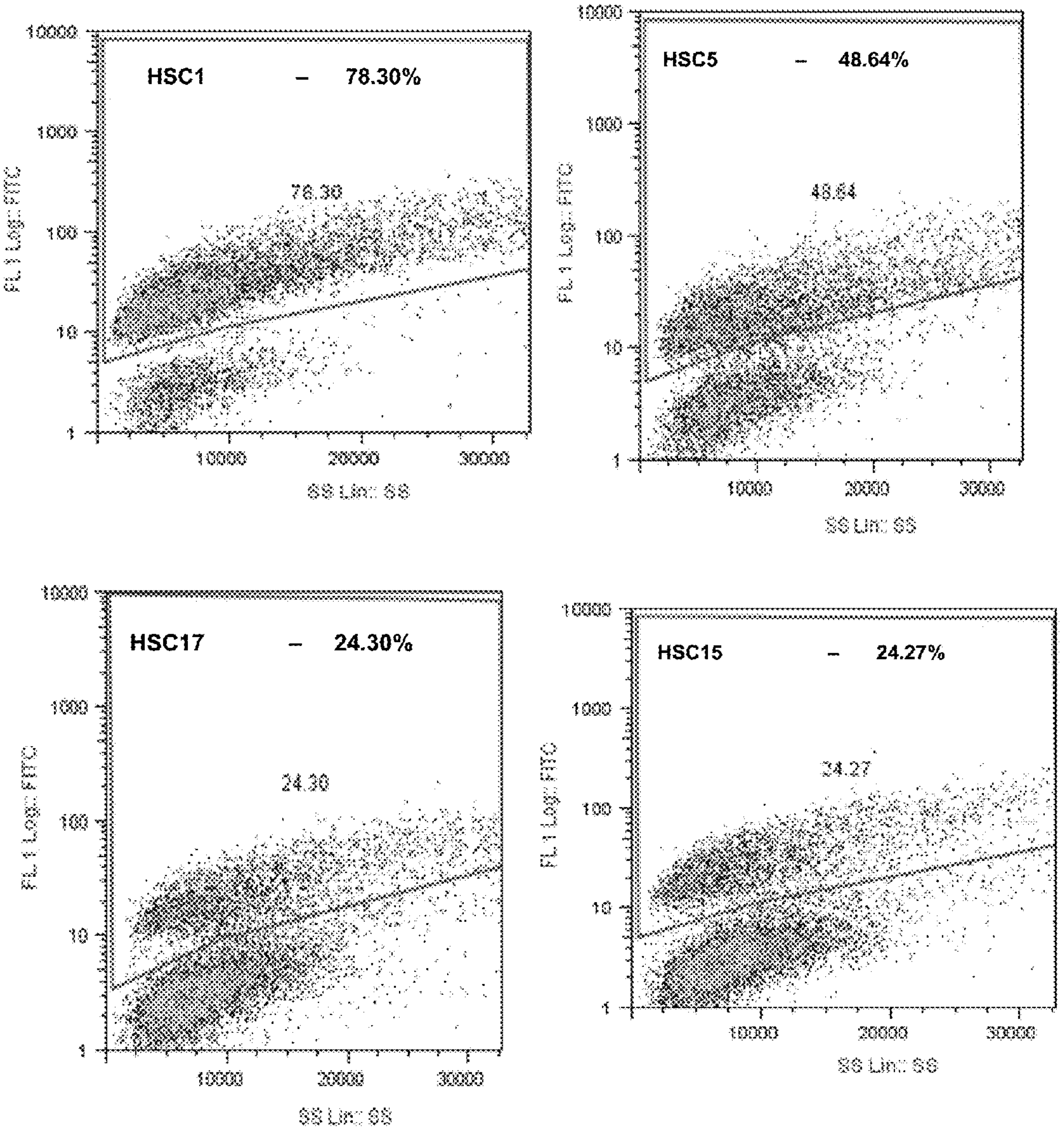
FIGS. 9A and 9B show enhanced green fluorescent protein (GFP) expression in pooled cord blood $CD34^+$ cells transduced with stem cell-derived AAV vectors in two representative experiments.
Figure 9A:
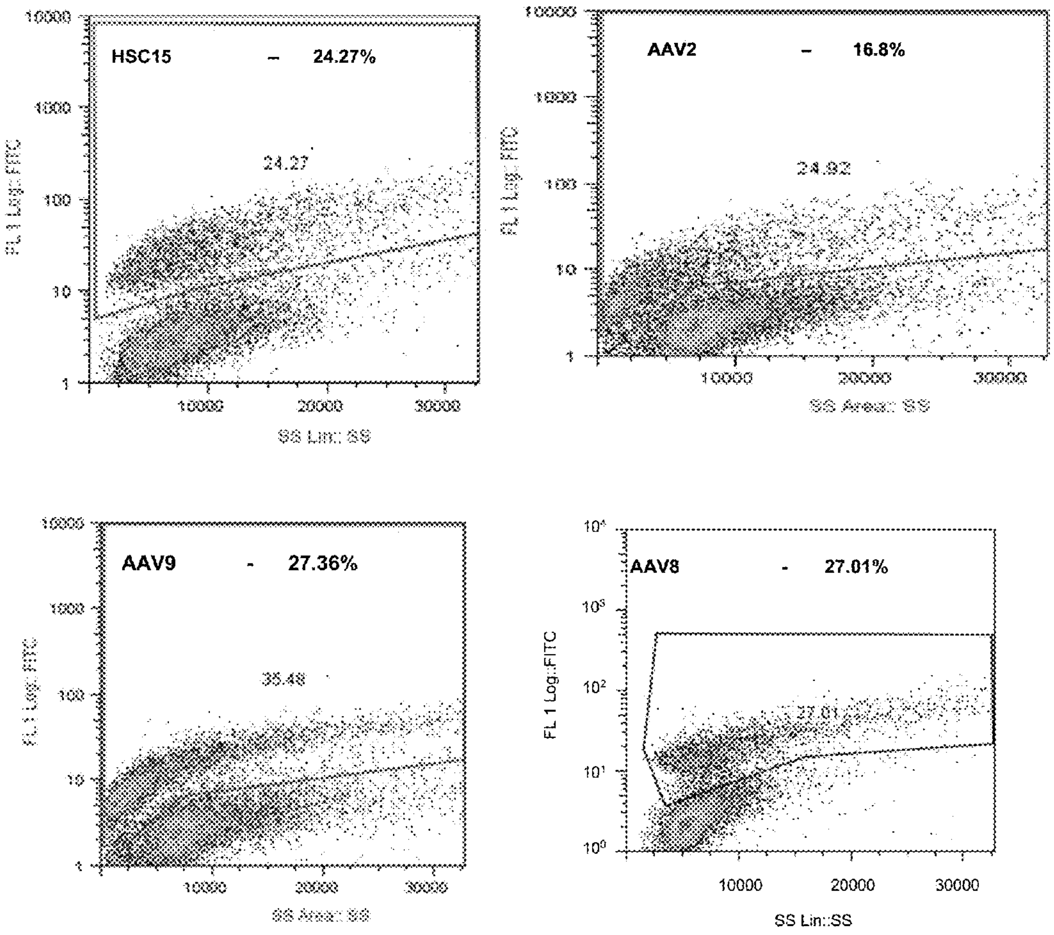
Figure 9B:
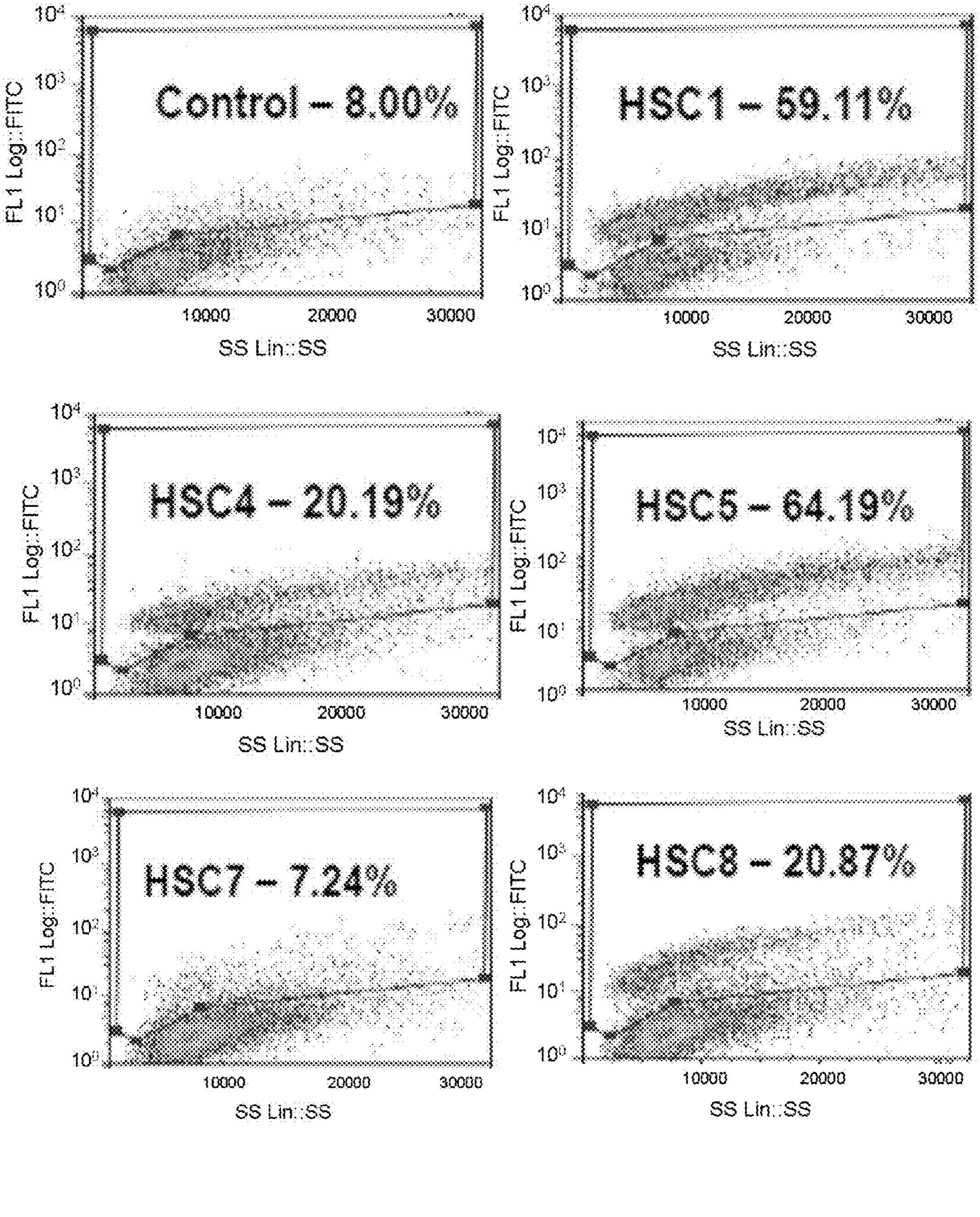
Figure 9B:
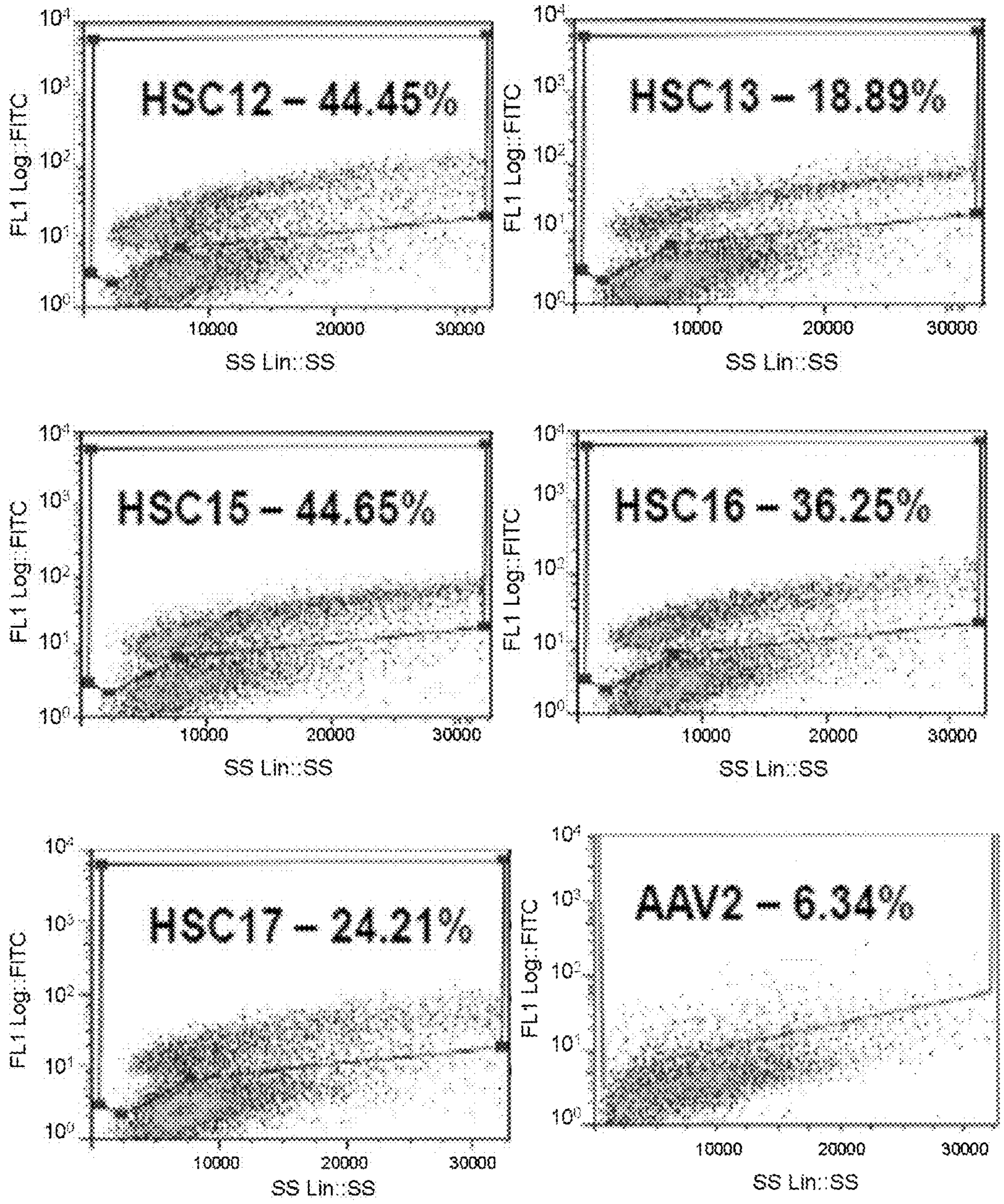
Figure 9B:
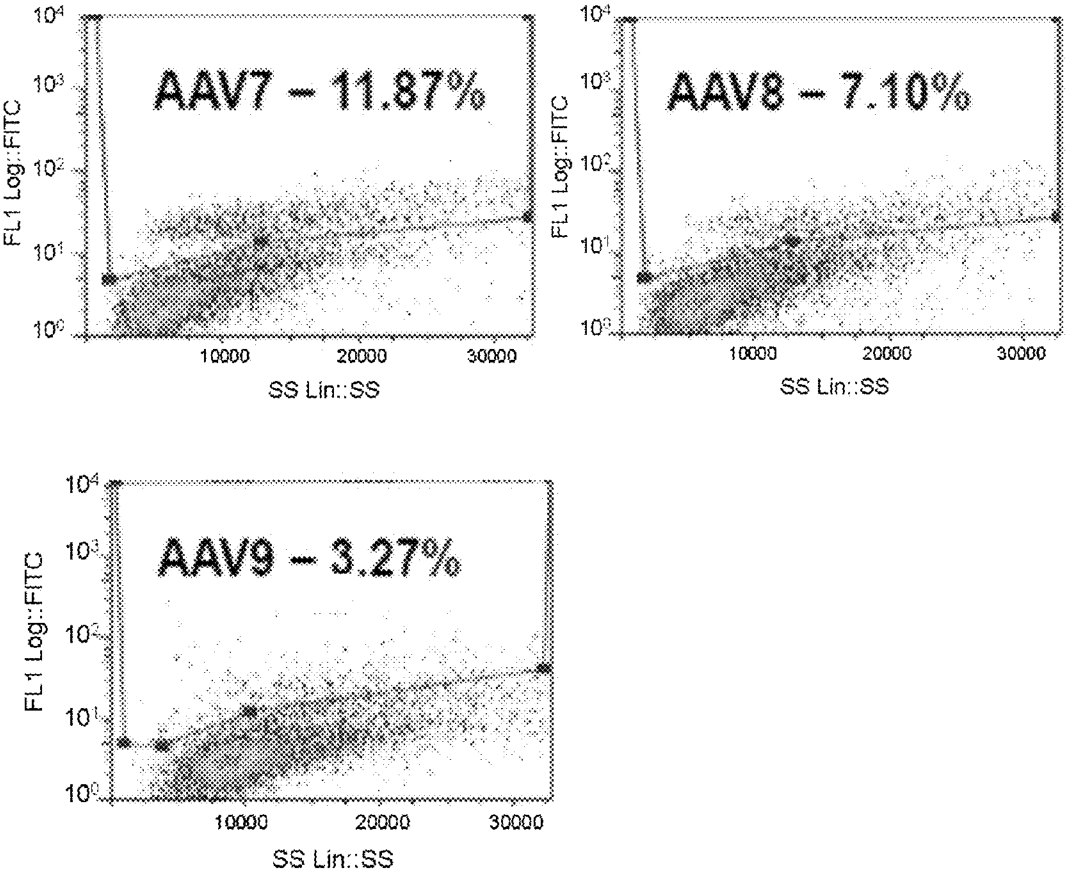
Figure 10A:
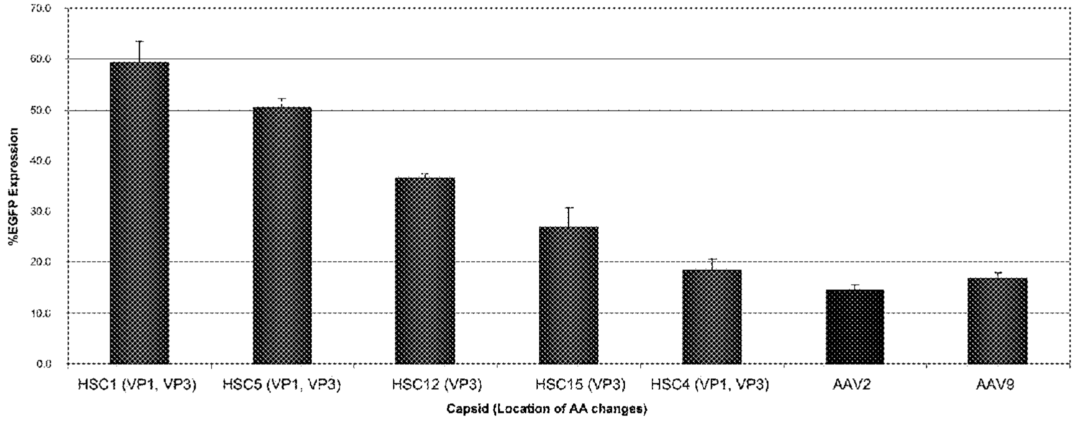
FIG. 10A shows GFP expression from four separate experiments and FIG. 10B shows GFP expression from five separate experiments using pooled cord blood $CD34^+$ HSC.
Figure 10B:
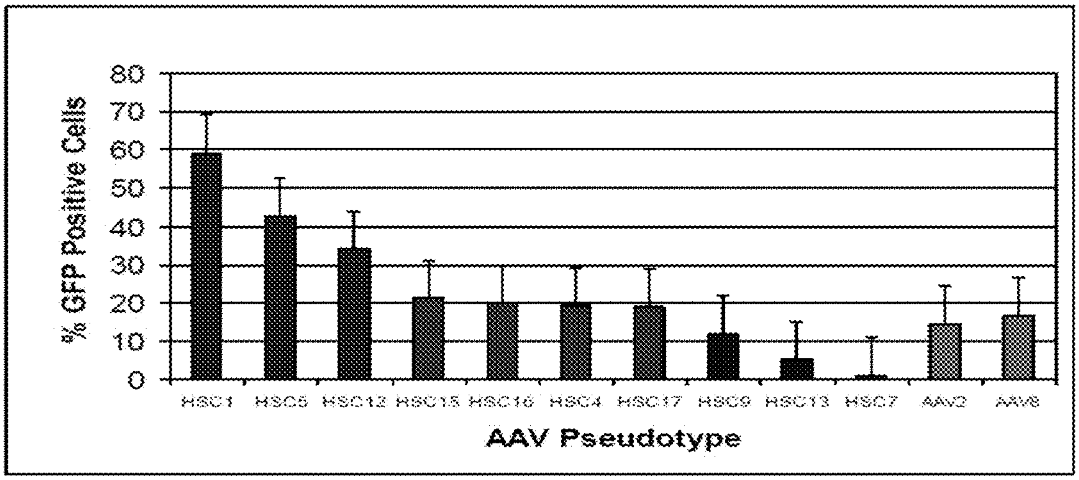

Novel AAV Capsids Mediate Enhanced In Vitro Transduction of Cord Blood $CD34^+$ Stem Cells To determine if the novel stem cell-derived rAAV vectors have increased tropism for human HSC, cord blood derived $CD34^+$ cells were transduced with rAAV-EGFP and analyzed by flow cytometry. FIGS. 9A and 9B show EGFP expression in pooled CB $CD34^+$ cells in two representative experiments. In FIG. 9A, capsids HSC1 and HSC5 transduced 78.3% and 48.6% of $CD34^+$ cells respectively. These represent one group of novel capsids that transduce $CD34^+$ cells at levels significantly higher than previously observed for any AAV serotype. Capsids HSC17, HSC15 and HSC4 transduced 22.6 to 24.3% of $CD34^+$ cells and represent a second group of novel capsids, transducing at levels comparable to that observed with standard serotypes. In FIG. 9B, rAAV HSC1 and HSC5 transduced 59.11% and 64.19% of CD34+ cells respectively. AAV isolates HSC4, HSC8, HSC13, HSC15, HSC16 and HSC 17 represent a second group of novel capsids that transduce human HSC in vitro at intermediate levels. GFP expression from four separate experiments using pooled cord blood $CD34^+$ HSC is shown in FIG. 10A and GFP from five experiments is shown in FIG. 10B. Consistently high levels of transduction were observed with stem cell capsids HSC1 and HSC5. HSC1, HSC5 and HSC12 display the highest gene in vitro transfer efficiencies on stem cells, reproducibly transducing at least 40 to 60% of CD34+ cells from different donors. For specific CB CD34+ samples, HSC1 displayed very high in vitro transduction efficiencies of up to 80%. Intermediate in vitro gene transfer efficiencies were observed with HSC4, HSC15, HSC16 and HSC 1, with an average of approximately 20% of CD34+ cells being transduced and >30% transduction of cells observed with specific CB samples. These represent far more efficient in vitro transduction of $CD34^+$ cells than that attained with the best standard rAAV serotype.

Stem Cell-Derived Capsids Support Sustained Long Term In Vivo Transduction of Human HSC.

Figure 11:
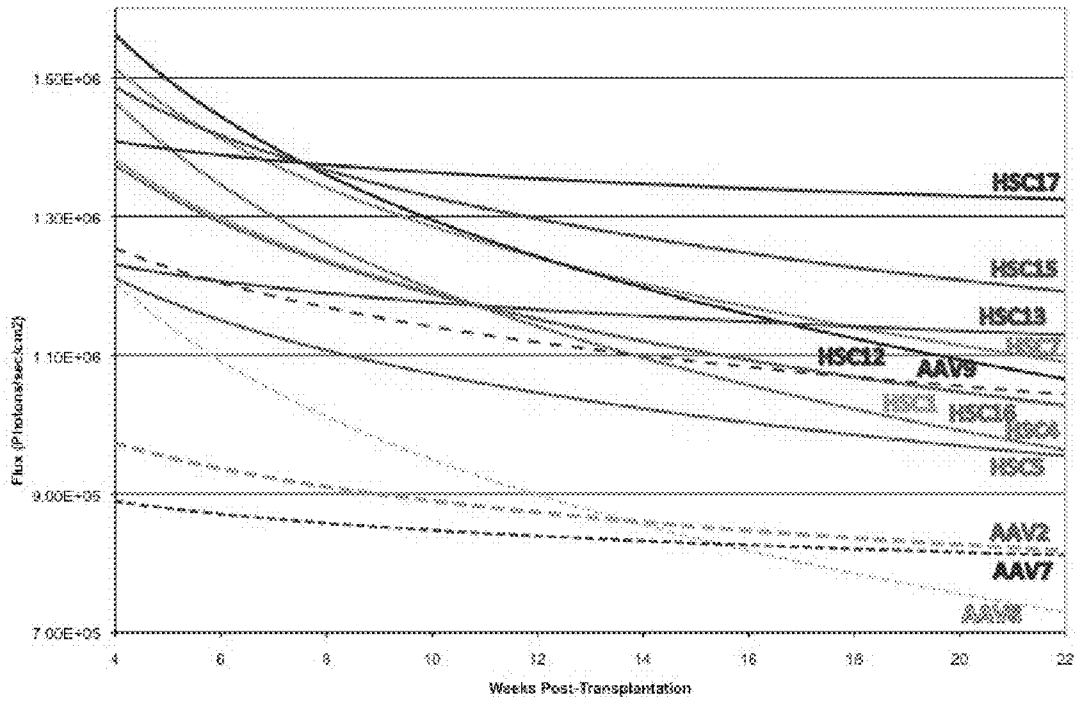
FIG. 11 is a graph showing quantitation via bioluminescence of NOD/SCID mice of long-term transgene expression in vivo transplanted with HSC transduced with stem cell-derived AAV. Novel vectors HSC17 and HSC15 support the highest level transduction. Also shown are the standard serotypes, which transduce to a significantly lower level than the stem cell-derived vectors. Recipients were followed up to 6 months post-transplantation.
Figure 12:
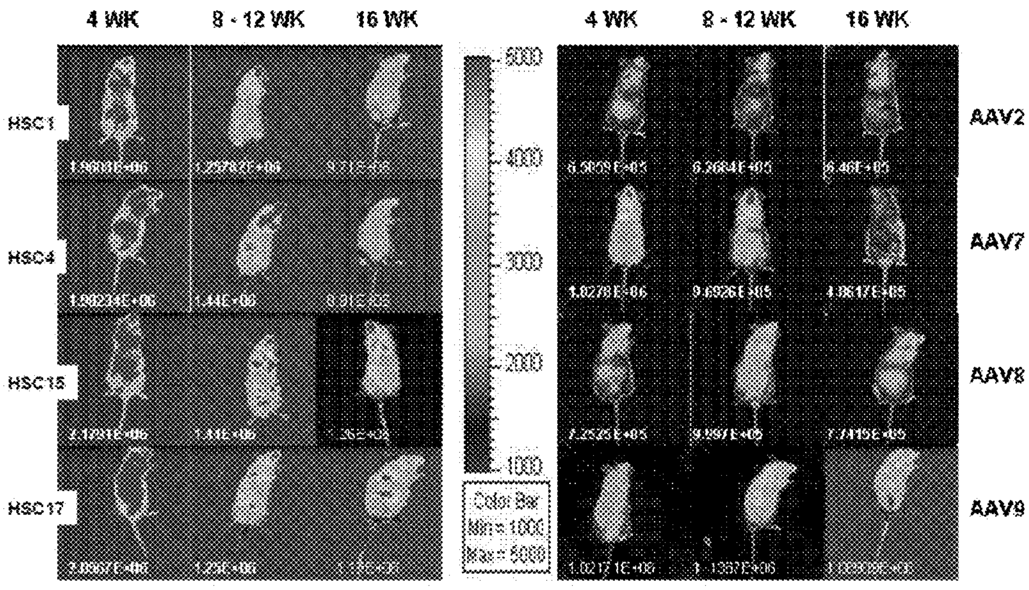
FIG. 12 shows in vivo luciferase expression in representative xenografts recipients.

Since stem cell-derived AAV capsids demonstrated very high transduction properties on $CD34^+$ cells in vitro, the ability of the novel vectors to support engraftment and sustained transgene expression in vivo was then evaluated. Human cord blood $CD34^+$ cells were transduced overnight, washed and transplanted into sublethally irradiated immune-deficient NOD/SCID mice. The rAAV encoded the firefly luciferase gene under the control of a constitutive CBA promoter. Serial bioluminescent imaging of transplant recipients performed biweekly after 4 weeks post-transplantation revealed that each novel capsid tested supported long-term engraftment, to at least 18-22 weeks, the end point of the experiment (FIGS. 11 and 12). Each pseudotype represents at least 4 mice per group for the new capsids. Dramatically high initial levels of luciferase expression were observed in vivo early after transplantation followed by a stabilization of expression. Notably, luciferase expression from stem cell derived AAV was approximately 1.5-2-fold higher than that seen with the best standard serotypes (FIG. 8).

Interestingly capsid HSC15 maintained an elevated level of expression throughout the experiment, up to 18 weeks post-transplantation. Capsids HSC1, HSC4, HSC12, HSC17 supported an intermediate level of expression, at 25-50% higher than the best standard serotypes. This is the highest level of sustained in vivo transgene expression observed in human $CD34^+$ cells and their progeny after transplantation.

These results indicate that these stem cell-derived rAAV vectors have the potential to be the optimal vectors for gene delivery to human HSC. FIG. 11 shows in vivo luciferase expression in representative xenografts recipients. Stem cell-derived AAV are capable of transferring genes to human HSC at much higher efficiencies than ever noted before with standard serotypes, making it essential to include them in the evaluation of pseudotyped AAV for the identification of the ideal candidate serotype for eventual clinical use.

The new stem cell-derived capsids support sustained and efficient transduction of $CD34^+$ HSC in vitro and in vivo after transplantation of rAAV-transduced cells into immune-deficient mice. Transplantation of transduced HSC within 24 hours of transduction in the presence of low cytokines results in long engraftment with primitive stem cells and sustained high level transduction in vivo. The levels of in vivo transduction observed with the AAV pseudotyped in the new capsids are significantly higher than that observed with the standard serotypes of AAV.

These novel AAV capsids are the most efficient transducers of human HSC in vitro which also support sustained long-term high level transduction in vivo. Preliminary in vivo transduction levels of HSC-derived rAAV suggest that they surpass that observed with the standard AAV serotypes. Thus results support the use of these novel AAV vectors for long term transduction of HSC in vivo.

In Vivo Engraftment of Transduced Human CD34+ Cells

Figure 13:
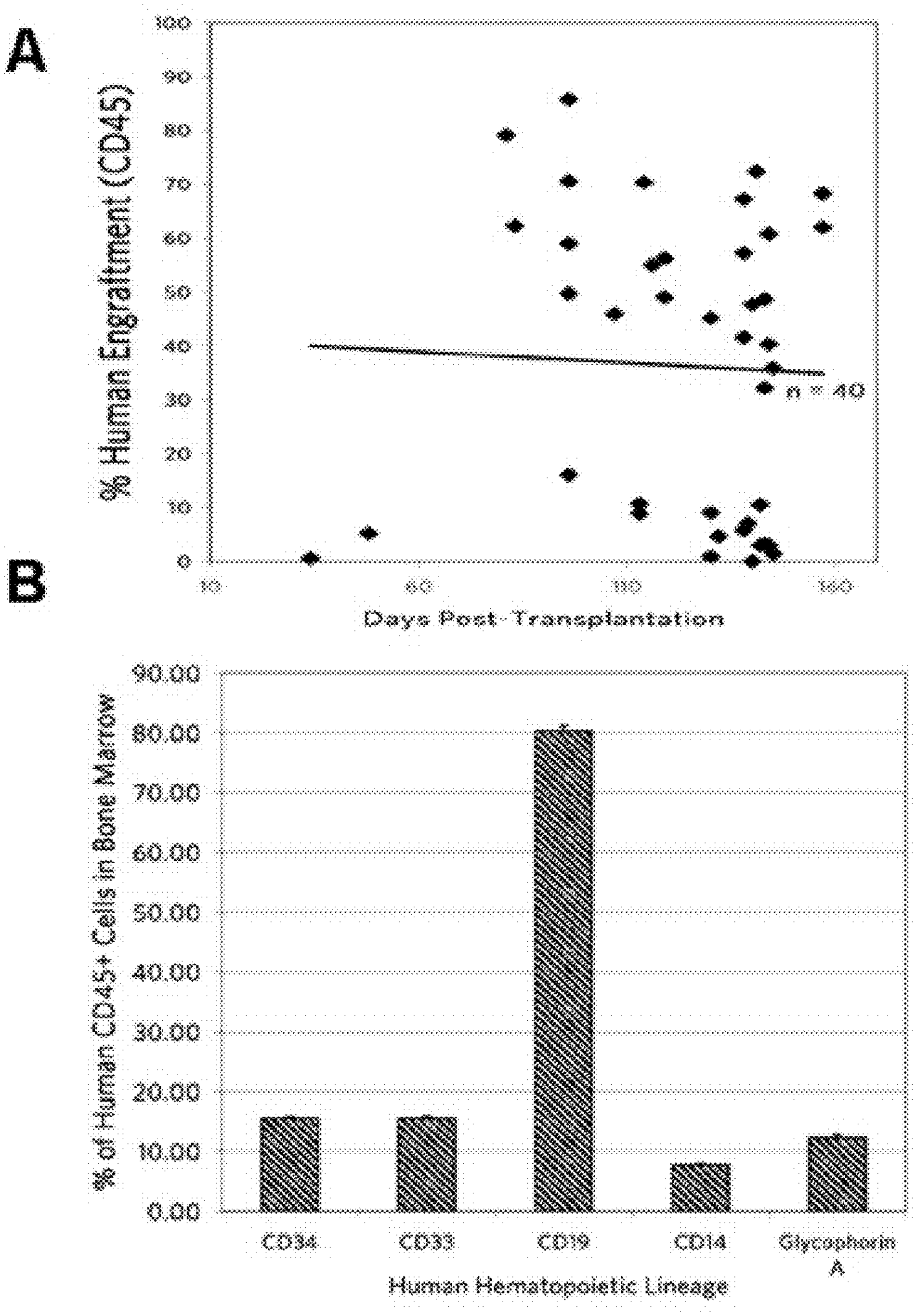
FIG. 13 shows engraftment of human CB $CD45^+$ cells transduced with recombinant AAV2 in NOD/SCID mice. Mice were transplanted with transduced $CD45^+$ cells pooled from 1-5 blood samples.

To determine whether cord blood CD34+ HSC transduced with rAAV2 could support long-term multilineage engraftment in immune deficient NOD/SCID mice, we evaluated human hematopoietic engraftment 16-22 weeks post-transplant in the bone marrow of xenograft recipients (FIG. 13A). Human cell engraftment in the bone marrow ranged from 0.5%-86% (median: 43.37%, n:40), as determined by the frequency of human CD45+ cells. Engraftment was found to be stable throughout the period of analysis, up to 22 weeks post-transplantation, suggesting a lack of toxicity associated with transduction of CD34+ cells with rAAV2, comparable to that observed with wt rAAV2 (29). In addition we conclude that CD34+ cells transduced with rAAV2 were capable of supporting long-term human hematopoietic engraftment.

The presence of differentiated human B lymphoid (CD19+), erythroid (glycophorin A+) and myeloid cells (CD14+ and CD33+) in the bone marrow up to 22 weeks post-transplantation, indicated that the highly purified input human CD34+ cells were capable of differentiation following transplantation (FIG. 13B). The continued presence of CD34+ stem/progenitor cells (15.54%+6.30) throughout the study indicated the ability of transplanted CD34+ cells to persist and/or self-renew in vivo. CD19+ B cells comprised the most frequent human cell subpopulation in the bone marrow (80.29%+19.70). CD33+ and CD14+ myeloid cells and glycophorin A+ erythroid cells accounted for 15.55%+8.11, 7.69%+3.49, 12.30%+8.46 of bone marrow cells, respectively (FIG. 13B). Importantly, no pathology or toxicity was associated with the transplant or engraftment of CD34+ cells transduced with rAAV2.

Analysis of the spleen in transplanted mice indicated that human CD45+ cells were also present (range: 0.2-47.5%, n=40), representing either direct homing or trafficking from the marrow. CD19+ B cells constituted most (89.7+16.2%) of the splenic human subpopulation. These results indicate the ability of transduced, transplanted human CD34+ cells to safely engraft, undergo multi-lineage differentiation and possibly traffic in vivo.

Transient High Level Transduction of CD34+ HSC In Vitro

As discussed in Paz et al, 2007, stable transduction of $CD34^+$ cells is dependent upon the culture conditions. Transduction for less than 24 hours in the presence cytokines followed by transplantation results in the retention of the stem cell properties of CD34+ cells and promotes stable transduction. One property of AAV in conjunction with the new capsids is exploited to transiently transduce HSC at high efficiency under conditions that encourage loss of vector genomes. This strategy is highly desirable for the delivery of genes which are required only transiently, without causing permanent genomic changes. Thus this approach can be used for the transient expression of reprogramming genes for the induction of induced pluripotent stem cells (iPSC); zinc fingers targeting specific genes; and miRNA/shRNA to specifically regulate temporal gene expression and induce differentiation along certain lineages. The data shows that AAV pseudotyped in HSC 5, 9, 12 and 17 capsids will transduce at very high efficiencies and the decline over time in culture to undetectable levels.

FIG. 14 shows transient transduction by the novel rAAV. rAAV genome copies per cells were quantitated by Taqman real time PCR between 1 and 7-14 days post-transduction. Initially high genome copy levels were observed at 24 hours post-transduction. This was followed by a decline of rAAV genomes in transduced CD34+ cells over time. Several log reduction in the genome copy number, as quantitated by Taqman real time PCR was observed by 7-14 days post-transduction. This was particularly notable with HSC5 and 12. Analysis of transgene expression revealed a parallel decline. These results strongly suggest that rAAV HSC5 and HSC12 represent good candidates for transient high level transgene expression in CD34+ cells without permanent genetic modification.

Efficient Transient Gene Transduction with Novel Non-Integrating AAV Vectors.

Figure 15:
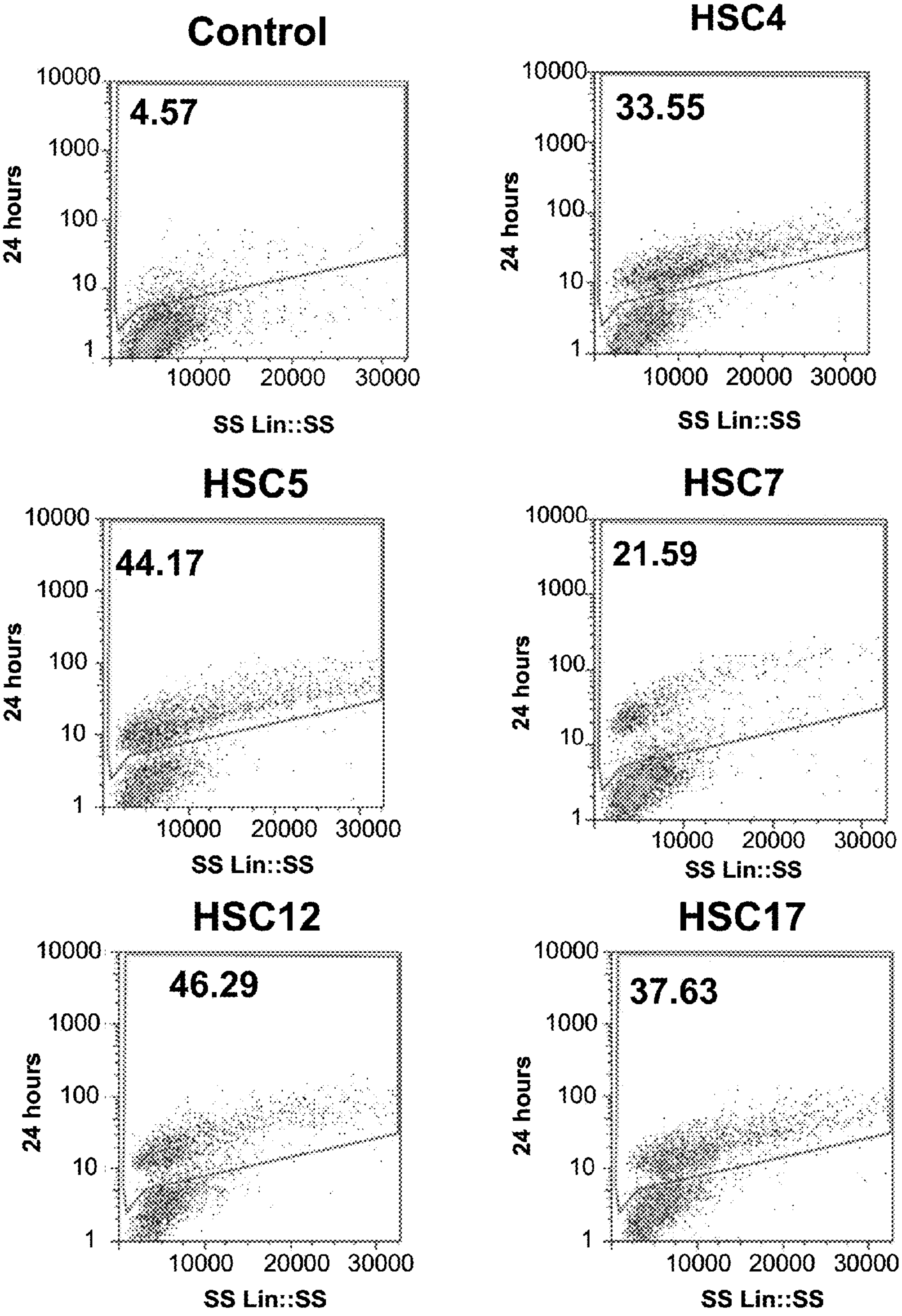
FIG. 15 shows EGFP expression in HSC transduced with representative AAV vectors pseudotyped in 4 different novel capsids. Under specific culture conditions that promote loss of episomal rAAV genomes, the novel isolates may be used to transiently transduce cells, without inducing permanent genetic change. Vectors may be used for inducing transient expression of induced pluripotent stem cells. EGFP expression is shown on Day 1, Day 4 and 1 Week after transduction of $CD34^+$ cells cultured under conditions that promote integration rather than loss of episomes.
Figure 15:
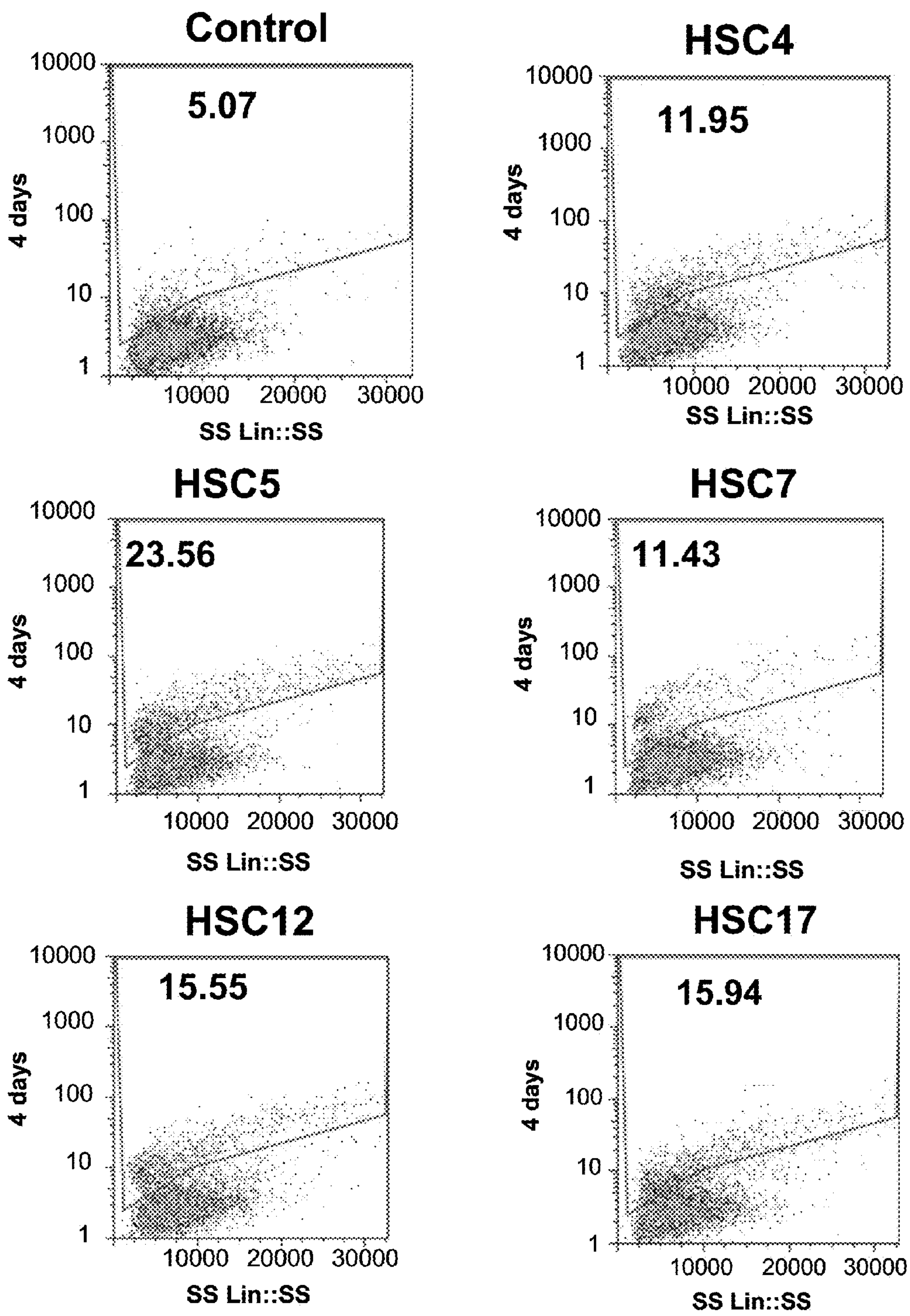
Figure 15:
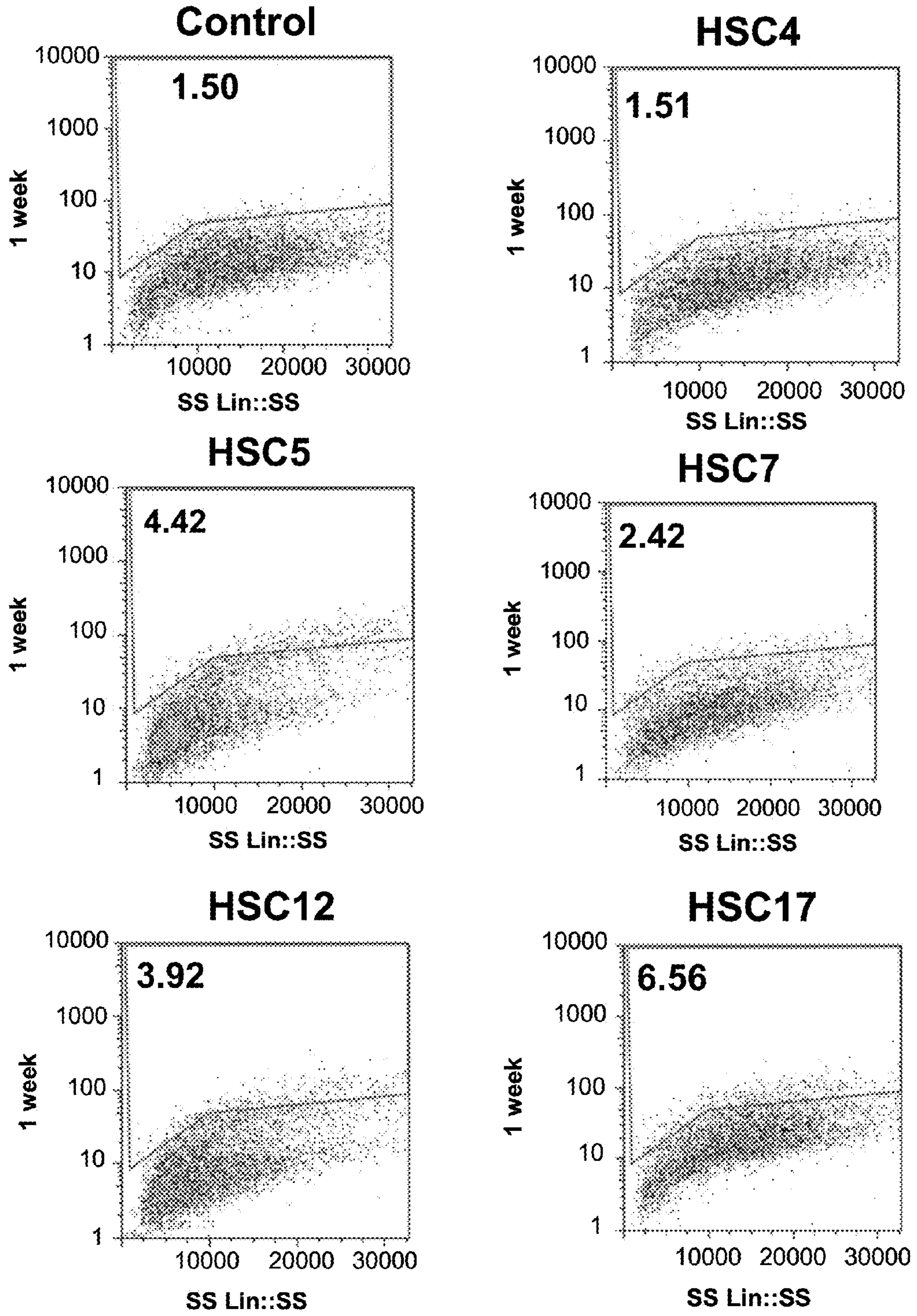

EGFP expression is shown in FIG. 15 on Day 1, Day 4 and Day 7 after transduction of $CD34^+$ cells cultured under conditions that promote integration rather than loss of episomes (8). Clearly high levels of EGFP expression are observed at 1 day after transduction, however even under the most stringent conditions, almost no transduction is observed after 1 week, showing that AAV vectors pseudotyped in these novel capsids display efficient transient transduction but do not persist long term.

Loss of AAV Vector Genomes in Culture

To quantitate the loss of AAV genomes from transduced cells, transduced $CD34^+$ cells were analyzed at 24 hours and 1 week post-transduction. Table 3 shows quantitation of loss of AAV genome copies per cell by real time Q-PCR. Pseudotype HSC5 showed a 40-fold decline and HSC12 showed a 566-fold decline, to undetectable levels within a week. Both of these serve as excellent candidates for the delivery of reprogramming genes. Both HSC5 and HSC12 transduce efficiently as shown by high EGFP expression at 1 day (FIG. 5), indicating that initial expression of reprogramming genes will be sufficiently high. Notably, EGFP, the transgene encoded by these vectors, showed a more modest decline, due to the half life of the protein. These results show that when pseudotyped in these capsids, AAV genomes are lost from transduced cells.

TABLE 3

Fold decreases in AAV transduction in HSC

| | Genome Copies | EGFP Expression |
|---|---|---|
| HSC5 | 40.32 | 13.12 |
| HSC12 | 566.10 | 11.81 |

The ability to efficiently generate induced pluripotent stem cells (iPSC) from somatic cells without the permanent introduction of foreign DNA holds tremendous promise for the production of patient-specific pluripotent stem cells for genetic correction of inherited diseases, regenerative medicine and transplantation. Reprogramming somatic cells of specific disease origin to iPSC has the potential to play a key role in developing human diseases models for testing promising therapies and studying pathophysiology. However, the most significant challenge with this promising technology lies in the use of integrating gene delivery vectors for the transduction of reprogramming genes while mitigating the risk of oncogenesis.

Systemic Delivery of AAV Pseudotyped in Novel Capsids

Figure 16:
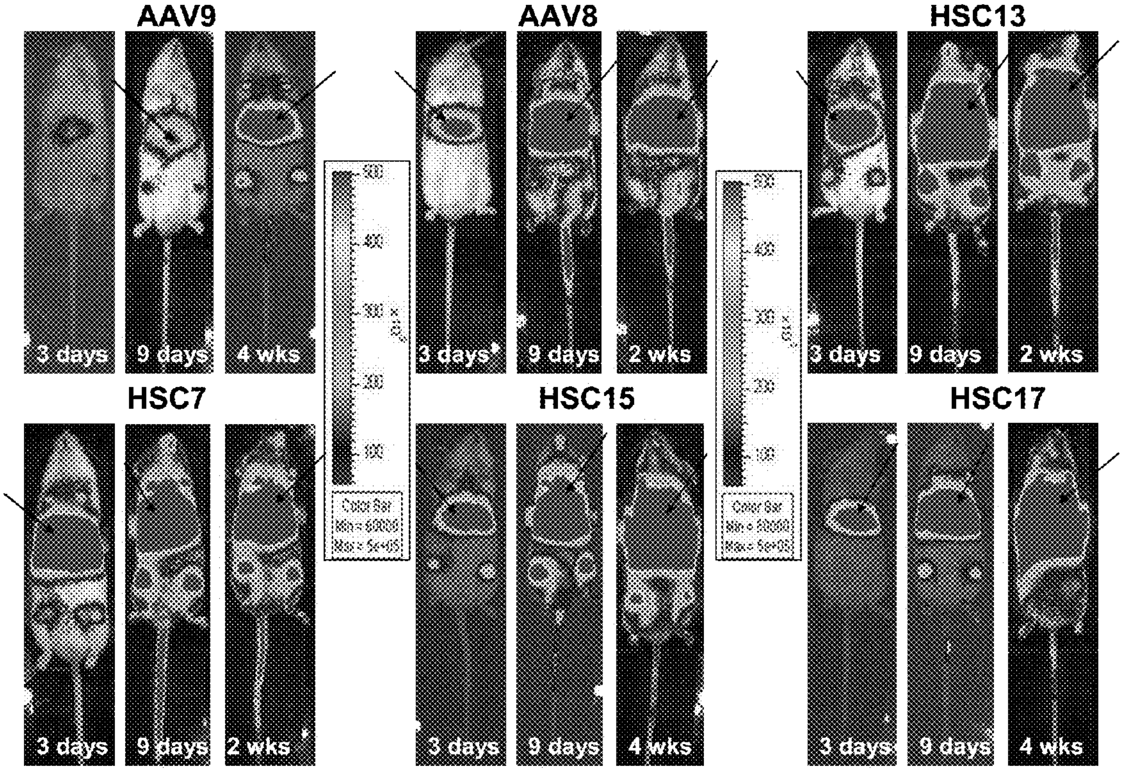
FIG. 16 shows systemic transduction after intra-venous delivery of AAV-Luciferase pseudotyped in novel capsids to mice. Arrows represents the strongest level of luciferase expression. In the standard serotype, AAV9, the initial 3 day image shows expression starting in the liver and joints. This expression continues to increase up to 4 weeks in both areas. HSC7, HSC13, HSC15, and HSC17 also show expression in the liver and joints starting at 3 days post-injection increase in localized areas gradually. HSC15 and HSC17 have high expression already at 3 days post injection and increase dramatically long term. This tropism to the liver can be advantageous for expression of therapeutic transgenes such as factor 9 for hemophilia B.

Many of the newly identified serotypes of AAV show novel tropisms for specific organs when delivered systemically in vivo. These tropisms appear to be independent of the tissue of origin. For example AAV9 targets the heart and AAV8 transduces the liver efficiently in mice. Similarly other specific serotypes show tropism for the eye, the CNS, the lung, the muscle, etc. Since in vivo tropisms are extremely valuable for use in gene therapy for organ-specific disorders, systemic delivery of AAV-luciferase pseudotyped was tested in our novel capsids. Serial in vivo bioluminescent imaging showed that a group of our novel capsids targeted the liver very strongly, with gene expression being evident as early as 3 days post-injection (FIG. 16) and persisting long-term. Comparison with AAV8, the current gold standard for the hepatic delivery of transgenes in mice, showed that injection of the same number of vector genomes resulted in resulted in significantly enhanced luciferase expression from our vectors than was significantly higher.

Figure 17:
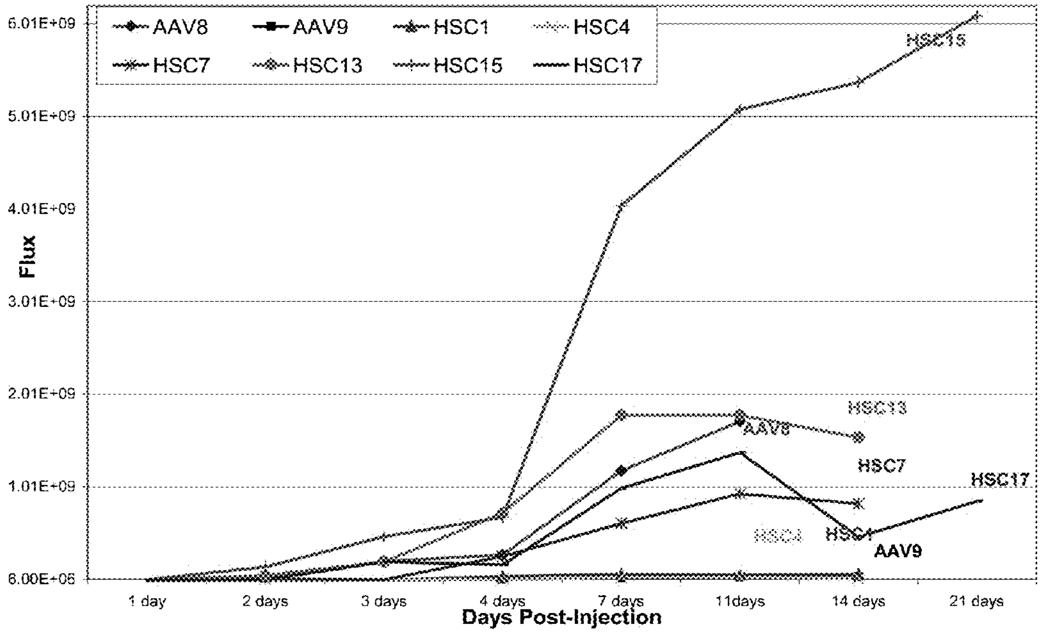
FIG. 17 is a graph representing the compiled results of in vivo serial bioluminescence measurements after systemic delivery of AAV-Luciferase pseudotyped in our novel capsids. Vectors pseudotyped in capsids HSC15, HSC17 and HSC13 clearly express superior to AAV8 and AAV9 in systemic expression of transgenes at persistently high levels in vivo.

FIG. 17 represents the compiled results of in vivo serial bioluminescence measurements after systemic delivery of AAV-Luciferase pseudotyped in our novel capsids. Vectors pseudotyped in capsids HSC15, HSC17 and HSC13 clearly express superior to AAV8 and AAV9 in systemic expression of transgenes at persistently high levels in vivo. These vectors are highly promising for the delivery of therapeutic transgenes such as Factor IX for the treatment of hemophilia or Apo lipoprotein A1 for the treatment of atherosclerosis or many enzymes for a variety of deficiency diseases. Thus these novel vectors also have clear significance for the use of these vectors for hepatic delivery of therapeutic transgenes.

Figure 18:
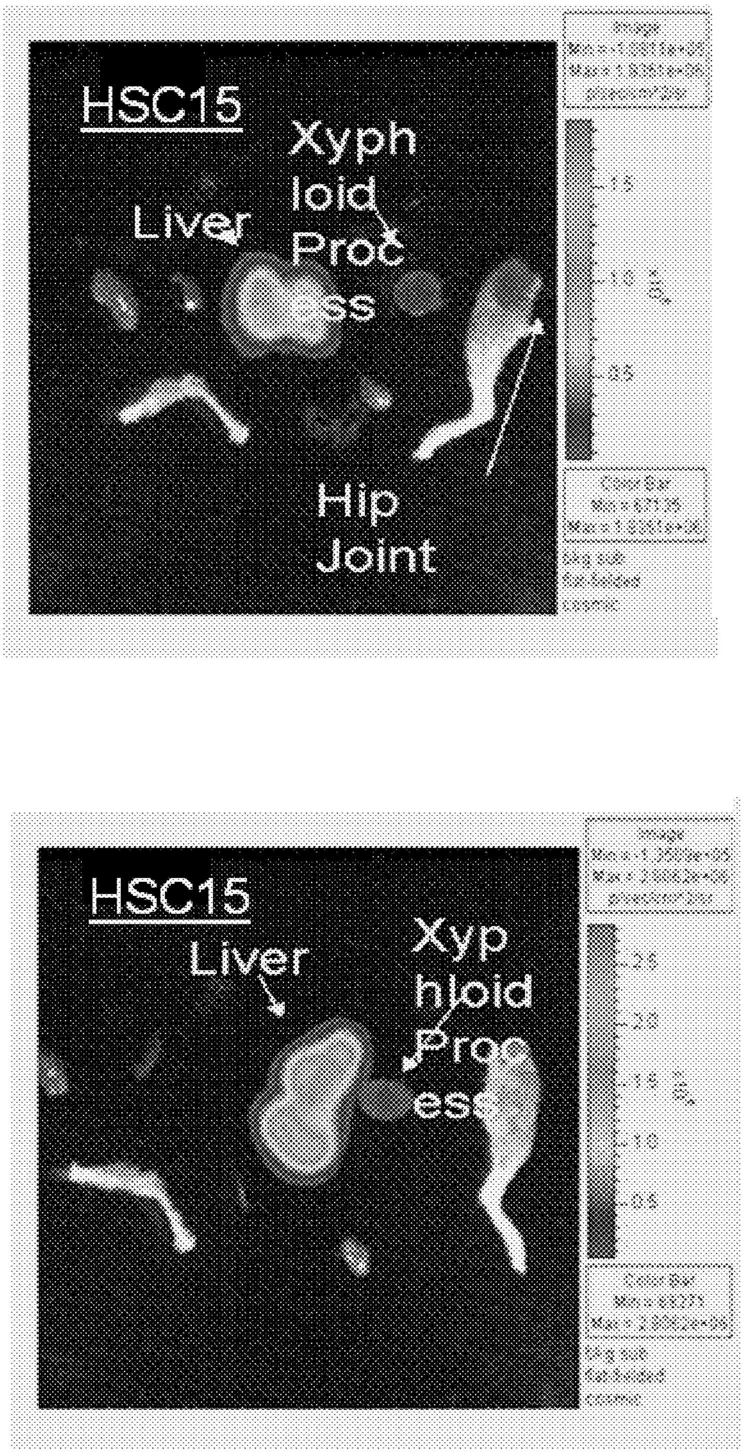
FIG. 18 shows luciferase expression in the liver and cartilage of a mouse injected with AAV-Luciferase pseudotyped in HSC15 and HSC17 capsids.
Figure 18:
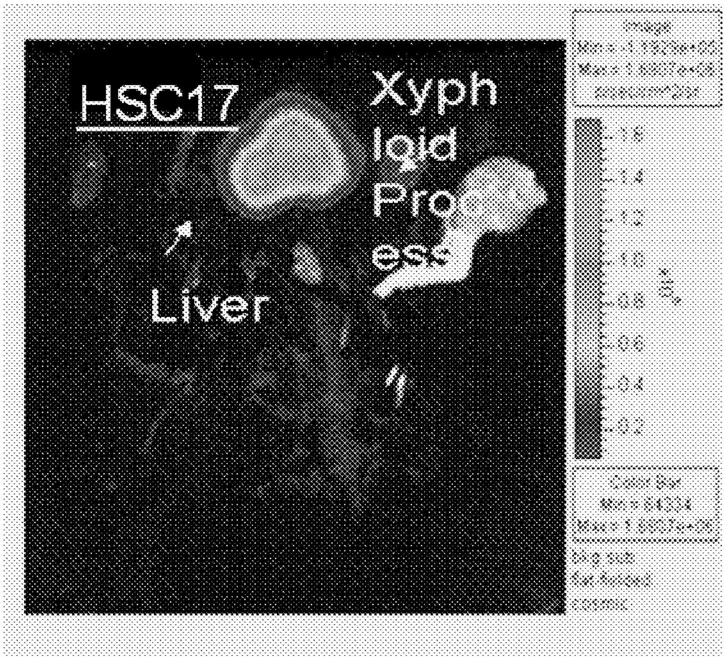
Figure 19:
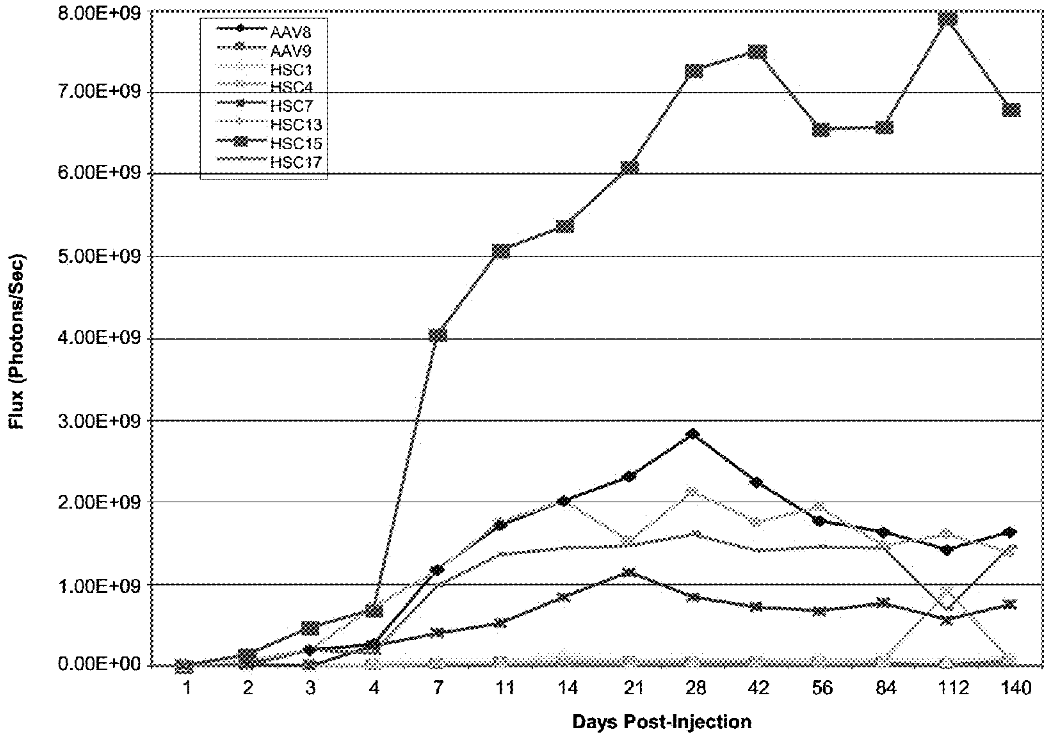
FIG. 19 shows long-term in vivo transgene expression following intra-venous injection of $10^{11}$ particles of stem cell-derived rAAV as measured by serial whole body bioluminescent imaging. Results represent averages of 4-6 mice per group. These results show that transgene expression from HSC15 is sustained and continues to be significantly higher than that from AAV8. In vivo imaging (FIG. 20) indicates that expression is primarily in the liver. Thus, HSC15 is a very promising vector for the treatment of a variety of genetic diseases including hemophilia, atherosclerosis, inborn errors of metabolism and other diseases or disorders.
Figure 20:
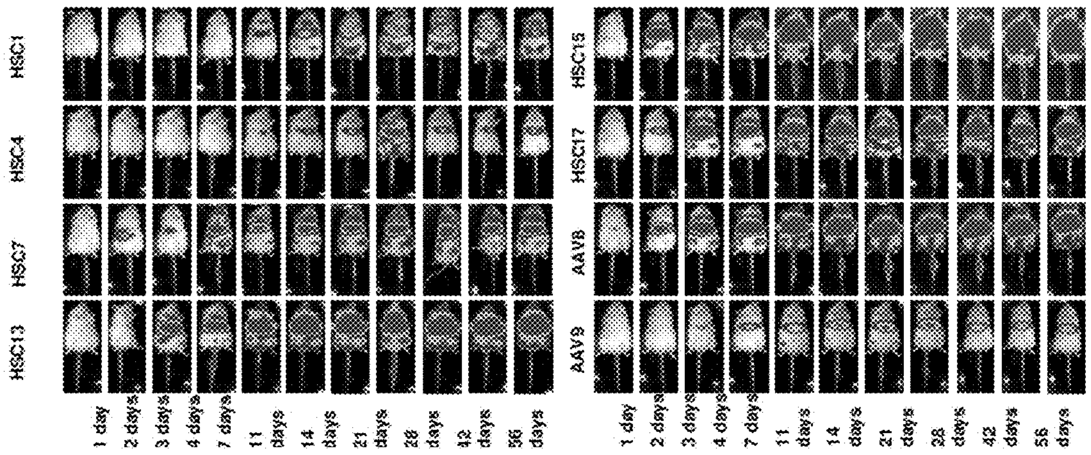
FIG. 20 shows serial bioluminescent imaging of whole body luciferase expression following systemic administration of rAAV-luciferase packaged in novel capsids. AAV8 and AAV9 controls are also shown. The strong sustained transduction of the liver with HSC15 is readily evident. In vivo transduction by HSC15 is stronger than that mediated by AAV8 in NOD/SCID mice. Before the present discovery, AAV8 was the best liver targeting gene transfer vector. Mice representative of the group are shown.

In addition to targeting the liver, there was also evidence for transduction of tissue in the knee, hip joints and the xyphoid process after systemic delivery. Organs dissected from mice given intra-venous injections of pseudotyped AAV-luciferase were imaged for luciferase expression. FIG. 18 shows luciferase expression in the liver, the xyphoid process and joints, suggesting transduction of cartilage in addition to the liver. FIGS. 19 and 20 show long-term in vivo transgene expression.

rAAV vectors pseudotyped with capsids HSC15 and HSC17 clearly target the liver very efficiently when delivered systemically through a tail vein injection. Transgene expression is sustained at elevated levels to >3 months post-injection. These results strongly support their use for expression of enzyme and factor replacement for gene therapy of inherited and acquired diseases.

Mapping Determinants of Liver Tropism

The genomic sequences of the stem cell-derived AAV isolates thus far map to AAV clade F and were most homologous to AAV9. However, each of the novel isolates tested had unique amino acids in their capsid genes, with the differences relative to AAV9 being limited to 1 to 4 amino acids.

Interestingly, in contrast to AAV9, particularly strong liver tropism was noted with specific isolates such as HSC15, upon systemic delivery by intravenous injection. (See, for example, FIGS. 21 and 22.) Liver tropism of these isolates was further studied by serial in vivo bioluminescent imaging (BLI) of recipient NOD/SCID mice following intravenous injection with rAAV encoding firefly luciferase. Results revealed that despite limited amino acid changes in the capsids, rAAVHSC13, rAAVHSC15 and rAAVHSC17 displayed significantly enhanced liver tropism as compared with AAV9. Importantly, rAAVHSC15 displayed 4-10-fold stronger liver transduction than AAV8. In an effort to elucidate factors which influence liver tropism, each variant amino acid in HSC15 and AAV9 were mutagenized singly and in combination. The luciferase transgene was then packaged in the mutant capsids and in vivo liver tropism was determined by BLI following systemic delivery, as described above (FIGS. 23A & B). Results revealed that when residue 505 is mutagenized from arginine (HSC15) to glycine (AAV9), liver tropism is significantly reduced. While mutagenizing residue 346 from alanine (HSC15) to threonine (AAV9) resulted in only a minor decline. These results indicate that the amino acid residue 505 located near the external surface of the capsid contributed to liver tropism. However, internally located residue at 346 also appeared to act synergistically to increase transduction.

Figure 24:
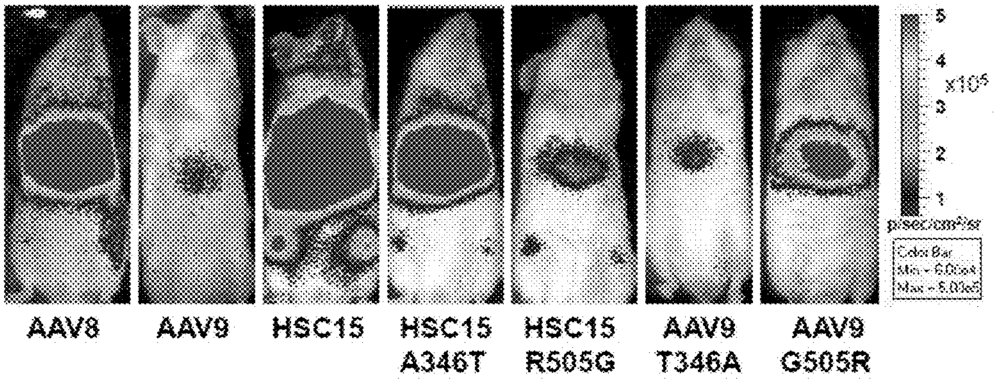
FIG. 24 shows in vivo bioluminescent imaging of bidirectional mutagenesis to map the determinants of liver tropism of HSC15.
Figure 25:
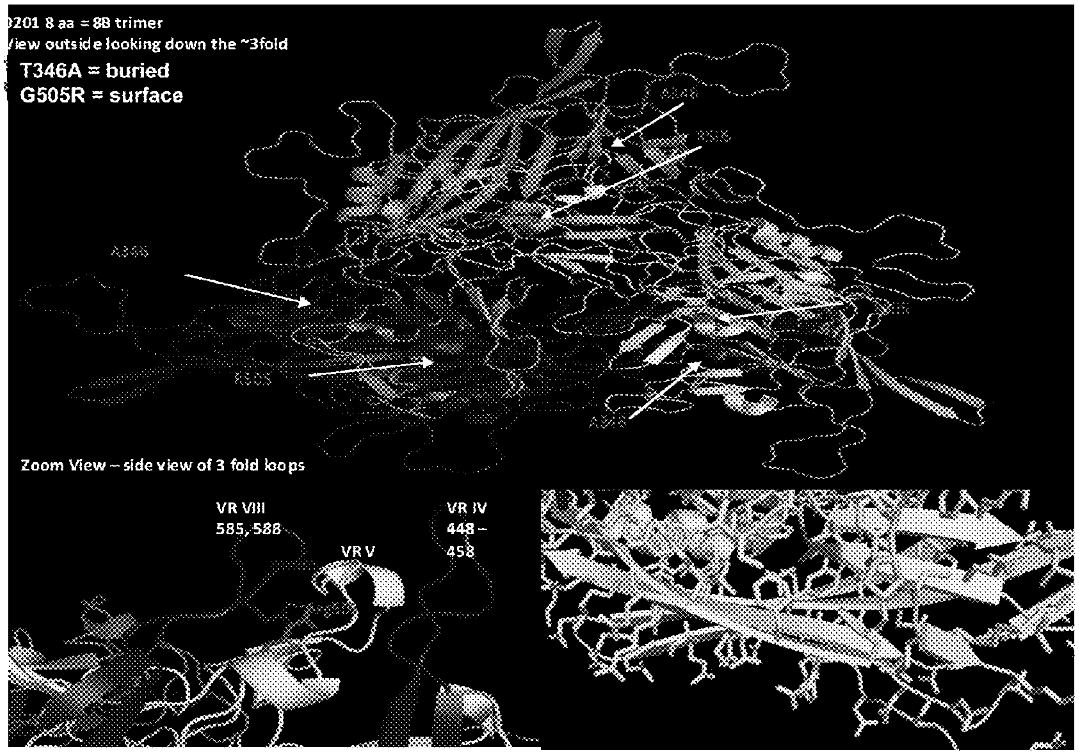
FIG. 25 shows structural analysis of HSC15 determinants of liver tropism. R505G was found to be located on the surface of the capsid at a site known to be involved in receptor interactions in other serotypes of AAV. Thus, residue 505 ("surface") was involved in binding the putative liver receptor for HSC15. Residue 346 is located internally ("buried") and may be involved in capsid uncoating. There is likely a synergistic effect of both changes resulting in the enhanced liver tropism observed with HSC15.
Figure 26:
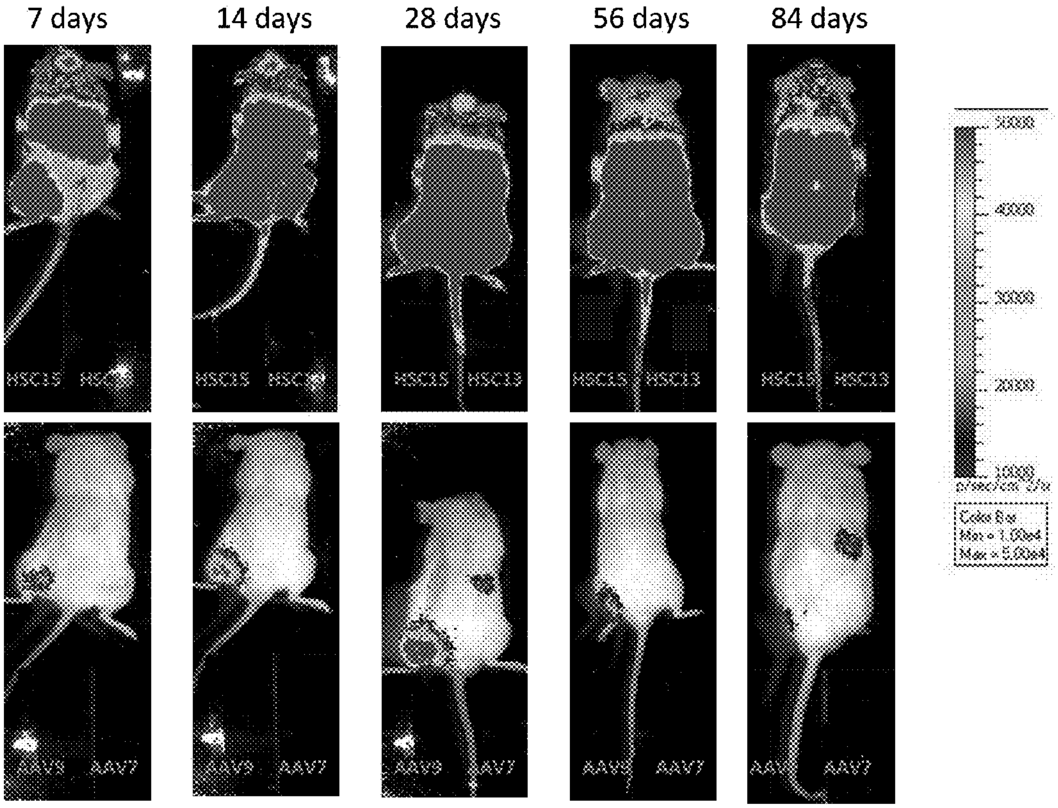
FIG. 26 shows intramuscular injection of 1E10 particles of rAAVHSC results in transgene expression in the brain. Mice were injected intramuscularly with 1E10P of vector in the designated leg. Vector biodistribution was assayed through serial bioluminescent imaging at select time points post injection.
Figure 27:
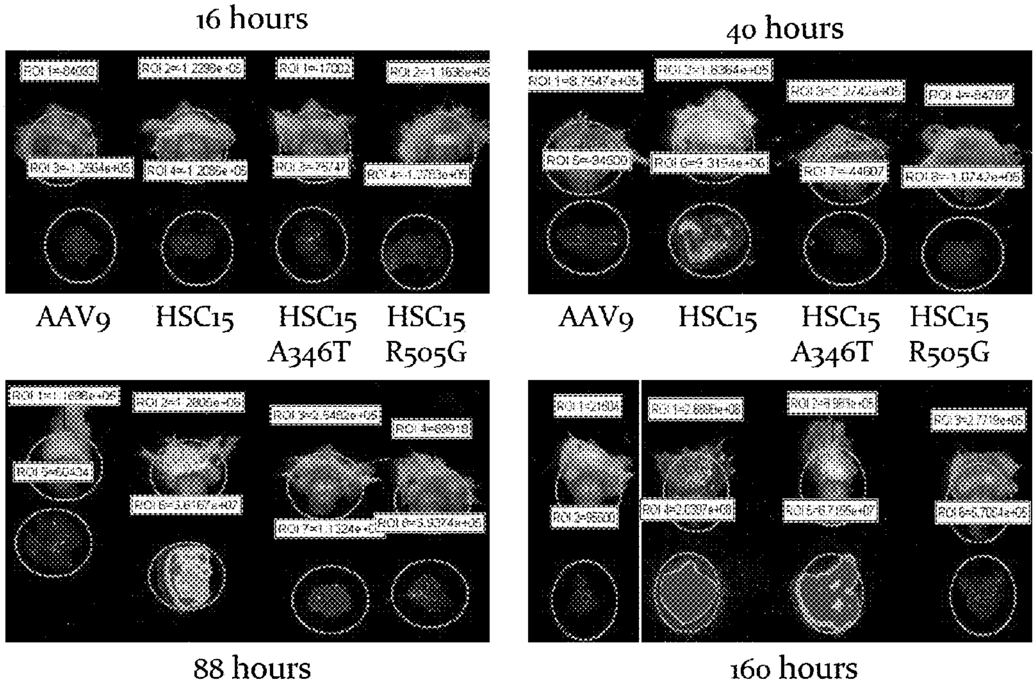
FIG. 27 shows transgene expression in the brain following intravenous injection of rAAVHSC15. Brains and livers were harvested from mice injected intravenously via tail vein with 1E11P of AAV9, HSC15 or HSC15 mutants at given time points post injection. Brains and livers were harvested within 20 minutes of luciferin injection and organs imaged using Xenogen to determine luminescence (transgene expression).
Figure 28:
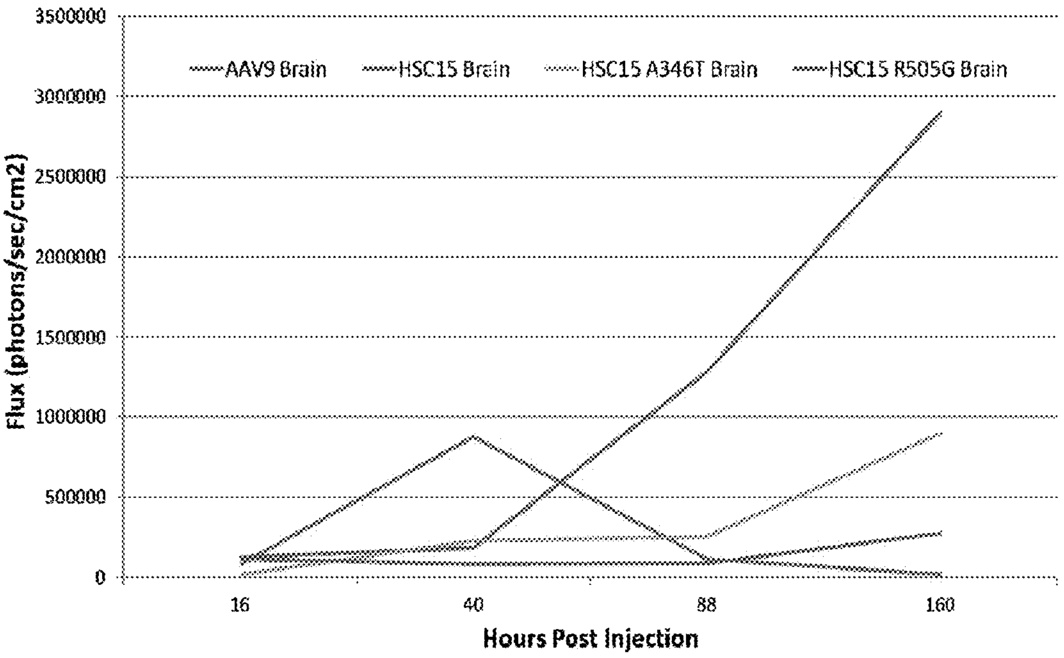
FIG. 28 shows transgene expression in brains harvested from mice following intravenous injection with 1E11P of vector IV via tail vein at each of the time points post injection. Transgene expression in the brains of mice injected with HSC15 is over 100 fold higher than AAV9 at 160 hours post IV injection.
Figure 30:
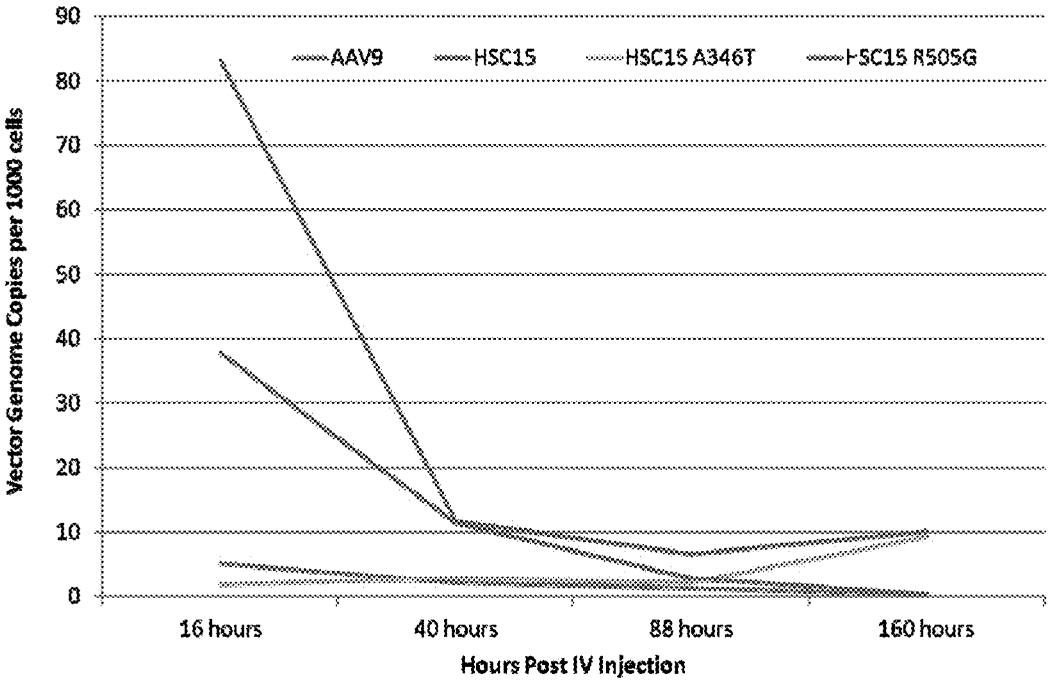
FIG. 30 shows rAAV genome copies in the brain. Brains were harvested from mice injected intravenously via tail vein with 1E11P of AAV9, HSC15 or HSC15 mutants at given time points post injection. Genomic DNA was isolated from harvested brain and vector genome copies were assayed through qPCR using primers specific for the transgene and housekeeping gene. HSC15 has between 5 to 40 fold increase in vector genome copies when compared to AAV9 in the brain after IV injection of 1E11 rAAV particles.
Figure 31:
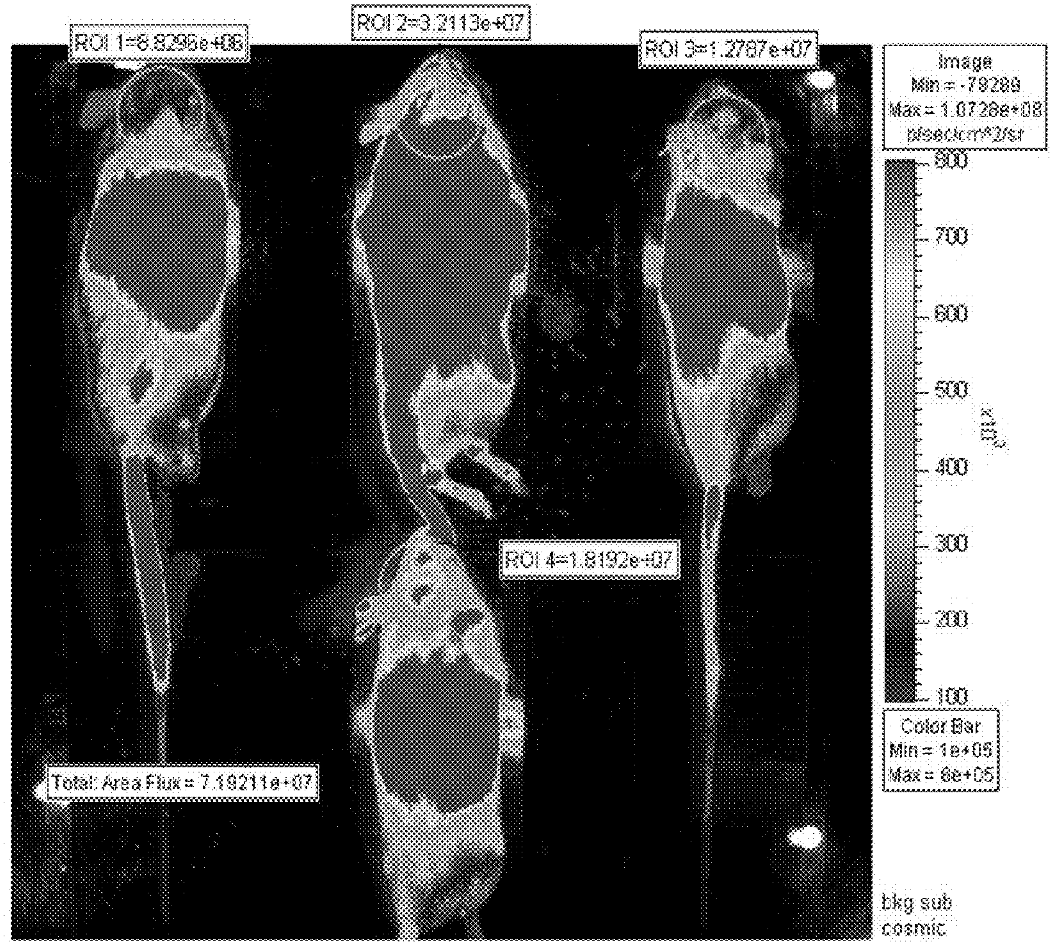
FIG. 31 shows transgene expression in the cranial region 21 days post-IV injection of 1e11 particles of HSC15. Mice were injected with 1E11P of ssluc vector via tail vein. Transgene expression was analyzed through serial bioluminescent imaging and these images show mice at 21 days post injection. A fixed area was used to measure bioluminescence or transgene expression in the cranial region. IV injection of 1E11P of HSC15 results in transgene expression in thr cranial region 21 days post injection. n=4 mice.
Figure 32:
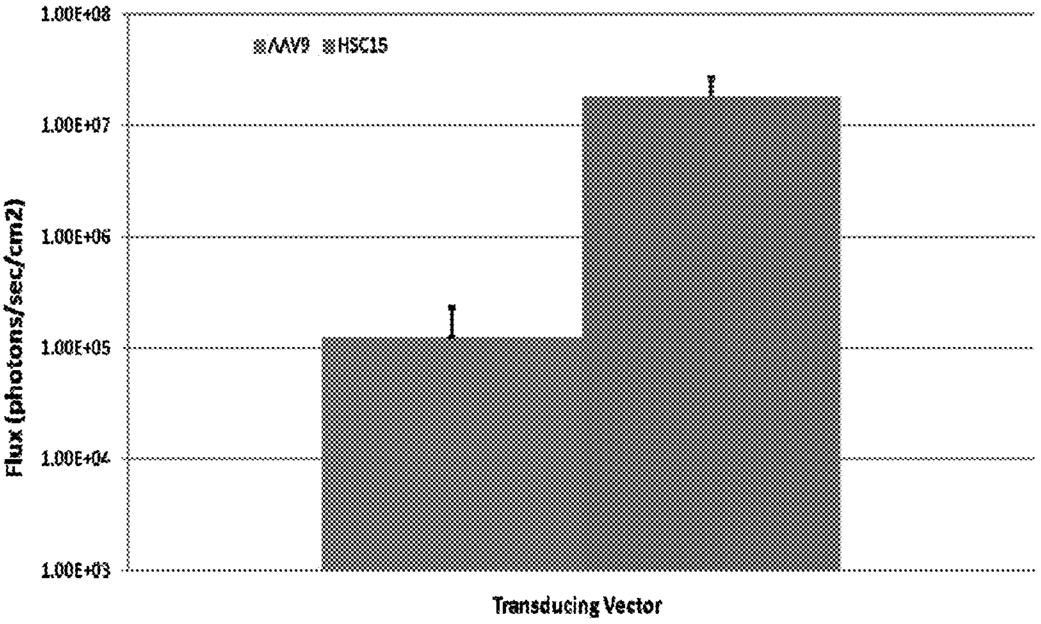
FIG. 32 shows average luciferase expression in the cranium of mice injected intravenously with AAV9 or HSC15. Mice were injected with 1E11P of ssluc vector via tail vein. Transgene expression was analyzed through serial bioluminescent imaging and these images show mice at 21 days post injection. A fixed area was used to measure bioluminescence or transgene expression in the cranial region. Average transgene expression from rAAVHSC15 in the cranium is 2 logs higher than AAV9 when 1E11 particles of vector is injected intravenously. Results shown are at 21 days post injection. N=4 mice.
Figure 34:
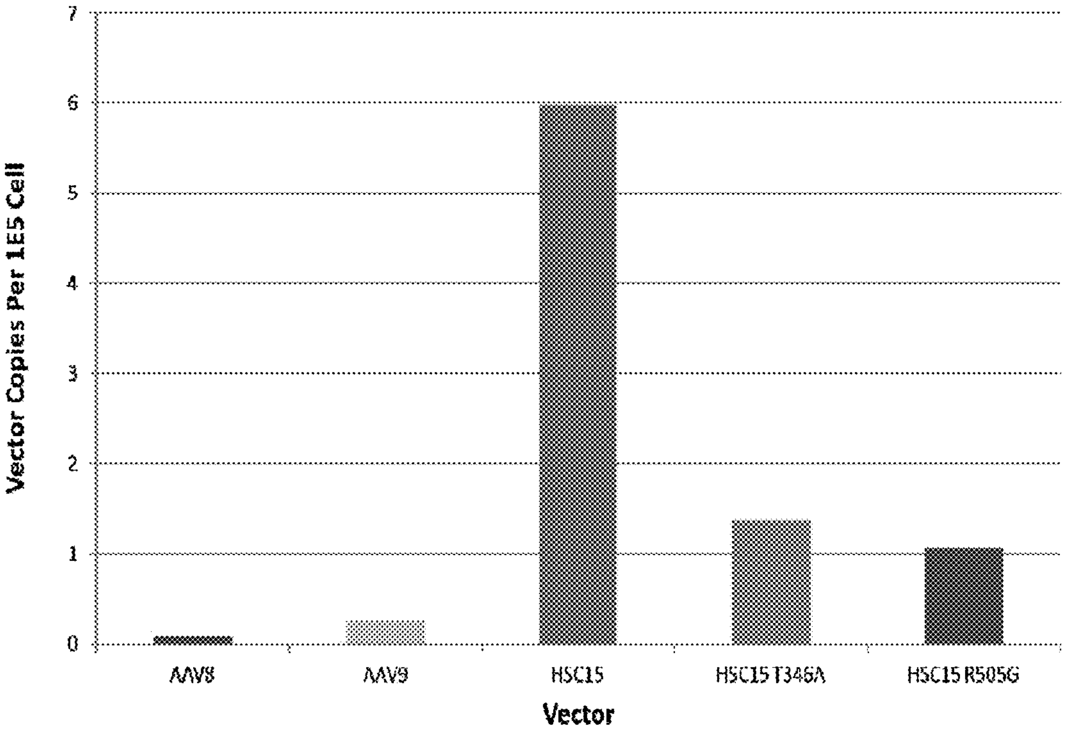
FIG. 34 shows vector genomes in brains of mice injected with 1E11 particles of ssrAAV-luc vector 56 days post injection. Mice were injected with 1E11P of ssluc via tail vein. 56 days post injection, brains were harvested and homogenized. Genomic DNA isolated from brains was analyzed for vector genome copies through qPCR using vector specific and housekeeping gene primers and probes. HSC15 has over 20 fold increase in average vector genome copies compared to AAV9 at 56 days post 1E11P IV injection. N=4 mice.
Figure 35:
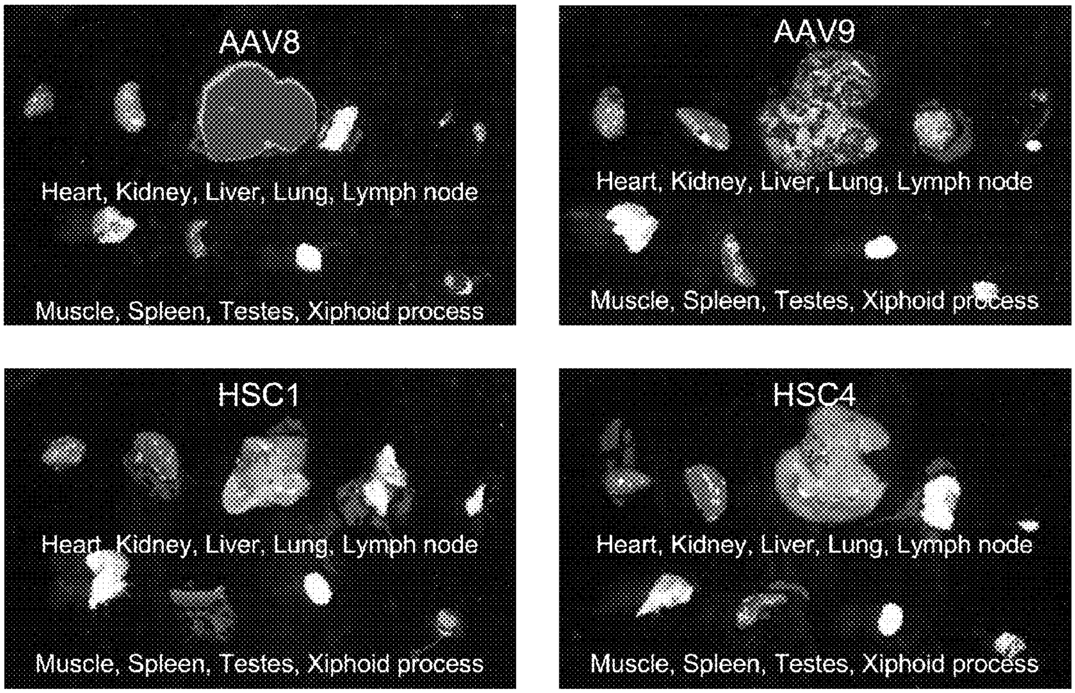
FIG. 35 shows transgene expression in isolated organs harvested from mice injected intravenously with 1E11P ssrAAV-luc. The heart, kidney, liver, lung, lymph nodes, muscle, spleen, testes, and xiphoid process (a cartilagenous area of the sternum) was harvested from mice 56 days after IV injection of 1E11P of ssluc vector. Organs were harvested within 20 minutes of luciferin injection and bioluminescence assayed by imaging in a Caliper Xenogen.
Figure 36:
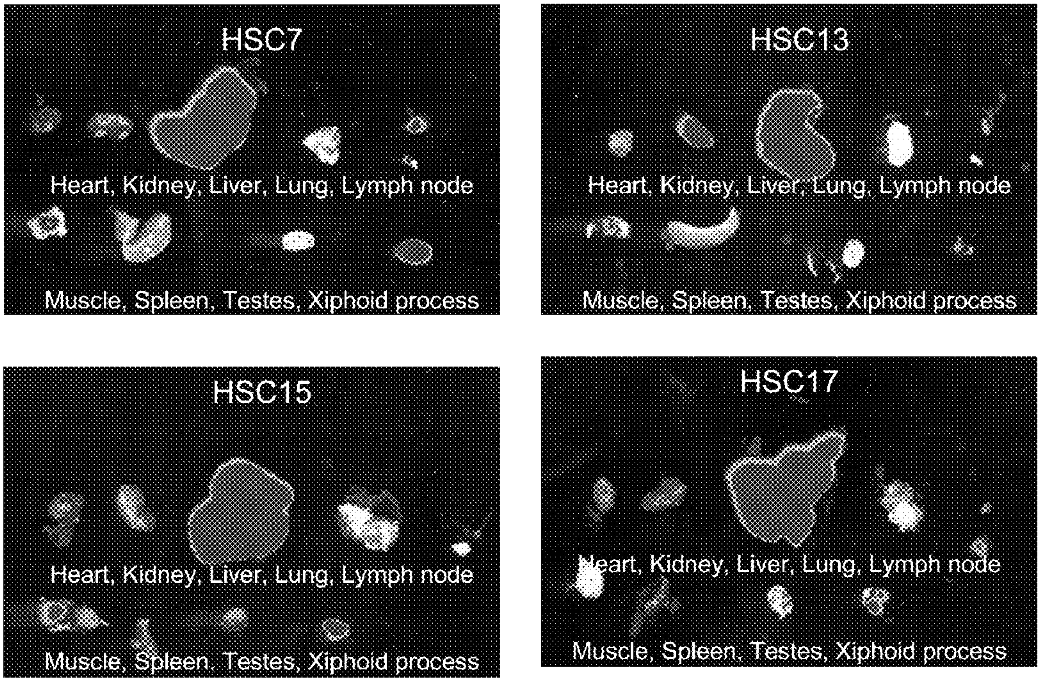
FIG. 36 also shows transgene expression in isolated organs harvested from mice injected intravenously with 1E11P ssrAAV-luc. The heart, kidney, liver, lung, lymph nodes, muscle, spleen, testes, and xiphoid process (a cartilagenous area of the sternum) was harvested from mice 56 days after IV injection of 1E11P of ssluc vector. Organs were harvested within 20 minutes of luciferin injection and bioluminescence assayed by imaging in a Caliper Xenogen.
Figure 37:
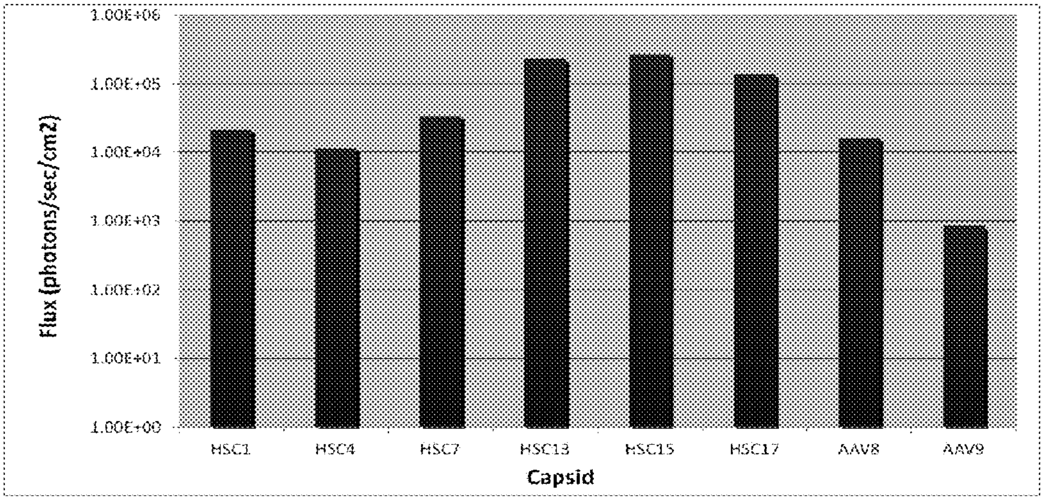
FIG. 37 shows transgene expression on day 56 in hearts of mice injected systemically with rAAVHSC. Hearts were harvested from mice injected IV via tail vein with 1E11P of ssluc vectors 56 days post injection. Organs were harvested from mice within 20 minutes of luciferin injection and bioluminescence was measured. All AAVHSC vectors transduce the heart more efficiently than AAV9. AAVHSC13 and AAVHSC15 transduce the heart almost 150-fold better than AAV9. AAVHSC17 also transduces the heart efficiently.
Figure 38:
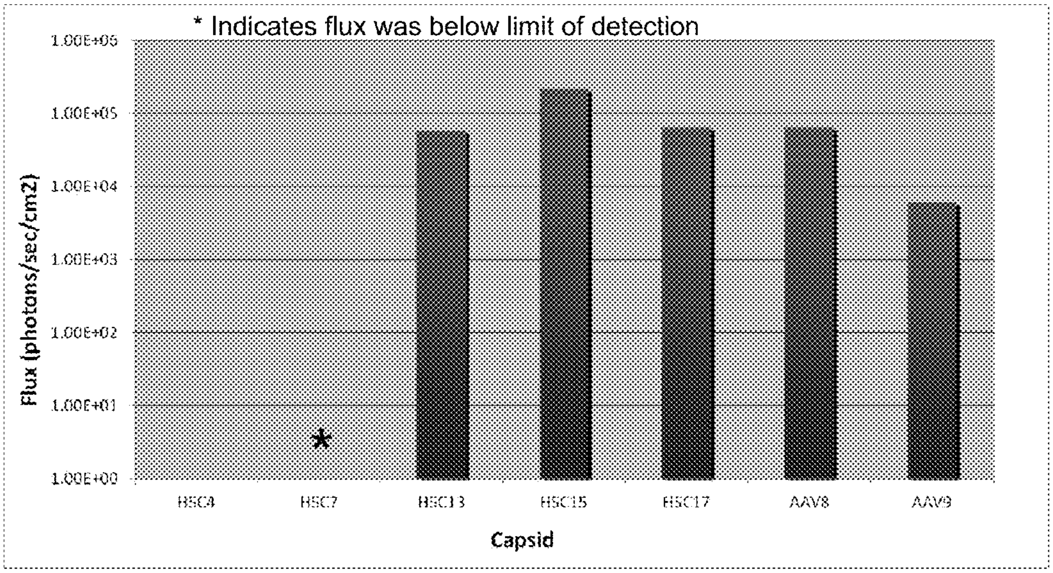
FIG. 38 shows transgene expression on day 56 in kidneys of mice injected systemically with rAAVHSC. Kidneys were harvested from mice injected IV via tail vein with 1E11P of ssluc vectors 56 days post injection. Organs were harvested from mice within 20 minutes of luciferin injection and bioluminescence was measured. AAVHSC15 transduces the kidney almost 15-fold better than AAV9. AAVHSC13 and AAVHSC17 also transduce the kidneys efficiently.
Figure 39:
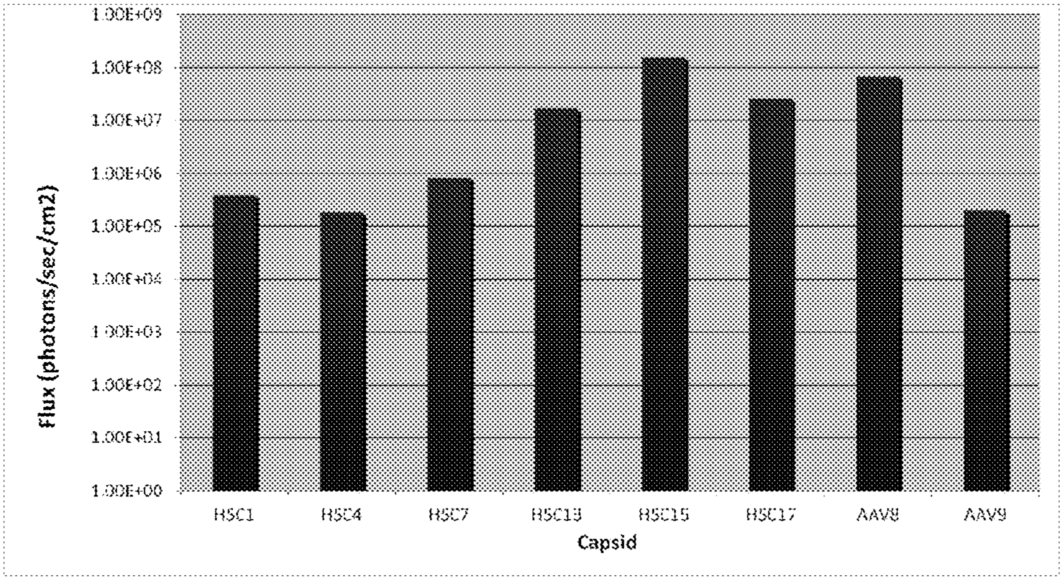
FIG. 39 shows transgene expression on day 56 in livers of mice injected systemically with rAAVHSC. Livers were harvested from mice injected IV via tail vein with 1E11P of ssluc vectors 56 days post injection. Organs were harvested from mice within 20 minutes of luciferin injection and bioluminescence was measured. AAVHSC15 transduces the liver approximately 1000 fold better than AAV9. AAVHSC13 and AAVHSC17 also transduce the liver efficiently.
Figure 40:
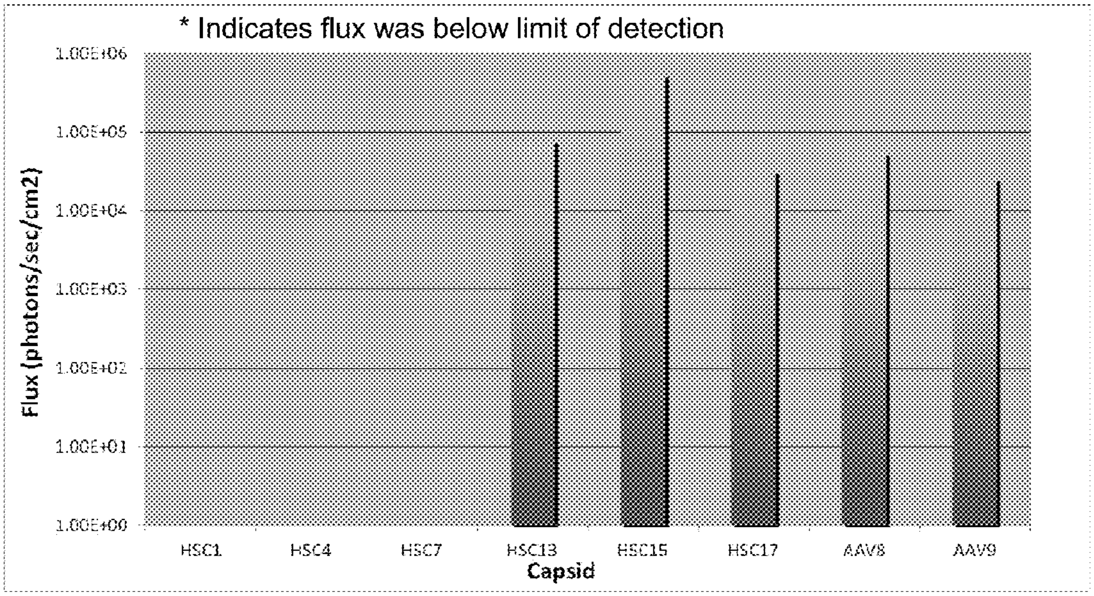
FIG. 40 shows transgene expression on day 56 in lungs of mice injected systemically with rAAVHSC. Lungs were harvested from mice injected IV via tail vein with 1E11P of ssluc vectors 56 days post injection. Organs were harvested from mice within 20 minutes of luciferin injection and bioluminescence was measured. AAVHSC15 transduce the lungs over 10 fold better than AAV9. AAVHSC13 and AAVHSC17 also transduce the lungs efficiently.
Figure 41:
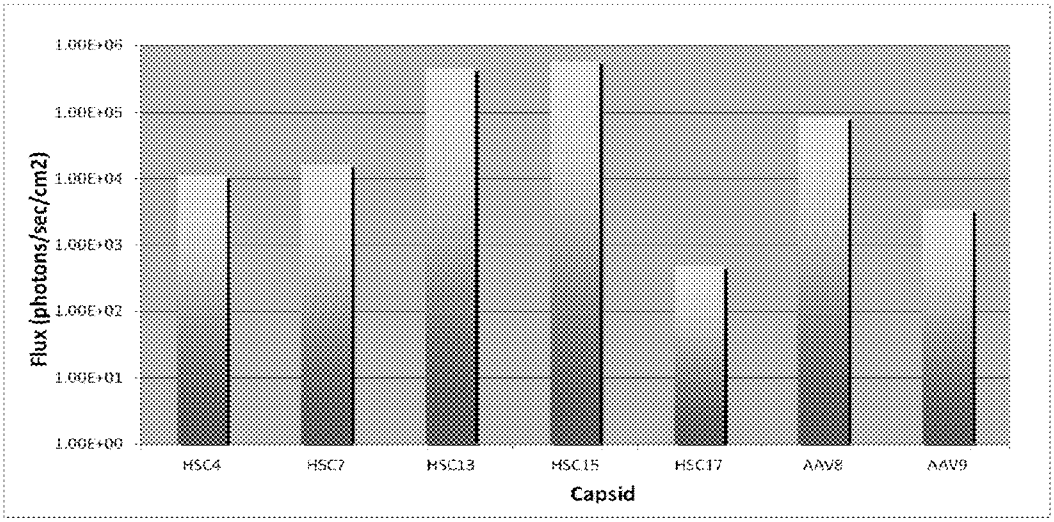
FIG. 41 shows transgene expression on day 56 in muscle of mice injected systemically with rAAVHSC. Muscle were harvested from mice injected IV via tail vein with 1E11P of ssluc vectors 56 days post injection. Organs were harvested from mice within 20 minutes of luciferin injection and bioluminescence was measured. AAVHSC13 and AAVHSC 15 transduce the muscle approximately 100 fold better than AAV9.
Figure 42:
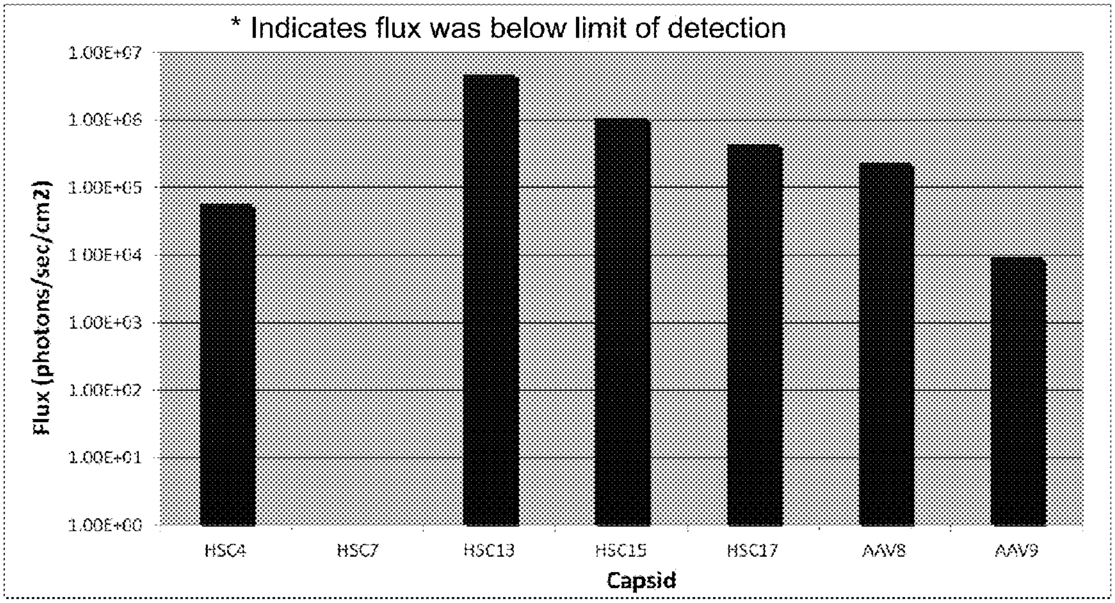
FIG. 42 shows transgene expression on day 56 in xiphoid processes of mice injected systemically with rAAVHSC. Xiphoid processes were harvested from mice injected IV via tail vein with 1E11P of ssluc vectors 56 days post injection. Organs were harvested from mice within 20 minutes of luciferin injection and bioluminescence was measured. AAVHSC13 transduce the xiphoid process, a cartilaginous structure of the sternum, 150 fold better than AAV9. AAVHSC15 and AAVHSC17 also transduce the xiphoid process efficiently.
Figure 43:
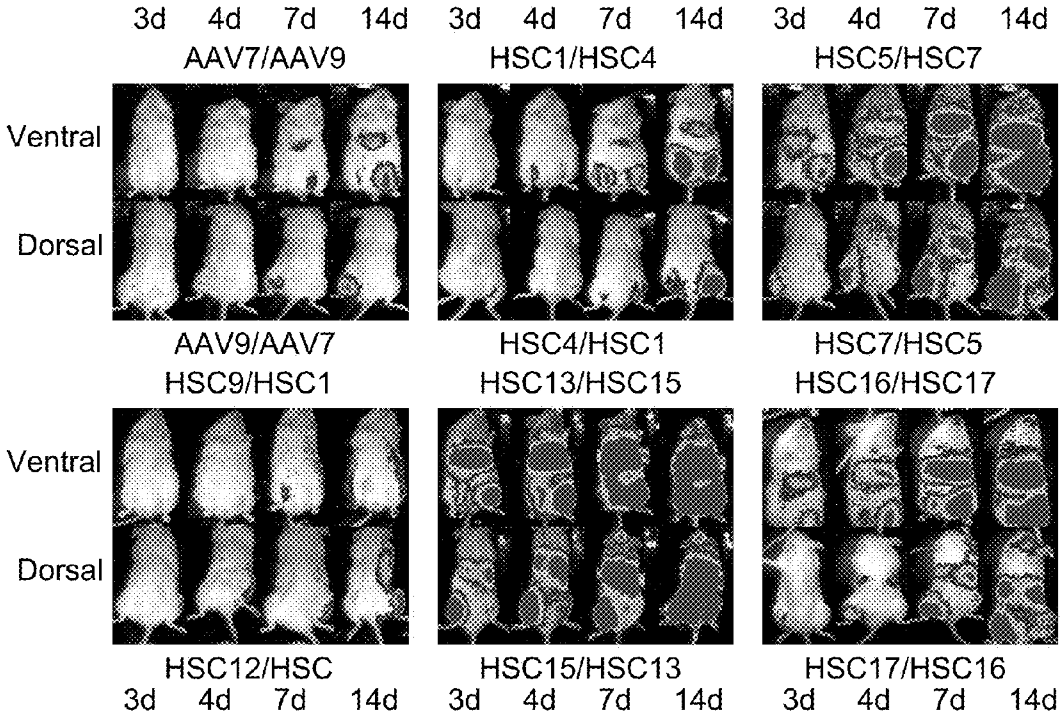
FIG. 43 shows transgene expression following intramuscular injection of 1E10P of rAAVHSC vector. Representative bioluminescent images of mice injected intramuscularly into the gastronemius with 1E10 P (HSC12 has 2E9 P), one vector per leg. HSC12 has 2E9 particles instead of 1E10 particles due to tittering and injection limits.
Figure 44:
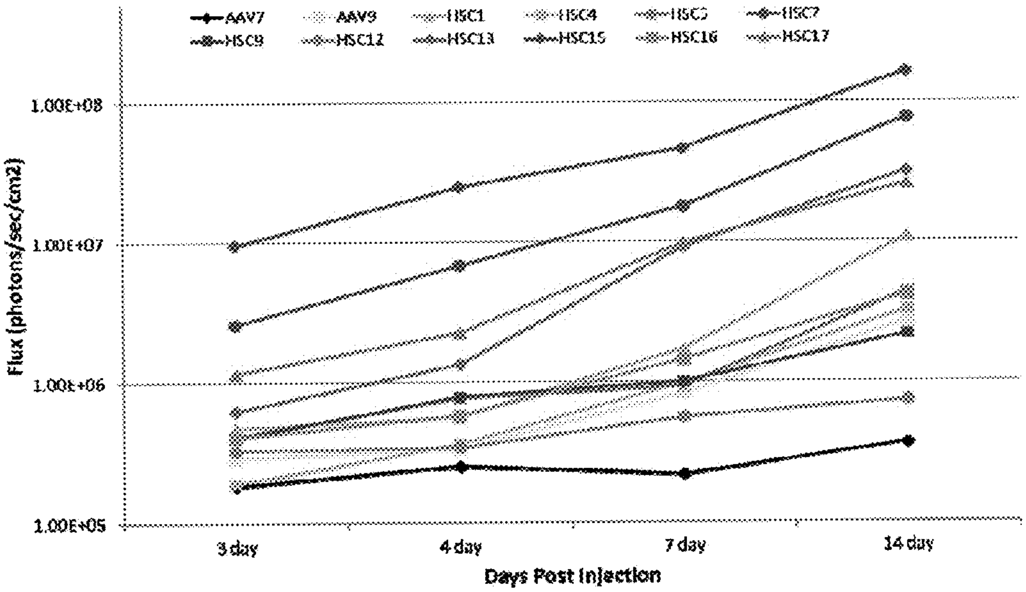
FIG. 44 shows transgene expression in muscle after intra-muscular injection of 1E10P of rAAVHSC vector. Bioluminescent images taken of mice injected intramuscularly into the gastronemius with ssluc vector at given time points post injection were used to measure flux in consistent area around the site of intramuscular injection. AAVHSC15, AAVHSC7 and AAVHSC13 show the highest muscle transduction, approximately 5 to 15 fold higher than AAV9. HSC12 has 2E09P instead of 1E10P due to tittering and injection limits.
Figure 45:
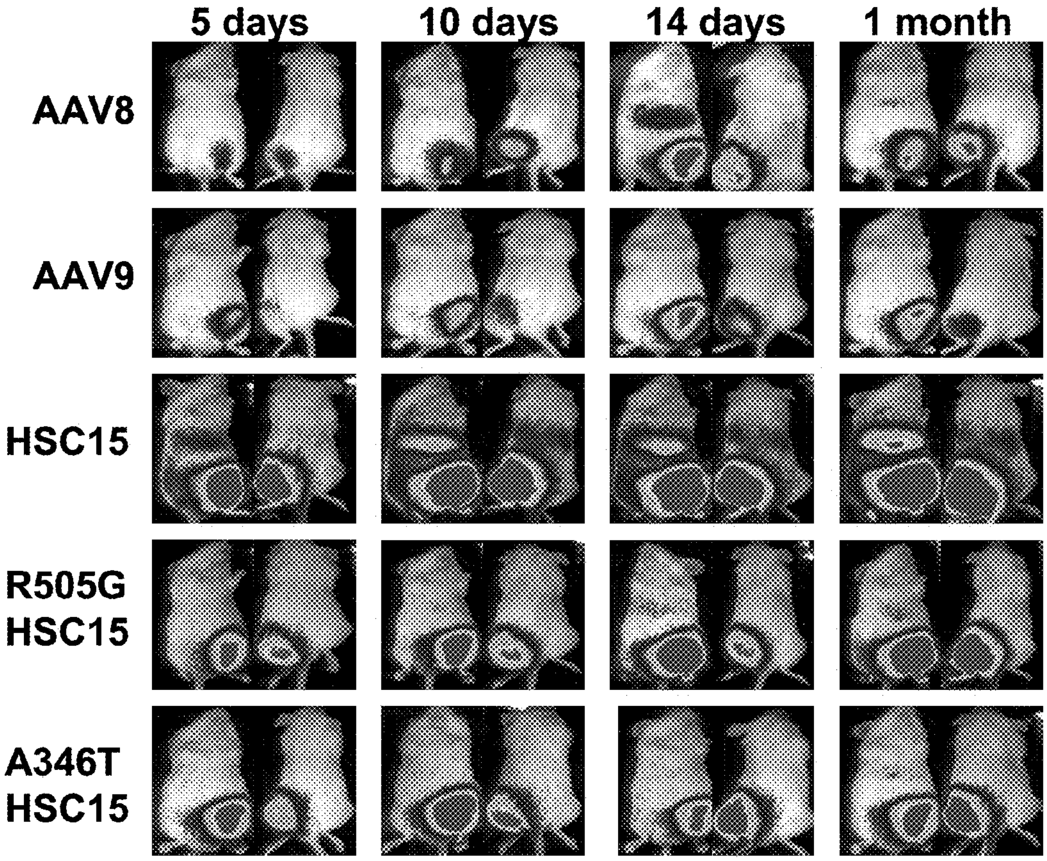
FIG. 45 shows transgene expression after intramuscular injection of 1E10 particles of ss rAAV-luc vector. 1E10P of ssluc vector was injected intramuscularly into the gastronemius of mice and transgene expression was assayed through serial bioluminescent imaging at given time points. HSC15 R505G and HSC15 A346T vectors are HSC15 capsids with either the 505 or 346 residue mutated back to the AAV9 residue to confirm that these two residues contribute to the enhanced transduction properties.
Figure 46:
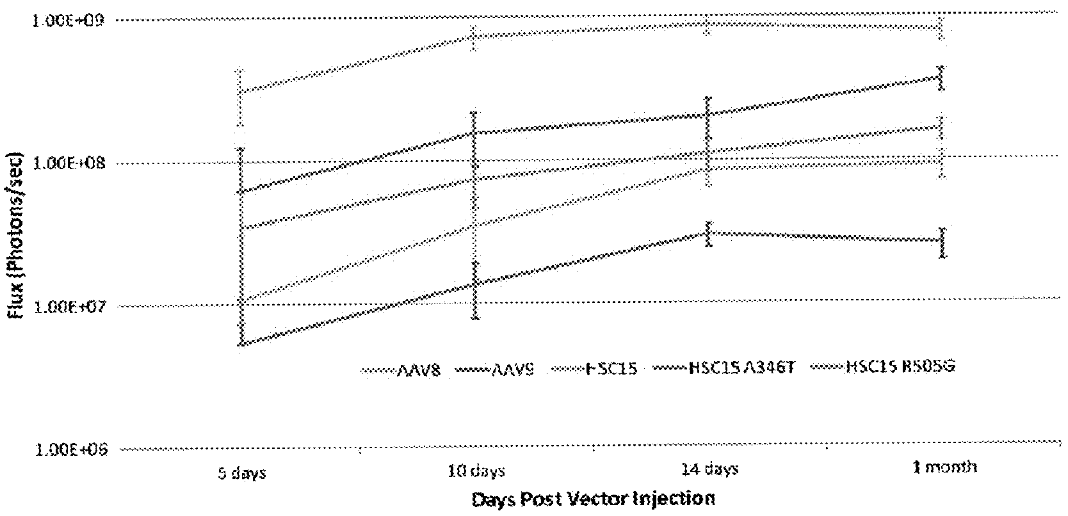
FIG. 46 shows average whole body flux measurements of mice after intramuscular injection with 1E10 particles of ss rAAV-luc. Average whole body flux measurements and standard error of mice (n=4) injected intramuscularly with 1E10 P of ssluc vector. AAVHSC15 shows a 15 fold increase in whole body transgene expression when compared to AAV9.
Figure 48:
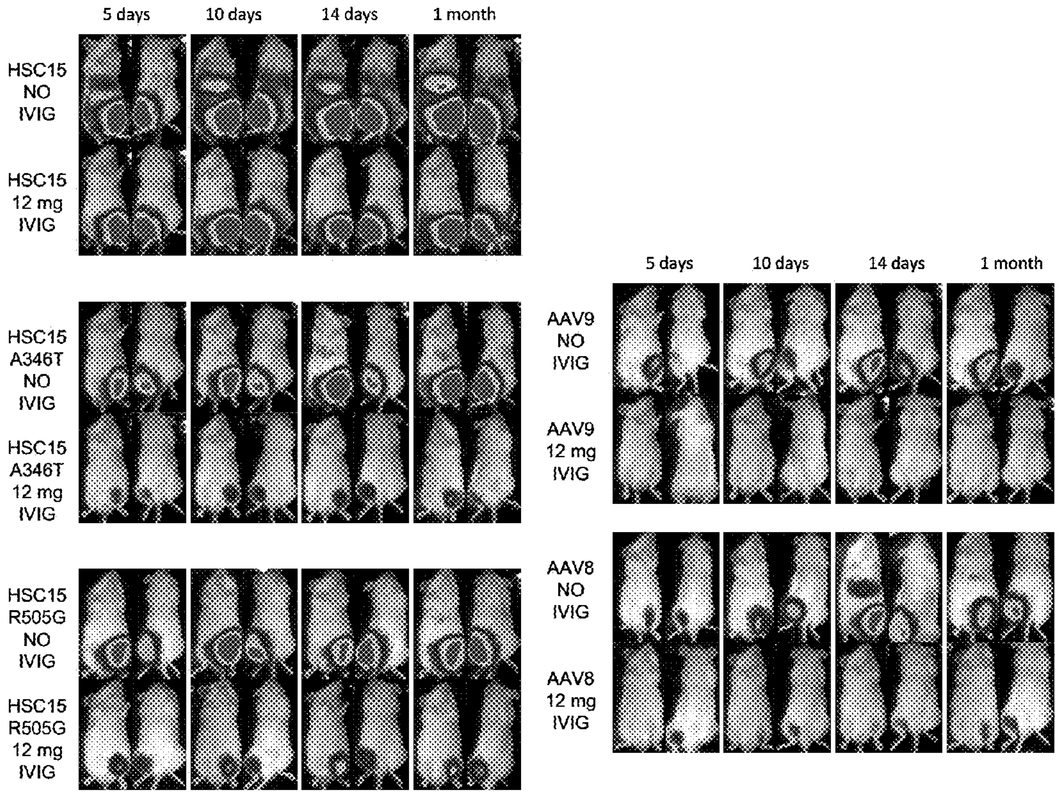
FIG. 48 shows systemic transgene expression in mice injected intra-muscularly with and without human IVIG pre-treatment. Representative serial bioluminescent images of mice taken at given time points post injections. Mice are injected IV with 12 mg of IVIG, while control mice are not.

Importantly, the reverse mutations in the AAV9 capsid, also clearly demonstrated that mutagenesis of residue 505 from glutamine to arginine conferred enhanced liver tropism (FIG. 24). These results show that residue 505 is clearly important in determining liver tropism of our novel AAV isolates. Further structural analysis of HSC15 revealed that amino acid 505 is located in an area of subunit interaction and possible receptor binding (FIG. 25). Thus the use of natural AAV capsid variants with limited amino acid alteration that differ widely with respect to in vivo tropisms may allow mapping of critical components necessary for efficient transduction.

Gene Transfer to the Brain Following Systemic Administration of rAAVHSC rAAVHSC15 traffics to the brain following systemic intravenous injection. The in vivo data, as demonstrated in FIGS. 26-34 and elsewhere, shows that HSC15 vectors may be used for gene delivery to the brain by non-invasive methods. Transgene expression in the brain via non-invasive means is a remarkable advancement in the art because it allows the gene of interest to cross the blood-brain barrier, which as previously been a major impediment. FIGS. 26-34 show vector-encoded luciferase expression in the brain after intravenous and intramuscular injections. Also shown is the frequency of vector genome copies in the brain after systemic injection. FIG. 54 shows an overview of the frequency of rAAV genomes per 1000 cells in four cell types.

Additional Data Supporting the Efficacy of Gene Transfer to Various Organs and Muscle Following Intravenous Systemic Injection of AAVHSC Certain AAVHSC vectors, such as HSC15, HSC13, and HSC17 transfer genes efficiently to the liver, heart, kidneys and lung after systemic injection, and transduce the target organs more effectively than the currently known AAV8 or AAV9. These novel vectors, particularly the top performing HSC15, may be used for the treatment of cardiac diseases such as heart, liver, kidney and lung-based diseases such as heart, hemophilia, atherosclerosis, hepatitis and congenital and acquired diseases.

Data supporting the efficacy of these vectors for in vivo transduction is found in FIGS. 22 and 35-42. For example, in one experiment, the tissue samples of liver, muscle, and brain were chopped from IVIG mice over dry ice and divided into multiple aliquots. One aliquot from each organ was placed in 300 μL digestion buffer with 1 μL Dnasefree Rnase and rotated at 37° C. for 1 and a half hours. 15 μL of 10% SDS and 1.5 μL protease K were added to all samples and incubated O/N at 65° C. The extracted samples were exposed to various amounts of IVIG and a vector (AAV9, AAV8, HSC15, or one of the HSC15 mutants), precipitated with 10M ammonium acetate at final concentration of 2.5M. Then, 1 mL of cold EtOH 100% was added, the sample was precipitated at 80° C. for about 2 hours, spun down and washed all genomic DNA, and dried overnight.

rAAVHSCs are also highly efficient at gene transfer to the muscle, with AAVHSC15 and AAVHSC7 being the most efficient of the vectors tested. These vectors may be used for delivery of gene-based vaccines, muscle diseases such muscular dystrophy and as depots for the secretions of enzymes and other biologics (FIGS. 43-47), in addition to the many therapeutic and diagnostic uses discussed herein.

Finally, additional data (FIGS. 48-53) supports the finding that neutralizing antibodies, which may be present in individuals previously exposed to AAVHSC, will have less effect on in vivo administered rAAVHSC15. Currently, these patients are excluded. However, the HSC15 vector would allow these same patients to be eligible to receive these vectors, including those with low level neutralizing antibodies.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All patents, patent applications, and references cited throughout the specification are expressly incorporated by reference.

REFERENCES

1. BAINBRIDGE, J. W., SMITH, A. J., BARKER, S. S., ROBBIE, S., HENDERSON, R., BALAGGAN, K., VISWANATHAN, A., HOLDER, G. E., STOCKMAN, A., TYLER, N., PETERSEN-JONES, S., BHATTACHARYA, S. S., THRASHER, A. J., FITZKE, F. W., CARTER, B. J., RUBIN, G. S., MOORE, A. T., and ALI, R. R. (2008). Effect of gene therapy on visual function in Leber's congenital amaurosis. N Engl J Med 358, 2231-2239.
2. BATCHU, R. B., SHAMMAS, M. A., WANG, J. Y., FREEMAN, J., ROSEN, N., and MUNSHI, N. C. (2002). Adeno-associated virus protects the retinoblastoma family of proteins from adenoviral-induced functional inactivation. Cancer Res 62, 2982-2985.
3. BELL, P., WANG, L., LEBHERZ, C., FLIEDER, D. B., BOVE, M. S., WU, D., GAO, G. P., WILSON, J. M., and WIVEL, N. A. (2005). No evidence for tumorigenesis of AAV vectors in a large-scale study in mice. Mol Ther 12, 299-306.
4. BERNS, K. I., and GIRAUD, C. (1996). Biology of adeno-associated virus. Curr Top Microbiol Immunol 218, 1-23.
5. BIFFI, A., and CESANI, M. (2008). Human hematopoietic stem cells in gene therapy: preclinical and clinical issues. Curr Gene Ther 8, 135-146.
6. BRANTLY, M. L., CHULAY, J. D., WANG, L., MUELLER, C., HUMPHRIES, M., SPENCER, L. T., ROUHANI, F., CONLON, T. J., CALCEDO, R., BETTS, M. R., SPENCER, C., BYRNE, B. J., WILSON, J. M., and FLOTTE, T. R. (2009). Sustained transgene expression despite T lymphocyte responses in a clinical trial of rAAV1-AAT gene therapy. Proc Natl Acad Sci USA.
7. CHATTERJEE, S., JOHNSON, P. R., and WONG, K. K., JR. (1992). Dual-target inhibition of HIV-1 in vitro by means of an adeno-associated virus antisense vector. Science 258, 1485-1488.
8. CHATTERJEE, S., LI, W., WONG, C. A., FISHER-ADAMS, G., LU, D., GUHA, M., MACER, J. A., FORMAN, S. J., and WONG, K. K., JR. (1999). Transduction of primitive human marrow and cord blood-derived hematopoietic progenitor cells with adeno-associated virus vectors. Blood 93, 1882-1894.
9. CHATTERJEE, S., WONG, KK. (1993). Adeno-Associated Viral Vectors for the Delivery of Antisense RNA. METHODS—LONDON—A COMPANION TO METHODS IN ENZYMOLOGY—5, 1.
10. CIDECIYAN, A. V., HAUSWIRTH, W. W., ALEMAN, T. S., KAUSHAL, S., SCHWARTZ, S. B., BOYE, S. L., WINDSOR, E. A., CONLON, T. J., SUMAROKA, A., PANG, J. J., ROMAN, A. J., BYRNE, B. J., and JACOBSON, S. G. (2009). Human RPE65 gene therapy for Leber congenital amaurosis: persistence of early visual improvements and safety at 1 year. Hum Gene Ther 20, 999-1004.
11. EINERHAND, M. P., ANTONIOU, M., ZOLOTUKHIN, S., MUZYCZKA, N., BERNS, K. I., GROSVELD, F., and VALERIO, D. (1995). Regulated high-level human beta-globin gene expression in erythroid cells following recombinant adeno-associated virus-mediated gene transfer. Gene Ther 2, 336-343.
12. FISHER-ADAMS, G., WONG, K. K., JR., PODSAKOFF, G., FORMAN, S. J., and CHATTERJEE, S. (1996). Integration of adeno-associated virus vectors in CD34+ human hematopoietic progenitor cells after transduction. Blood 88, 492-504.
13. FLOTTE, T. R., BRANTLY, M. L., SPENCER, L. T., BYRNE, B. J., SPENCER, C. T., BAKER, D. J., and HUMPHRIES, M. (2004). Phase I trial of intramuscular injection of a recombinant adeno-associated virus alpha 1-antitrypsin (rAAV2-CB-hAAT) gene vector to AAT-deficient adults. Hum Gene Ther 15, 93-128.
14. GAO, G., VANDENBERGHE, L. H., ALVIRA, M. R., LU, Y., CALCEDO, R., ZHOU, X., and WILSON, J. M. (2004). Clades of Adeno-associated viruses are widely disseminated in human tissues. J Virol 78, 6381-6388.
15. HACEIN-BEY-ABINA, S., VON KALLE, C., SCHMIDT, M., LE DEIST, F., WULFFRAAT, N., MCINTYRE, E., RADFORD, I., VILLEVAL, J. L., FRASER, C. C., CAVAZZANA-CALVO, M., and FISCHER, A. (2003). A serious adverse event after successful gene therapy for X-linked severe combined immunodeficiency. N Engl J Med 348, 255-256.
16. HAN, Z., ZHONG, L., MAINA, N., HU, Z., LI, X., CHOUTHAI, N. S., BISCHOF, D., WEIGEL-VAN AKEN, K. A., SLAYTON, W. B., YODER, M. C., and SRIVASTAVA, A. (2008). Stable integration of recombinant adeno-associated virus vector genomes after transduction of murine hematopoietic stem cells. Hum Gene Ther 19, 267-278.
17. JAYANDHARAN, G. R., ZHONG, L., LI, B., KACHNIARZ, B., and SRIVASTAVA, A. (2008). Strategies for improving the transduction efficiency of single-stranded adeno-associated virus vectors in vitro and in vivo. Gene Ther 15, 1287-1293.
18. KAPLITT, M. G., FEIGIN, A., TANG, C., FITZSIMONS, H. L., MATTIS, P., LAWLOR, P. A., BLAND, R. J., YOUNG, D., STRYBING, K., EIDELBERG, D., and DURING, M. J. (2007). Safety and tolerability of gene therapy with an adeno-associated virus (AAV) borne GAD gene for Parkinson's disease: an open label, phase I trial. Lancet 369, 2097-2105.
19. KELLS, A. P., HADACZEK, P., YIN, D., BRINGAS, J., VARENIKA, V., FORSAYETH, J., and BANKIEWICZ, K. S. (2009). Efficient gene therapy-based method for the delivery of therapeutics to primate cortex. Proc Natl Acad Sci USA 106, 2407-2411.

20. KESSLER, P. D., PODSAKOFF, G. M., CHEN, X., MCQUISTON, S. A., COLOSI, P. C., MATELIS, L. A., KURTZMAN, G. J., and BYRNE, B. J. (1996). Gene delivery to skeletal muscle results in sustained expression and systemic delivery of a therapeutic protein. Proc Natl Acad Sci USA 93, 14082-14087.

21. MANNO, C. S., CHEW, A. J., HUTCHISON, S., LARSON, P. J., HERZOG, R. W., ARRUDA, V. R., TAI, S. J., RAGNI, M. V., THOMPSON, A., OZELO, M., COUTO, L. B., LEONARD, D. G., JOHNSON, F. A., MCCLELLAND, A., SCALLAN, C., SKARSGARD, E., FLAKE, A. W., KAY, M. A., HIGH, K. A., and GLADER, B. (2003). AAV-mediated factor IX gene transfer to skeletal muscle in patients with severe hemophilia B. Blood 101, 2963-2972.

22. MCCORMACK, M. P., and RABBITTS, T. H. (2004). Activation of the T-cell oncogene LMO2 after gene therapy for X-linked severe combined immunodeficiency. N Engl J Med 350, 913-922.

23. MILLER, D. G., ADAM, M. A., and MILLER, A. D. (1990). Gene transfer by retrovirus vectors occurs only in cells that are actively replicating at the time of infection. Mol Cell Biol 10, 4239-4242.

24. PAZ, H., WONG, C. A., LI, W., SANTAT, L., WONG, K. K., and CHATTERJEE, S. (2007). Quiescent subpopulations of human CD34-positive hematopoietic stem cells are preferred targets for stable recombinant adeno-associated virus type 2 transduction. Hum Gene Ther 18, 614-626.

25. PETRS-SILVA, H., DINCULESCU, A., LI, Q., MIN, S. H., CHIODO, V., PANG, J. J., ZHONG, L., ZOLOTUKHIN, S., SRIVASTAVA, A., LEWIN, A. S., and HAUSWIRTH, W. W. (2009). High-efficiency transduction of the mouse retina by tyrosine-mutant AAV serotype vectors. Mol Ther 17, 463-471.

26. PODSAKOFF, G., WONG, K. K., JR., and CHATTERJEE, S. (1994). Efficient gene transfer into nondividing cells by adeno-associated virus-based vectors. J Virol 68, 5656-5666.

27. PONNAZHAGAN, S., YODER, M. C., and SRIVASTAVA, A. (1997). Adeno-associated virus type 2-mediated transduction of murine hematopoietic cells with long-term repopulating ability and sustained expression of a human globin gene in vivo. J Virol 71, 3098-3104.

28. RAJ, K., OGSTON, P., and BEARD, P. (2001). Virus-mediated killing of cells that lack p53 activity. Nature 412, 914-917.

29. SANTAT, L., PAZ, H., WONG, C., LI, L., MACER, J., FORMAN, S., WONG, K. K., and CHATTERJEE, S. (2005). Recombinant AAV2 transduction of primitive human hematopoietic stem cells capable of serial engraftment in immune-deficient mice. Proc Natl Acad Sci USA 102, 11053-11058.

30. SRIVASTAVA, A. (2004). Gene delivery to human and murine primitive hematopoietic stem and progenitor cells by AAV2 vectors. Methods Mol Biol 246, 245-254.

31. TOWNE, C., SCHNEIDER, B. L., KIERAN, D., REDMOND, D. E., JR., and AEBISCHER, P. (2009). Efficient transduction of non-human primate motor neurons after intramuscular delivery of recombinant AAV serotype 6. Gene Ther.

32. ZHONG, L., CHEN, L., LI, Y., QING, K., WEIGEL-KELLEY, K. A., CHAN, R. J., YODER, M. C., and SRIVASTAVA, A. (2004a). Self-complementary adeno-associated virus 2 (AAV)-T cell protein tyrosine phosphatase vectors as helper viruses to improve transduction efficiency of conventional single-stranded AAV vectors in vitro and in vivo. Mol Ther 10, 950-957.

33. ZHONG, L., LI, B., JAYANDHARAN, G., MAH, C. S., GOVINDASAMY, L., AGBANDJEMCKENNA, M., HERZOG, R. W., WEIGEL-VAN AKEN, K. A., HOBBS, J. A., ZOLOTUKHIN, S., MUZYCZKA, N., and SRIVASTAVA, A. (2008a). Tyrosine phosphorylation of AAV2 vectors and its consequences on viral intracellular trafficking and transgene expression. Virology 381, 194-202.

34. ZHONG, L., LI, B., MAH, C. S., GOVINDASAMY, L., AGBANDJE-MCKENNA, M., COOPER, M., HERZOG, R. W., ZOLOTUKHIN, I., WARRINGTON, K. H., JR., WEIGEL-VAN AKEN, K. A., HOBBS, J. A., ZOLOTUKHIN, S., MUZYCZKA, N., and SRIVASTAVA, A. (2008b). Next generation of adeno-associated virus 2 vectors: point mutations in tyrosines lead to high-efficiency transduction at lower doses. Proc Natl Acad Sci USA 105, 7827-7832.

35. ZHONG, L., LI, W., YANG, Z., QING, K., TAN, M., HANSEN, J., LI, Y., CHEN, L., CHAN, R. J., BISCHOF, D., MAINA, N., WEIGEL-KELLEY, K. A., ZHAO, W., LARSEN, S. H., YODER, M. C., SHOU, W., and SRIVASTAVA, A. (2004b). Impaired nuclear transport and uncoating limit recombinant adeno-associated virus 2 vector-mediated transduction of primary murine hematopoietic cells. Hum Gene Ther 15, 1207-1218.

36. ZHONG, L., ZHAO, W., WU, J., LI, B., ZOLOTUKHIN, S., GOVINDASAMY, L., AGBANDJEMCKENNA, M., and SRIVASTAVA, A. (2007). A dual role of EGFR protein tyrosine kinase signaling in ubiquitination of AAV2 capsids and viral second-strand DNA synthesis. Mol Ther 15, 1323-1330.

37. ZHOU, S. Z., BROXMEYER, H. E., COOPER, S., HARRINGTON, M. A., and SRIVASTAVA, A. (1993). Adeno-associated virus 2-mediated gene transfer in murine hematopoietic progenitor cells. Exp Hematol 21, 928-933.

The invention claimed is:

1. A method for transduction of a cell, the method comprising contacting the cell with a recombinant adeno-associated virus (rAAV) vector comprising a capsid protein comprising an amino acid sequence having at least 95% sequence identity with the amino acid sequence of amino acids 203-736 of SEQ ID NO:2, wherein: the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G, and wherein the cell is transduced by the rAAV.

2. The method of claim 1, wherein:

(a) the amino acid in the capsid protein corresponding to amino acid 626 of SEQ ID NO: 2 is G, and the amino acid in the capsid protein corresponding to amino acid 718 of SEQ ID NO: 2 is G;

(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(c) the amino acid in the capsid protein corresponding to amino acid 505 of SEQ ID NO: 2 is R, and the amino acid in the capsid protein corresponding to amino acid 687 of SEQ ID NO: 2 is R;

(d) the amino acid in the capsid protein corresponding to amino acid 346 of SEQ ID NO: 2 is A, and the amino acid in the capsid protein corresponding to amino acid 505 of SEQ ID NO: 2 is R;

or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

3. The method of claim 1, wherein the capsid protein comprises the amino acid sequence of amino acids 203-736 of SEQ ID NO: 2, 3, 4, 6, 7, 10, 11, 12, 13, 15, 16, or 17.

4. The method of claim 3, wherein the capsid protein comprises the amino acid sequence of amino acids 203-736 of SEQ ID NO: 11.

5. The method of claim 3, wherein the capsid protein comprises the amino acid sequence of amino acids 203-736 of SEQ ID NO: 16.

6. The method of claim 3, wherein the capsid protein comprises the amino acid sequence of amino acids 203-736 of SEQ ID NO: 13.

7. The method of claim 1, wherein transduction of the cell introduces a therapeutic nucleotide sequence into the cell.

8. The method of claim 7, wherein the therapeutic nucleotide sequence encodes a protein.

9. The method of claim 7, wherein the therapeutic nucleotide sequence encodes a miRNA, shRNA, or siRNA.

10. The method of claim 1, wherein the cell is a blood, liver, heart, joint tissue, muscle, brain, kidney, or lung cell.

11. The method of claim 1, wherein the cell is a hematopoietic stem cell.

12. The method of claim 11, wherein the cell is a human $CD34^+$ hematopoietic stem cell.

13. The method of claim 1, wherein the cell is in a subject and the rAAV is administered to the subject.

14. The method of claim 13, wherein the rAAV is administered to the subject intravenously, intraperitoneally, subcutaneously, intramuscularly, or intradermally.

15. The method of claim 13, wherein the subject is a human subject.

16. A method for transduction of a cell, the method comprising contacting the cell with an rAAV vector comprising a capsid protein comprising an amino acid sequence having at least 95% sequence identity with the amino acid sequence of amino acids 138-736 of SEQ ID NO:2, wherein: the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G, and wherein the cell is transduced by the rAAV.

17. The method of claim 16, wherein:

(a) the amino acid in the capsid protein corresponding to amino acid 626 of SEQ ID NO: 2 is G, and the amino acid in the capsid protein corresponding to amino acid 718 of SEQ ID NO: 2 is G;

(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(c) the amino acid in the capsid protein corresponding to amino acid 505 of SEQ ID NO: 2 is R, and the amino acid in the capsid protein corresponding to amino acid 687 of SEQ ID NO: 2 is R;

(d) the amino acid in the capsid protein corresponding to amino acid 346 of SEQ ID NO: 2 is A, and the amino acid in the capsid protein corresponding to amino acid 505 of SEQ ID NO: 2 is R;

or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

18. The method of claim 16, wherein the capsid protein comprises the amino acid sequence of amino acids 138-736 of SEQ ID NO: 2, 3, 4, 5, 6, 7, 9, 10, 11, 12, 13, 15, 16, or 17.

19. The method of claim 18, wherein the capsid protein comprises the amino acid sequence of amino acids 138-736 of SEQ ID NO: 11.

20. The method of claim 18, wherein the capsid protein comprises the amino acid sequence of amino acids 138-736 of SEQ ID NO: 16.

21. The method of claim 18, wherein the capsid protein comprises the amino acid sequence of amino acids 138-736 of SEQ ID NO: 13.

22. A method for transduction of a cell, the method comprising contacting the cell with an rAAV vector comprising a capsid protein comprising an amino acid sequence having at least 95% sequence identity with the amino acid sequence of amino acids 1-736 of SEQ ID NO:2, wherein: the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G, and wherein the cell is transduced by the rAAV.

23. The method of claim 22, wherein:

(a) the amino acid in the capsid protein corresponding to amino acid 2 of SEQ ID NO: 2 is T, and the amino acid in the capsid protein corresponding to amino acid 312 of SEQ ID NO: 2 is Q;

(b) the amino acid in the capsid protein corresponding to amino acid 65 of SEQ ID NO: 2 is I, and the amino acid in the capsid protein corresponding to amino acid 626 of SEQ ID NO: 2 is Y;

(c) the amino acid in the capsid protein corresponding to amino acid 77 of SEQ ID NO: 2 is R, and the amino acid in the capsid protein corresponding to amino acid 690 of SEQ ID NO: 2 is K;

(d) the amino acid in the capsid protein corresponding to amino acid 119 of SEQ ID NO: 2 is L, and the amino acid in the capsid protein corresponding to amino acid 468 of SEQ ID NO: 2 is S;

(e) the amino acid in the capsid protein corresponding to amino acid 626 of SEQ ID NO: 2 is G, and the amino acid in the capsid protein corresponding to amino acid 718 of SEQ ID NO: 2 is G;

(f) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;

(g) the amino acid in the capsid protein corresponding to amino acid 505 of SEQ ID NO: 2 is R, and the amino acid in the capsid protein corresponding to amino acid 687 of SEQ ID NO: 2 is R;

(h) the amino acid in the capsid protein corresponding to amino acid 346 of SEQ ID NO: 2 is A, and the amino acid in the capsid protein corresponding to amino acid 505 of SEQ ID NO: 2 is R;

or (i) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

24. The method of claim 22, wherein the capsid protein comprises the amino acid sequence of SEQ ID NO: 2, 3, 4, 5, 6, 7, 8, 9, 10, 11, 12, 13, 15, 16, or 17.

25. The method of claim 24, wherein the capsid protein comprises the amino acid sequence of SEQ ID NO: 11.

26. The method of claim 24, wherein the capsid protein comprises the amino acid sequence SEQ ID NO: 8.

27. The method of claim 24, wherein the capsid protein comprises the amino acid sequence of SEQ ID NO: 16.

28. The method of claim 24, wherein the capsid protein comprises the amino acid sequence of SEQ ID NO: 13.

29. The method of claim 16, wherein transduction of the cell introduces a therapeutic nucleotide sequence into the cell.

30. The method of claim 29, wherein the therapeutic nucleotide sequence encodes a protein.

31. The method of claim 29, wherein the therapeutic nucleotide sequence encodes a miRNA, shRNA, or siRNA.

32. The method of claim 16, wherein the cell is a blood, liver, heart, joint tissue, muscle, brain, kidney, or lung cell.

33. The method of claim 16, wherein the cell is a hematopoietic stem cell.

34. The method of claim 33, wherein the cell is a human $CD34^+$ hematopoietic stem cell.

35. The method of claim 16, wherein the cell is in a subject and the rAAV is administered to the subject.

36. The method of claim 35, wherein the rAAV is administered to the subject intravenously, intraperitoneally, subcutaneously, intramuscularly, or intradermally.

37. The method of claim 35, wherein the subject is a human subject.

38. The method of claim 22, wherein transduction of the cell introduces a therapeutic nucleotide sequence into the cell.

39. The method of claim 38, wherein the therapeutic nucleotide sequence encodes a protein.

40. The method of claim 38, wherein the therapeutic nucleotide sequence encodes a miRNA, shRNA, or siRNA.

41. The method of claim 22, wherein the cell is a blood, liver, heart, joint tissue, muscle, brain, kidney, or lung cell.

42. The method of claim 22, wherein the cell is a hematopoietic stem cell.

43. The method of claim 42, wherein the cell is a human $CD34^+$ hematopoietic stem cell.

44. The method of claim 22, wherein the cell is in a subject and the rAAV is administered to the subject.

45. The method of claim 44, wherein the rAAV is administered to the subject intravenously, intraperitoneally, subcutaneously, intramuscularly, or intradermally.

46. The method of claim 44, wherein the subject is a human subject.

* * * * *